(12) United States Patent
Cogan et al.

(10) Patent No.: US 11,780,849 B2
(45) Date of Patent: Oct. 10, 2023

(54) IMINO SULFANONE INHIBITORS OF ENPP1

(71) Applicant: Volastra Therapeutics, Inc., New York, NY (US)

(72) Inventors: Derek A. Cogan, New York, NY (US); Sarah Bettigole, New York, NY (US); Leon Van Berkom, Nijmegen (NL); Piotr Nieczypor, Nijmegen (NL); Michael Su, New York, NY (US); Rutger Folmer, Nijmegen (NL)

(73) Assignee: Volastra Therapeutics, Inc., New York, NY (US)

( * ) Notice: Subject to any disclaimer, the term of this patent is extended or adjusted under 35 U.S.C. 154(b) by 0 days.

(21) Appl. No.: 17/306,690

(22) Filed: May 3, 2021

(65) Prior Publication Data

US 2023/0002406 A1   Jan. 5, 2023

Related U.S. Application Data

(60) Provisional application No. 63/093,709, filed on Oct. 19, 2020, provisional application No. 63/019,853, filed on May 4, 2020.

(51) Int. Cl.

| | | |
|---|---|---|
| C07D 495/10 | (2006.01) |
| C07D 215/233 | (2006.01) |
| C07D 215/56 | (2006.01) |
| C07D 237/28 | (2006.01) |
| C07D 239/74 | (2006.01) |
| C07D 239/88 | (2006.01) |
| C07D 401/04 | (2006.01) |
| C07D 401/06 | (2006.01) |
| C07D 403/04 | (2006.01) |
| C07D 405/12 | (2006.01) |
| C07D 409/04 | (2006.01) |
| C07D 409/12 | (2006.01) |
| C07D 409/14 | (2006.01) |
| C07D 417/06 | (2006.01) |
| C07D 417/14 | (2006.01) |
| C07D 471/04 | (2006.01) |
| C07D 471/10 | (2006.01) |
| C07D 487/10 | (2006.01) |
| C07D 239/94 | (2006.01) |

(52) U.S. Cl.
CPC ....... *C07D 495/10* (2013.01); *C07D 215/233* (2013.01); *C07D 215/56* (2013.01); *C07D 237/28* (2013.01); *C07D 239/74* (2013.01); *C07D 239/88* (2013.01); *C07D 239/94* (2013.01); *C07D 401/04* (2013.01); *C07D 401/06* (2013.01); *C07D 403/04* (2013.01); *C07D 405/12* (2013.01); *C07D 409/04* (2013.01); *C07D 409/12* (2013.01); *C07D 409/14* (2013.01); *C07D 417/06* (2013.01); *C07D 417/14* (2013.01); *C07D 471/04* (2013.01); *C07D 471/10* (2013.01); *C07D 487/10* (2013.01)

(58) Field of Classification Search
CPC .. C07D 401/04; C07D 401/06; C07D 403/04; C07D 405/12; C07D 409/04; C07D 409/12; C07D 417/06; C07D 417/14; C07D 471/04; C07D 471/10; C07D 487/10; C07D 237/28; C07D 215/56; C07D 239/74; C07D 239/88; C07D 495/10; C07D 215/33
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 2014/0378408 A1 | 12/2014 | Fischet et al. |
| 2019/0201423 A1 | 7/2019 | Deb et al. |
| 2019/0282703 A1 | 9/2019 | Gallatin et al. |
| 2023/0036933 A1 | 2/2023 | Bettigole |

FOREIGN PATENT DOCUMENTS

| | | |
|---|---|---|
| EP | 2 003 132 | 12/2008 |
| JP | 2020-015670 | 1/2020 |
| WO | WO 1991/008211 | 6/1991 |
| WO | WO 2012/032513 | 3/2012 |
| WO | WO 2012/116137 | 8/2012 |
| WO | WO 2014/134772 | 9/2014 |
| WO | WO 2016/090296 | 6/2016 |
| WO | WO 2017/198756 | 11/2017 |
| WO | WO 2018/119325 | 6/2018 |
| WO | WO 2019/046778 | 3/2019 |
| WO | WO 2019/051269 | 3/2019 |
| WO | WO 2019/149660 | 8/2019 |
| WO | WO 2019/177971 | 9/2019 |
| WO | WO 2019/191504 | 10/2019 |
| WO | WO 2020/035052 | 2/2020 |
| WO | WO 2020/140001 | 7/2020 |
| WO | WO 2020/160333 | 8/2020 |
| WO | WO 2020/190912 | 9/2020 |
| WO | WO 2021/061803 | 4/2021 |
| WO | WO 2021/225969 | 11/2021 |

OTHER PUBLICATIONS

Berge et al., "Pharmaceutical Salts," J Pharmaceutical Sciences (1977) 66(1):1-19.

Carozza et al., "Structure-Aided Development of Small-Molecule Inhibitors of ENPP1, the Extracellular Phosphodiesterase of the Immunotransmitter cGAMP," Cell Chem Biol (2020) 27:1347-1358.

(Continued)

*Primary Examiner* — Rebecca L Anderson
(74) *Attorney, Agent, or Firm* — Morrison & Foerster LLP

(57) ABSTRACT

The present disclosure relates generally to inhibitors of ectonucleotide pyrophosphatase/phosphodiesterase 1 (ENPP1), compositions thereof, and methods of using said compounds and compositions thereof. More specifically, the present disclosure relates to sulfoximine-based inhibitors of ENPP1 and methods of their use for treating disease mediated by ENPP1.

10 Claims, No Drawings

(56) References Cited

OTHER PUBLICATIONS

Danino et al., "Inhibition of nucleotide pyrophosphatase/phosphodiesterase 1: implications for developing a calcium pyrophosphate deposition disease modifying drug," Rheumatology (2018) 57:1472-1480.
Dean et al., "Recent Advances in the Synthesis and Applications of Radiolabeled Compounds for Drug Discovery and Development," Curr Pharm Des (2000) 6(10).
Dennis et al., "Crystal structures of human ENPP1 in apo and bound forms," Acta Crystallogr Sect D 76, 889-898 (2020).
Evans et al., "Synthesis of radiolabeled compounds," J Radioanal Xhem (1981) 64(1-2):9-32.
Hessle et al., "Tissue-nonspecific alkaline phosphatase and plasma cell membrane glycoprotein-1 are central antagonistic regulators of bone mineralization," PNAS (2002) 99(14):9445-9449.
Jafari et al., Synthesis of 2-arylated thiadiazolopyrimidones by Suzuki-Miyaura cross-coupling: a new class of nucleotide pyrophosphatase (NPPs) inhibitors. Rsc Adv 6:107556-107571 (2016).
Kabalka et al., "The Synthesis of Radiolabeled Compounds via Organometallic Intermediates," Tetrahedron (1989) 45(21): 6601-21.
Kawaguchi et al., "Development of an ENPP1 Fluorescence Probe for Inhibitor Screening, Cellular Imaging, and Prognostic Assessment of Malignant Breast Cancer," Journal of Medicinal Chemistry (2019) 62(20), 9254-9269.
Lee et al., "Substrate-dependence of competitive nucleotide pyrophosphatase/phosphodiesterasel (NPP1) inhibitors," Frontiers Pharma (2017) 8:Article 54.
Mardjuki et al., "Development of cGAMP-Luc, a sensitive and precise coupled enzyme assay to measure cGAMP in complex biological samples," J Biol Chem (2020) 295(15):4881-4892.
Onyedibe et al., "ENPP1, an Old Enzyme with New Functions, and Small Molecule Inhibitors—A STING in the Tale of ENPP1" Molecules (2019) 24:4192.
Patel et al., "Quinazolin-4-Piperidin-4-Methyl Sulfamide PC-1 Inhibitors: Alleviating HERG Interactions through Structure Based Design," Bioorganic Med. Chem. Lett. (2009) 19 (12):3339-3343.
Rosenthal et al., "Calcium Pyrophosphate Deposition Disease," N Engl J Med (2016) 374(26) :2575-2584.
Shayhidin et al., "Quinazoline-4-Piperidine Sulfamides Are Specific Inhibitors of Human NPP1 and Prevent Pathological Mineralization of Valve Interstitial Cells," Br. J. Pharmacol. (2015) 172 (16): 4189-4199.
Ullah et al., "Synthesis, biological evaluation, and docking studies of new pyrazole-based thiourea and sulfonamide derivatives as inhibitors of nucleotide pyrophosphatase/phosphodiesterase," Bioorg Chem (2020) 99:103783.
Zelikman et al., "Highly Selective and Potent Ectonucleotide Pyrophosphatase-1 (NPP1) Inhibitors Based on Uridine 5'-P $\alpha,\alpha$-Dithiophosphate Analogues," J Med Chem (2018) 61:3939-3951.
STN-Chemical database registry RN 949716-61-4 for N-Hydroxy-5,7-dimethyl[1,2,4]triazolo[1,5-a]pyrimidine-6-propanamide, Entered STN: Oct. 9, 2007, LC STN Files: CHEMCATS.
Wislicenus, J. "Adolph Strecker's Short Textbook of Organic Chemistry" 1881, Spottiswoode: London, pp. 38-39.

IMINO SULFANONE INHIBITORS OF ENPP1

CROSS-REFERENCE TO RELATED APPLICATIONS

This application claims priority to and the benefit of U.S. Provisional Application No. 63/019,853, filed on May 4, 2020, and U.S. Provisional Application No. 63/093,709, filed on Oct. 19, 2020, the entire disclosures of which are incorporated herein by reference in their entireties.

FIELD

The present disclosure relates generally to inhibitors of ectonucleotide pyrophosphatase/phosphodiesterase 1 (ENPP1), compositions thereof, and methods of using said compounds and compositions thereof. More specifically, the present disclosure relates to sulfoximine-based inhibitors of ENPP1 and methods of their use for treating disease mediated by ENPP1.

BACKGROUND

In certain human diseases, maintenance of the phosphorylated nucleotides can be dysregulated resulting in poor outcomes, severe complications, and even death. Ectonucleotide Pyrophosphatase/Phosphodiesterase 1 (ENPP1), also known as ARHR2, COLED, M6S1, NPP1, NPPS, PC-1, PCA1 and PDNP1, is an enzyme that hydrolyzes phosphorylated nucleotides, including adenosine triphosphate (ATP) and 2',3'-cyclic adenosine monophosphate-guanidine monophosphate (cGAMP). In some cases, ENPP1 consumes substrates preventing their role in resolving disease. The concomitant increase in hydrolysis products can also have detrimental effects. Therefore, inhibitors of ENNP1's enzyme activity will have a beneficial effect in certain human diseases.

Cells detecting aberrant DNA in the cytosol generate cGAMP, which is an activator of the immune response via the STING pathway. ATP activates immune cells via purinergic receptor signaling. ENPP1 can be expressed as a mechanism to degrade cGAMP and ATP and evade the immune response. Such expression of ENPP1 has been identified in cancers with especially poor prognosis. Therefore, ENPP1 inhibition can be an effective treatment in cancers, especially in cases where ENPP1 expression is high or cytosolic DNA levels are elevated. Adenosine monophosphate (AMP) is also a product of both ATP and cGAMP hydrolysis. Adenosine is generated from AMP by enzymes such as CD73, and further suppresses the immune response and supports tumor survival by adenosine receptor pathways.

ENPP1 has also been implicated in bacterial or viral infections, insulin resistance and type II diabetes, chondrocalcinosis and osteoarthritis, calcium pyrophosphate deposition disorder (CPPD), hypophosphatasia, and soft-tissue calcification disorders such as cardiac calcification after heart injury. Therefore, ENPP1 inhibition can be used to treat any of these disorders.

BRIEF SUMMARY

The present disclosure provides compounds of Formula (I), compositions thereof, and methods of using said compounds and compositions thereof for the treatment of diseases or conditions associated with ENPP1. In one aspect, provided is a compound of Formula (I)

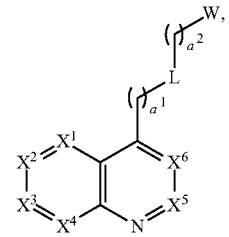

or a pharmaceutically acceptable salt thereof, wherein W is

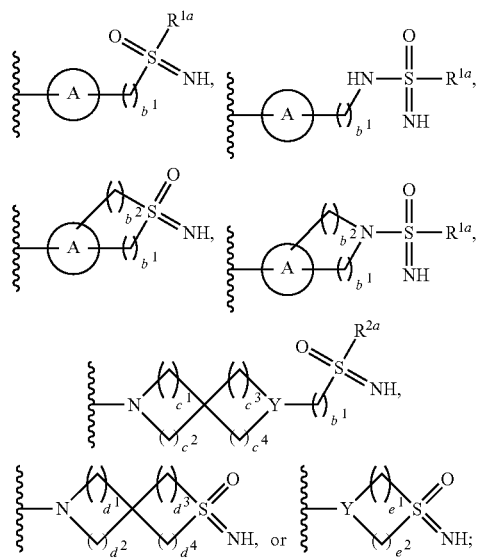

ring A is aryl, heteroaryl, cycloalkyl, cycloalkenyl, heterocycloalkyl or heterocycloalkenyl, each of which is substituted or unsubstituted;

$R^{1a}$ and $R^{2a}$ are each independently hydrogen, optionally substituted $C_{1-6}$ alkyl, optionally substituted $C_{3-6}$ cycloalkyl, optionally substituted 3-6 membered heterocycloalkyl, or optionally substituted $C_{1-6}$ haloalkyl;

Y is —N— or —CH—;
$X^1$ is —$CR^{1b}$— or —N—;
$X^2$ is —$CR^{2b}$— or —N—;
$X^3$ is —$CR^{3b}$— or —N—;
$X^4$ is —$CR^{4b}$— or —N—;
$X^5$ is —$CR^{5b}$— or —N—;
$X^6$ is —$CR^{6b}$— or —N—;
$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, —$NR^{6c}$—, or —$OCR^{7c}$—*, wherein * represents the point of attachment to

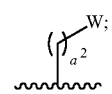

$R^{1c}$-$R^{7c}$ are each independently hydrogen or $C_{1-3}$ alkyl;
$a^1$, $a^2$, $b^1$, and $c^4$ are each independently 0, 1, 2, or 3; and
$b^2$, $c^1$-$c^3$, $d^1$-$d^4$, $e^1$, and $e^2$ are each independently 1, 2, or 3.

In another aspect, provided is pharmaceutical composition comprising a compound of Formula (I), or a pharmaceutically acceptable salt thereof, and a pharmaceutically acceptable carrier or excipient.

In another aspect, provided is a method of inhibiting ENPP1 comprising contacting a cell with an effective amount of a compound of Formula (I), or a pharmaceutically acceptable salt thereof.

In another aspect, provided is a method of treating cancer, a bacterial and/or viral infection, insulin resistance, type II diabetes, chondrocalcinosis, osteoarthritis, a soft-tissue calcification disorder, calcium pyrophosphate deposition disorder, or hypophosphatasia in a subject in need thereof, comprising administering to the subject a therapeutically effective amount of a compound of Formula (I), or a pharmaceutically acceptable salt thereof.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), including all substructures, subgenera, preferences, embodiments, examples and particular compounds defined and/or described herein. In some embodiments, references to a compound of Formula (I) and subgroups thereof, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), include polymorphs, solvates, co-crystals, isomers, tautomers and/or oxides thereof. In some embodiments, references to a compound of Formula (I) and subgroups thereof, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), include polymorphs, solvates, and/or co-crystals thereof. In some embodiments, references to a compound of Formula (I) and subgroups thereof, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), include isomers, tautomers and/or oxides thereof. In some embodiments, references to a compound of Formula (I) and subgroups thereof, such as Formula (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, 5 membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluoro, chloro, bromo or iodo.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2$H, $^3$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient, individual, or subject is a human, for example a human that has been or will be the object of treatment, observation or experiment. The compounds, compositions and methods described herein can be useful in both human therapy and veterinary applications.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation (e.g., inhibition) of ENPP1. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

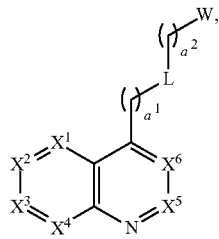

(I)

or a pharmaceutically acceptable salt thereof, wherein:
W is

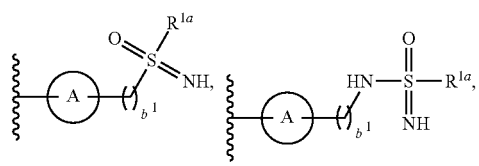

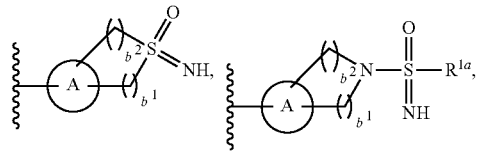

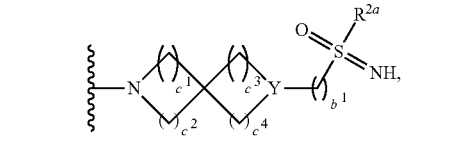

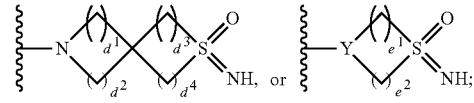

ring A is aryl, heteroaryl, cycloalkyl, cycloalkenyl, heterocycloalkyl or heterocycloalkenyl, each of which is substituted or unsubstituted;
$R^{1a}$ and $R^{2a}$ are each independently hydrogen, optionally substituted $C_{1-6}$ alkyl, optionally substituted $C_{3-6}$ cycloalkyl, optionally substituted 3-6 membered heterocycloalkyl, or optionally substituted $C_{1-6}$ haloalkyl;
Y is —N— or —CH—;
$X^1$ is —$CR^{1b}$— or —N—;
$X^2$ is —$CR^{2b}$— or —N—;
$X^3$ is —$CR^{3b}$— or —N—;
$X^4$ is —$CR^{4b}$— or —N—;
$X^5$ is —$CR^{5b}$— or —N—;
$X^6$ is —$CR^{6b}$— or —N—;
$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, —$NR^{6c}$—, or —$OCR^{7c}$—*, wherein * represents the point of attachment to

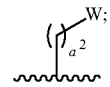

$R^{1c}$-$R^{7c}$ are each independently hydrogen or $C_{1-3}$ alkyl;
$a^1$, $a^2$, $b^1$, and $c^4$ are each independently 0, 1, 2, or 3; and
$b^2$, $c^1$-$c^3$, $d^1$-$d^4$, $e^1$, and $e^2$ are each independently 1, 2, or 3.

In some embodiments of Formula (I), or a pharmaceutically acceptable salt thereof, the compound is not (9-imino-9-oxido-1-oxa-9λ⁶-thia-4-azaspiro[5.5]undecan-4-yl)(2-methylquinolin-4-yl)methanone. In some embodiments, W is not

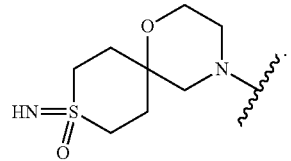 [SMILES: *N1CCOC2(CCS(=N)(=O)CC2)C1]

In some embodiments, W comprises a fused ring structure when W is

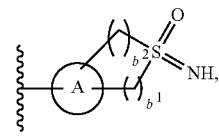

where two or more rings share a bond. In some embodiments, A is not heterocycloalkyl when W is

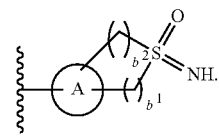

In some embodiments, W comprises a fused ring structure when W is

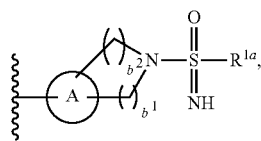

where two or more rings share a bond. In some embodiments, W comprises a fused ring structure when W is

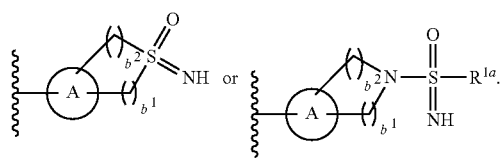

In some embodiments, $R^{1b}$-$R^{6b}$ are not morpholinyl or pyrazolyl. In some embodiments, $R^{1b}$-$R^{6b}$ are not heterocycloalkyl or heteroaryl. In some embodiments, L is not —C(O)N(CH$_3$)—*, wherein * represents the point of attachment to

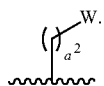

In some embodiments of Formula (I), or a pharmaceutically acceptable salt thereof, W is

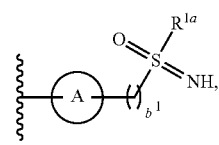

wherein ring A, $b^1$, and $R^{1a}$ are as defined for Formula I or any variation or embodiment thereof. In some embodiments, W is

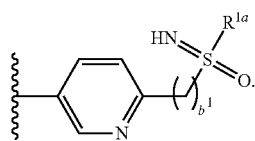

In some such embodiments, $b^1$ is 0. In some such embodiments, $b^1$ is 1. In some such embodiments, $b^1$ is 2. In some embodiments, $b^1$ is 3. In some embodiments, W is

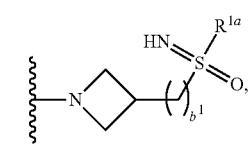 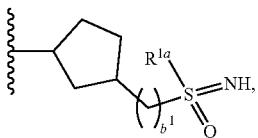

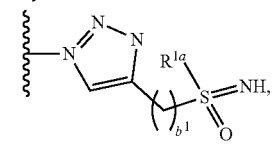 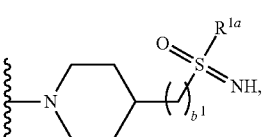

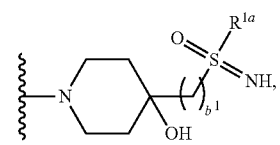 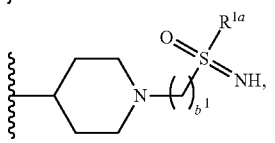

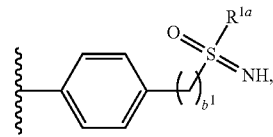 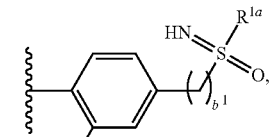

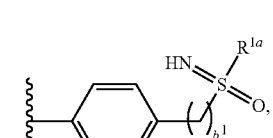 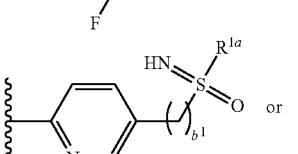

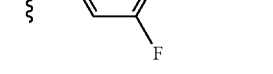  or

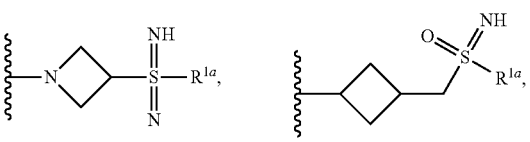

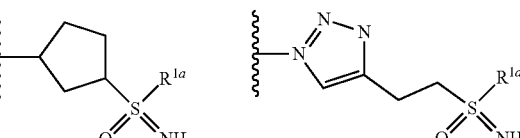

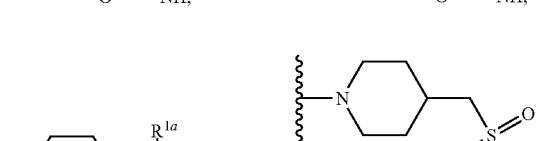

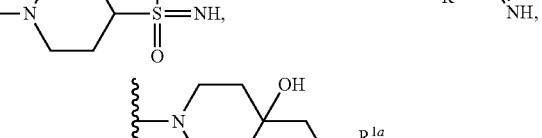

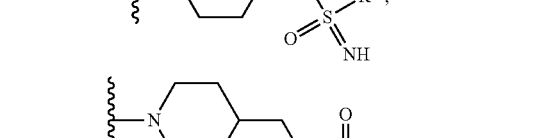

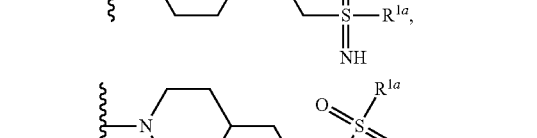

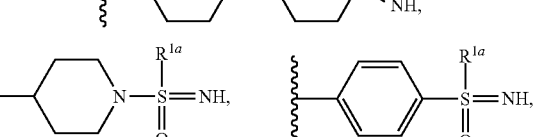

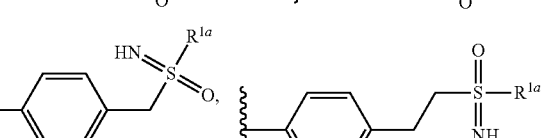

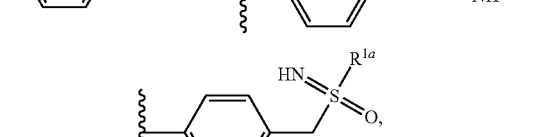

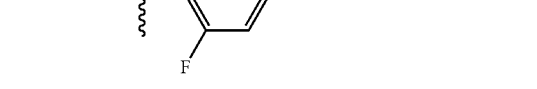

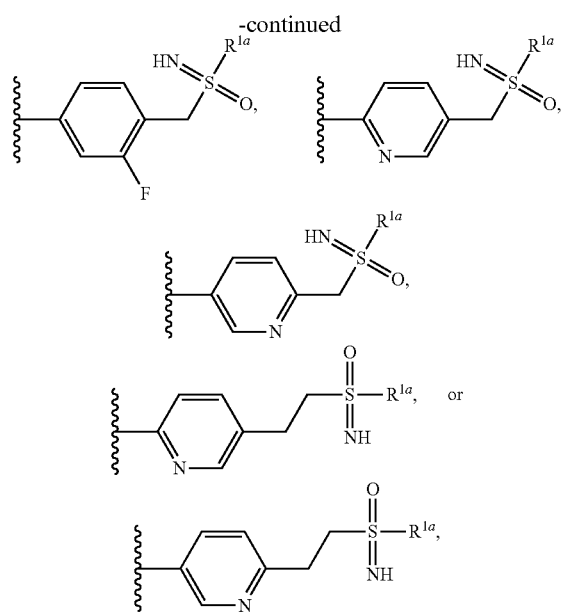

In some embodiments, W is

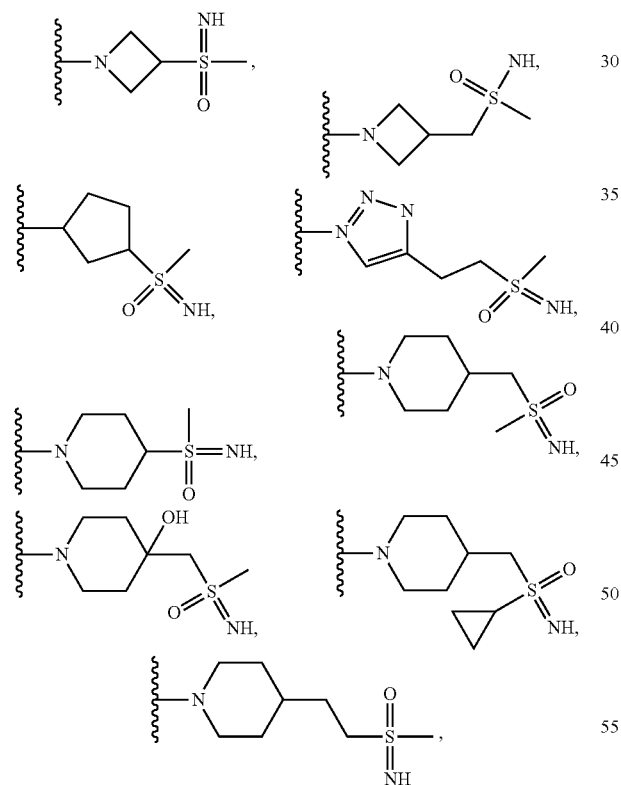

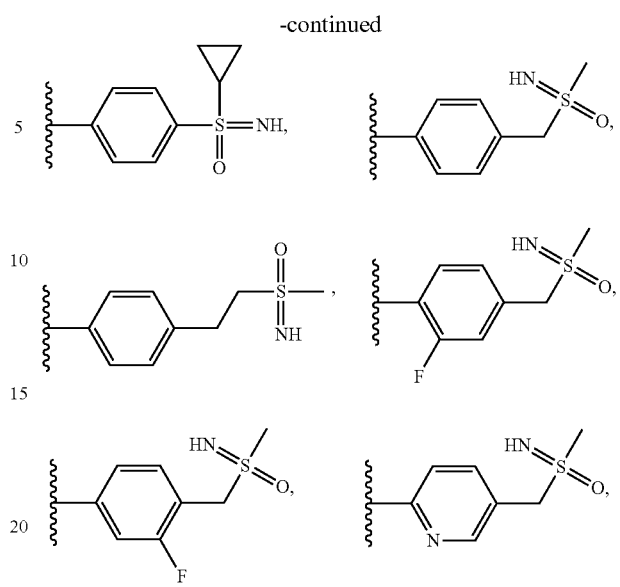

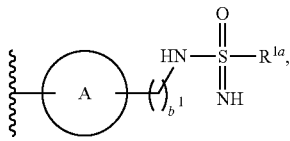

In some embodiments of Formula (I), or a pharmaceutically acceptable salt thereof, W is

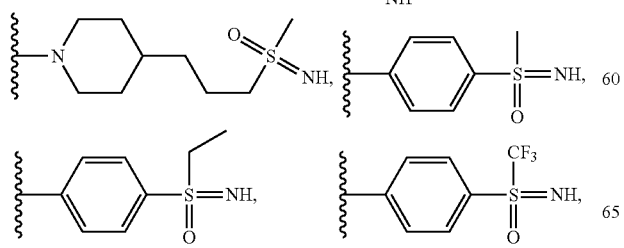

wherein ring A, $b^1$, and $R^{1a}$ are as defined for Formula (I) or any variation or embodiment thereof. In some embodiments, W is

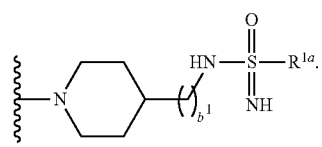

In some such embodiments, $b^1$ is 0. In some such embodiments, $b^1$ is 1. In some such embodiments, $b^1$ is 2. In some embodiments, $b^1$ is 3. In some embodiments, W is In some embodiments, W is

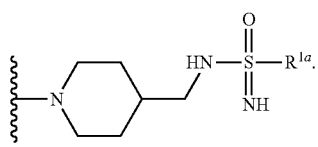

In some embodiments, W is

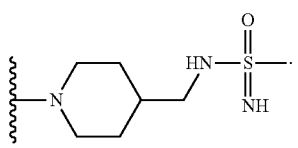

In some embodiments of Formula (I), or a pharmaceutically acceptable salt thereof, W is

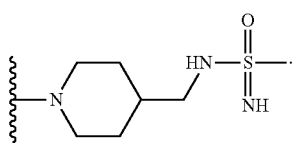

wherein ring A, $b^1$, and $b^2$ are as defined for Formula (I) or any variation or embodiment thereof. In some embodiments, W is

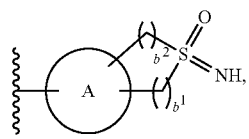

In some such embodiments, $b^1$ is 1 and $b^2$ is 2. In some embodiments, W is

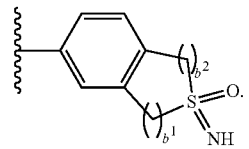

In some embodiments of Formula (I), or a pharmaceutically acceptable salt thereof, W is

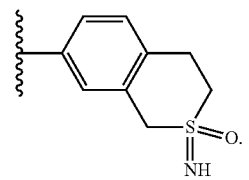 [SMILES: *c1ccc2c(c1)CS(=N)(=O)CC2]

wherein ring A, $b^1$, $b^2$, and $R^{1a}$ are as defined for Formula (I) or an variation or embodiment thereof. In some embodiments, W is

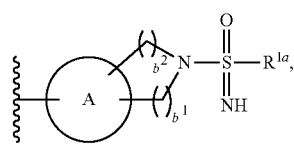

In some such embodiments, $b^1$ is 1 and $b^2$ is 2. In some embodiments, W is

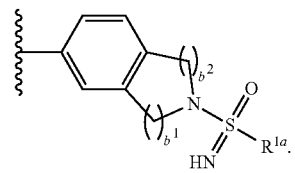

In some embodiments, W is

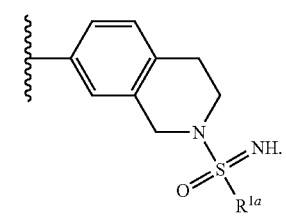

In some embodiments of Formula (I), or a pharmaceutically acceptable salt thereof, ring A is aryl, heteroaryl, cycloalkyl, cycloalkenyl, heterocycloalkyl, or hetereocycloalkenyl, each of which is substituted or unsubstituted. In some embodiments, ring A is $C_{6-14}$ aryl, 4- to 14-membered heteroaryl, $C_{3-10}$ cycloalkyl, $C_{3-10}$ cycloalkenyl, 3- to 18-membered heterocycloalkyl, or 3- to 18-membered hetereocycloalkenyl, each of which is substituted or unsubstituted. In some embodiments, ring A is 4- to 14-membered heteroaryl, 3- to 18-membered heterocycloalkyl, or 3- to 18-membered heterocycloalkenyl, each of which is substituted or unsubstituted, wherein the 4- to 14-membered heteroaryl, 3- to 18-membered heterocycloalkyl, or 3- to 18-membered hetereocycloalkenyl contains one, two, three, four, five, or six heteroatoms. In some embodiments, each heteroatom is independently selected from nitrogen, oxygen, and sulfur.

In some embodiments, ring A is aryl (e.g., phenyl). In some embodiments, ring A is phenyl substituted with halo (e.g., fluoro). In some embodiments, ring A is heteroaryl. In some embodiments, ring A is pyridyl (e.g., 2-pyridyl or 3-pyridyl). In some embodiments, ring A is cycloalkyl (e.g., cyclopentyl). In some embodiments, ring A is heterocyloalkyl (e.g., piperidinyl). In some embodiments, ring A is

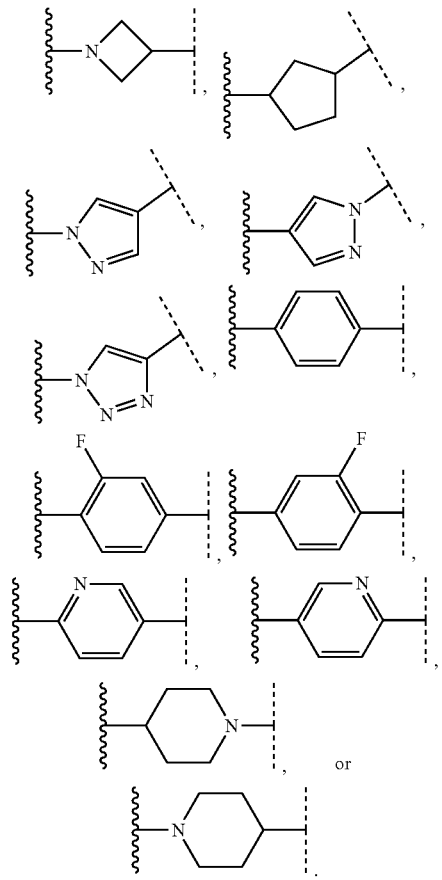

In some embodiments, ring A

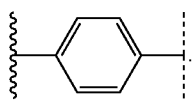

In some embodiments, ring A is

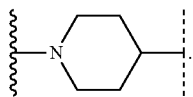

In some embodiments, ring A is substituted with one, two, three, four, five, or more substituents independently selected from halo, hydroxyl, $C_{3-10}$ cycloalkyl, or $C_{1-6}$ alkyl. In some embodiments, ring A is $C_{6-14}$ aryl substituted with halo. In some embodiments, ring A is phenyl substituted with fluoro. In some embodiments, ring A is phenyl substituted with bromo. In some embodiments, ring A is 3- to 18-membered heterocycloalkyl substituted with hydroxyl. In some embodiments, ring A is piperidinyl substituted with hydroxyl. In some embodiments, ring A is 3- to 18-membered heterocycloalkyl substituted with $C_{3-10}$ cycloalkyl. In some embodiments, ring A is piperidinyl substituted with $C_{3-10}$ cycloalkyl.

It will be understood that when a moiety depicted herein is bonded to the remainder of a molecule at more than one position, the directionality of the moiety can be indicated by showing differentiated symbols, such as a squiggly line ∼∼∼ and a dotted line ------, to represent the positions of such bonds with respect to the remainder of the molecule. For example, when W is

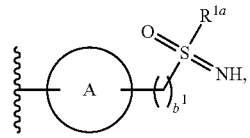

wherein ring A is

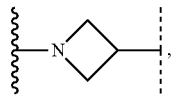

this denotes that bond shown with a squiggly line ∼∼∼ in the azetidine ring corresponds to the bond shown with a squiggly line ∼∼∼ in the

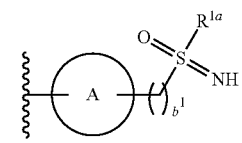

moiety, thereby providing the moiety

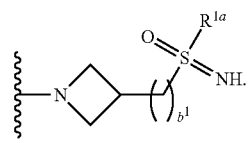

In some embodiments of Formula (I), or a pharmaceutically acceptable salt thereof, $R^{1a}$ is $C_{1-6}$ alkyl, wherein the $C_{1-6}$ alkyl is optionally substituted by halo, hydroxyl, $C_{1-3}$ alkoxy, or $C_{3-6}$ cycloalkyl. In some embodiments of Formula (I), or a pharmaceutically acceptable salt thereof, $R^{1a}$ is $C_{1-6}$ alkyl. In some embodiments, $R^{1a}$ is methyl, ethyl, n-propyl, isopropyl, n-butyl, isobutyl, sec-butyl, or tert-butyl. In some embodiments, $R^{1a}$ is methyl. In some embodiments, $R^{1a}$ is $C_{1-6}$ alkyl substituted by hydroxyl. In some embodiments, $R^{1a}$ is methyl substituted by hydroxyl, ethyl substituted by hydroxyl, n-propyl substituted by hydroxyl, isopropyl substituted by hydroxyl, n-butyl substituted by hydroxyl, isobutyl substituted by hydroxyl, sec-butyl substituted by hydroxyl, or tert-butyl substituted by hydroxyl. In some embodiments, $R^{1a}$ is $C_{1-6}$ alkyl substituted by $C_{1-3}$ alkoxy. In some embodiments, $R^{1a}$ is methyl substituted by $C_{1-3}$ alkoxy, ethyl substituted by $C_{1-3}$ alkoxy, n-propyl substituted by $C_{1-3}$ alkoxy, isopropyl substituted by $C_{1-3}$ alkoxy, n-butyl substituted by $C_{1-3}$ alkoxy, isobutyl substituted by $C_{1-3}$ alkoxy, sec-butyl substituted by $C_{1-3}$ alkoxy, or tert-butyl substituted by $C_{1-3}$ alkoxy. In some embodiments, $R^{1a}$ is methyl substituted by methoxy or ethyl substituted by methoxy. In some embodiments, $R^{1a}$ is $C_{1-6}$ alkyl substituted by $C_{3-6}$ cycloalkyl. In some embodiments, $R^{1a}$ is methyl substituted by $C_{3-6}$ cycloalkyl, ethyl substituted by $C_{3-6}$ cycloalkyl, n-propyl substituted by $C_{3-6}$ cycloalkyl, isopropyl substituted by $C_{3-6}$ cycloalkyl, n-butyl substituted by $C_{3-6}$ cycloalkyl, isobutyl substituted by $C_{3-6}$ cycloalkyl, sec-butyl substituted by $C_{3-6}$ cycloalkyl, or tert-butyl substituted by $C_{3-6}$ cycloalkyl. In some embodiments, $R^{1a}$ is methyl substituted by cyclopropyl.

In some embodiments, $R^{1a}$ and $R^{2a}$ are hydrogen, $C_{1-6}$ alkyl, $C_{3-6}$ cycloalkyl, 3-6 membered heterocycloalkyl, or $C_{1-6}$ haloalkyl. In some embodiments, $R^{1a}$ and $R^{2a}$ are optionally substituted with one, two, three, four, five, or more substituents each independently selected from halo, hydroxyl, $C_{1-3}$ alkoxy, $C_{3-6}$ cycloalkyl, and acyl. In some embodiments, acyl is $—C(O)R^{1a1}$, wherein $R^{1a1}$ is H or $C_{1-6}$ alkyl. In some embodiments, $R^{1a}$ and $R^{2a}$ are optionally substituted with one, two, three, four, five, or more substituents each independently selected from fluoro, chloro, methoxy, ethoxy, cyclopropyl, and $—C(O)CH_3$.

In some embodiments of Formula (I), or a pharmaceutically acceptable salt thereof, $b^1$ is 0, 1, or 2. In some embodiments, $b^1$ is 0. In some embodiments, $b^1$ is 1. In some embodiments, $b^1$ is 2. In some embodiments, $b^1$ is 3.

In some embodiments of Formula (I), or a pharmaceutically acceptable salt thereof, W is

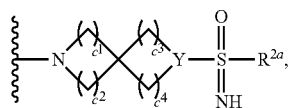

wherein $c^1$-$c^4$, Y, and $R^{2a}$ are as defined for Formula (I) or any variation or embodiment thereof. In some embodiments, Y is —N—. In some embodiments, Y is —CH—. In some embodiments, $c^1$ is 2 and $c^2$ is 2. In some embodiments, $c^3$ is 1 and $c^4$ is 1. In some embodiments, $c^3$ is 2 and $c^4$ is 1. In some embodiments, $c^1$ is 2, $c^2$ is 2, $c^3$ is 1, and $c^4$ is 1. In some embodiments, $c^1$ is 2, $c^2$ is 2, $c^3$ is 2, and $c^4$ is 1. In some embodiments, $c^4$ is 0. In some embodiments, $c^1$ is 2, $c^2$ is 2, $c^3$ is 1, and $c^4$ is 0.

In some embodiments, W is

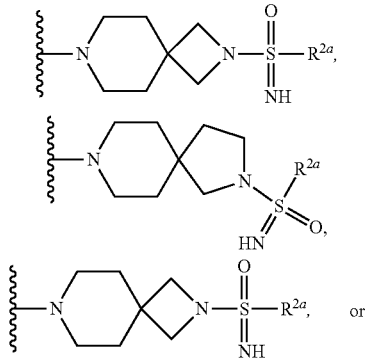

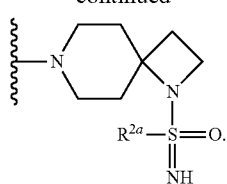

In some embodiments, $R^{2a}$ is hydrogen, $C_{1-6}$ alkyl, $C_{3-6}$ cycloalkyl, 3-6 membered heterocycloalkyl, or $C_{1-6}$ haloalkyl. In some embodiments, $R^{2a}$ is methyl. In some embodiments, $R^{2a}$ is optionally substituted with one, two, three, four, five, or more groups selected from halo, hydroxyl, $C_{1-3}$ alkoxy, $C_{3-6}$ cycloalkyl, and $—C(O)R^{1a1}$, wherein $R^{1a1}$ is H or $C_{1-6}$ alkyl. In some embodiments, $R^{2a}$ is $C_{1-6}$ alkyl optionally substituted with hydroxyl.

In some embodiments, W is

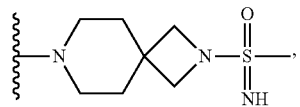

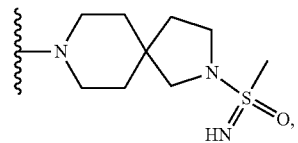

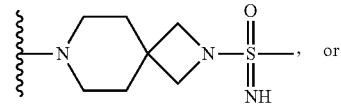

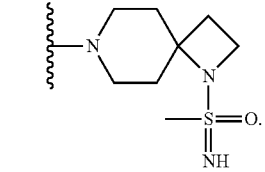

In some embodiments of Formula (I), or a pharmaceutically acceptable salt thereof, W is

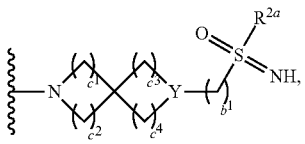

wherein $c^1$-$c^4$, Y, $b^1$, and $R^{2a}$ are as defined for Formula (I) or any variation or embodiment thereof. In some embodiments, Y is —N—. In some embodiments, Y is —CH—. In some embodiments, $c^1$ is 2 and $c^2$ is 2. In some embodiments, $c^3$ is 1 and $c^4$ is 1. In some embodiments, $c^3$ is 2 and $c^4$ is 1. In some embodiments, $c^1$ is 2, $c^2$ is 2, $c^3$ is 1, and $c^4$ is 1. In some embodiments, $c^1$ is 2, $c^2$ is 2, $c^3$ is 2, and $c^4$ is 1. In some embodiments, $c^1$ is 1 and $c^2$ is 1. In some embodiments, $c^1$ is 1, $c^2$ is 1, $c^3$ is 1, and $c^4$ is 1.

In some embodiments, W is

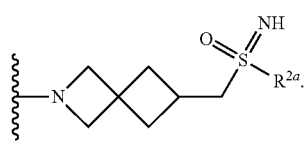

In some embodiments, $R^{2a}$ is hydrogen, $C_{1-6}$ alkyl, $C_{3-6}$ cycloalkyl, 3-6 membered heterocycloalkyl, or $C_{1-6}$ haloalkyl. In some embodiments, $R^{2a}$ is methyl. In some embodiments, $R^{2a}$ is optionally substituted with one, two, three, four, five, or more groups selected from halo, hydroxyl, $C_{1-3}$ alkoxy, $C_{3-6}$ cycloalkyl, and —C(O)$R^{1a1}$, wherein $R^{1a1}$ is H or $C_{1-6}$ alkyl. In some embodiments, $R^{2a}$ is $C_{1-6}$ alkyl optionally substituted with hydroxyl. In some embodiments, W is

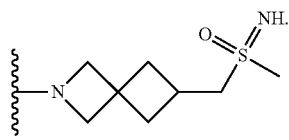 [SMILES: *N1CC2(CC(CS(C)(=N)=O)C2)C1]

In some embodiments of Formula (I), or a pharmaceutically acceptable salt thereof, W is

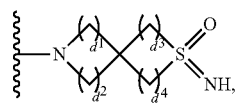

wherein $d^1$-$d^4$ are as defined for Formula (I) or any variation or embodiment thereof. In some embodiments, $d^1$ is 2 and $d^2$ is 2. In some embodiments, $d^1$ is 1 and $d^2$ is 1. In some embodiments, $d^3$ is 2 and $d^4$ is 1. In some embodiments, $d^3$ is 1 and $d^4$ is 1. In some embodiments, $d^1$ is 2, $d^2$ is 2, $d^3$ is 2, and $d^4$ is 1. In some embodiments, $d^1$ is 1, $d^2$ is 1, $d^3$ is 1, and $d^4$ is 1. In some embodiments, W is

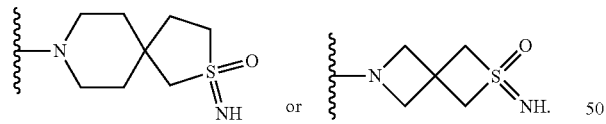

In some embodiments of Formula (I), or a pharmaceutically acceptable salt thereof, W is

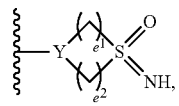

wherein Y, $e^1$, and $e^2$ are as defined for Formula (I) or any variation or embodiment thereof. In some embodiments, Y is —N—. In some embodiments, Y is —CH—. In some embodiments, $e^1$ is 2 and $e^2$ is 2. In some embodiments, $e^1$ is 1 and $e^2$ is 2. In some embodiments, $e^1$ is 3 and $e^2$ is 2. In some embodiments, W is

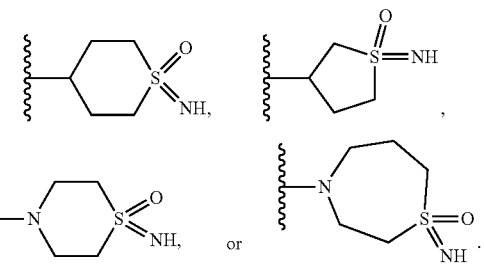

In some embodiments, W is

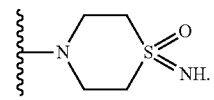 [SMILES: *N1CCS(=N)(=O)CC1]

In another aspect, the compound of Formula (I) is a compound of Formula (Ia), (Ib), (Ic), (Id), (Ie), (If), or (Ig):

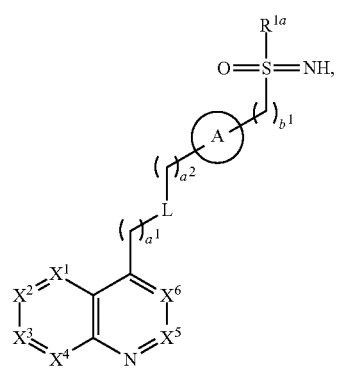

(Ia)

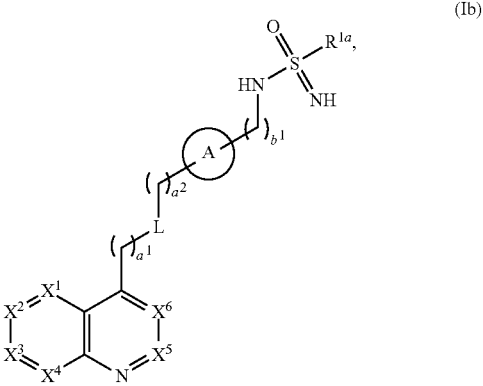

(Ib)

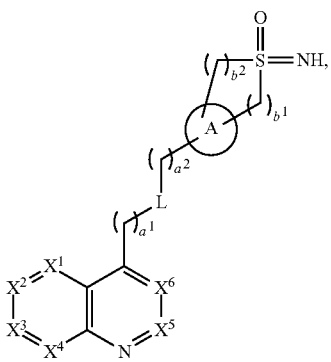
(Ic)

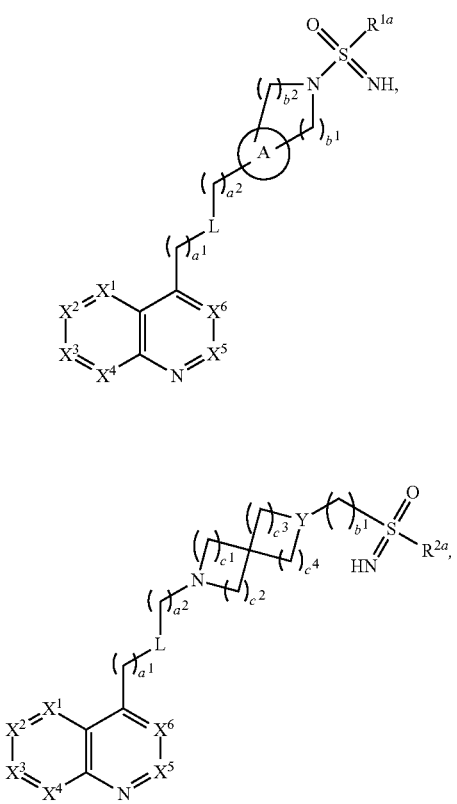
(Id)

(Ie)

(If)

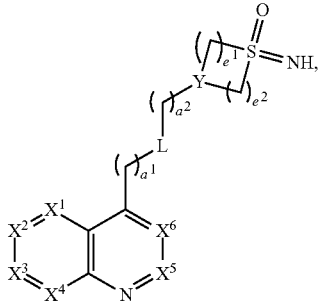
(Ig)

or a pharmaceutically acceptable salt thereof, wherein ring A, $R^{1a}$, $R^{2a}$, Y, $X^1$-$X^6$, $R^{1b}$-$R^{6b}$, L, $R^{1c}$-$R^{6c}$, $a^1$, $a^2$, $b^1$, $b^2$, $c^1$-$c^4$, $d^1$-$d^4$, $e^1$, and $e^2$ are as defined for Formula (I) or any variation or embodiment thereof.

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, $X^1$ is —$CR^{1b}$—. In some embodiments, $X^1$ is —N—. In some embodiments, $X^2$ is —$CR^{2b}$—. In some embodiments, $X^2$ is —N—. In some embodiments, $X^3$ is —$CR^{3b}$—. In some embodiments, $X^3$ is —N—. In some embodiments, $X^4$ is —$CR^{4b}$—. In some embodiments, $X^4$ is —N—. In some embodiments, $X^5$ is —$CR^{5b}$—. In some embodiments, $X^5$ is —N—. In some embodiments, $X^6$ is —$CR^{6b}$—. In some embodiments, $X^6$ is —N—. In some embodiments, $X^1$ is —$CR^{1b}$—, $X^2$ is —$CR^{2b}$—, $X^3$ is —$CR^{3b}$—, $X^4$ is —$CR^{4b}$—, $X^5$ is —$CR^{5b}$—, and $X^6$ is —$CR^{6b}$—. In some embodiments, $X^1$ is —N—, $X^2$ is —$CR^{2b}$—, $X^3$ is —$CR^{3b}$—, $X^4$ is —$CR^{4b}$—, $X^5$ is —$CR^{5b}$—, and $X^6$ is —$CR^{6b}$—. In some embodiments, $X^1$ is —$CR^{1b}$—, $X^2$ is —N—, $X^3$ is —$CR^{3b}$—, $X^4$ is —$CR^{4b}$—, $X^5$ is —$CR^{5b}$—, and $X^6$ is —$CR^{6b}$—. In some embodiments, $X^1$ is —$CR^{1b}$—, $X^2$ is —$CR^{2b}$—, $X^3$ is —N—, $X^4$ is —$CR^{4b}$—, $X^5$ is —$CR^{5b}$—, and $X^6$ is —$CR^{6b}$—. In some embodiments, $X^1$ is —$CR^{1b}$—, $X^2$ is —$CR^{2b}$—, $X^3$ is —$CR^{3b}$—, $X^4$ is —N—, $X^5$ is —$CR^{5b}$—, and $X^6$ is —$CR^{6b}$—. In some embodiments, $X^1$ is —$CR^{1b}$—, $X^2$ is —$CR^{2b}$—, $X^3$ is —$CR^{3b}$—, $X^4$ is —$CR^{4b}$—, $X^5$ is —N—, and $X^6$ is —$CR^{6b}$—. In some embodiments, $X^1$ is —$CR^{1b}$—, $X^2$ is —$CR^{2b}$—, $X^3$ is —$CR^{3b}$—, $X^4$ is —$CR^{4b}$—, $X^5$ is —$CR^{5b}$—, and $X^6$ is —N—.

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the

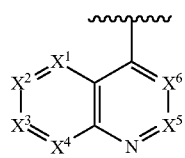

portion is quinolin-4-yl, 1,5-naphthyridinyl-4-yl, 1,6-naphthyridinyl-4-yl, 1,7-naphthyridin-4-yl, 1,8-naphthyridin-4-yl, cinnolin-4-yl, or quinazolin-4-yl, each of which is substituted or unsubstituted. In some embodiments, the

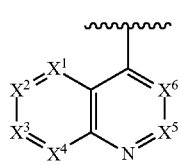

portion is 6,7-dimethoxyquinolin-4-yl. In some embodiments, the

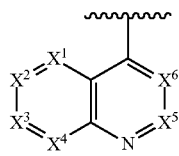

portion is 7-methoxyquinolin-4-yl.

In some embodiments of Formula (I), (I-1), (I-2), (I-3), (I-4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the

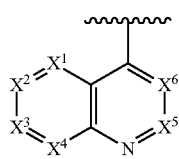

portion is

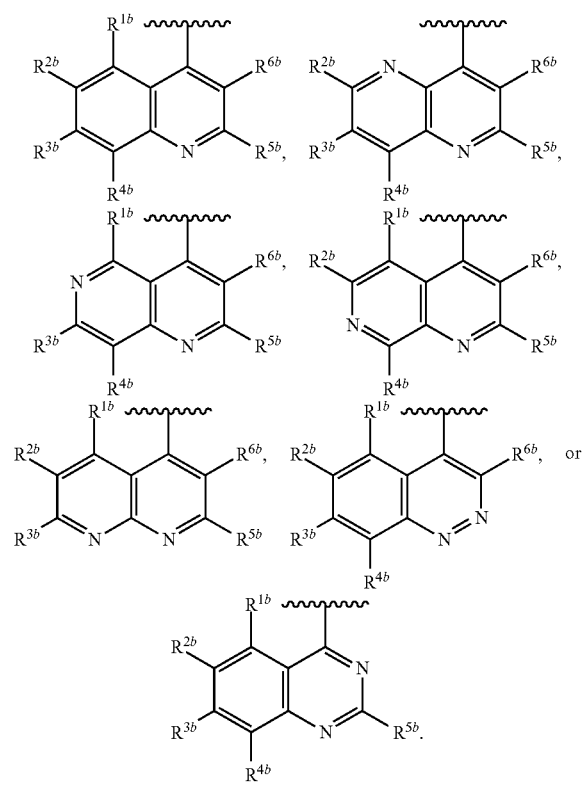

some embodiments, the

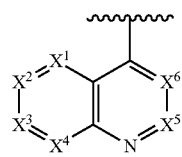

portion of Formula (I) is

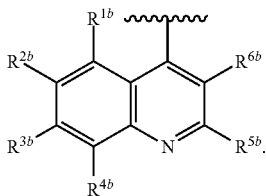

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, $X^2$ is $R^{2b}$ and $X^3$ is $R^{3b}$, wherein $R^{2b}$ and $R^{3b}$ are methoxy. In some embodiments, $X^1$ is Rib, $X^2$ is $R^{2b}$, $X^3$ is $R^{3b}$, and $X^4$ is $R^{4b}$, wherein $R^{2b}$ and $R^{3b}$ are methoxy, and Rib and $R^{4b}$ are hydrogen. In some embodiments, $X^1$ is $R^{1b}$, $X^2$ is $R^{2b}$, $X^3$ is $R^{3b}$, and $X^4$ is $R^{4b}$, wherein $R^{3b}$ is methoxy, and Rib, $R^{2b}$, and $R^{4b}$ are hydrogen.

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, or a pharmaceutically acceptable salt thereof, the

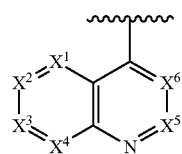

portion is

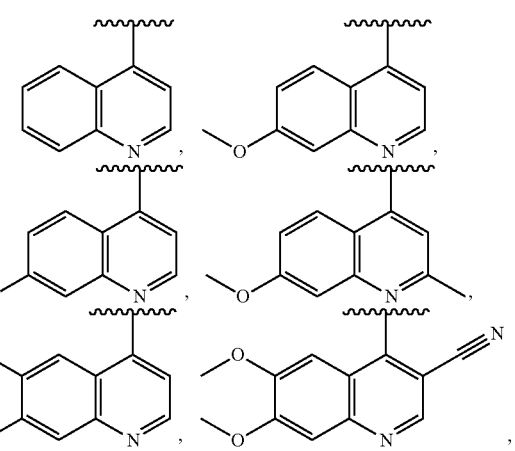

-continued
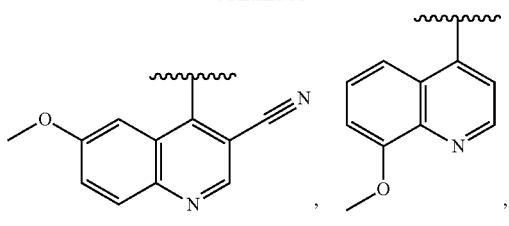
,
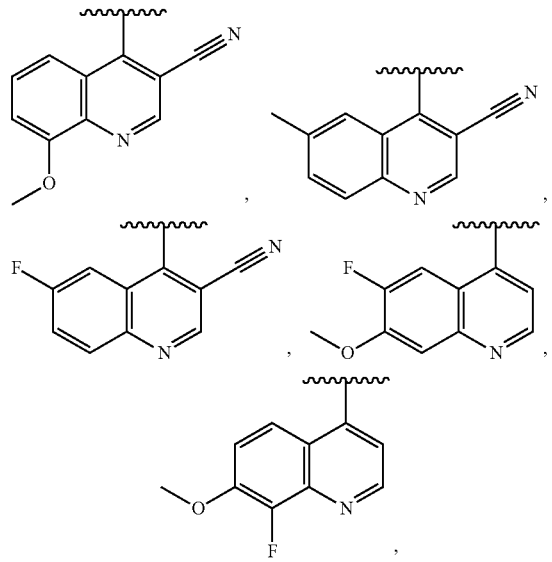
,
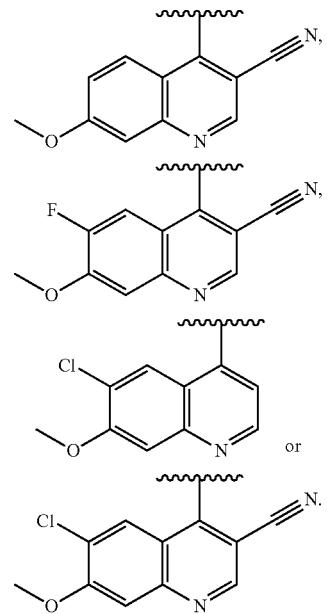
In some embodiments, the
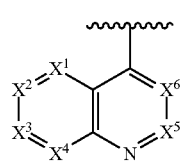
portion is
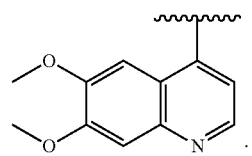 [SMILES: *c1ccnc2cc(OC)c(OC)cc12]
.
In some embodiments, the
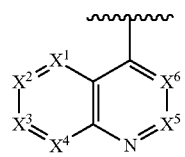
portion is
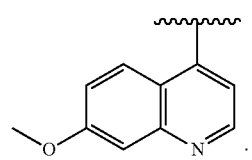
.
In some embodiments, the
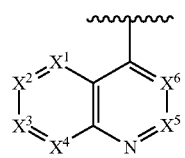
portion is
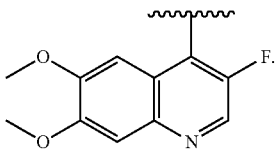 [SMILES: *c1c(F)cnc2cc(OC)c(OC)cc12]
.
In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the
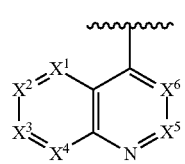

portion is

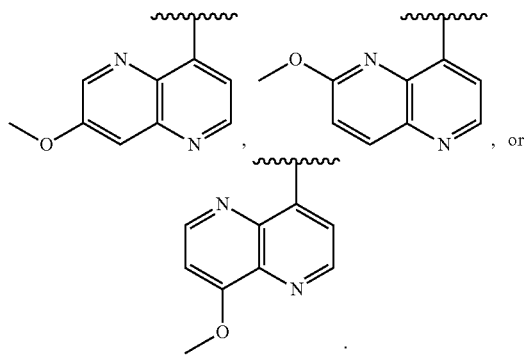

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the

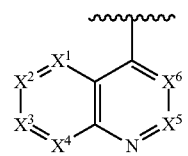

portion of Formula (I) is

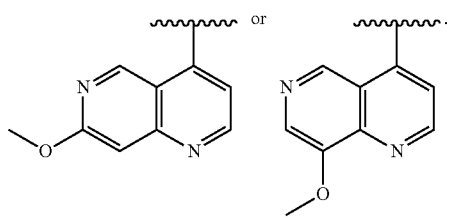

In some embodiments of Formula (I), (I-1), (I-2), (I-3), (I-4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the

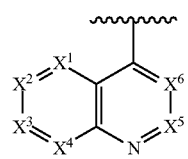

portion is

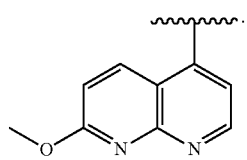 [SMILES: *c1ccnc2nc(OC)ccc12]

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a acceptable salt thereof, the

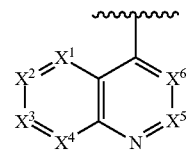

portion of Formula (I) is

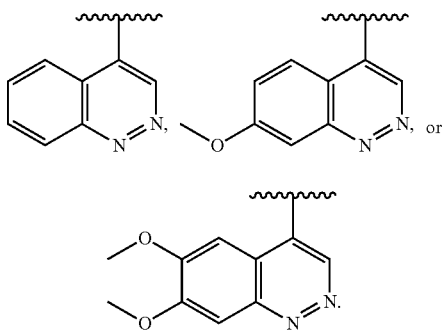

In some embodiments, the

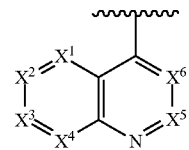

portion of Formula (I) is

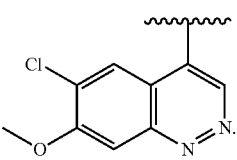 [SMILES: *c1cnnc2cc(OC)c(Cl)cc12]

In some embodiments of Formula (I), (I-1), (I-2), (I-3), (I4), (I-5), (Ia), (Ia-4), (Ia-5), (Ia-6), (Ib), (Ic), (Id), (Ie), (Ie-1), (Ie-2), (If), or (Ig), or a pharmaceutically acceptable salt thereof, the

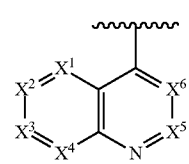

portion of Formula (I) is

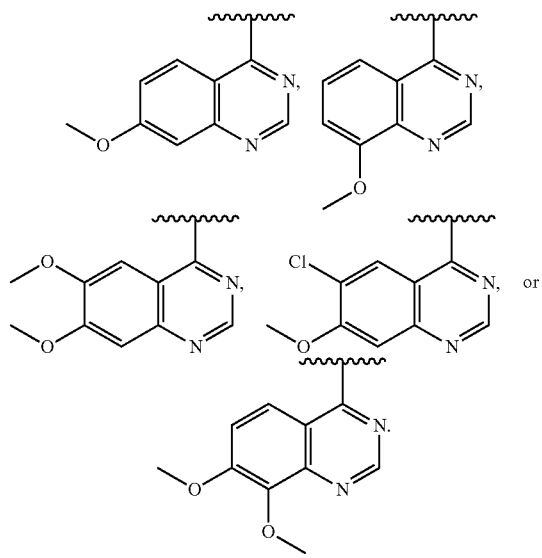

In some embodiments of Formula (I), (I-1), (I-2), (I-3), (I-4), (I-5), (Ia), (Ib), (Ic), (Id), (Ie), (If), or (Ig), or a pharmaceutically acceptable salt thereof, L is a bond, —O—, —C(O)—, —NR$^{6c}$—, or —OCR$^{7c}$—*, wherein R$^{6c}$ is as defined for Formula (I) or any variation or embodiment thereof, and wherein * represents the point of attachment to

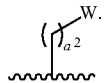

In some embodiments, L is a bond. In some embodiments, L is —O—. In some embodiments, L is —C(O)—. In some embodiments, L is —NR$^{6c}$—. In some embodiments, L is —NH—. In some embodiments, L is —N(CH$_3$)—. In some embodiments, L is —OCR$^{7c}$—*, wherein * represents the point of attachment to

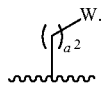

In some embodiments, L is —OC(CH$_3$)—*.

In some embodiments of Formula (I), (I-1), (I-2), (I-3), (I4), (I-5), (Ia), (Ia-1), (Ib), (Ic), (Id), (Ie), (If), or (Ig), or a pharmaceutically acceptable salt thereof, a$^1$ and a$^2$ are each independently 0, 1, or 2. In some embodiments, a$^1$ is 0. In some embodiments, a$^1$ is 1. In some embodiments, a$^1$ is 2. In some embodiments, a$^2$ is 0. In some embodiments, a$^2$ is 1. In some embodiments, a$^2$ is 2. In some embodiments, a$^1$ is 0, and a$^2$ is 0. In some embodiments, a$^1$ is 0, and a$^2$ is 1. In some embodiments, a$^1$ is 0, and a$^2$ is 2. In some embodiments, a$^1$ is 1, and a$^2$ is 0. In some embodiments, a$^1$ is 2, and a$^2$ is 0.

In some embodiments of Formula (I), (I-1), (I-2), (I-3), (I4), (I-5), (Ia), (Ib), (Ic), (Id), (Ie), (If), or (Ig), or a pharmaceutically acceptable salt thereof, the

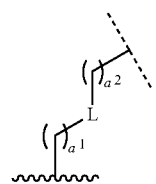

portion is a bond, —CH$_2$—, —CH$_2$CH$_2$—, —O—, —OCH$_2$—, —CH$_2$O—, —CH$_2$OCH$_2$—, —C(O)—, —C(O)CH$_2$—, —CH$_2$C(O)—, —NH—, —NHCH$_2$—, or —CH$_2$NH—, wherein the left-hand side of each listed moiety is bonded to the remainder of the molecule on the side represented by the squiggly line ∿∿, and the right-hand side of each listed moiety is bonded to the remainder of the molecule on the side represented by the dotted line ------.

In some embodiments of Formula (I), or a pharmaceutically acceptable salt thereof, W is

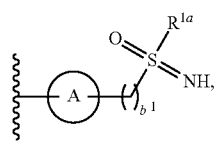

and the

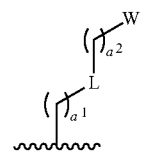

portion of Formula (I) is

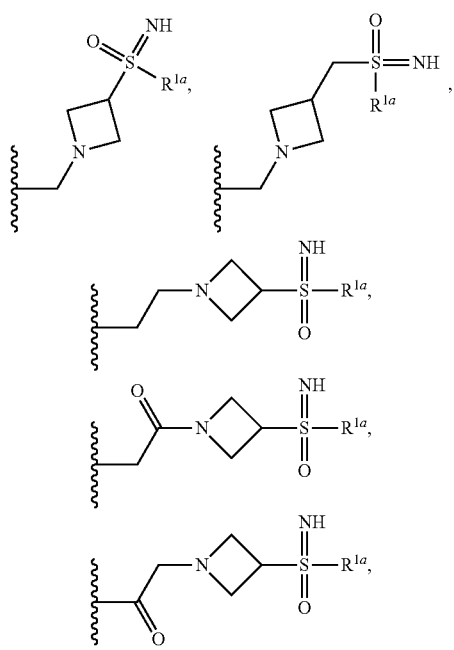

-continued
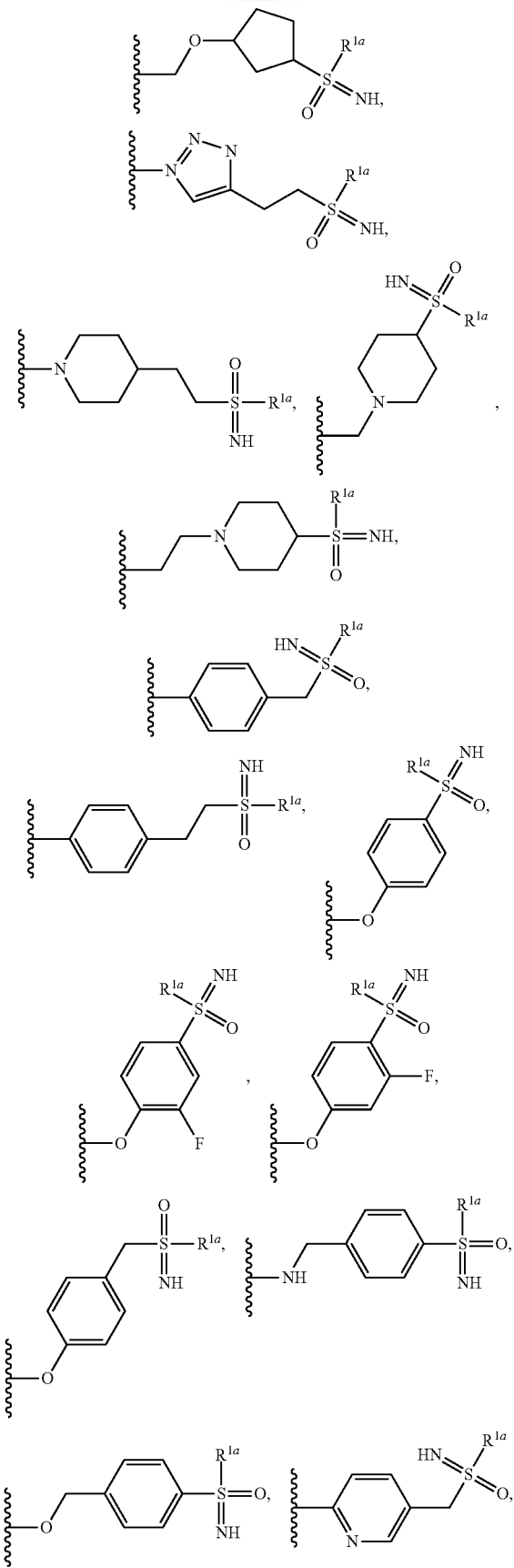
-continued
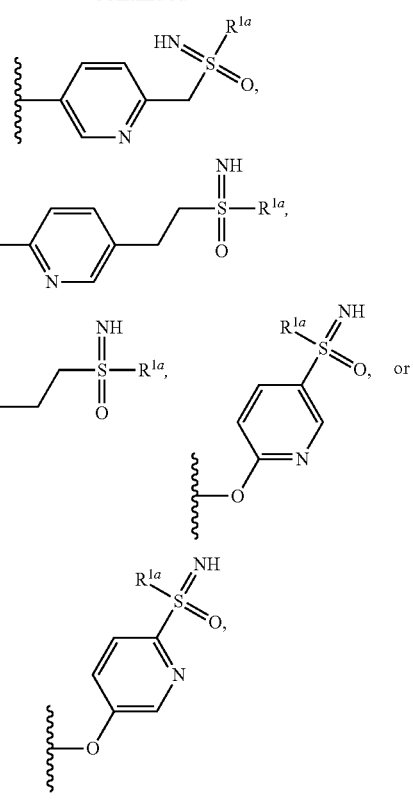
In some embodiments, the
$$\underset{\substack{(\phantom{x})_{a^1}\\\mathclap{\sim\sim\sim}}}{\overset{(\phantom{x})_{a^2}\!\!-\!\!W}{L}}$$
portion of Formula (I) is
[structure shown]
In some embodiments, the
$$\underset{\substack{(\phantom{x})_{a^1}\\\mathclap{\sim\sim\sim}}}{\overset{(\phantom{x})_{a^2}\!\!-\!\!W}{L}}$$

portion of Formula (I) is
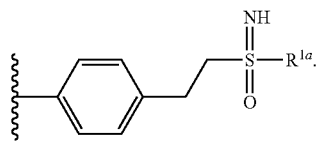
In some embodiments, the
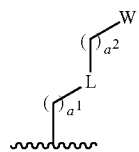
portion of Formula (I) is
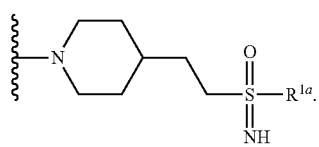
In some embodiments, the
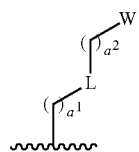
portion of Formula (I), or a pharmaceutically acceptable salt thereof, is
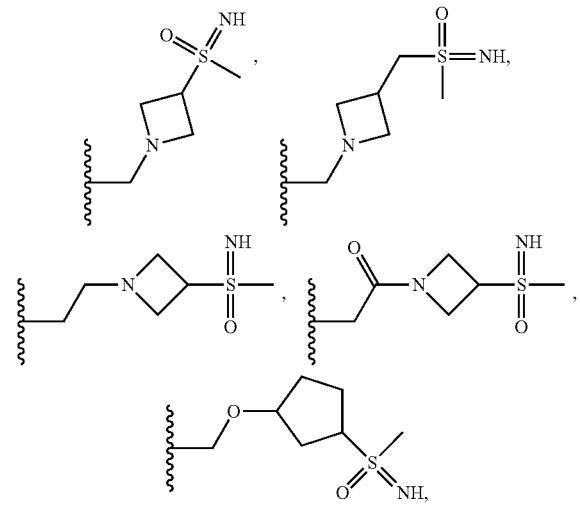
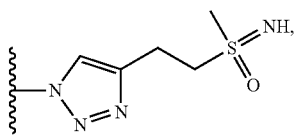
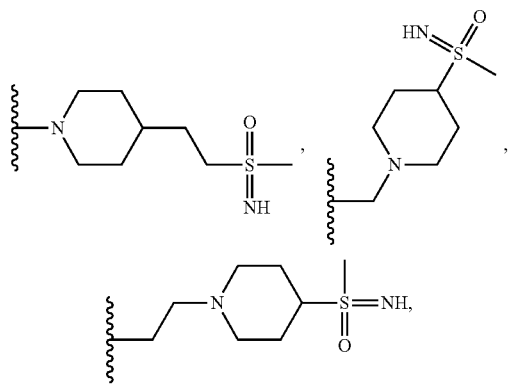
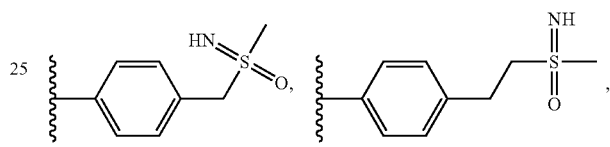
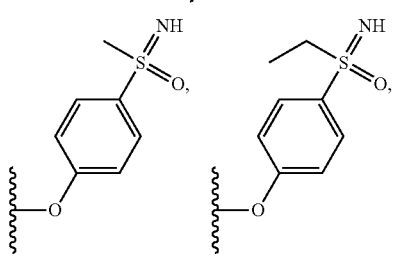
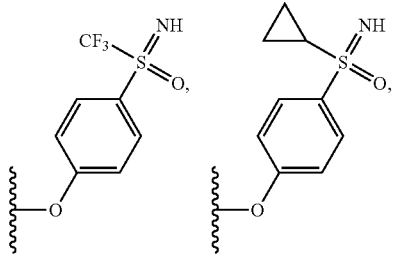
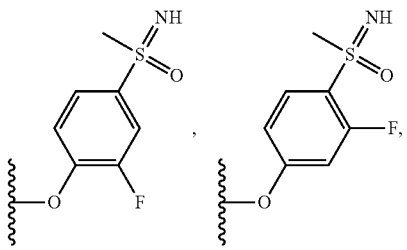
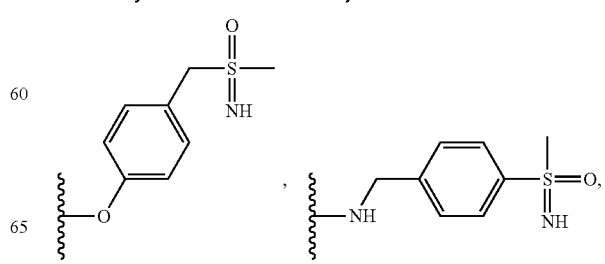

-continued
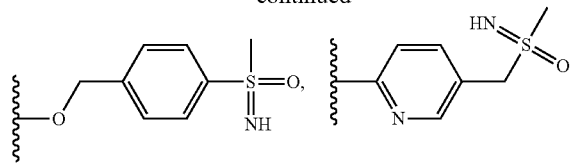
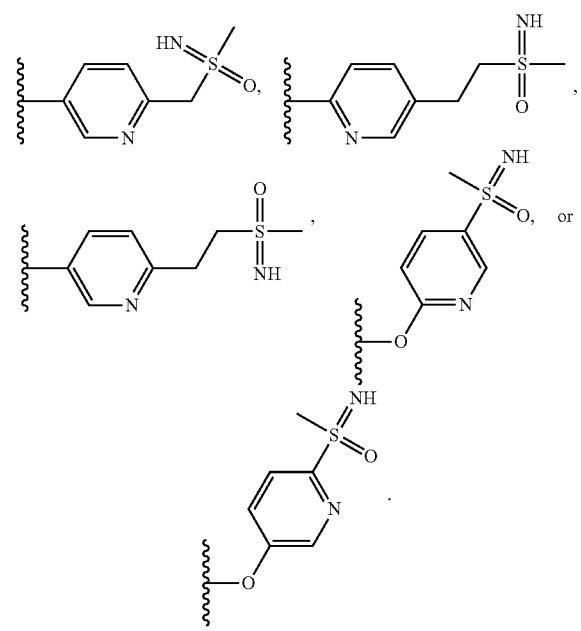
In some embodiments, the
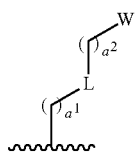
portion of Formula (I) is
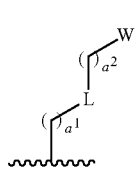
In some embodiments, the
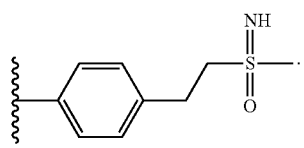 [SMILES: *c1ccc(CCS(C)(=N)=O)cc1]
portion of Formula (I) is
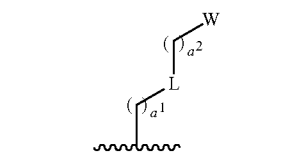
In some embodiments, the
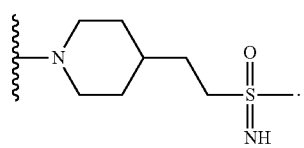 [SMILES: *N1CCC(CCS(C)(=N)=O)CC1]
portion of Formula (I) is
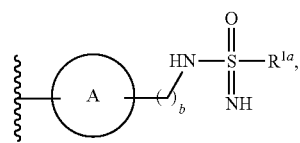
In some embodiments of Formula (I), or a pharmaceutically acceptable salt thereof, W is
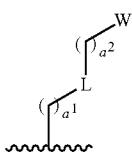
and the
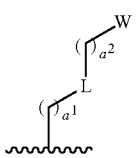
portion of Formula (I) is
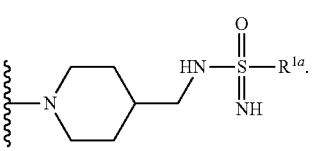
In some embodiments, the portion of Formula (I) is

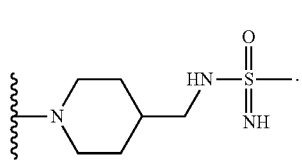 [SMILES: *N1CCC(CNS(C)(=N)=O)CC1]

In some embodiments of Formula (I), or a pharmaceutically acceptable salt thereof, W is

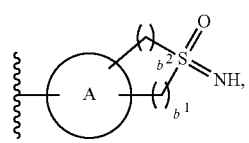

and the

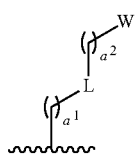

portion of Formula (I) is

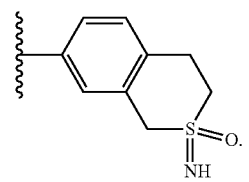 [SMILES: *c1ccc2c(c1)CS(=N)(=O)CC2]

In some embodiments of Formula (I), or a pharmaceutically acceptable salt thereof, W is

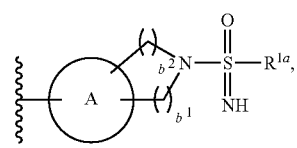

and the

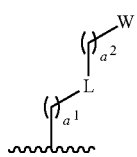

portion of Formula (I) is. In some embodiments, the

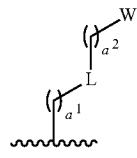

portion of Formula (I) is

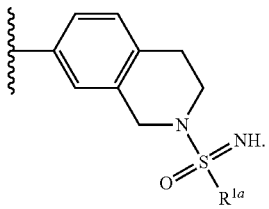

In some embodiments, the

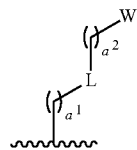

portion of Formula (I) is

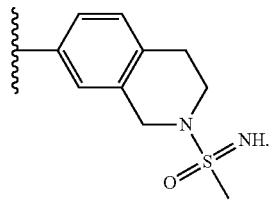 [SMILES: *c1ccc2c(c1)CN(S(C)(=N)=O)CC2]

In some embodiments of Formula (I), or a pharmaceutically acceptable salt thereof, W is

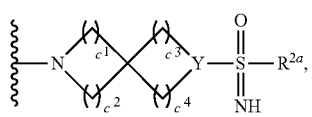

and the

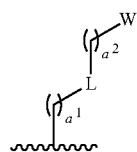

portion of Formula (I) is
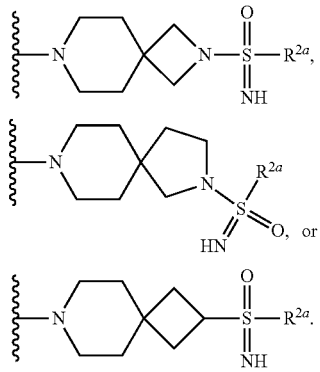
In some embodiments, the
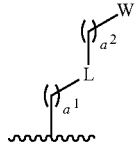
portion of Formula (I) is
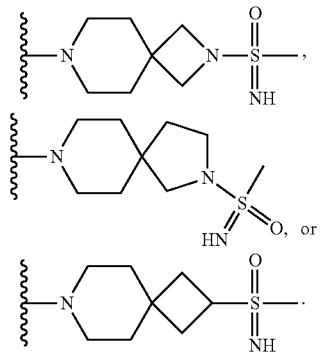
In some embodiments of Formula (I), or a pharmaceutically acceptable salt thereof, W is
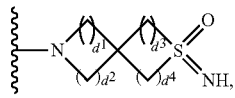
and the
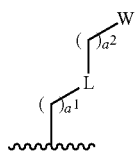
portion of Formula (I) is
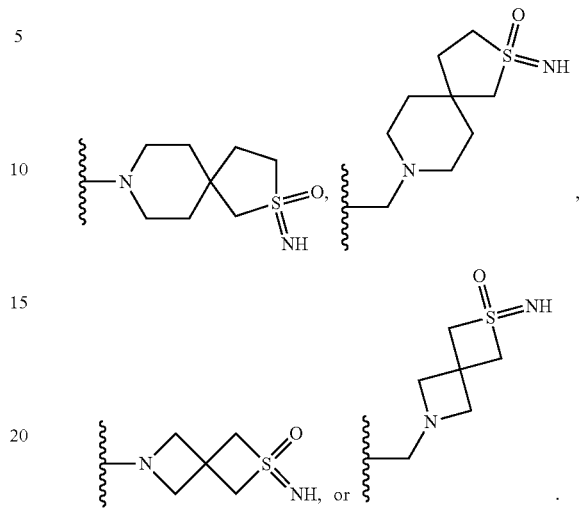
In some embodiments of Formula (I), or a pharmaceutically acceptable salt thereof, W is
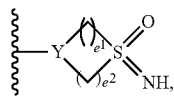
and the
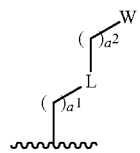
portion of Formula (I) is
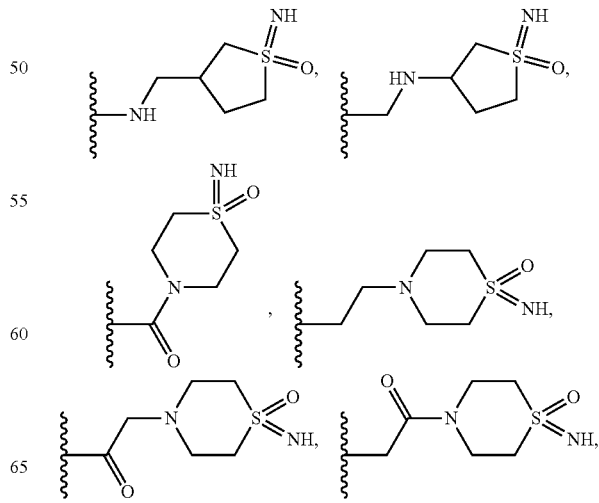

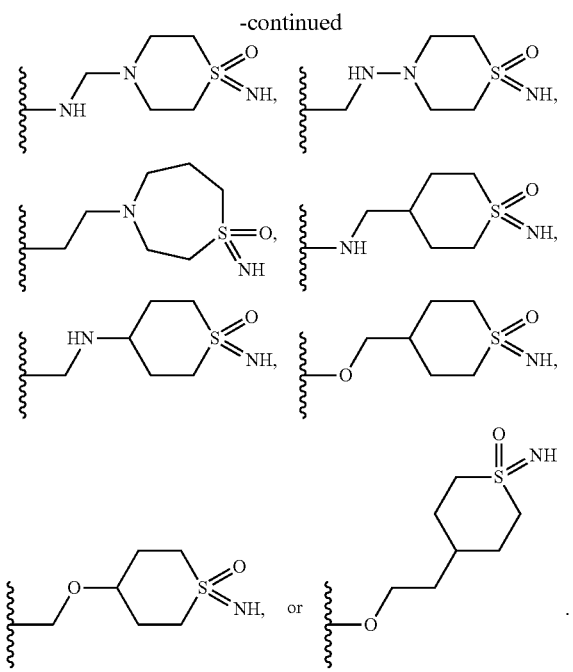

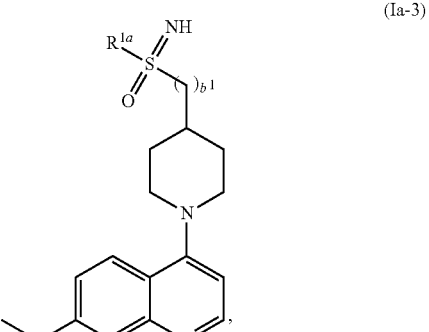

In one aspect, provided are compounds of Formula (Ia-1):

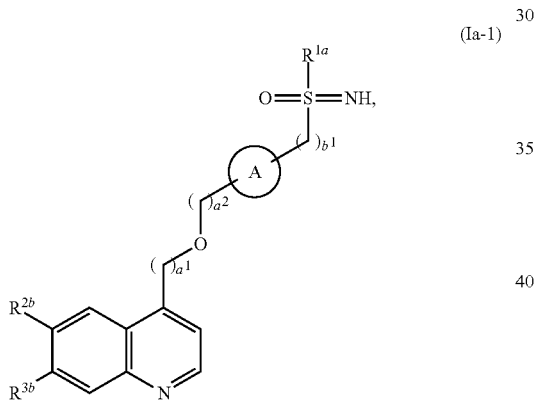

or a pharmaceutically acceptable salt thereof, wherein $R^{2b}$, $R^{3b}$, $a^1$, $a^2$, ring A, $b^1$, and $R^{1a}$ are as defined for Formula (I) or any variation or embodiment thereof.

In one aspect, provided are compounds of Formula (Ia-2):

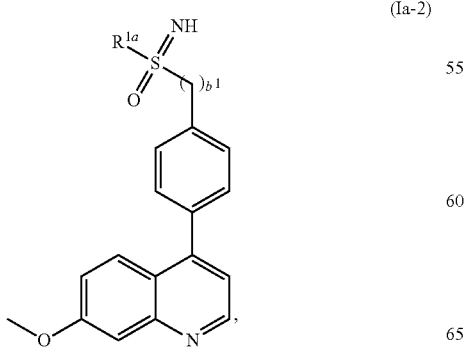

or a pharmaceutically acceptable salt thereof, wherein $R^{1a}$ and $b^1$ are as defined for Formula (I) or any variation or embodiment thereof.

In one aspect, provided are compounds of Formula (Ia-3):

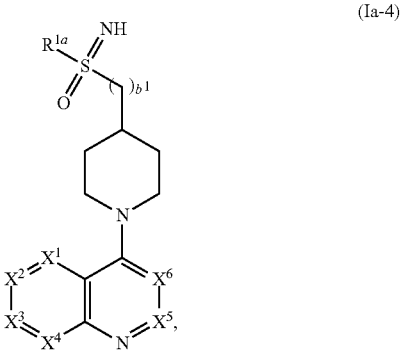

or a pharmaceutically acceptable salt thereof, wherein $R^{1a}$ and $b^1$ are as defined for Formula (I) or any variation or embodiment thereof.

In one aspect, provided are compounds of Formula (Ia-4):

(Ia-4)

[structure image for Ia-4]

or a pharmaceutically acceptable salt thereof, wherein $R^{1a}$, $b^1$, $X^1$, $X^2$, $X^3$, $X^4$, $X^5$, and $X^6$ are as defined for Formula (I) or any variation or embodiment thereof.

In one aspect, provided are compounds of Formula (Ia-5):

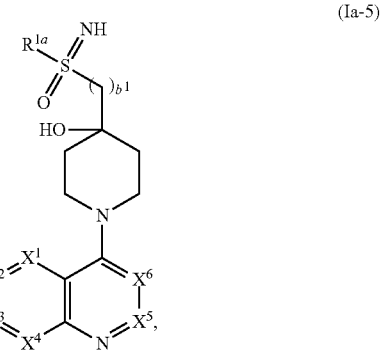

or a pharmaceutically acceptable salt thereof, wherein $R^{1a}$, $b^1$, $X^1$, $X^2$, $X^3$, $X^4$, $X^5$, and $X^6$ are as defined for Formula (I) or any variation or embodiment thereof.

In one aspect, provided are compounds of Formula (Ia-6):

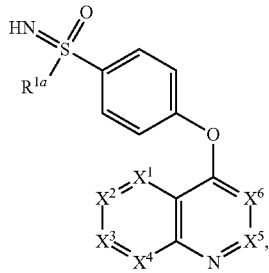

(Ia-6)

or a pharmaceutically acceptable salt thereof, wherein $R^{1a}$, $X^1$, $X^2$, $X^3$, $X^4$, $X^5$, and $X^6$ are as defined for Formula (I) or any variation or embodiment thereof.

In one aspect, provided are compounds of Formula (Ie-1):

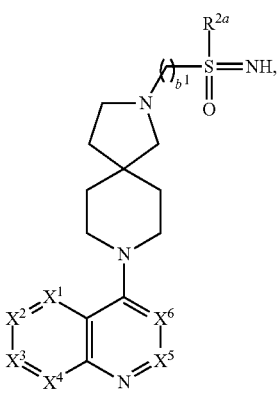

(Ie-1)

or a pharmaceutically acceptable salt thereof, wherein $R^{2a}$, $b^1$, $X^1$, $X^2$, $X^3$, $X^4$, $X^5$, and $X^6$ are as defined for Formula (I) or any variation or embodiment thereof.

In one aspect, provided are compounds of Formula (Ie-2):

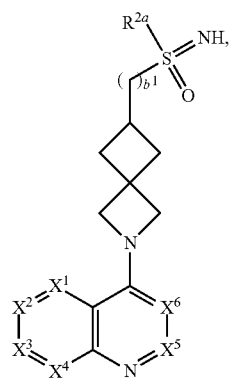

(Ie-2)

or a pharmaceutically acceptable salt thereof, wherein $R^{2a}$, $b^1$, $X^1$, $X^2$, $X^3$, $X^4$, $X^5$, and $X^6$ are as defined for Formula (I) or any variation or embodiment thereof.

In another aspect, the compound of Formula (I) is a compound of Formula (I-1):

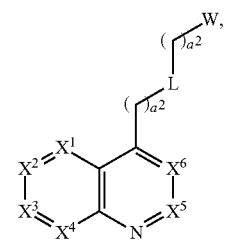

(I-1)

or a pharmaceutically acceptable salt thereof, wherein:

W is

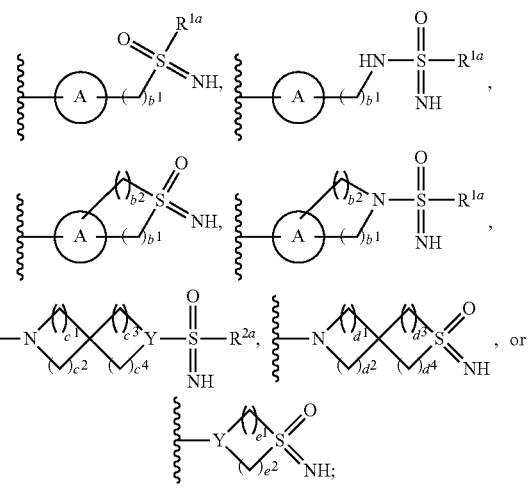

ring A is aryl, heteroaryl, cycloalkyl, cycloalkenyl, heterocycloalkyl or heterocycloalkenyl, each of which is substituted or unsubstituted;

$R^{1a}$ and $R^{2a}$ are each independently hydrogen, $C_{1-6}$ alkyl, $C_{3-6}$ cycloalkyl, 3-6 membered heterocycloalkyl, or $C_{1-6}$ haloalkyl;

Y is —N— or —CH—;

$X^1$ is —$CR^{1b}$— or —N—;

$X^2$ is —$CR^{2b}$— or —N—;

$X^3$ is —$CR^{3b}$— or —N—;

$X^4$ is —$CR^{4b}$— or —N—;

$X^5$ is —$CR^{5b}$— or —N—;

$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, or —$NR^6$—;

$R^{1c}$-$R^{6c}$ are each independently hydrogen or $C_{1-3}$ alkyl;

$a^1$, $a^2$, and $b^1$ are each independently 0, 1, or 2; and $b^2$, $c^1$-$c^4$, $d^1$-$d^4$, $e^1$, and $e^2$ are each independently 1, 2, or 3.

In another aspect, the compound of Formula (I) is a compound of Formula (I-2):

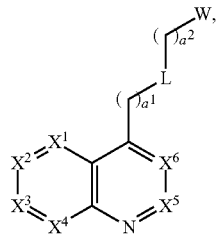

(I-2)

or a pharmaceutically acceptable salt thereof, wherein:
W is

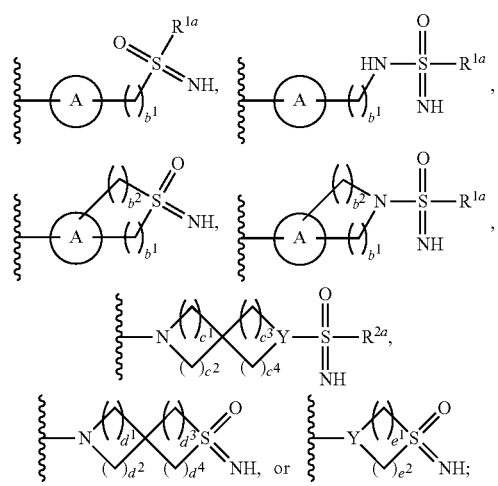

ring A is aryl, heteroaryl, cycloalkyl, cycloalkenyl, heterocycloalkyl or heterocycloalkenyl, each of which is substituted or unsubstituted;

$R^{1a}$ and $R^{2a}$ are each independently hydrogen, $C_{1-6}$ alkyl, $C_{3-6}$ cycloalkyl, 3-6 membered heterocycloalkyl, or $C_{1-6}$ haloalkyl, wherein the $C_{1-6}$ alkyl is optionally substituted by hydroxyl, $C_{1-3}$ alkoxy, or $C_{3-6}$ cycloalkyl;

Y is —N— or —CH—;
$X^1$ is —$CR^{1b}$— or —N—;
$X^2$ is —$CR^{2b}$— or —N—;
$X^3$ is —$CR^{3b}$— or —N—;
$X^4$ is —$CR^{b}$— or —N—;
$X^5$ is —$CR^{5b}$— or —N—;
$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, or —$NR^{6c}$—;
$R^{1c}$-$R^{6c}$ are each independently hydrogen or $C_{1-3}$ alkyl;
$a^1$, $a^2$, and $b^1$ are each independently 0, 1, 2, or 3; and
$b^2$, $c^1$-$c^4$, $d^1$-$d^4$, $e^1$, and $e^2$ are each independently 1, 2, or 3.

In one aspect, provided are compounds of Formula (I-3):

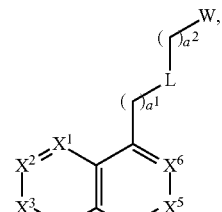

(I-3)

or a pharmaceutically acceptable salt thereof, wherein:
W is

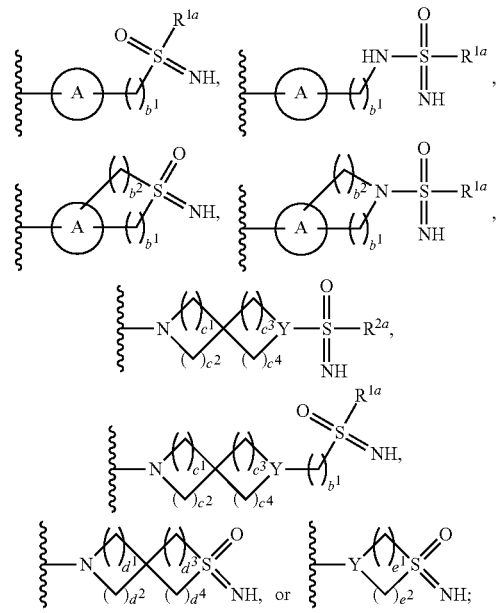

ring A is aryl, heteroaryl, cycloalkyl, cycloalkenyl, heterocycloalkyl or heterocycloalkenyl, each of which is substituted or unsubstituted;

$R^{1a}$ and $R^{2a}$ are each independently hydrogen, optionally substituted $C_{1-6}$ alkyl, optionally substituted $C_{3-6}$ cycloalkyl, optionally substituted 3-6 membered heterocycloalkyl, or optionally substituted $C_{1-6}$ haloalkyl;

Y is —N— or —CH—;
$X^1$ is —$CR^{1b}$— or —N—;
$X^2$ is —$CR^{2b}$— or —N—;
$X^3$ is —$CR^{3b}$— or —N—;
$X^4$ is —$CR^{4b}$— or —N—;
$X^5$ is —$CR^{5b}$— or —N—;
$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is —$OCR^{7c}$—*, wherein * represents the point of attachment to

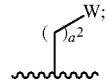

$R^{1c}$-$R^{5c}$ and $R^{7c}$ are each independently hydrogen or $C_{1-3}$ alkyl;

$a^1$, $a^2$, $b^1$, and $c^4$ are each independently 0, 1, 2, or 3; and $b^2$, $c^1$-$c^3$, $d^1$-$d^4$, $e^1$, and $e^2$ are each independently 1, 2, or 3.

In one aspect, provided are compounds of Formula (I4):

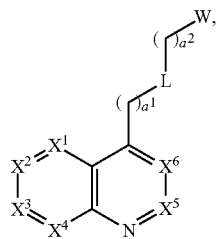

(I-4)

or a pharmaceutically acceptable salt thereof, wherein:

W is

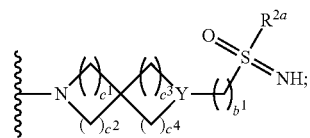

$R^{2a}$ is hydrogen, optionally substituted $C_{1-6}$ alkyl, optionally substituted $C_{3-6}$ cycloalkyl, optionally substituted 3-6 membered heterocycloalkyl, or optionally substituted $C_{1-6}$ haloalkyl;

Y is —N— or —CH—;

$X^1$ is —$CR^{1b}$— or —N—;

$X^2$ is —$CR^{2b}$— or —N—;

$X^3$ is —$CR^{3b}$— or —N—;

$X^4$ is —$CR^{4b}$— or —N—;

$X^5$ is —$CR^{5b}$— or —N—;

$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, —$NR^{6c}$—, or —$OCR^{7c}$—*, wherein * represents the point of attachment to

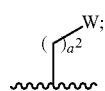

$R^{1c}$-$R^{7c}$ are each independently hydrogen or $C_{1-3}$ alkyl;

$a^1$, $a^2$, $b^1$, and $c^4$ are each independently 0, 1, 2, or 3; and $c^1$-$c^3$ are each independently 1, 2, or 3.

In one aspect, provided are compounds of Formula (I-5):

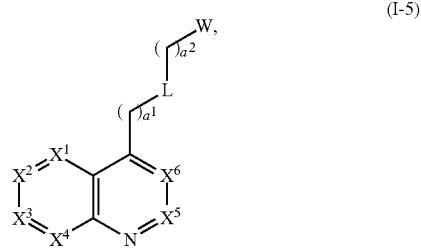

(I-5)

or a pharmaceutically acceptable salt thereof, wherein:

W is

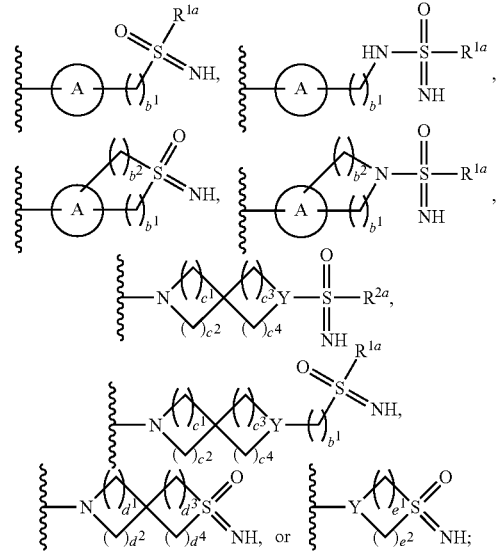

ring A is aryl, heteroaryl, cycloalkyl, cycloalkenyl, heterocycloalkyl or heterocycloalkenyl, each of which is substituted or unsubstituted;

$R^{1a}$ and $R^{2a}$ are each independently $C_{1-6}$ alkyl substituted with halo or 3-6 membered heterocycloalkyl substituted with acyl;

Y is —N— or —CH—;

$X^1$ is —$CR^{1b}$— or —N—;

$X^2$ is —$CR^{2b}$— or —N—;

$X^3$ is —$CR^{3b}$— or —N—;

$X^4$ is —$CR^{4b}$— or —N—;

$X^5$ is —$CR^{5b}$— or —N—;

$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, —$NR^{6c}$—, or —$OCR^{7c}$—*, wherein * represents the point of attachment to

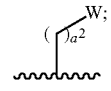

$R^{1c}$-$R^{7c}$ are each independently hydrogen or $C_{1-3}$ alkyl;

$a^1$, $a^2$, $b^1$, and $c^4$ are each independently 0, 1, 2, or 3; and $b^2$, $c^1$-$c^3$, $d^1$-$d^4$, $e^1$, and $e^2$ are each independently 1, 2, or 3.

In some embodiments, provided herein are compounds and salts thereof described in Table 1.

TABLE 1

| Compound No. | Structure | Name |
|---|---|---|
| 1 | 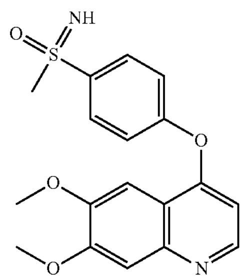 [SMILES: COc1cc2nccc(Oc3ccc(S(C)(=N)=O)cc3)c2cc1OC] | (4-((6,7-dimethoxyquinolin-4-yl)oxy)phenyl)(imino)(methyl)-$\lambda^6$-sulfanone |
| 1R | 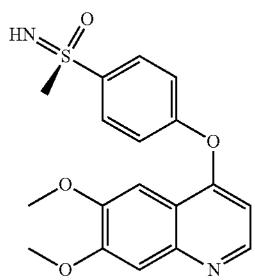 [SMILES: COc1cc2nccc(Oc3ccc([S@](C)(=N)=O)cc3)c2cc1OC] | (R)-(4-((6,7-dimethoxyquinolin-4-yl)oxy)phenyl)(imino)(methyl)-$\lambda^6$-sulfanone |
| 1S | 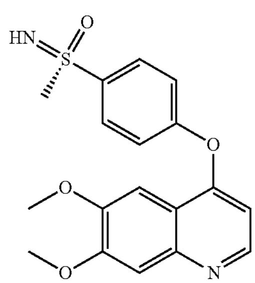 [SMILES: COc1cc2nccc(Oc3ccc([S@@](C)(=N)=O)cc3)c2cc1OC] | (S)-(4-((6,7-dimethoxyquinolin-4-yl)oxy)phenyl)(imino)(methyl)-$\lambda^6$-sulfanone |
| 2 | 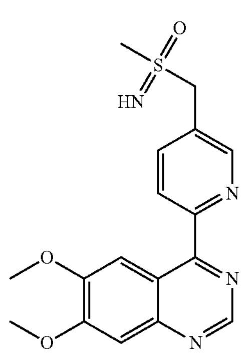 [SMILES: COc1cc2ncnc(-c3ccc(CS(C)(=N)=O)cn3)c2cc1OC] | ((6-(6,7-dimethoxyquinazolin-4-yl)pyridin-3-yl)methyl)(imino)(methyl)-$\lambda^6$-sulfanone |

TABLE 1-continued

| Compound No. | Structure | Name |
|---|---|---|
| 3 | 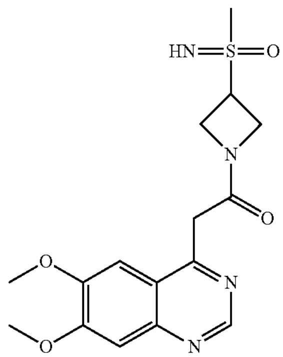 [SMILES: COc1cc2ncnc(CC(=O)N3CC(S(C)(=N)=O)C3)c2cc1OC] | (1-(2-(6,7-dimethoxyquinazolin-4-yl)acetyl)azetidin-3-yl)(imino)(methyl)-$\lambda^6$-sulfanone |
| 4 | 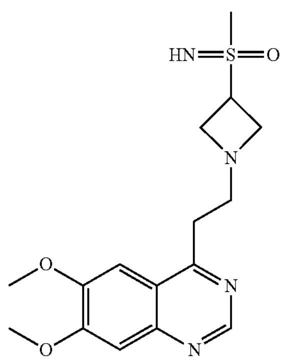 [SMILES: COc1cc2ncnc(CCN3CC(S(C)(=N)=O)C3)c2cc1OC] | (1-(2-(6,7-dimethoxyquinazolin-4-yl)ethyl)azetidin-3-yl)(imino)(methyl)-$\lambda^6$-sulfanone |
| 5 | 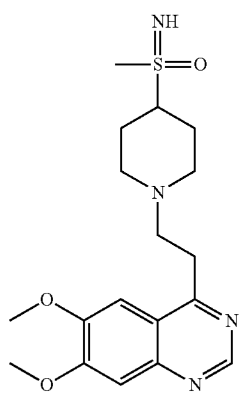 [SMILES: COc1cc2ncnc(CCN3CCC(S(C)(=N)=O)CC3)c2cc1OC] | (1-(2-(6,7-dimethoxyquinazolin-4-yl)ethyl)piperidin-4-yl)(imino)(methyl)-$\lambda^6$-sulfanone |
| 6 | 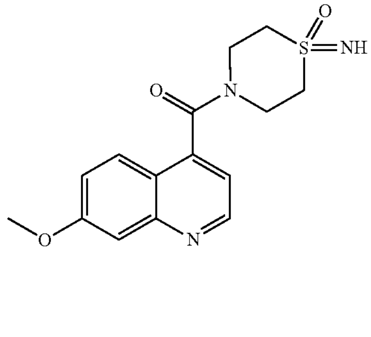 [SMILES: COc1ccc2c(C(=O)N3CCS(=N)(=O)CC3)ccnc2c1] | (1-imino-1-oxido-1$\lambda^6$-thiomorpholino)(7-methoxyquinolin-4-yl)methanone |

TABLE 1-continued

| Compound No. | Structure | Name |
| --- | --- | --- |
| 7 | 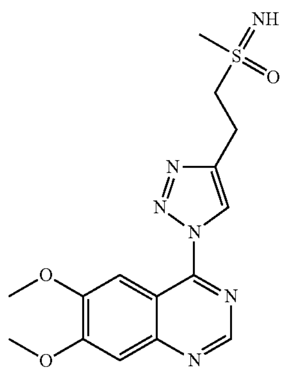 [SMILES: COc1cc2ncnc(-n3cc(CCS(C)(=N)=O)nn3)c2cc1OC] | (2-(1-(6,7-dimethoxyquinazolin-4-yl)-1H-1,2,3-triazol-4-yl)ethyl)(imino)(methyl)-$\lambda^6$-sulfanone |
| 8 | 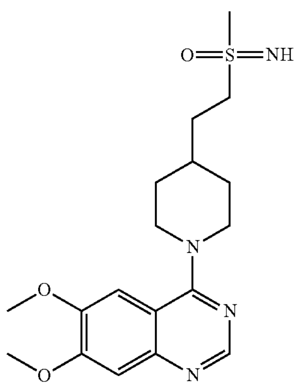 [SMILES: COc1cc2ncnc(N3CCC(CCS(C)(=N)=O)CC3)c2cc1OC] | (2-(1-(6,7-dimethoxyquinazolin-4-yl)piperidin-4-yl)ethyl)(imino)(methyl)-$\lambda^6$-sulfanone |
| 9 | 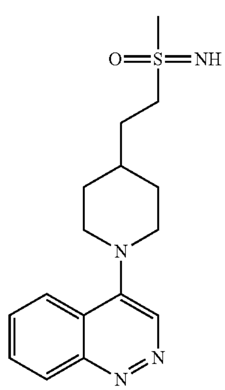 [SMILES: CS(=N)(=O)CCC1CCN(c2cnnc3ccccc23)CC1] | (2-(1-(cinnolin-4-yl)piperidin-4-yl)ethyl)(imino)(methyl)-$\lambda^6$-sulfanone |
| 10 | 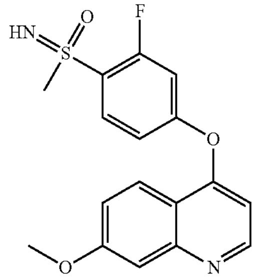 [SMILES: COc1ccc2c(Oc3ccc(S(C)(=N)=O)c(F)c3)ccnc2c1] | (2-fluoro-4-((7-methoxyquinolin-4-yl)oxy)phenyl)(imino)(methyl)-$\lambda^6$-sulfanone |

TABLE 1-continued

| Compound No. | Structure | Name |
| --- | --- | --- |
| 11 | 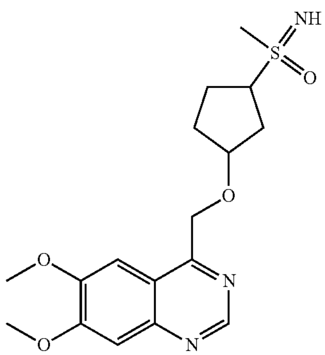 [SMILES: COc1cc2ncnc(COC3CCC(S(C)(=N)=O)C3)c2cc1OC] | (3-(((6,7-dimethoxyquinazolin-4-yl)methoxy)cyclopentyl)(imino)(methyl)-$\lambda^6$-sulfanone |
| 12 | 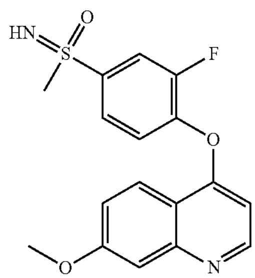 [SMILES: COc1ccc2c(Oc3ccc(S(C)(=N)=O)cc3F)ccnc2c1] | (3-fluoro-4-((7-methoxyquinolin-4-yl)oxy)phenyl)(imino)(methyl)-$\lambda^6$-sulfanone |
| 13 | 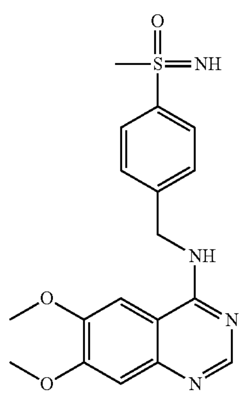 [SMILES: COc1cc2ncnc(NCc3ccc(S(C)(=N)=O)cc3)c2cc1OC] | (4-(((6,7-dimethoxyquinazolin-4-yl)amino)methyl)phenyl)(imino)(methyl)-$\lambda^6$-sulfanone |
| 14 | 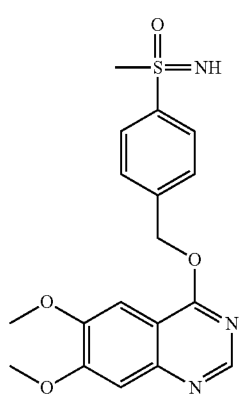 [SMILES: COc1cc2ncnc(OCc3ccc(S(C)(=N)=O)cc3)c2cc1OC] | (4-(((6,7-dimethoxyquinazolin-4-yl)oxy)methyl)phenyl)(imino)(methyl)-$\lambda^6$-sulfanone |

TABLE 1-continued

| Compound No. | Structure | Name |
|---|---|---|
| 15 | 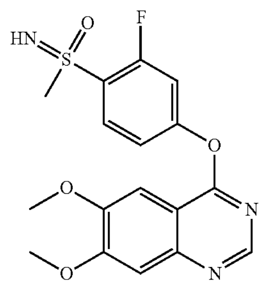 [SMILES: COc1cc2ncnc(Oc3ccc(S(C)(=N)=O)c(F)c3)c2cc1OC] | (4-((6,7-dimethoxyquinazolin-4-yl)oxy)-2-fluorophenyl)(imino)(methyl)-$\lambda^6$-sulfanone |
| 16 | 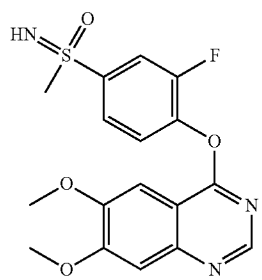 [SMILES: COc1cc2ncnc(Oc3ccc(S(C)(=N)=O)cc3F)c2cc1OC] | (4-((6,7-dimethoxyquinazolin-4-yl)oxy)-3-fluorophenyl)(imino)(methyl)-$\lambda^6$-sulfanone |
| 17 | 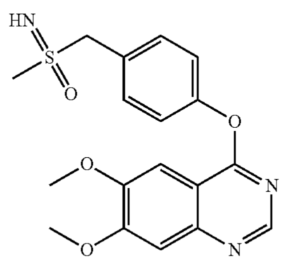 [SMILES: COc1cc2ncnc(Oc3ccc(CS(C)(=N)=O)cc3)c2cc1OC] | (4-((6,7-dimethoxyquinazolin-4-yl)oxy)benzyl)(imino)(methyl)-$\lambda^6$-sulfanone |
| 18 | 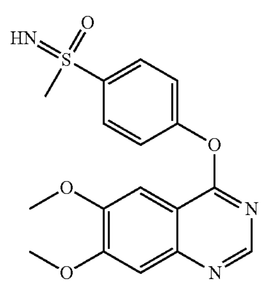 [SMILES: COc1cc2ncnc(Oc3ccc(S(C)(=N)=O)cc3)c2cc1OC] | (4-((6,7-dimethoxyquinazolin-4-yl)oxy)phenyl)(imino)(methyl)-$\lambda^6$-sulfanone |
| 19 | 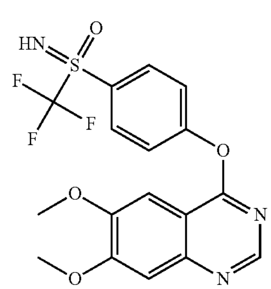 [SMILES: COc1cc2ncnc(Oc3ccc(S(=N)(=O)C(F)(F)F)cc3)c2cc1OC] | (4-((6,7-dimethoxyquinazolin-4-yl)oxy)phenyl)(imino)(trifluoromethyl)-$\lambda^6$-sulfanone |

TABLE 1-continued

| Compound No. | Structure | Name |
| --- | --- | --- |
| 20 | 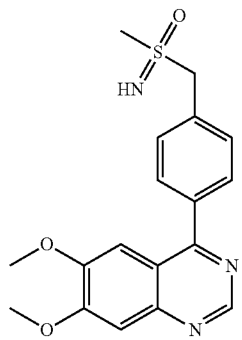 [SMILES: COc1cc2ncnc(-c3ccc(CS(C)(=N)=O)cc3)c2cc1OC] | (4-(6,7-dimethoxyquinazolin-4-yl)benzyl)(imino)(methyl)-$\lambda^6$-sulfanone |
| 21 | 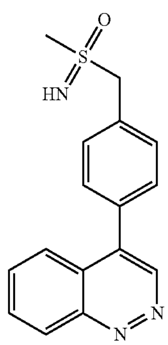 [SMILES: CS(=N)(=O)Cc1ccc(-c2cnnc3ccccc23)cc1] | (4-(cinnolin-4-yl)benzyl)(imino)(methyl)-$\lambda^6$-sulfanone |
| 22 | 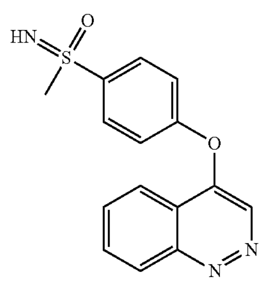 [SMILES: CS(=N)(=O)c1ccc(Oc2cnnc3ccccc23)cc1] | (4-(cinnolin-4-yloxy)phenyl)(imino)(methyl)-$\lambda^6$-sulfanone |
| 23 | 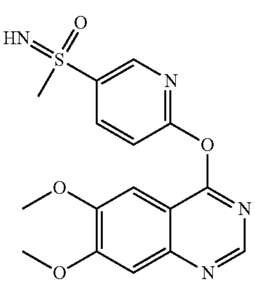 [SMILES: COc1cc2ncnc(Oc3ccc(S(C)(=N)=O)cn3)c2cc1OC] | (6-((6,7-dimethoxyquinazolin-4-yl)oxy)pyridin-3-yl)(imino)(methyl)-$\lambda^6$-sulfanone |
| 24 | 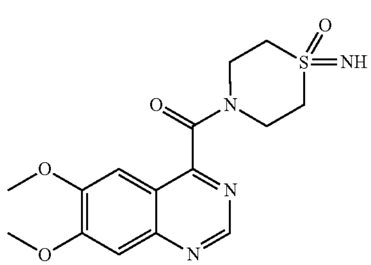 [SMILES: COc1cc2ncnc(C(=O)N3CCS(=N)(=O)CC3)c2cc1OC] | (6,7-dimethoxyquinazolin-4-yl)(1-imino-1-oxido-1$\lambda^6$-thiomorpholino)methanone |

TABLE 1-continued
| Compound No. | Structure | Name |
|---|---|---|
| 25 | 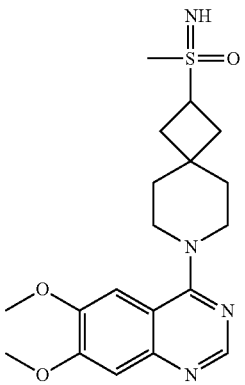 | (7-(6,7-dimethoxyquinazolin-4-yl)-7-azaspiro[3.5]nonan-2-yl)(imino)(methyl)-$\lambda^6$-sulfanone |
| 26 | 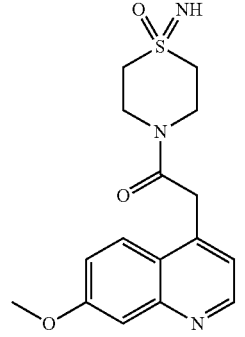 [SMILES: COc1ccc2c(CC(=O)N3CCS(=N)(=O)CC3)ccnc2c1] | 1-(1-imino-1-oxido-1$\lambda^6$-thiomorpholino)-2-(7-methoxyquinolin-4-yl)ethan-1-one |
| 27 | 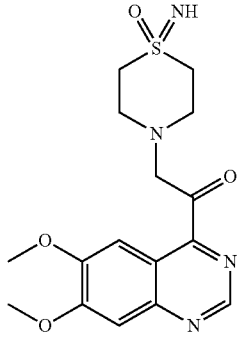 [SMILES: COc1cc2ncnc(C(=O)CN3CCS(=N)(=O)CC3)c2cc1OC] | 1-(6,7-dimethoxyquinazolin-4-yl)-2-(1-imino-1-oxido-1$\lambda^6$-thiomorpholino)ethan-1-one |
| 28 | 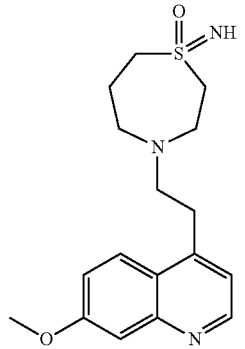 [SMILES: COc1ccc2c(CCN3CCCS(=N)(=O)CC3)ccnc2c1] | 1-imino-4-(2-(7-methoxyquinolin-4-yl)ethyl)-1$\lambda^6$,4-thiazepane 1-oxide |

TABLE 1-continued

| Compound No. | Structure | Name |
|---|---|---|
| 29 | 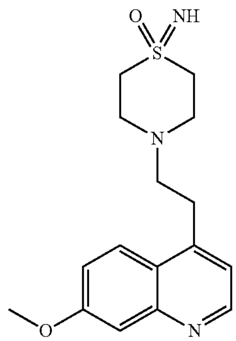 [SMILES: COc1ccc2c(CCN3CCS(=N)(=O)CC3)ccnc2c1] | 1-imino-4-(2-(7-methoxyquinolin-4-yl)ethyl)-1$\lambda^6$-thiomorpholine 1-oxide |
| 30 | 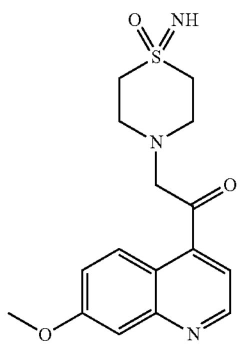 [SMILES: COc1ccc2c(C(=O)CN3CCS(=N)(=O)CC3)ccnc2c1] | 2-(1-imino-1-oxido-1$\lambda^6$-thiomorpholino)-1-(7-methoxyquinolin-4-yl)ethan-1-one |
| 31 | 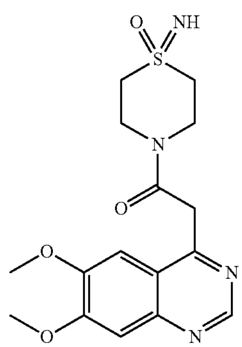 [SMILES: COc1cc2ncnc(CC(=O)N3CCS(=N)(=O)CC3)c2cc1OC] | 2-(6,7-dimethoxyquinazolin-4-yl)-1-(1-imino-1-oxido-1$\lambda^6$-thiomorpholino)ethan-1-one |
| 32 | 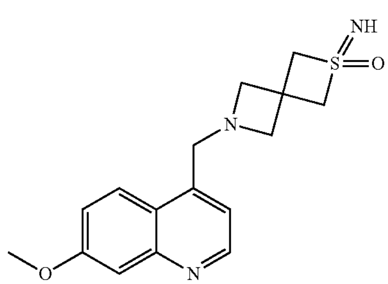 [SMILES: COc1ccc2c(CN3CC4(C3)CS(=N)(=O)C4)ccnc2c1] | 2-imino-6-((7-methoxyquinolin-4-yl)methyl)-2$\lambda^6$-thia-6-azaspiro[3.3]heptane 2-oxide |

TABLE 1-continued

| Compound No. | Structure | Name |
|---|---|---|
| 33 | 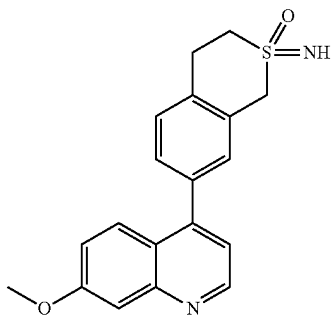 [SMILES: COc1ccc2c(-c3ccc4c(c3)CS(=N)(=O)CC4)ccnc2c1] | 2-imino-7-(7-methoxyquinolin-4-yl)-2l4-isothiochromane 2-oxide |
| 34 | 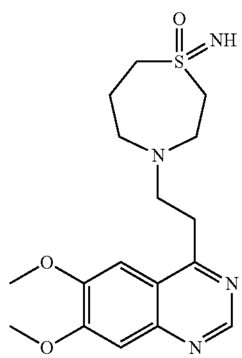 [SMILES: COc1cc2ncnc(CCN3CCCS(=N)(=O)CC3)c2cc1OC] | 4-(2-(6,7-dimethoxyquinazolin-4-yl)ethyl)-1-imino-1l6,4-thiazepane 1-oxide |
| 35 | 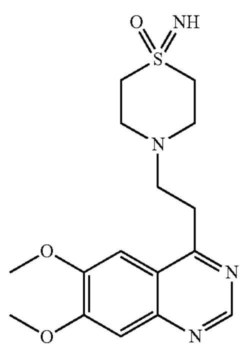 [SMILES: COc1cc2ncnc(CCN3CCS(=N)(=O)CC3)c2cc1OC] | 4-(2-(6,7-dimethoxyquinazolin-4-yl)ethyl)-1-imino-1$\lambda^6$-thiomorpholine 1-oxide |
| 36 | 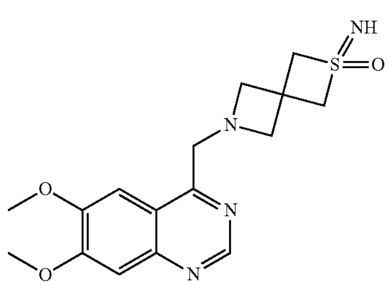 [SMILES: COc1cc2ncnc(CN3CC4(C3)CS(=N)(=O)C4)c2cc1OC] | 6-((6,7-dimethoxyquinazolin-4-yl)methyl)-2-imino-2$\lambda^6$-thia-6-azaspiro[3.3]heptane 2-oxide |

TABLE 1-continued

| Compound No. | Structure | Name |
|---|---|---|
| 37 | 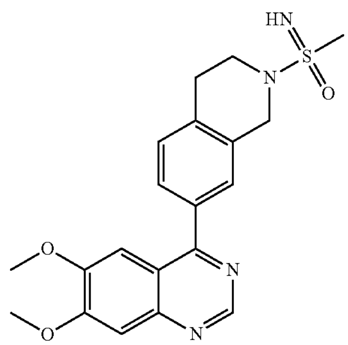 | 6,7-dimethoxy-4-(2-(S-methylsulfonimidoyl)-1,2,3,4-tetrahydroisoquinolin-7-yl)quinazoline |
| 37S | 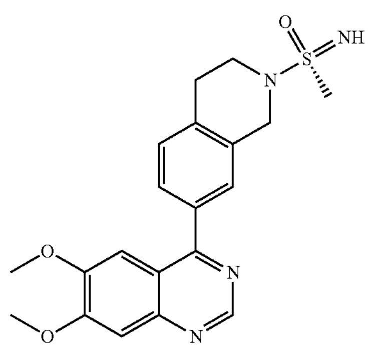 [SMILES: COc1cc2ncnc(-c3ccc4c(c3)CN([S@](C)(=N)=O)CC4)c2cc1OC] | (S)-6,7-dimethoxy-4-(2-(S-methylsulfonimidoyl)-1,2,3,4-tetrahydroisoquinolin-7-yl)quinazoline |
| 37R | 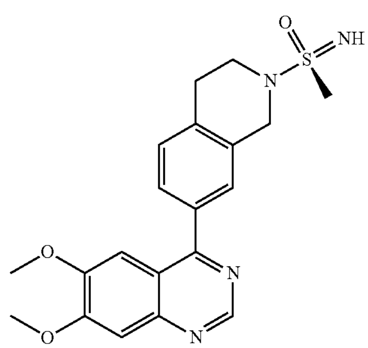 [SMILES: COc1cc2ncnc(-c3ccc4c(c3)CN([S@@](C)(=N)=O)CC4)c2cc1OC] | (R)-6,7-dimethoxy-4-(2-(S-methylsulfonimidoyl)-1,2,3,4-tetrahydroisoquinolin-7-yl)quinazoline |
| 38 | 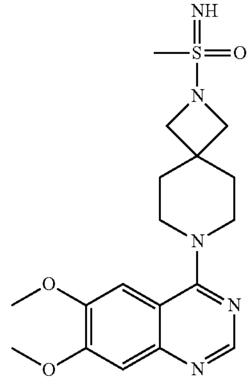 [SMILES: COc1cc2ncnc(N3CCC4(CC3)CN(S(C)(=N)=O)C4)c2cc1OC] | 6,7-dimethoxy-4-(2-(S-methylsulfonimidoyl)-2,7-diazaspiro[3.5]nonan-7-yl)quinazoline |

TABLE 1-continued

| Compound No. | Structure | Name |
| --- | --- | --- |
| 39 | 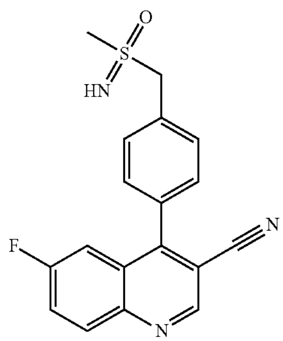 [SMILES: CS(=N)(=O)Cc1ccc(-c2c(C#N)cnc3ccc(F)cc23)cc1] | 6-fluoro-4-(4-((S-methylsulfonimidoyl)methyl)phenyl)quinoline-3-carbonitrile |
| 40 | 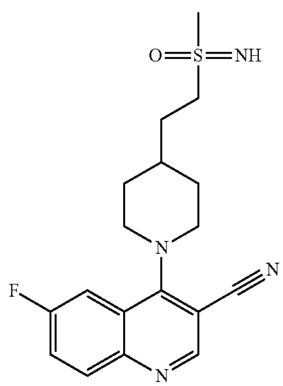 [SMILES: CS(=N)(=O)CCC1CCN(c2c(C#N)cnc3ccc(F)cc23)CC1] | 6-fluoro-4-(4-(2-(S-methylsulfonimidoyl)ethyl)piperidin-1-yl)quinoline-3-carbonitrile |
| 41 | 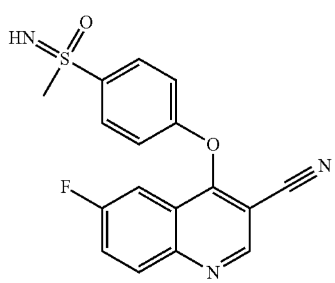 [SMILES: CS(=N)(=O)c1ccc(Oc2c(C#N)cnc3ccc(F)cc23)cc1] | 6-fluoro-4-(4-(S-methylsulfonimidoyl)phenoxy)quinoline-3-carbonitrile |
| 42 | 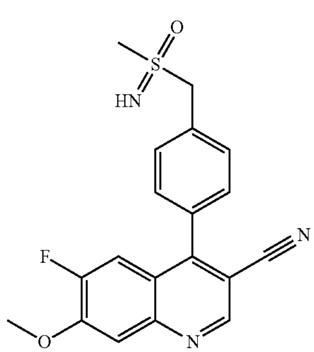 [SMILES: COc1cc2ncc(C#N)c(-c3ccc(CS(C)(=N)=O)cc3)c2cc1F] | 6-fluoro-7-methoxy-4-(4-((S-methylsulfonimidoyl)methyl)phenyl)quinoline-3-carbonitrile |

TABLE 1-continued

| Compound No. | Structure | Name |
|---|---|---|
| 43 | 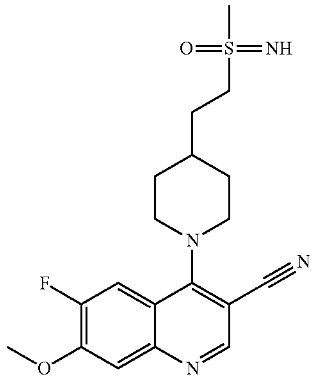 [SMILES: COc1cc2ncc(C#N)c(N3CCC(CCS(C)(=N)=O)CC3)c2cc1F] | 6-fluoro-7-methoxy-4-(4-(2-(S-methylsulfonimidoyl)ethyl)piperidin-1-yl)quinoline-3-carbonitrile |
| 44 | 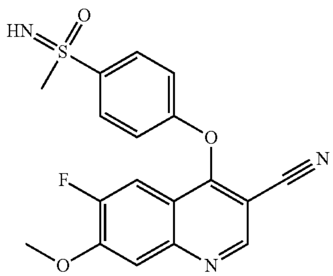 [SMILES: COc1cc2ncc(C#N)c(Oc3ccc(S(C)(=N)=O)cc3)c2cc1F] | 6-fluoro-7-methoxy-4-(4-(S-methylsulfonimidoyl)phenoxy)quinoline-3-carbonitrile |
| 44R | 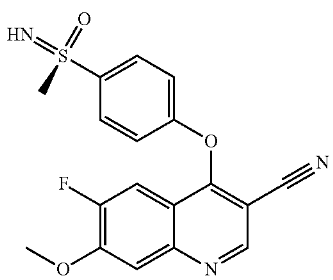 [SMILES: COc1cc2ncc(C#N)c(Oc3ccc([S@](C)(=N)=O)cc3)c2cc1F] | (R)-6-fluoro-7-methoxy-4-(4-(S-methylsulfonimidoyl)phenoxy)quinoline-3-carbonitrile |
| 44S | 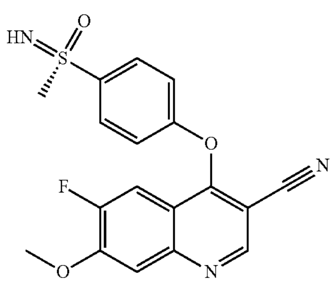 [SMILES: COc1cc2ncc(C#N)c(Oc3ccc([S@@](C)(=N)=O)cc3)c2cc1F] | (S)-6-fluoro-7-methoxy-4-(4-(S-methylsulfonimidoyl)phenoxy)quinoline-3-carbonitrile |
| 45 | 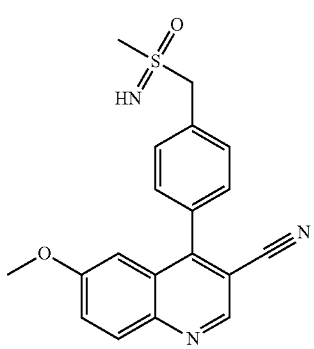 [SMILES: COc1ccc2ncc(C#N)c(-c3ccc(CS(C)(=N)=O)cc3)c2c1] | 6-methoxy-4-(4-((S-methylsulfonimidoyl)methyl)phenyl)quinoline-3-carbonitrile |

TABLE 1-continued

| Compound No. | Structure | Name |
|---|---|---|
| 46 | 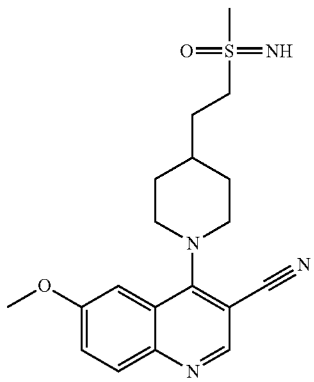 [SMILES: COc1ccc2ncc(C#N)c(N3CCC(CCS(C)(=N)=O)CC3)c2c1] | 6-methoxy-4-(4-(2-(S-methylsulfonimidoyl)ethyl)piperidin-1-yl)quinoline-3-carbonitrile |
| 47 | 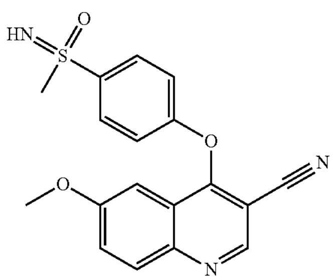 [SMILES: COc1ccc2ncc(C#N)c(Oc3ccc(S(C)(=N)=O)cc3)c2c1] | 6-methoxy-4-(4-(S-methylsulfonimidoyl)phenoxy)quinoline-3-carbonitrile |
| 48 | 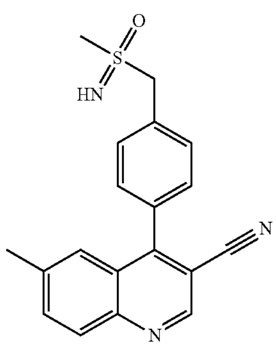 [SMILES: Cc1ccc2ncc(C#N)c(-c3ccc(CS(C)(=N)=O)cc3)c2c1] | 6-methyl-4-(4-((S-methylsulfonimidoyl)methyl)phenyl)quinoline-3-carbonitrile |
| 49 | 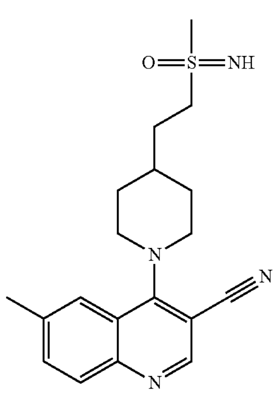 [SMILES: Cc1ccc2ncc(C#N)c(N3CCC(CCS(C)(=N)=O)CC3)c2c1] | 6-methyl-4-(4-(2-(S-methylsulfonimidoyl)ethyl)piperidin-1-yl)quinoline-3-carbonitrile |

TABLE 1-continued

| Compound No. | Structure | Name |
|---|---|---|
| 50 | 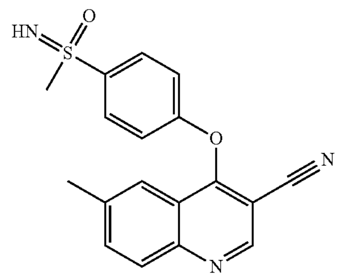 [SMILES: Cc1ccc2ncc(C#N)c(Oc3ccc(S(C)(=N)=O)cc3)c2c1] | 6-methyl-4-(4-(S-methylsulfonimidoyl)phenoxy)quinoline-3-carbonitrile |
| 51 | 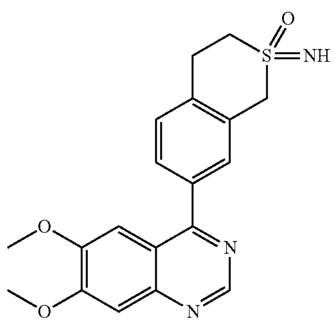 [SMILES: COc1cc2ncnc(-c3ccc4c(c3)CS(=N)(=O)CC4)c2cc1OC] | 7-(6,7-dimethoxyquinazolin-4-yl)-2-imino-2l4-isothiochromane 2-oxide |
| 52 | 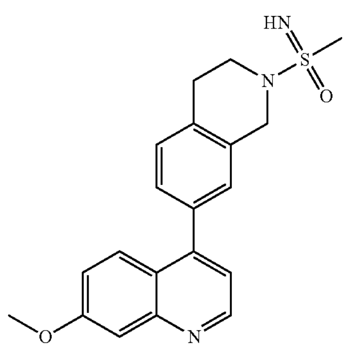 | 7-methoxy-4-(2-(S-methylsulfonimidoyl)-1,2,3,4-tetrahydroisoquinolin-7-yl)quinoline |
| 52S | 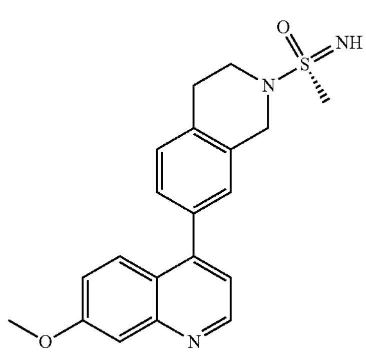 [SMILES: COc1ccc2c(-c3ccc4c(c3)CN([S@](C)(=N)=O)CC4)ccnc2c1] | (S)-7-methoxy-4-(2-(S-methylsulfonimidoyl)-1,2,3,4-tetrahydroisoquinolin-7-yl)quinoline |

TABLE 1-continued

| Compound No. | Structure | Name |
|---|---|---|
| 52R | 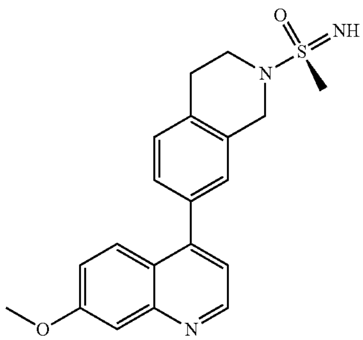 [SMILES: COc1ccc2c(-c3ccc4c(c3)CN([S@@](C)(=N)=O)CC4)ccnc2c1] | (R)-7-methoxy-4-(2-(S-methylsulfonimidoyl)-1,2,3,4-tetrahydroisoquinolin-7-yl)quinoline |
| 53 | 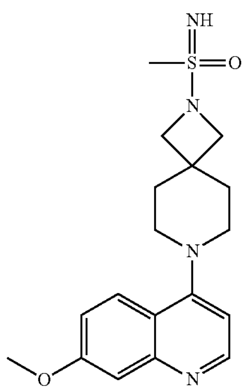 [SMILES: COc1ccc2c(N3CCC4(CC3)CN(S(C)(=N)=O)C4)ccnc2c1] | 7-methoxy-4-(2-(S-methylsulfonimidoyl)-2,7-diazaspiro[3.5]nonan-7-yl)quinoline |
| 54 | 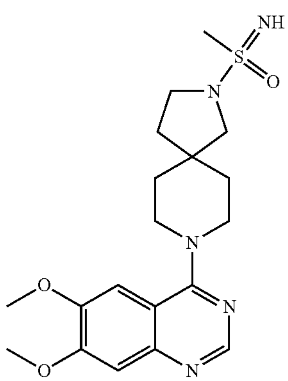 [SMILES: COc1cc2ncnc(N3CCC4(CC3)CCN(S(C)(=N)=O)C4)c2cc1OC] | 8-(6,7-dimethoxyquinazolin-4-yl)-2-(S-methylsulfonimidoyl)-2,8-diazaspiro[4.5]decane |
| 54S | 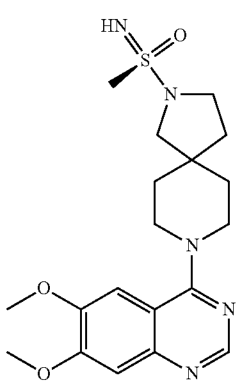 [SMILES: COc1cc2ncnc(N3CCC4(CC3)CCN([S@](C)(=N)=O)C4)c2cc1OC] | (S)-8-(6,7-dimethoxyquinazolin-4-yl)-2-(S-methylsulfonimidoyl)-2,8-diazaspiro[4.5]decane |

TABLE 1-continued

| Compound No. | Structure | Name |
|---|---|---|
| 54R | 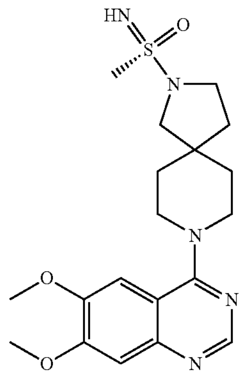 [SMILES: COc1cc2ncnc(N3CCC4(CC3)CCN([S@@](C)(=N)=O)C4)c2cc1OC] | (R)-8-(6,7-dimethoxyquinazolin-4-yl)-2-(S-methylsulfonimidoyl)-2,8-diazaspiro[4.5]decane |
| 55 | 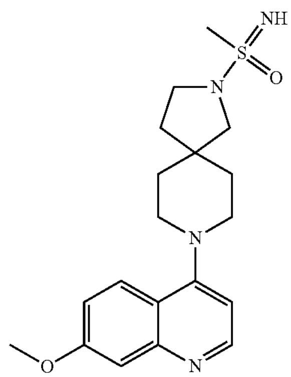 [SMILES: COc1ccc2c(N3CCC4(CC3)CCN(S(C)(=N)=O)C4)ccnc2c1] | 8-(7-methoxyquinolin-4-yl)-2-(S-methylsulfonimidoyl)-2,8-diazaspiro[4.5]decane |
| 55S | 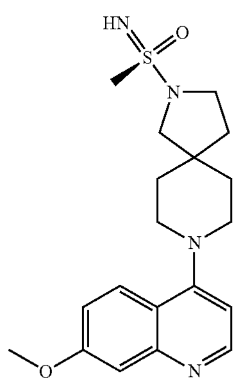 [SMILES: COc1ccc2c(N3CCC4(CC3)CCN([S@](C)(=N)=O)C4)ccnc2c1] | (S)-8-(7-methoxyquinolin-4-yl)-2-(S-methylsulfonimidoyl)-2,8-diazaspiro[4.5]decane |
| 55R | 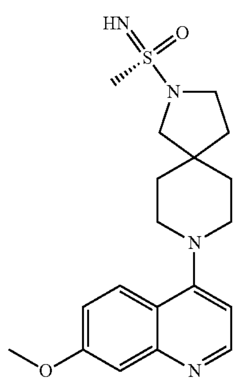 [SMILES: COc1ccc2c(N3CCC4(CC3)CCN([S@@](C)(=N)=O)C4)ccnc2c1] | (R)-8-(7-methoxyquinolin-4-yl)-2-(S-methylsulfonimidoyl)-2,8-diazaspiro[4.5]decane |

TABLE 1-continued

| Compound No. | Structure | Name |
|---|---|---|
| 56 | 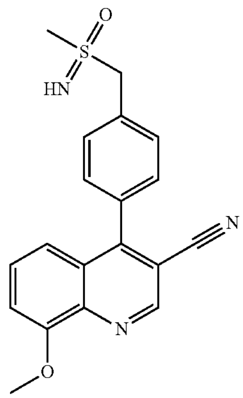 [SMILES: COc1cccc2c(-c3ccc(CS(C)(=N)=O)cc3)c(C#N)cnc12] | 8-methoxy-4-(4-((S-methylsulfonimidoyl)methyl)phenyl)quinoline-3-carbonitrile |
| 57 | 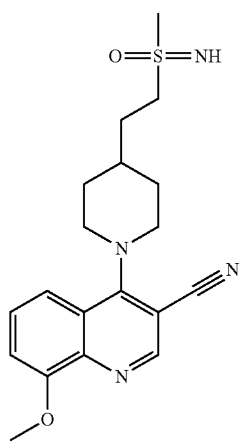 [SMILES: COc1cccc2c(N3CCC(CCS(C)(=N)=O)CC3)c(C#N)cnc12] | 8-methoxy-4-(4-(2-(S-methylsulfonimidoyl)ethyl)piperidin-1-yl)quinoline-3-carbonitrile |
| 58 | 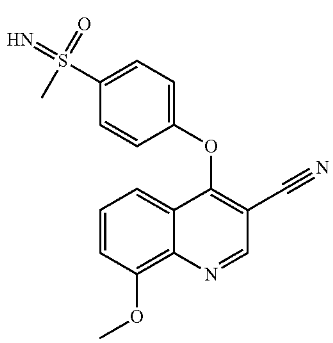 [SMILES: COc1cccc2c(Oc3ccc(S(C)(=N)=O)cc3)c(C#N)cnc12] | 8-methoxy-4-(4-(S-methylsulfonimidoyl)phenoxy)quinoline-3-carbonitrile |
| 59 | 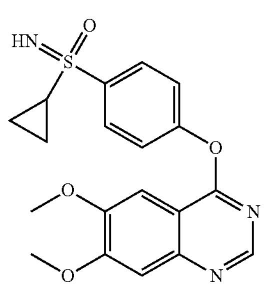 [SMILES: COc1cc2ncnc(Oc3ccc(S(=N)(=O)C4CC4)cc3)c2cc1OC] | cyclopropyl(4-((6,7-dimethoxyquinazolin-4-yl)oxy)phenyl)(imino)-$\lambda^6$-sulfanone |

TABLE 1-continued

| Compound No. | Structure | Name |
|---|---|---|
| 60 | 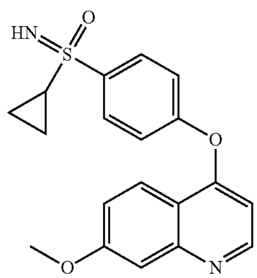 [SMILES: COc1ccc2c(Oc3ccc(S(=N)(=O)C4CC4)cc3)ccnc2c1] | cyclopropyl(imino)(4-((7-methoxyquinolin-4-yl)oxy)phenyl)-$\lambda^6$-sulfanone |
| 60R | 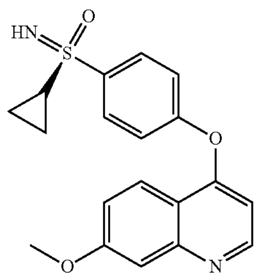 [SMILES: COc1ccc2c(Oc3ccc([S@](=N)(=O)C4CC4)cc3)ccnc2c1] | (R)-cyclopropyl(imino)(4-((7-methoxyquinolin-4-yl)oxy)phenyl)-$\lambda^6$-sulfanone |
| 60S | 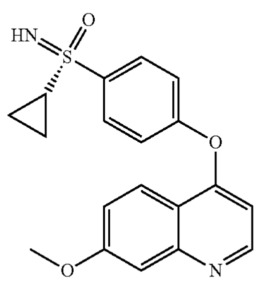 | (S)-cyclopropyl(imino)(4-((7-methoxyquinolin-4-yl)oxy)phenyl)-$\lambda^6$-sulfanone |
| 61 | 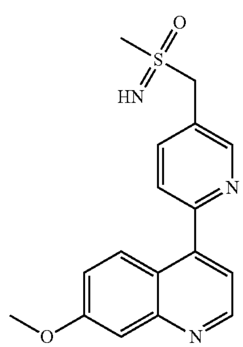 [SMILES: COc1ccc2c(-c3ccc(CS(C)(=N)=O)cn3)ccnc2c1] | imino((6-(7-methoxyquinolin-4-yl)pyridin-3-yl)methyl)(methyl)-$\lambda^6$-sulfanone |
| 62 | 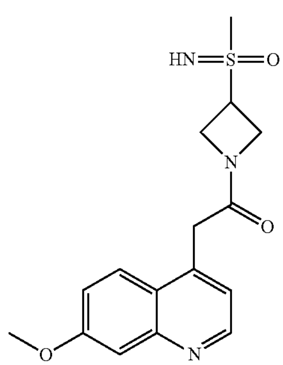 [SMILES: COc1ccc2c(CC(=O)N3CC(S(C)(=N)=O)C3)ccnc2c1] | imino(1-(2-(7-methoxyquinolin-4-yl)acetyl)azetidin-3-yl)(methyl)-$\lambda^6$-sulfanone |

TABLE 1-continued

| Compound No. | Structure | Name |
|---|---|---|
| 63 | 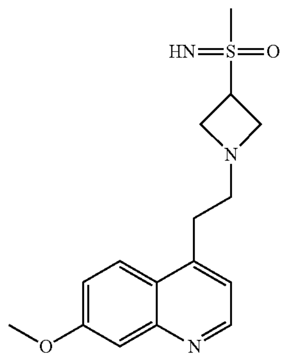 [SMILES: COc1ccc2c(CCN3CC(S(C)(=N)=O)C3)ccnc2c1] | imino(1-(2-(7-methoxyquinolin-4-yl)ethyl)azetidin-3-yl)(methyl)-$\lambda^6$-sulfanone |
| 64 | 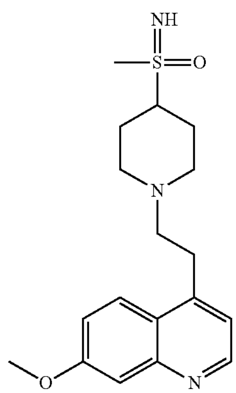 [SMILES: COc1ccc2c(CCN3CCC(S(C)(=N)=O)CC3)ccnc2c1] | imino(1-(2-(7-methoxyquinolin-4-yl)ethyl)piperidin-4-yl)(methyl)-$\lambda^6$-sulfanone |
| 65 | 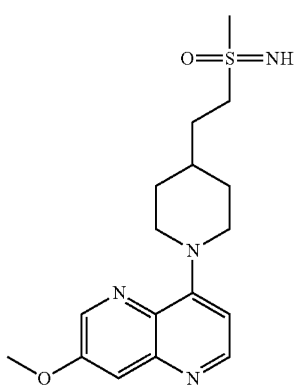 | imino(2-(1-(7-methoxy-1,5-naphthyridin-4-yl)piperidin-4-yl)ethyl)(methyl)-$\lambda^6$-sulfanone |
| 66 | 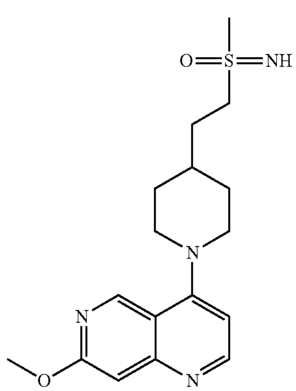 [SMILES: COc1cc2nccc(N3CCC(CCS(C)(=N)=O)CC3)c2cn1] | imino(2-(1-(7-methoxy-1,6-naphthyridin-4-yl)piperidin-4-yl)ethyl)(methyl)-$\lambda^6$-sulfanone |

TABLE 1-continued
| Compound No. | Structure | Name |
|---|---|---|
| 67 | 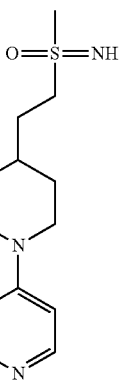 | imino(2-(1-(7-methoxy-1,8-naphthyridin-4-yl)piperidin-4-yl)ethyl)(methyl)-$\lambda^6$-sulfanone |
| 68 | 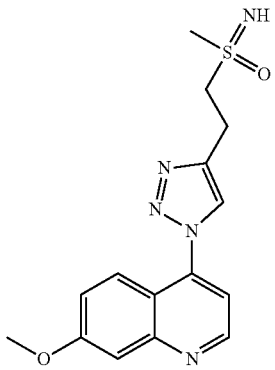 [SMILES: COc1ccc2c(-n3cc(CCS(C)(=N)=O)nn3)ccnc2c1] | imino(2-(1-(7-methoxyquinolin-4-yl)-1H-1,2,3-triazol-4-yl)ethyl)(methyl)-$\lambda^6$-sulfanone |
| 69 | 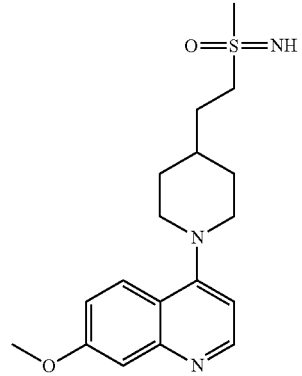 [SMILES: COc1ccc2c(N3CCC(CCS(C)(=N)=O)CC3)ccnc2c1] | imino(2-(1-(7-methoxyquinolin-4-yl)piperidin-4-yl)ethyl)(methyl)-$\lambda^6$-sulfanone |
| 70 | 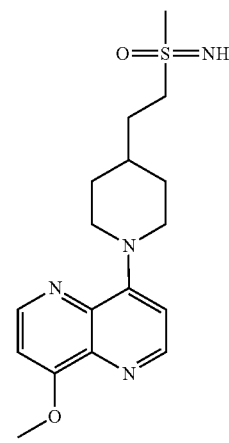 [SMILES: COc1ccnc2c(N3CCC(CCS(C)(=N)=O)CC3)ccnc12] | imino(2-(1-(8-methoxy-1,5-naphthyridin-4-yl)piperidin-4-yl)ethyl)(methyl)-$\lambda^6$-sulfanone |

TABLE 1-continued
| Compound No. | Structure | Name |
|---|---|---|
| 71 | 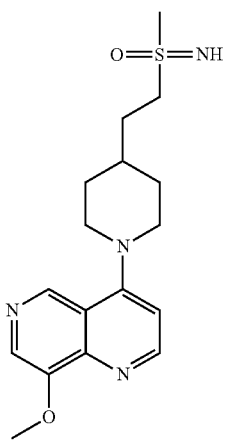 [SMILES: COc1cncc2c(N3CCC(CCS(C)(=N)=O)CC3)ccnc12] | imino(2-(1-(8-methoxy-1,6-naphthyridin-4-yl)piperidin-4-yl)ethyl)(methyl)-$\lambda^6$-sulfanone |
| 72 | 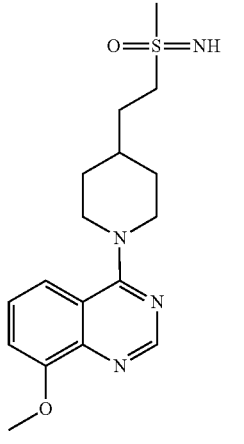 [SMILES: COc1cccc2c(N3CCC(CCS(C)(=N)=O)CC3)ncnc12] | imino(2-(1-(8-methoxyquinazolin-4-yl)piperidin-4-yl)ethyl)(methyl)-$\lambda^6$-sulfanone |
| 73 | 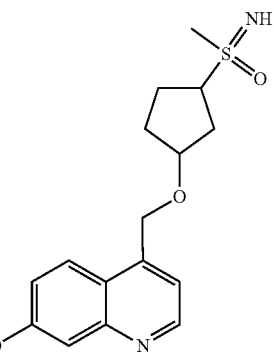 | imino(3-((7-methoxyquinolin-4-yl)methoxy)cyclopentyl)(methyl)-$\lambda^6$-sulfanone |

TABLE 1-continued
| Compound No. | Structure | Name |
|---|---|---|
| 74 | 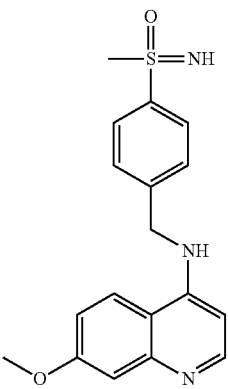 [SMILES: COc1ccc2c(NCc3ccc(S(C)(=N)=O)cc3)ccnc2c1] | imino(4-(((7-methoxyquinolin-4-yl)amino)methyl)phenyl)(methyl)-$\lambda^6$-sulfanone |
| 75 | 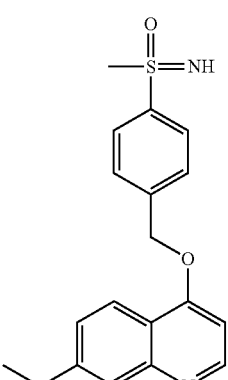 | imino(4-(((7-methoxyquinolin-4-yl)oxy)methyl)phenyl)(methyl)-$\lambda^6$-sulfanone |
| 75R | 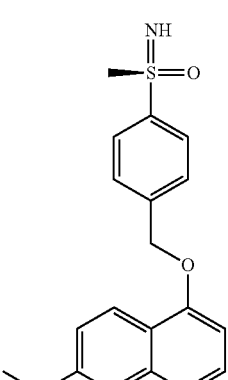 | (R)-imino(4-(((7-methoxyquinolin-4-yl)oxy)methyl)phenyl)(methyl)-l6-sulfanone |
| 75S | 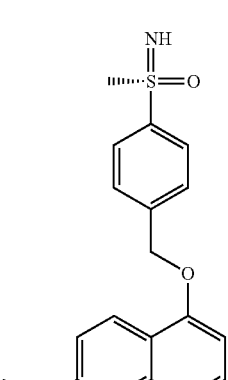 | (S)-imino(4-(((7-methoxyquinolin-4-yl)oxy)methyl)phenyl)(methyl)-l6-sulfanone |

TABLE 1-continued

| Compound No. | Structure | Name |
|---|---|---|
| 76 | 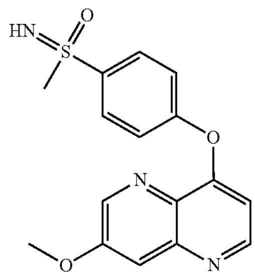 [SMILES: COc1cnc2c(Oc3ccc(S(C)(=N)=O)cc3)ccnc2c1] | imino(4-((7-methoxy-1,5-naphthyridin-4-yl)oxy)phenyl)(methyl)-$\lambda^6$-sulfanone |
| 77 | 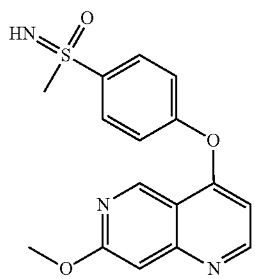 [SMILES: COc1cc2nccc(Oc3ccc(S(C)(=N)=O)cc3)c2cn1] | imino(4-((7-methoxy-1,6-naphthyridin-4-yl)oxy)phenyl)(methyl)-$\lambda^6$-sulfanone |
| 78 | 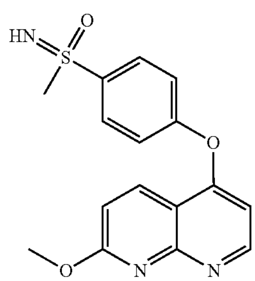 | imino(4-((7-methoxy-1,8-naphthyridin-4-yl)oxy)phenyl)(methyl)-$\lambda^6$-sulfanone |
| 79 | 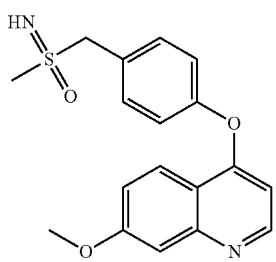 [SMILES: COc1ccc2c(Oc3ccc(CS(C)(=N)=O)cc3)ccnc2c1] | imino(4-((7-methoxyquinolin-4-yl)oxy)benzyl)(methyl)-$\lambda^6$-sulfanone |
| 80 | 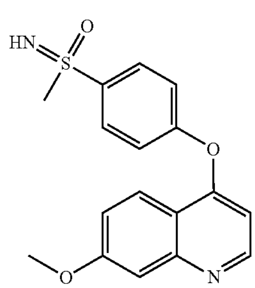 | imino(4-((7-methoxyquinolin-4-yl)oxy)phenyl)(methyl)-$\lambda^6$-sulfanone |

TABLE 1-continued

| Compound No. | Structure | Name |
|---|---|---|
| 80R | 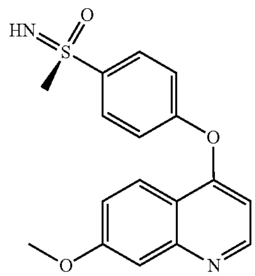 [SMILES: COc1ccc2c(Oc3ccc([S@](C)(=N)=O)cc3)ccnc2c1] | (R)-imino(4-((7-methoxyquinolin-4-yl)oxy)phenyl)(methyl)-$\lambda^6$-sulfanone |
| 80S | 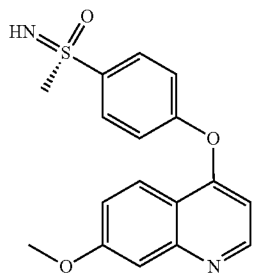 [SMILES: COc1ccc2c(Oc3ccc([S@@](C)(=N)=O)cc3)ccnc2c1] | (S)-imino(4-((7-methoxyquinolin-4-yl)oxy)phenyl)(methyl)-$\lambda^6$-sulfanone |
| 81 | 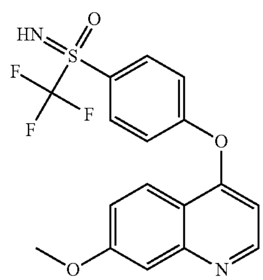 [SMILES: COc1ccc2c(Oc3ccc(S(=N)(=O)C(F)(F)F)cc3)ccnc2c1] | imino(4-((7-methoxyquinolin-4-yl)oxy)phenyl)(trifluoromethyl)-$\lambda^6$-sulfanone |
| 82 | 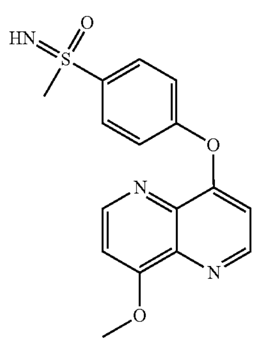 [SMILES: COc1ccnc2c(Oc3ccc(S(C)(=N)=O)cc3)ccnc12] | imino(4-((8-methoxy-1,5-naphthyridin-4-yl)oxy)phenyl)(methyl)-$\lambda^6$-sulfanone |
| 83 | 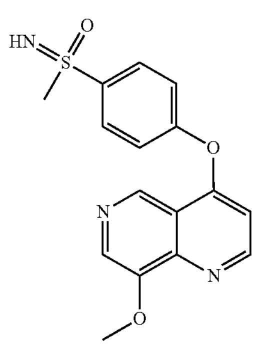 [SMILES: COc1cncc2c(Oc3ccc(S(C)(=N)=O)cc3)ccnc12] | imino(4-((8-methoxy-1,6-naphthyridin-4-yl)oxy)phenyl)(methyl)-$\lambda^6$-sulfanone |

TABLE 1-continued

| Compound No. | Structure | Name |
|---|---|---|
| 84 | 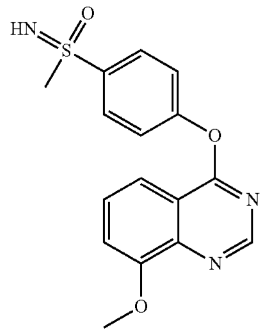 [SMILES: COc1cccc2c(Oc3ccc(S(C)(=N)=O)cc3)ncnc12] | imino(4-((8-methoxyquinazolin-4-yl)oxy)phenyl)(methyl)-$\lambda^6$-sulfanone |
| 85 | 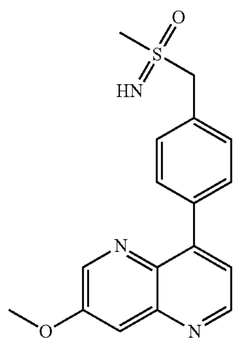 [SMILES: COc1cnc2c(-c3ccc(CS(C)(=N)=O)cc3)ccnc2c1] | imino(4-(7-methoxy-1,5-naphthyridin-4-yl)benzyl)(methyl)-$\lambda^6$-sulfanone |
| 86 | 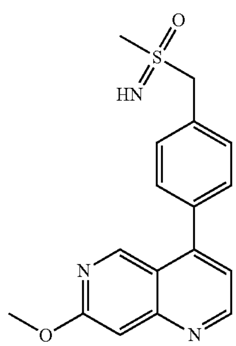 [SMILES: COc1cc2nccc(-c3ccc(CS(C)(=N)=O)cc3)c2cn1] | imino(4-(7-methoxy-1,6-naphthyridin-4-yl)benzyl)(methyl)-$\lambda^6$-sulfanone |
| 87 | 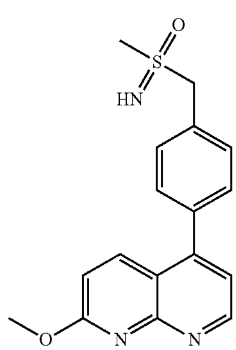 [SMILES: COc1ccc2c(-c3ccc(CS(C)(=N)=O)cc3)ccnc2n1] | imino(4-(7-methoxy-1,8-naphthyridin-4-yl)benzyl)(methyl)-$\lambda^6$-sulfanone |

TABLE 1-continued

| Compound No. | Structure | Name |
|---|---|---|
| 88 | 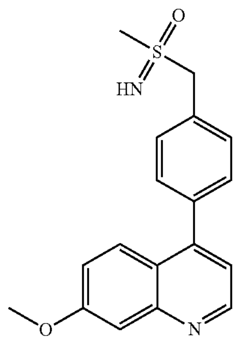 [SMILES: COc1ccc2c(-c3ccc(CS(C)(=N)=O)cc3)ccnc2c1] | imino(4-(7-methoxyquinolin-4-yl)benzyl)(methyl)-$\lambda^6$-sulfanone |
| 89 | 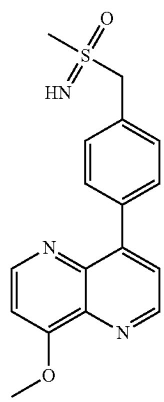 [SMILES: COc1ccnc2c(-c3ccc(CS(C)(=N)=O)cc3)ccnc12] | imino(4-(8-methoxy-1,5-naphthyridin-4-yl)benzyl)(methyl)-$\lambda^6$-sulfanone |
| 90 | 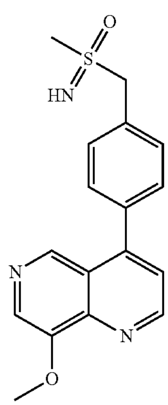 [SMILES: COc1cncc2c(-c3ccc(CS(C)(=N)=O)cc3)ccnc12] | imino(4-(8-methoxy-1,6-naphthyridin-4-yl)benzyl)(methyl)-$\lambda^6$-sulfanone |
| 91 | 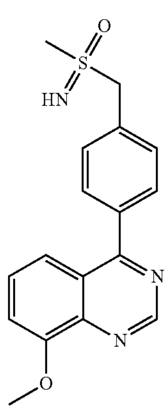 [SMILES: COc1cccc2c(-c3ccc(CS(C)(=N)=O)cc3)ncnc12] | imino(4-(8-methoxyquinazolin-4-yl)benzyl)(methyl)-$\lambda^6$-sulfanone |

TABLE 1-continued
| Compound No. | Structure | Name |
|---|---|---|
| 92 | 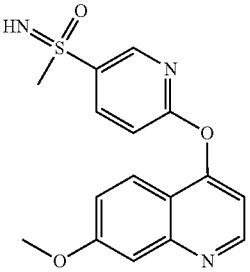 [SMILES: COc1ccc2c(Oc3ccc(S(C)(=N)=O)cn3)ccnc2c1] | imino(6-((7-methoxyquinolin-4-yl)oxy)pyridin-3-yl)(methyl)-$\lambda^6$-sulfanone |
| 93 | 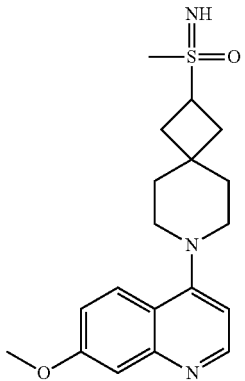 [SMILES: COc1ccc2c(N3CCC4(CC3)CC(S(C)(=N)=O)C4)ccnc2c1] | imino(7-(7-methoxyquinolin-4-yl)-7-azaspiro[3.5]nonan-2-yl)(methyl)-$\lambda^6$-sulfanone |
| 94 | 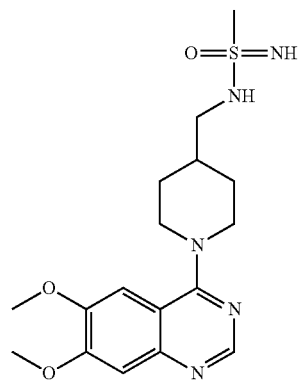 | N-((1-(6,7-dimethoxyquinazolin-4-yl)piperidin-4-yl)methyl)methanesulfonimidamide |
| 94S | 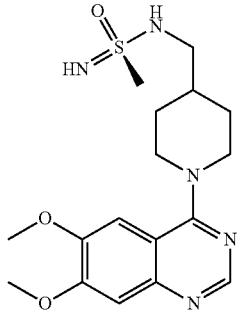 [SMILES: COc1cc2ncnc(N3CCC(CN[S@](C)(=N)=O)CC3)c2cc1OC] | (S)-N-((1-(6,7-dimethoxyquinazolin-4-yl)piperidin-4-yl)methyl)methanesulfonimidamide |

TABLE 1-continued

| Compound No. | Structure | Name |
|---|---|---|
| 94R | 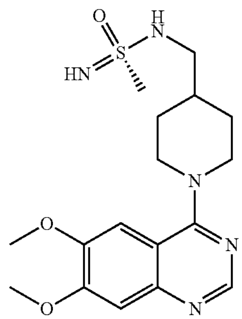 [SMILES: COc1cc2ncnc(N3CCC(CN[S@@](C)(=N)=O)CC3)c2cc1OC] | (R)-N-((1-(6,7-dimethoxyquinazolin-4-yl)piperidin-4-yl)methyl)methanesulfonimidamide |
| 95 | 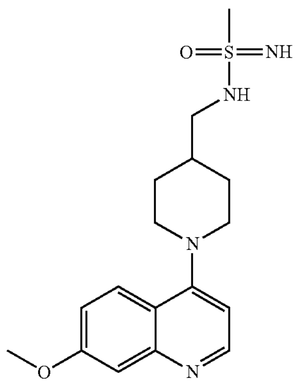 [SMILES: COc1ccc2c(N3CCC(CNS(C)(=N)=O)CC3)ccnc2c1] | N-((1-(7-methoxyquinolin-4-yl)piperidin-4-yl)methyl)methanesulfonimidamide |
| 96 | 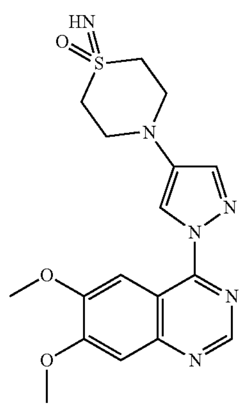 [SMILES: COc1cc2ncnc(-n3cc(N4CCS(=N)(=O)CC4)cn3)c2cc1OC] | 4-(1-(6,7-dimethoxyquinolin-4-yl)-1H-pyrazol-4-yl)-1-imino-1$\lambda^6$-thiomorpholine 1-oxide |
| 97 | 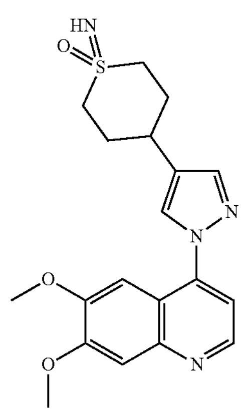 [SMILES: COc1cc2nccc(-n3cc(C4CCS(=N)(=O)CC4)cn3)c2cc1OC] | 4-(1-(6,7-dimethoxyquinolin-4-yl)-1H-pyrazol-4-yl)-1-iminohexahydro-1$\lambda^6$-thiopyran 1-oxide |

TABLE 1-continued

| Compound No. | Structure | Name |
|---|---|---|
| 98 | 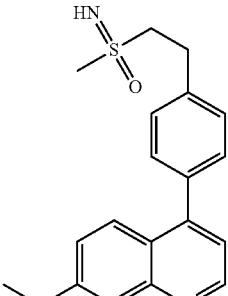 | imino(4-(7-methoxyquinolin-4-yl)phenethyl)(methyl)-$\lambda^6$-sulfanone |
| 99 | 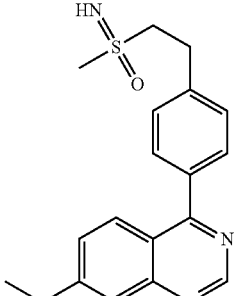 | (4-(6,7-dimethoxyquinazolin-4-yl)phenethyl)(imino)(methyl)-$\lambda^6$-sulfanone |
| 100 | 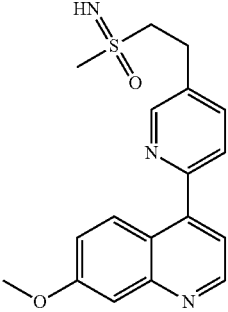 [SMILES: COc1ccc2c(-c3ccc(CCS(C)(=N)=O)cn3)ccnc2c1] | imino(2-(6-(7-methoxyquinolin-4-yl)pyridin-3-yl)ethyl)(methyl)-$\lambda^6$-sulfanone |
| 101 | 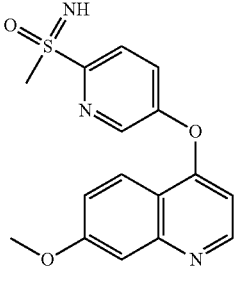 [SMILES: COc1ccc2c(Oc3ccc(S(C)(=N)=O)nc3)ccnc2c1] | imino(5-((7-methoxyquinolin-4-yl)oxy)pyridin-2-yl)(methyl)-$\lambda^6$-sulfanone |
| 102 | 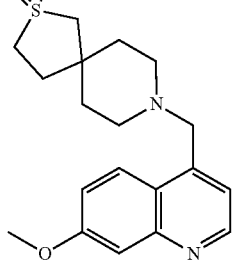 | 2-imino-8-((7-methoxyquinolin-4-yl)methyl)-2$\lambda^6$-thia-8-azaspiro[4.5]decane 2-oxide |

TABLE 1-continued

| Compound No. | Structure | Name |
|---|---|---|
| 103 | 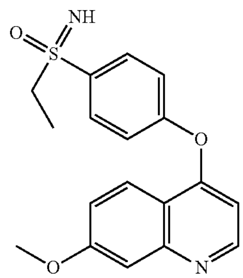 [SMILES: CCS(=N)(=O)c1ccc(Oc2ccnc3cc(OC)ccc23)cc1] | ethyl(imino)(4-((7-methoxyquinolin-4-yl)oxy)phenyl)-λ⁶-sulfanone |
| 103R | 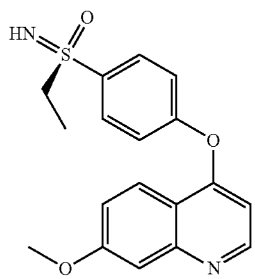 [SMILES: CC[S@@](=N)(=O)c1ccc(Oc2ccnc3cc(OC)ccc23)cc1] | (R)-ethyl(imino)(4-((7-methoxyquinolin-4-yl)oxy)phenyl)-λ⁶-sulfanone |
| 103S | 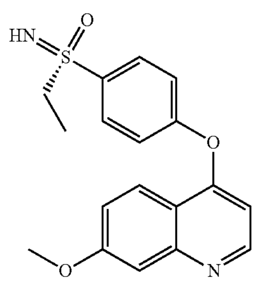 [SMILES: CC[S@](=N)(=O)c1ccc(Oc2ccnc3cc(OC)ccc23)cc1] | (S)-ethyl(imino)(4-((7-methoxyquinolin-4-yl)oxy)phenyl)-λ⁶-sulfanone |
| 104 | 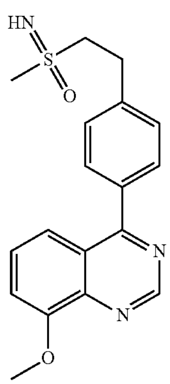 [SMILES: COc1cccc2c(-c3ccc(CCS(C)(=N)=O)cc3)ncnc12] | imino(4-(8-methoxyquinazolin-4-yl)phenethyl)(methyl)-λ⁶-sulfanone |
| 105 | 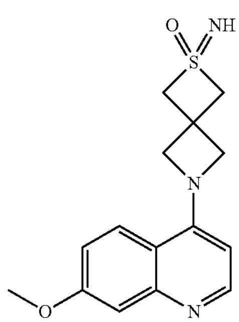 [SMILES: COc1ccc2c(N3CC4(C3)CS(=N)(=O)C4)ccnc2c1] | 2-imino-6-(7-methoxyquinolin-4-yl)-2λ⁶-thia-6-azaspiro[3.3]heptane 2-oxide |

TABLE 1-continued

| Compound No. | Structure | Name |
| --- | --- | --- |
| 106 | 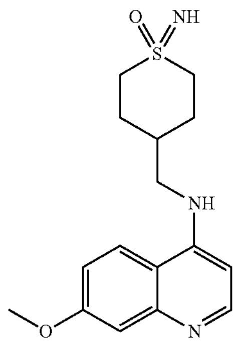 [SMILES: COc1ccc2c(NCC3CCS(=N)(=O)CC3)ccnc2c1] | 1-imino-4-(((7-methoxyquinolin-4-yl)amino)methyl)hexahydro-$\lambda^6$-thiopyran 1-oxide |
| 107 | 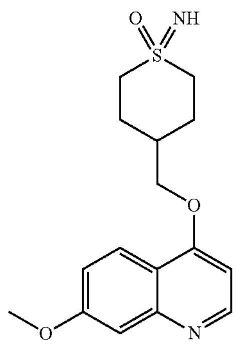 [SMILES: COc1ccc2c(OCC3CCS(=N)(=O)CC3)ccnc2c1] | 1-imino-4-(((7-methoxyquinolin-4-yl)oxy)methyl)hexahydro-1$\lambda^6$-thiopyran 1-oxide |
| 107rr | 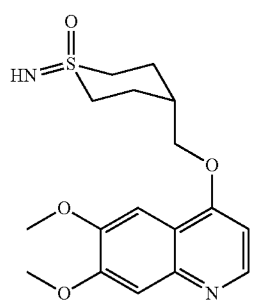 [SMILES: COc1cc2nccc(OCC3CCS(=N)(=O)CC3)c2cc1OC] | (1r,4r)-4-(((6,7-dimethoxyquinolin-4-yl)oxy)methyl)-1-iminohexahydro-1$\lambda^6$-thiopyran 1-oxide |
| 107ss | 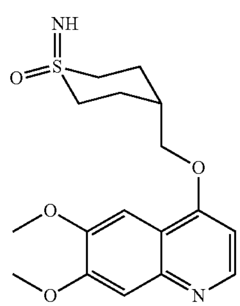 [SMILES: COc1cc2nccc(OCC3CCS(=N)(=O)CC3)c2cc1OC] | (1s,4s)-4-(((6,7-dimethoxyquinolin-4-yl)oxy)methyl)-1-iminohexahydro-1$\lambda^6$-thiopyran 1-oxide |
| 108 | 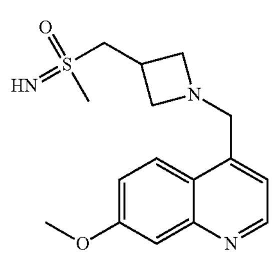 [SMILES: COc1ccc2c(CN3CC(CS(C)(=N)=O)C3)ccnc2c1] | imino((1-((7-methoxyquinolin-4-yl)methyl)azetidin-3-yl)methyl)(methyl)-$\lambda^6$-sulfanone |

TABLE 1-continued

| Compound No. | Structure | Name |
|---|---|---|
| 109 | 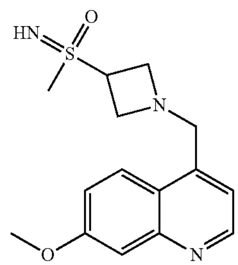 [SMILES: COc1ccc2c(CN3CC(S(C)(=N)=O)C3)ccnc2c1] | imino(1-((7-methoxyquinolin-4-yl)methyl)azetidin-3-yl)(methyl)-λ⁶-sulfanone |
| 110 | 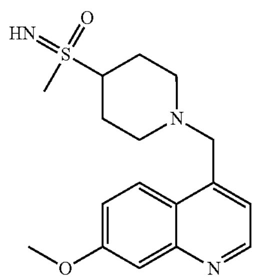 [SMILES: COc1ccc2c(CN3CCC(S(C)(=N)=O)CC3)ccnc2c1] | imino(1-((7-methoxyquinolin-4-yl)methyl)piperidin-4-yl)(methyl)-λ⁶-sulfanone |
| 111 | 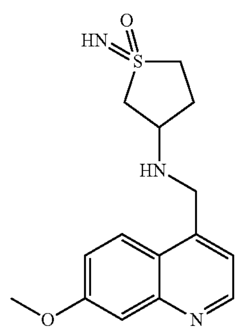 [SMILES: COc1ccc2c(CNC3CCS(=N)(=O)C3)ccnc2c1] | 1-imino-3-(((7-methoxyquinolin-4-yl)methyl)amino)tetrahydro-1H-1λ⁶-thiophene 1-oxide |
| 112 | 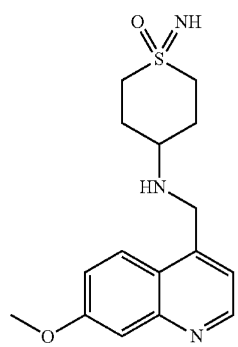 [SMILES: COc1ccc2c(CNC3CCS(=N)(=O)CC3)ccnc2c1] | 1-imino-4-(((7-methoxyquinolin-4-yl)methyl)amino)hexahydro-1λ⁶-thiopyran 1-oxide |
| 113 | 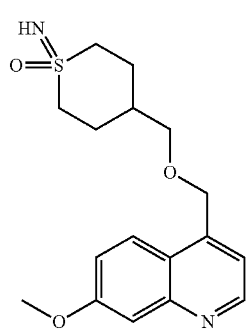 [SMILES: COc1ccc2c(COCC3CCS(=N)(=O)CC3)ccnc2c1] | 1-imino-4-(((7-methoxyquinolin-4-yl)methoxy)methyl)hexahydro-1λ⁶-thiopyran 1-oxide |

TABLE 1-continued

| Compound No. | Structure | Name |
|---|---|---|
| 114 | 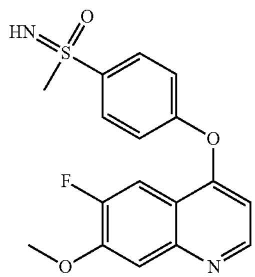 [SMILES: COc1cc2nccc(Oc3ccc(S(C)(=N)=O)cc3)c2cc1F] | {4-[(6-fluoro-7-methoxyquinolin-4-yl)oxy]phenyl}(imino)methyl-λ⁶-sulfanone |
| 114R | 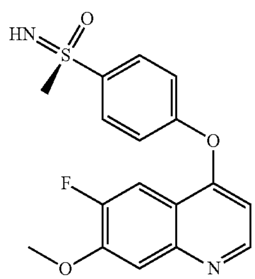 [SMILES: COc1cc2nccc(Oc3ccc([S@](C)(=N)=O)cc3)c2cc1F] | (R)-{4-[(6-fluoro-7-methoxyquinolin-4-yl)oxy]phenyl}(imino)methyl-λ⁶-sulfanone |
| 114S | 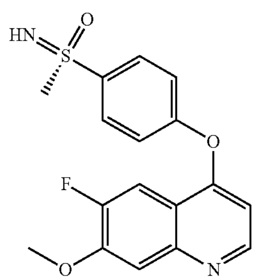 | (S)-{4-[(6-fluoro-7-methoxyquinolin-4-yl)oxy]phenyl}(imino)methyl-λ⁶-sulfanone |
| 115 | 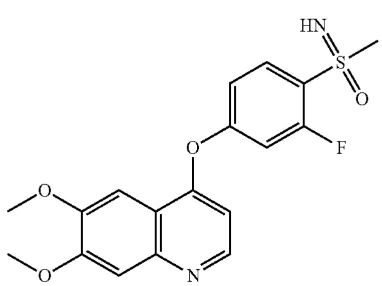 | {4-[(6,7-dimethoxyquinolin-4-yl)oxy]-2-fluorophenyl}(imino)methyl-λ⁶-sulfanone |
| 116 | 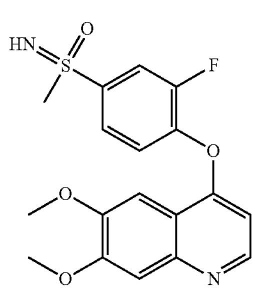 [SMILES: COc1cc2nccc(Oc3ccc(S(C)(=N)=O)cc3F)c2cc1OC] | {4-[(6,7-dimethoxyquinolin-4-yl)oxy]-3-fluorophenyl}(imino)methyl-λ⁶-sulfanone |

TABLE 1-continued

| Compound No. | Structure | Name |
|---|---|---|
| 117 | 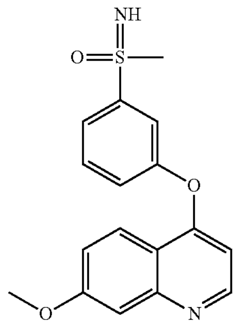 [SMILES: COc1ccc2c(Oc3cccc(S(C)(=N)=O)c3)ccnc2c1] | imino({3-[(7-methoxyquinolin-4-yl)oxy]phenyl})methyl-$\lambda^6$-sulfanone |
| 118 | 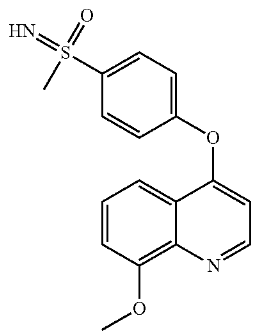 | imino({4-[(8-methoxyquinolin-4-yl)oxy]phenyl})methyl-$\lambda^6$-sulfanone |
| 119 | 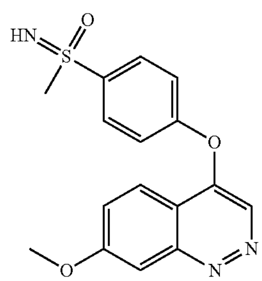 [SMILES: COc1ccc2c(Oc3ccc(S(C)(=N)=O)cc3)cnnc2c1] | imino({4-[(7-methoxycinnolin-4-yl)oxy]phenyl})methyl-$\lambda^6$-sulfanone |
| 120 | 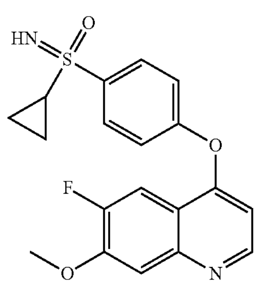 [SMILES: COc1cc2nccc(Oc3ccc(S(=N)(=O)C4CC4)cc3)c2cc1F] | [cyclopropyl({4-[(6-fluoro-7-methoxyquinolin-4-yl)oxy]phenyl})imino-$\lambda^6$-sulfanyl]one |
| 120R | 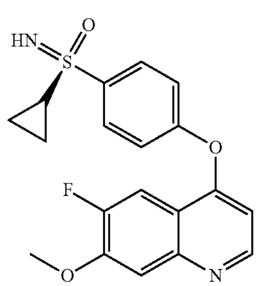 [SMILES: COc1cc2nccc(Oc3ccc([S@](=N)(=O)C4CC4)cc3)c2cc1F] | (R)-[cyclopropyl({4-[(6-fluoro-7-methoxyquinolin-4-yl)oxy]phenyl})imino-$\lambda 6$-sulfanyl]one |

TABLE 1-continued

| Compound No. | Structure | Name |
|---|---|---|
| 120S | 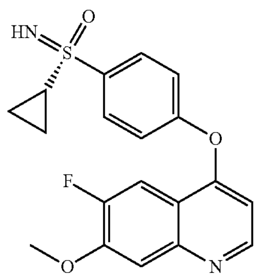 [SMILES: COc1cc2nccc(Oc3ccc([S@@](=N)(=O)C4CC4)cc3)c2cc1F] | (S)-[cyclopropyl({4-[(6-fluoro-7-methoxyquinolin-4-yl)oxy]phenyl})imino-λ6-sulfanyl]one |
| 121 | 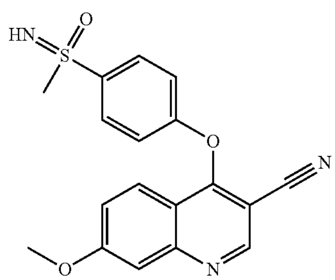 [SMILES: COc1ccc2c(Oc3ccc(S(C)(=N)=O)cc3)c(C#N)cnc2c1] | 4-{4-[imino(methyl)oxo-λ6-sulfanyl]phenoxy}-7-methoxyquinoline-3-carbonitrile |
| 122 | 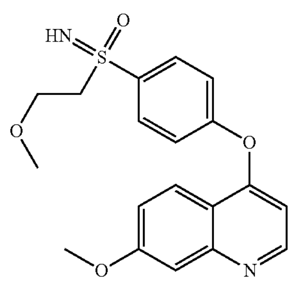 [SMILES: COCCS(=N)(=O)c1ccc(Oc2ccnc3cc(OC)ccc23)cc1] | imino(2-methoxyethyl){4-[(7-methoxyquinolin-4-yl)oxy]phenyl}-λ6-sulfanone |
| 123 | 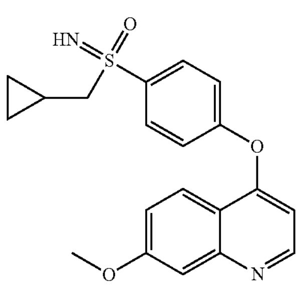 [SMILES: COc1ccc2c(Oc3ccc(S(=N)(=O)CC4CC4)cc3)ccnc2c1] | (cyclopropylmethyl)(imino){4-[(7-methoxyquinolin-4-yl)oxy]phenyl}-λ6-sulfanone |
| 124 | 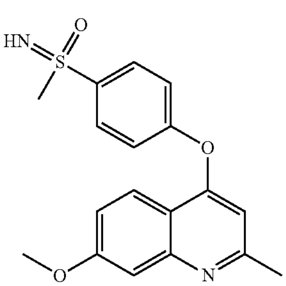 | imino({4-[(7-methoxy-2-methylquinolin-4-yl)oxy]phenyl})methyl-λ6-sulfanone |

TABLE 1-continued

| Compound No. | Structure | Name |
|---|---|---|
| 125 | 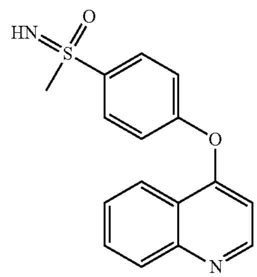 [SMILES: CS(=N)(=O)c1ccc(Oc2ccnc3ccccc23)cc1] | imino(methyl)[4-(quinolin-4-yloxy)phenyl]-λ⁶-sulfanone |
| 126 | 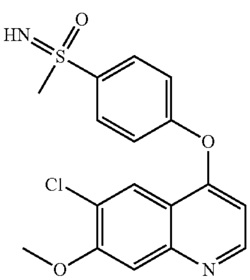 [SMILES: COc1cc2nccc(Oc3ccc(S(C)(=N)=O)cc3)c2cc1Cl] | {4-[(6-chloro-7-methoxyquinolin-4-yl)oxy]phenyl}(imino)methyl-λ⁶-sulfanone |
| 127 | 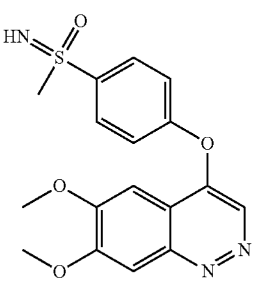 [SMILES: COc1cc2nncc(Oc3ccc(S(C)(=N)=O)cc3)c2cc1OC] | {4-[(6,7-dimethoxycinnolin-4-yl)oxy]phenyl}(imino)methyl-λ⁶-sulfanone |
| 128 | 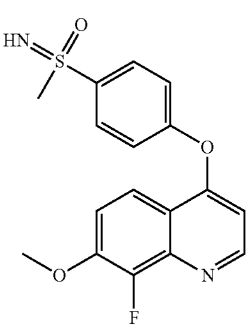 [SMILES: COc1ccc2c(Oc3ccc(S(C)(=N)=O)cc3)ccnc2c1F] | {4-[(8-fluoro-7-methoxyquinolin-4-yl)oxy]phenyl}(imino)methyl-λ⁶-sulfanone |
| 129 | 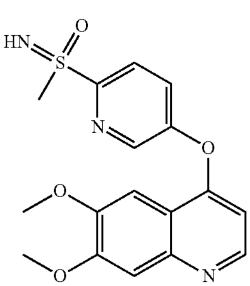 [SMILES: COc1cc2nccc(Oc3ccc(S(C)(=N)=O)nc3)c2cc1OC] | {5-[(6,7-dimethoxyquinolin-4-yl)oxy]pyridin-2-yl}(imino)methyl-λ⁶-sulfanone |

TABLE 1-continued

| Compound No. | Structure | Name |
|---|---|---|
| 130 | 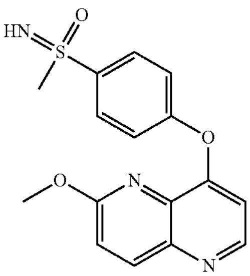 [SMILES: COc1ccc2nccc(Oc3ccc(S(C)(=N)=O)cc3)c2n1] | imino({4-[(6-methoxy-1,5-naphthyridin-4-yl)oxy]phenyl})methyl-λ⁶-sulfanone |
| 131 | 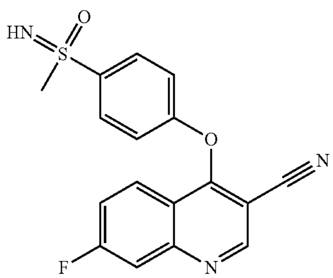 [SMILES: CS(=N)(=O)c1ccc(Oc2c(C#N)cnc3cc(F)ccc23)cc1] | 7-fluoro-4-{4-[imino(methyl)oxo-λ⁶-sulfanyl]phenoxy}quinoline-3-carbonitrile |
| 132 | 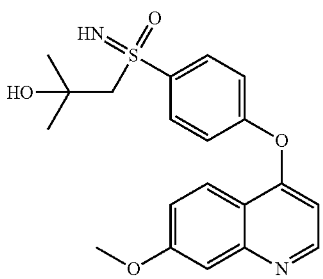 [SMILES: COc1ccc2c(Oc3ccc(S(=N)(=O)CC(C)(C)O)cc3)ccnc2c1] | (2-hydroxy-2-methylpropyl)(imino){4-[(7-methoxyquinolin-4-yl)oxy]phenyl}-λ⁶-sulfanone |
| 133 | 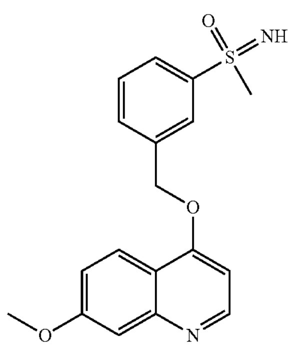 [SMILES: COc1ccc2c(OCc3cccc(S(C)(=N)=O)c3)ccnc2c1] | imino(3-{[(7-methoxyquinolin-4-yl)oxy]methyl}phenyl)methyl-λ⁶-sulfanone |
| 133R | 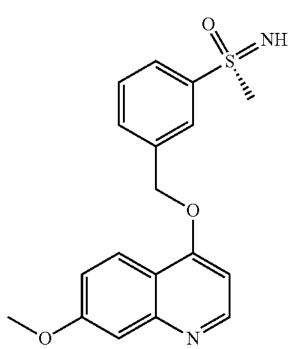 [SMILES: COc1ccc2c(OCc3cccc([S@](C)(=N)=O)c3)ccnc2c1] | (R)-imino(3-{[(7-methoxyquinolin-4-yl)oxy]methyl}phenyl)methyl-λ6-sulfanone |

TABLE 1-continued

| Compound No. | Structure | Name |
|---|---|---|
| 133S | 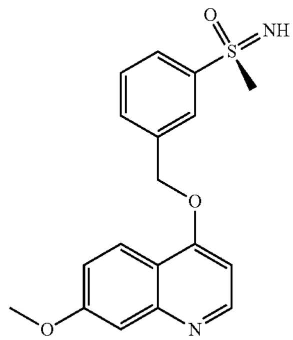 [SMILES: COc1ccc2c(OCc3cccc([S@@](C)(=N)=O)c3)ccnc2c1] | (S)-imino(3-{[(7-methoxyquinolin-4-yl)oxy]methyl}phenyl)methyl-λ6-sulfanone |
| 134 | 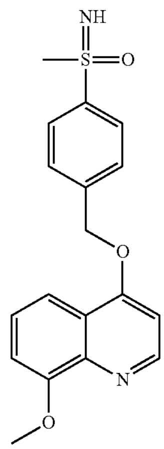 [SMILES: COc1cccc2c(OCc3ccc(S(C)(=N)=O)cc3)ccnc12] | imino(4-{[(8-methoxyquinolin-4-yl)oxy]methyl}phenyl)methyl-$\lambda^6$-sulfanone |
| 135 | 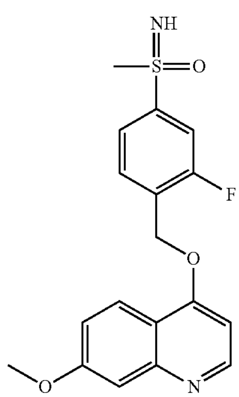 [SMILES: COc1ccc2c(OCc3ccc(S(C)(=N)=O)cc3F)ccnc2c1] | (3-fluoro-4-{[(7-methoxyquinolin-4-yl)oxy]methyl}phenyl)(imino)methyl-$\lambda^6$-sulfanone |
| 136 | 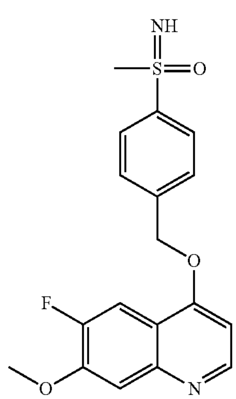 [SMILES: COc1cc2nccc(OCc3ccc(S(C)(=N)=O)cc3)c2cc1F] | (4-{[6-fluoro-7-methoxyquinolin-4-yl)oxy]methyl}phenyl)(imino)methyl-$\lambda^6$-sulfanone |

TABLE 1-continued
| Compound No. | Structure | Name |
|---|---|---|
| 137 | 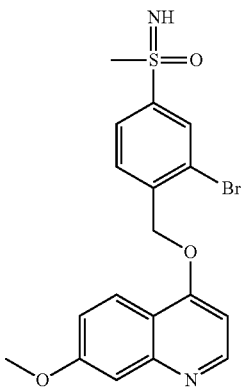 [SMILES: COc1ccc2c(OCc3ccc(S(C)(=N)=O)cc3Br)ccnc2c1] | (3-bromo-4-{[(7-methoxyquinolin-4-yl)oxy]methyl}phenyl)(imino)methyl-$\lambda^6$-sulfanone |
| 138 | 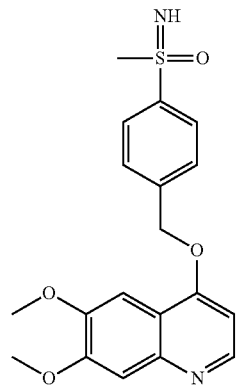 [SMILES: COc1cc2nccc(OCc3ccc(S(C)(=N)=O)cc3)c2cc1OC] | (4-{[(6,7-dimethoxyquinolin-4-yl)oxy]methyl}phenyl)(imino)methyl-$\lambda^6$-sulfanone |
| 139 | 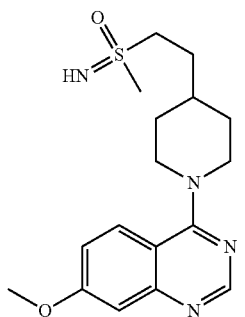 [SMILES: COc1ccc2c(N3CCC(CCS(C)(=N)=O)CC3)ncnc2c1] | imino({2-[1-(7-methoxyquinazolin-4-yl)piperidin-4-yl]ethyl})methyl-$\lambda^6$-sulfanone |
| 140 | 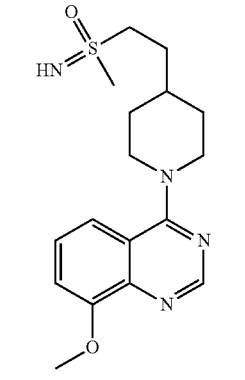 [SMILES: COc1cccc2c(N3CCC(CCS(C)(=N)=O)CC3)ncnc12] | imino({2-[1-(8-methoxyquinolin-4-yl)piperidin-4-yl]ethyl})methyl-$\lambda^6$-sulfanone |

TABLE 1-continued

| Compound No. | Structure | Name |
|---|---|---|
| 141 | 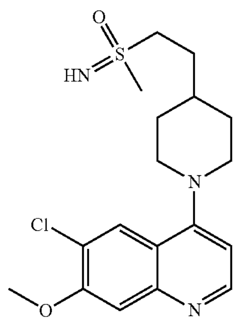 [SMILES: COc1cc2nccc(N3CCC(CCS(C)(=N)=O)CC3)c2cc1Cl] | {2-[1-(6-chloro-7-methoxyquinolin-4-yl)piperidin-4-yl]ethyl}(imino)methyl-$\lambda^6$-sulfanone |
| 141R | 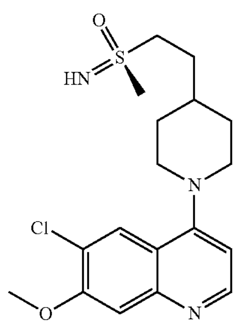 [SMILES: COc1cc2nccc(N3CCC(CC[S@](C)(=N)=O)CC3)c2cc1Cl] | (R)-{2-[1-(6-chloro-7-methoxyquinolin-4-yl)piperidin-4-yl]ethyl}(imino)methyl-$\lambda$6-sulfanone |
| 141S | 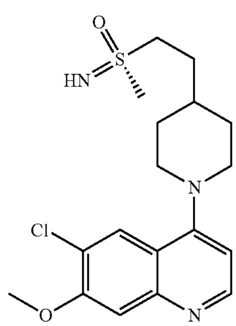 | (S)-{2-[1-(6-chloro-7-methoxyquinolin-4-yl)piperidin-4-yl]ethyl}(imino)methyl-$\lambda$6-sulfanone |
| 142 | 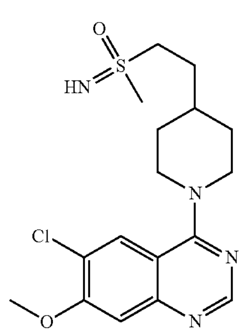 [SMILES: COc1cc2ncnc(N3CCC(CCS(C)(=N)=O)CC3)c2cc1Cl] | {2-[1-(6-chloro-7-methoxyquinazolin-4-yl)piperidin-4-yl]ethyl}(imino)methyl-$\lambda^6$-sulfanone |

TABLE 1-continued

| Compound No. | Structure | Name |
|---|---|---|
| 142R | 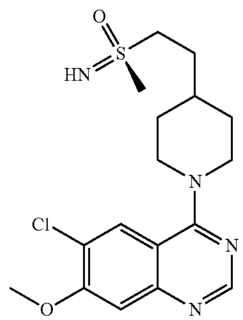 [SMILES: COc1cc2ncnc(N3CCC(CC[S@](C)(=N)=O)CC3)c2cc1Cl] | (R)-{2-[1-(6-chloro-7-methoxyquinazolin-4-yl)piperidin-4-yl]ethyl}(imino)methyl-λ6-sulfanone |
| 142S | 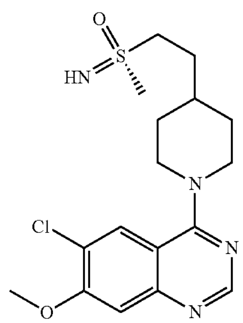 [SMILES: COc1cc2ncnc(N3CCC(CC[S@@](C)(=N)=O)CC3)c2cc1Cl] | (S)-{2-[1-(6-chloro-7-methoxyquinazolin-4-yl)piperidin-4-yl]ethyl}(imino)methyl-λ6-sulfanone |
| 143 | 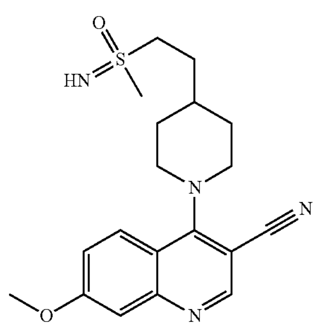 [SMILES: COc1ccc2c(N3CCC(CCS(C)(=N)=O)CC3)c(C#N)cnc2c1] | 4-(4-{2-[imino(methyl)oxo-λ6-sulfanyl]ethyl}piperidin-1-yl)-7-methoxyquinoline-3-carbonitrile |
| 144 | 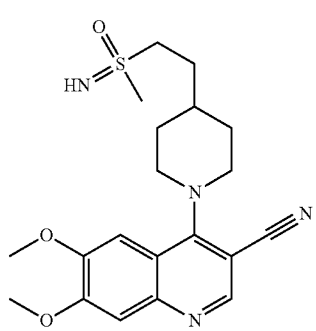 [SMILES: COc1cc2ncc(C#N)c(N3CCC(CCS(C)(=N)=O)CC3)c2cc1OC] | 4-(4-{2-[imino(methyl)oxo-λ6-sulfanyl]ethyl}piperidin-1-yl)-6,7-dimethoxyquinoline-3-carbonitrile |

TABLE 1-continued

| Compound No. | Structure | Name |
|---|---|---|
| 145 | 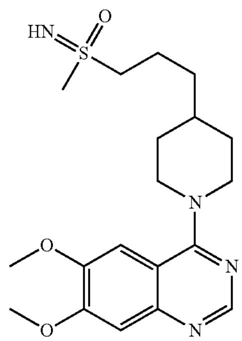 [SMILES: COc1cc2ncnc(N3CCC(CCCS(C)(=N)=O)CC3)c2cc1OC] | {3-[1-(6,7-dimethoxyquinazolin-4-yl)piperidin-4-yl]propyl}(imino)methyl-$\lambda^6$-sulfanone |
| 146 | 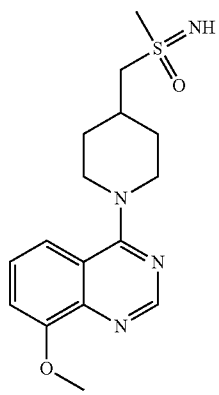 [SMILES: COc1cccc2c(N3CCC(CS(C)(=N)=O)CC3)ncnc12] | imino({[1-(8-methoxyquinazolin-4-yl)piperidin-4-yl]methyl})methyl-$\lambda^6$-sulfanone |
| 146R | 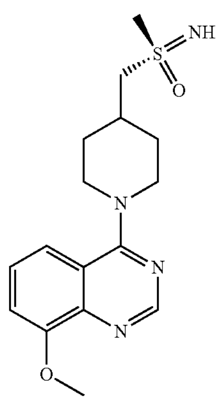 [SMILES: COc1cccc2c(N3CCC(C[S@](C)(=N)=O)CC3)ncnc12] | (R)-imino({[1-(8-methoxyquinazolin-4-yl)piperidin-4-yl]methyl})methyl-$\lambda^6$-sulfanone |
| 146S | 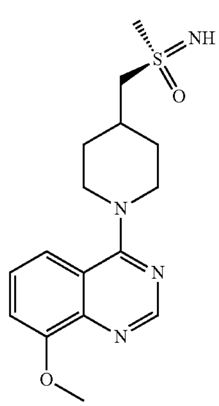 [SMILES: COc1cccc2c(N3CCC(C[S@@](C)(=N)=O)CC3)ncnc12] | (S)-imino({[1-(8-methoxyquinazolin-4-yl)piperidin-4-yl]methyl})methyl-$\lambda^6$-sulfanone |

TABLE 1-continued

| Compound No. | Structure | Name |
|---|---|---|
| 147 | 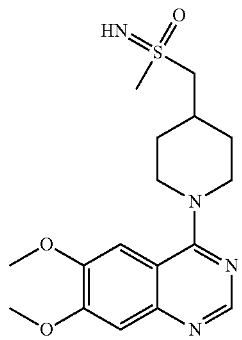 [SMILES: COc1cc2ncnc(N3CCC(CS(C)(=N)=O)CC3)c2cc1OC] | {[1-(6,7-dimethoxyquinazolin-4-yl)piperidin-4-yl]methyl}(imino)methyl-λ⁶-sulfanone |
| 148 | 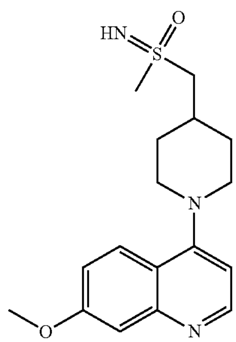 [SMILES: COc1ccc2c(N3CCC(CS(C)(=N)=O)CC3)ccnc2c1] | imino({[1-(7-methoxyquinolin-4-yl)piperidin-4-yl]methyl})methyl-λ⁶-sulfanone |
| 149 | 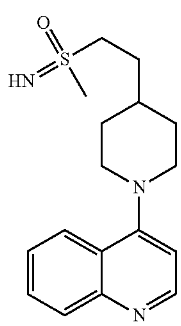 [SMILES: CS(=N)(=O)CCC1CCN(c2ccnc3ccccc23)CC1] | imino(methyl){2-[1-(quinolin-4-yl)piperidin-4-yl]ethyl}-λ⁶-sulfanone |
| 150 | 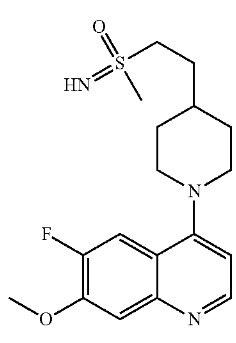 [SMILES: COc1cc2nccc(N3CCC(CCS(C)(=N)=O)CC3)c2cc1F] | {2-[1-(6-fluoro-7-methoxyquinolin-4-yl)piperidin-4-yl]ethyl}(imino)methyl-λ⁶-sulfanone |

TABLE 1-continued

| Compound No. | Structure | Name |
|---|---|---|
| 151 | 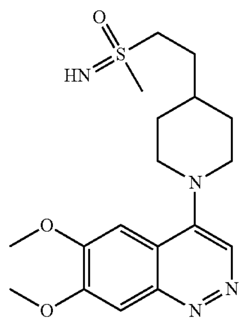 [SMILES: COc1cc2nncc(N3CCC(CCS(C)(=N)=O)CC3)c2cc1OC] | {2-[1-(6,7-dimethoxycinnolin-4-yl)piperidin-4-yl]ethyl}(imino)methyl-$\lambda^6$-sulfanone |
| 152 | 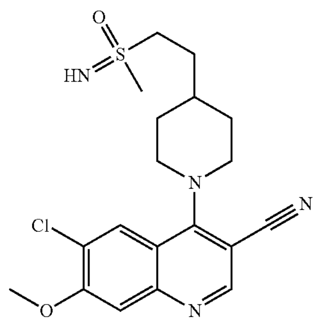 [SMILES: COc1cc2ncc(C#N)c(N3CCC(CCS(C)(=N)=O)CC3)c2cc1Cl] | 6-chloro-4-(4-{2-[imino(methyl)oxo-$\lambda^6$-sulfanyl]ethyl}piperidin-1-yl)-7-methoxyquinoline-3-carbonitrile |
| 153 | 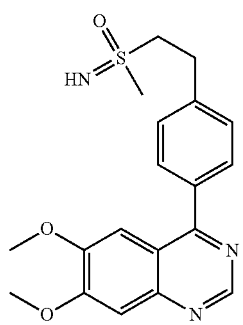 [SMILES: COc1cc2ncnc(-c3ccc(CCS(C)(=N)=O)cc3)c2cc1OC] | {2-[4-(6,7-dimethoxyquinazolin-4-yl)phenyl]ethyl}(imino)methyl-$\lambda^6$-sulfanone |
| 154 | 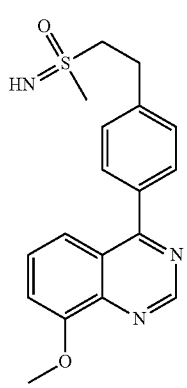 [SMILES: COc1cccc2c(-c3ccc(CCS(C)(=N)=O)cc3)ncnc12] | imino({2-[4-(8-methoxyquinazolin-4-yl)phenyl]ethyl})methyl-$\lambda^6$-sulfanone |

TABLE 1-continued

| Compound No. | Structure | Name |
| --- | --- | --- |
| 155 | 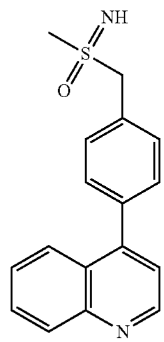 [SMILES: CS(=N)(=O)Cc1ccc(-c2ccnc3ccccc23)cc1] | imino(methyl){[4-(quinolin-4-yl)phenyl]methyl}-$\lambda^6$-sulfanone |
| 156 | 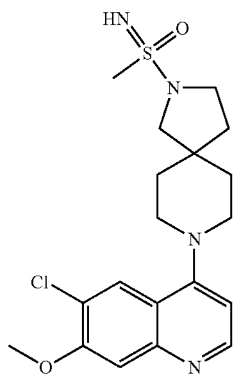 [SMILES: COc1cc2nccc(N3CCC4(CC3)CCN(S(C)(=N)=O)C4)c2cc1Cl] | [8-(6-chloro-7-methoxyquinolin-4-yl)-2,8-diazaspiro[4.5]decan-2-yl](imino)methyl-$\lambda^6$-sulfanone |
| 156S | 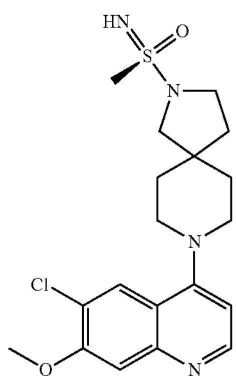 [SMILES: COc1cc2nccc(N3CCC4(CC3)CCN([S@](C)(=N)=O)C4)c2cc1Cl] | (S)-[8-(6-chloro-7-methoxyquinolin-4-yl)-2,8-diazaspiro[4.5]decan-2-yl](imino)methyl-λ6-sulfanone |
| 156R | 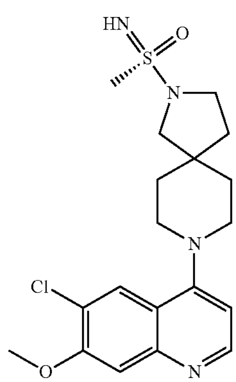 [SMILES: COc1cc2nccc(N3CCC4(CC3)CCN([S@@](C)(=N)=O)C4)c2cc1Cl] | (R)-[8-(6-chloro-7-methoxyquinolin-4-yl)-2,8-diazaspiro[4.5]decan-2-yl](imino)methyl-λ6-sulfanone |

TABLE 1-continued

| Compound No. | Structure | Name |
|---|---|---|
| 157 | 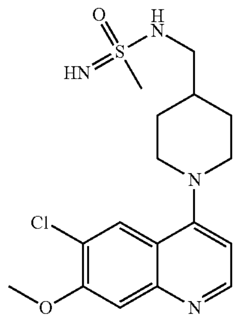 [SMILES: COc1cc2nccc(N3CCC(CNS(C)(=N)=O)CC3)c2cc1Cl] | N-{[1-(6-chloro-7-methoxyquinolin-4-yl)piperidin-4-yl]methyl}methanesulfonoimidamide |
| 158 | 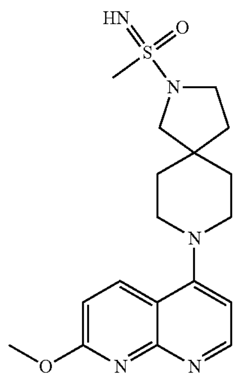 [SMILES: COc1ccc2c(N3CCC4(CC3)CCN(S(C)(=N)=O)C4)ccnc2n1] | imino[8-(7-methoxy-1,8-naphthyridin-4-yl)-2,8-diazaspiro[4.5]decan-2-yl]methyl-$\lambda^6$-sulfanone |
| 159 | 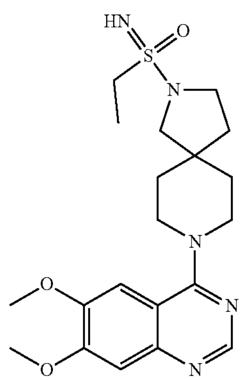 [SMILES: CCS(=N)(=O)N1CCC2(CCN(c3ncnc4cc(OC)c(OC)cc34)CC2)C1] | [8-(6,7-dimethoxyquinazolin-4-yl)-2,8-diazaspiro[4.5]decan-2-yl](ethyl)imino-$\lambda^6$-sulfanone |
| 160 | 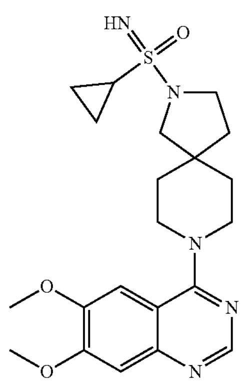 [SMILES: COc1cc2ncnc(N3CCC4(CC3)CCN(S(=N)(=O)C3CC3)C4)c2cc1OC] | {cyclopropyl[8-(6,7-dimethoxyquinazolin-4-yl)-2,8-diazaspiro[4.5]decan-2-yl]imino-$\lambda^6$-sulfanyl}one |

TABLE 1-continued

| Compound No. | Structure | Name |
| --- | --- | --- |
| 160R | 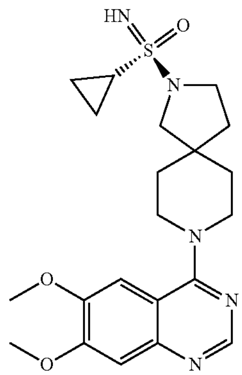 [SMILES: COc1cc2ncnc(N3CCC4(CC3)CCN([S@@](=N)(=O)C3CC3)C4)c2cc1OC] | (R)-{cyclopropyl[8-(6,7-dimethoxyquinazolin-4-yl)-2,8-diazaspiro[4.5]decan-2-yl]imino-$\lambda^6$-sulfanyl}one |
| 160S | 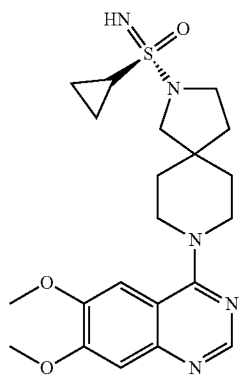 [SMILES: COc1cc2ncnc(N3CCC4(CC3)CCN([S@](=N)(=O)C3CC3)C4)c2cc1OC] | (S)-{cyclopropyl[8-(6,7-dimethoxyquinazolin-4-yl)-2,8-diazaspiro[4.5]decan-2-yl]imino-$\lambda^6$-sulfanyl}one |
| 161 | 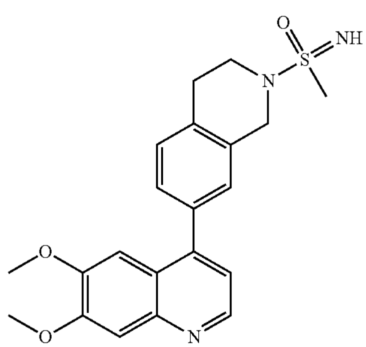 [SMILES: COc1cc2nccc(-c3ccc4c(c3)CN(S(C)(=N)=O)CC4)c2cc1OC] | [7-(6,7-dimethoxyquinolin-4-yl)-1,2,3,4-tetrahydroisoquinolin-2-yl](imino)methyl-$\lambda^6$-sulfanone |
| 161S | 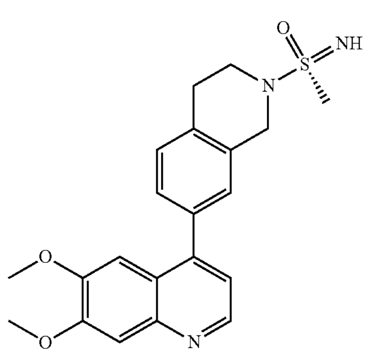 [SMILES: COc1cc2nccc(-c3ccc4c(c3)CN([S@](C)(=N)=O)CC4)c2cc1OC] | (S)-[7-(6,7-dimethoxyquinolin-4-yl)-1,2,3,4-tetrahydroisoquinolin-2-yl](imino)methyl-$\lambda$6-sulfanone |

TABLE 1-continued

| Compound No. | Structure | Name |
| --- | --- | --- |
| 161R | 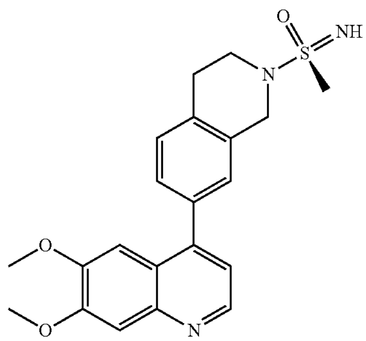 [SMILES: COc1cc2nccc(-c3ccc4c(c3)CN([S@@](C)(=N)=O)CC4)c2cc1OC] | (R)-[7-(6,7-dimethoxyquinolin-4-yl)-1,2,3,4-tetrahydroisoquinolin-2-yl](imino)methyl-$\lambda^6$-sulfanone |
| 162 | 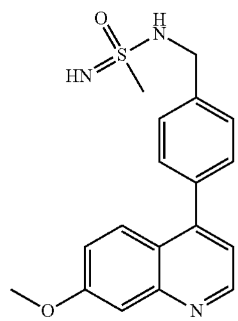 [SMILES: COc1ccc2c(-c3ccc(CNS(C)(=N)=O)cc3)ccnc2c1] | N-{[4-(7-methoxyquinolin-4-yl)phenyl]methyl}methanesulfonoimidamide |
| 163 | 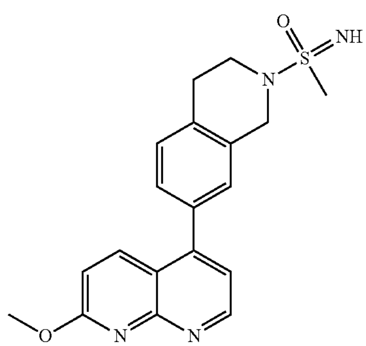 [SMILES: COc1ccc2c(-c3ccc4c(c3)CN(S(C)(=N)=O)CC4)ccnc2n1] | imino[7-(7-methoxy-1,8-naphthyridin-4-yl)-1,2,3,4-tetrahydroisoquinolin-2-yl]methyl-$\lambda^6$-sulfanone |
| 164 | 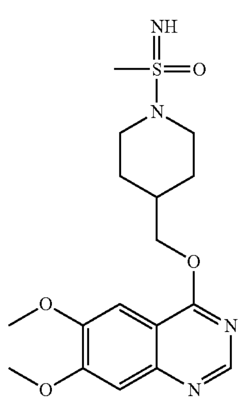 [SMILES: COc1cc2ncnc(OCC3CCN(S(C)(=N)=O)CC3)c2cc1OC] | (4-{[(6,7-dimethoxyquinazolin-4-yl)oxy]methyl}piperidin-1-yl)(imino)methyl-$\lambda^6$-sulfanone |

TABLE 1-continued

| Compound No. | Structure | Name |
| --- | --- | --- |
| 165 | 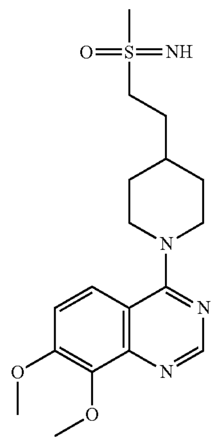 [SMILES: COc1ccc2c(N3CCC(CCS(C)(=N)=O)CC3)ncnc2c1OC] | (2-(1-(7,8-dimethoxyquinazolin-4-yl)piperidin-4-yl)ethyl)(imino)(methyl)-l6-sulfanone |
| 166 | 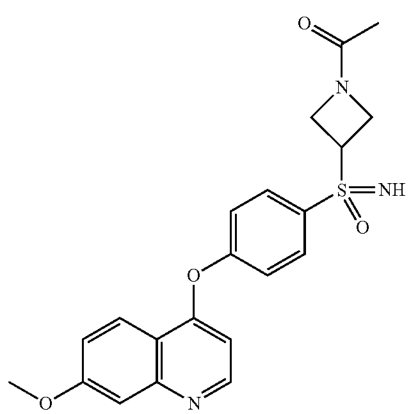 [SMILES: COc1ccc2c(Oc3ccc(S(=N)(=O)C4CN(C(C)=O)C4)cc3)ccnc2c1] | 1-[3-({4-[(7-methoxyquinolin-4-yl)oxy]phenyl}imino-$\lambda^6$-sulfanyl)azetidin-1-yl]ethan-1-one |
| 167 | 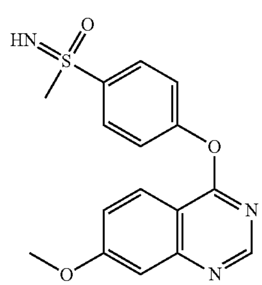 [SMILES: COc1ccc2c(Oc3ccc(S(C)(=N)=O)cc3)ncnc2c1] | imino({4-[(7-methoxyquinazolin-4-yl)oxy]phenyl})methyl-$\lambda^6$-sulfanone |
| 168 | 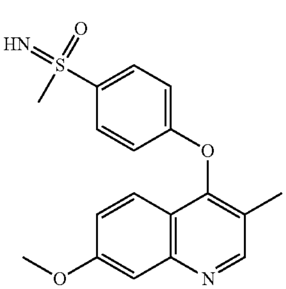 | imino({4-[(7-methoxy-3-methylquinolin-4-yl)oxy]phenyl})methyl-$\lambda^6$-sulfanone |

TABLE 1-continued

| Compound No. | Structure | Name |
|---|---|---|
| 169 | 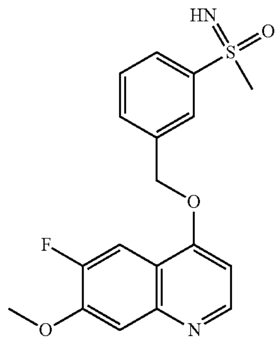 [SMILES: COc1cc2nccc(OCc3cccc(S(C)(=N)=O)c3)c2cc1F] | (3-{[(6-fluoro-7-methoxyquinolin-4-yl)oxy]methyl}phenyl)(imino)methyl-$\lambda^6$-sulfanone |
| 169R | 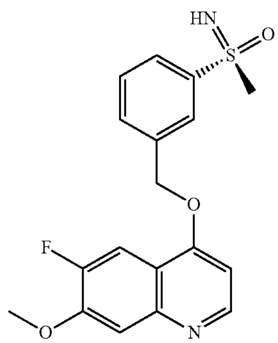 [SMILES: COc1cc2nccc(OCc3cccc([S@](C)(=N)=O)c3)c2cc1F] | (R)-(3-{[(6-fluoro-7-methoxyquinolin-4-yl)oxy]methyl}phenyl)(imino)methyl-$\lambda^6$-sulfanone |
| 169S | 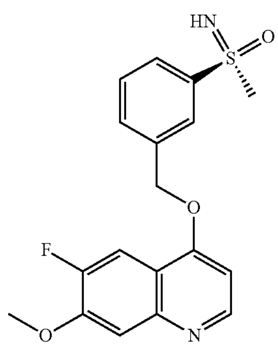 [SMILES: COc1cc2nccc(OCc3cccc([S@@](C)(=N)=O)c3)c2cc1F] | (S)-(3-{[(6-fluoro-7-methoxyquinolin-4-yl)oxy]methyl}phenyl)(imino)methyl-$\lambda^6$-sulfanone |
| 170 | 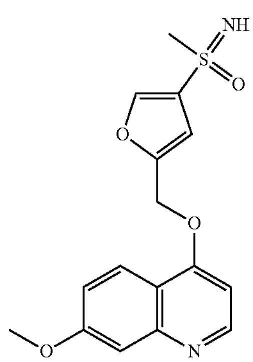 [SMILES: COc1ccc2c(OCc3cc(S(C)(=N)=O)co3)ccnc2c1] | imino(5-{[(7-methoxyquinolin-4-yl)oxy]methyl}furan-3-yl)methyl-$\lambda^6$-sulfanone |

TABLE 1-continued

| Compound No. | Structure | Name |
|---|---|---|
| 171 | 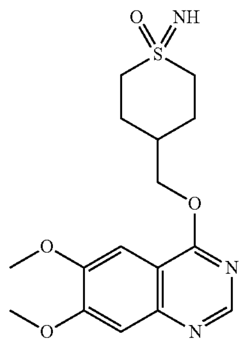 [SMILES: COc1cc2ncnc(OCC3CCS(=N)(=O)CC3)c2cc1OC] | 4-{[(6,7-dimethoxyquinazolin-4-yl)oxy]methyl}-1-imino-1λ⁶-thian-1-one |
| 172 | 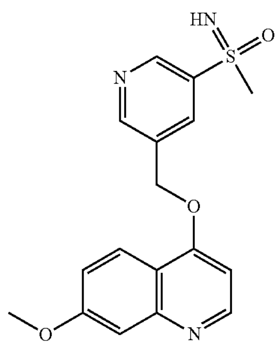 [SMILES: COc1ccc2c(OCc3cncc(S(C)(=N)=O)c3)ccnc2c1] | imino(5-{[(7-methoxyquinolin-4-yl)oxy]methyl}pyridin-3-yl)methyl-λ⁶-sulfanone |
| 173 | 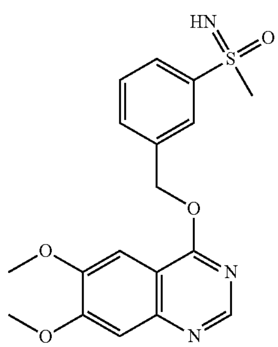 [SMILES: COc1cc2ncnc(OCc3cccc(S(C)(=N)=O)c3)c2cc1OC] | (3-{[(6,7-dimethoxyquinazolin-4-yl)oxy]methyl}phenyl)(imino)methyl-λ⁶-sulfanone |
| 174 | 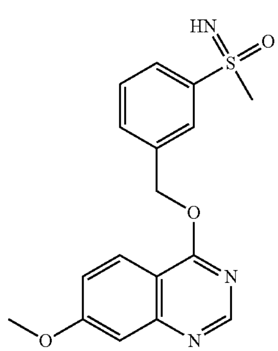 [SMILES: COc1ccc2c(OCc3cccc(S(C)(=N)=O)c3)ncnc2c1] | imino(3-{[(7-methoxyquinazolin-4-yl)oxy]methyl}phenyl)methyl-λ⁶-sulfanone |

TABLE 1-continued

| Compound No. | Structure | Name |
|---|---|---|
| 175 | 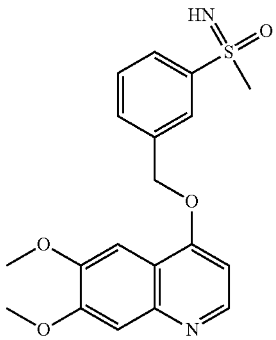 [SMILES: COc1cc2nccc(OCc3cccc(S(C)(=N)=O)c3)c2cc1OC] | (3-{[(6,7-dimethoxyquinolin-4-yl)oxy]methyl}phenyl)(imino)methyl-$\lambda^6$-sulfanone |
| 175R | 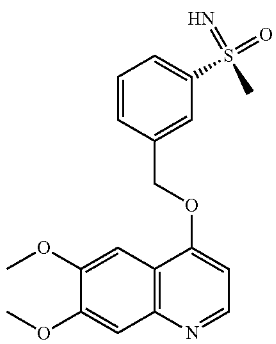 [SMILES: COc1cc2nccc(OCc3cccc([S@](C)(=N)=O)c3)c2cc1OC] | (R)-(3-{[(6,7-dimethoxyquinolin-4-yl)oxy]methyl}phenyl)(imino)methyl-$\lambda^6$-sulfanone |
| 175S | 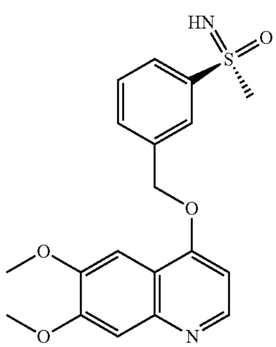 [SMILES: COc1cc2nccc(OCc3cccc([S@@](C)(=N)=O)c3)c2cc1OC] | (S)-(3-{[(6,7-dimethoxyquinolin-4-yl)oxy]methyl}phenyl)(imino)methyl-$\lambda^6$-sulfanone |
| 176 | 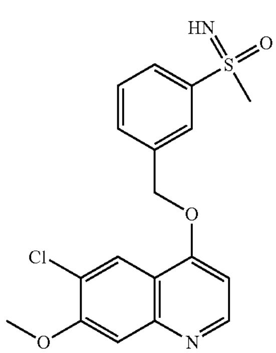 [SMILES: COc1cc2nccc(OCc3cccc(S(C)(=N)=O)c3)c2cc1Cl] | (3-{[(6-chloro-7-methoxyquinolin-4-yl)oxy]methyl}phenyl)(imino)methyl-$\lambda^6$-sulfanone |

TABLE 1-continued

| Compound No. | Structure | Name |
| --- | --- | --- |
| 177 | 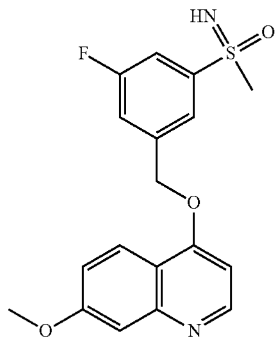 [SMILES: COc1ccc2c(OCc3cc(F)cc(S(C)(=N)=O)c3)ccnc2c1] | (3-fluoro-5-{[(7-methoxyquinolin-4-yl)oxy]methyl}phenyl)(imino)methyl-$\lambda^6$-sulfanone |
| 177R | 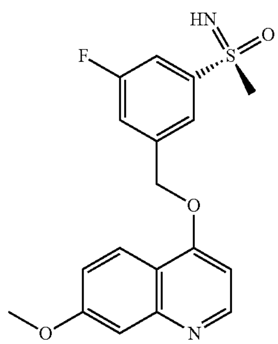 [SMILES: COc1ccc2c(OCc3cc(F)cc([S@](C)(=N)=O)c3)ccnc2c1] | (R)-(3-fluoro-5-{[(7-methoxyquinolin-4-yl)oxy]methyl}phenyl)(imino)methyl-$\lambda^6$-sulfanone |
| 177S | 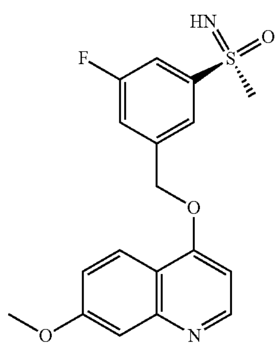 [SMILES: COc1ccc2c(OCc3cc(F)cc([S@@](C)(=N)=O)c3)ccnc2c1] | (S)-(3-fluoro-5-{[(7-methoxyquinolin-4-yl)oxy]methyl}phenyl)(imino)methyl-$\lambda^6$-sulfanone |
| 178 | 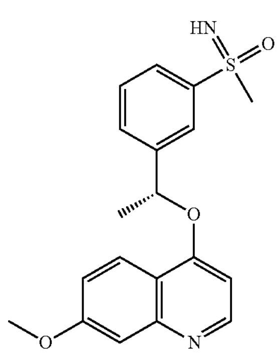 [SMILES: COc1ccc2c(O[C@H](C)c3cccc(S(C)(=N)=O)c3)ccnc2c1] | imino({3-[(1R)-1-[(7-methoxyquinolin-4-yl)oxy]ethyl]phenyl})methyl-$\lambda^6$-sulfanone |

TABLE 1-continued

| Compound No. | Structure | Name |
|---|---|---|
| 178R | 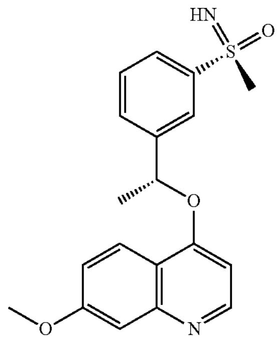 [SMILES: COc1ccc2c(O[C@H](C)c3cccc([S@](C)(=N)=O)c3)ccnc2c1] | (R)-imino({3-[(1R)-1-[(7-methoxyquinolin-4-yl)oxy]ethyl]phenyl})methyl-$\lambda^6$-sulfanone |
| 178S | 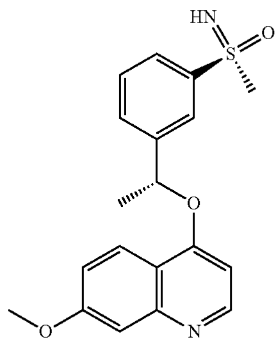 [SMILES: COc1ccc2c(O[C@H](C)c3cccc([S@@](C)(=N)=O)c3)ccnc2c1] | (S)-imino({3-[(1R)-1-[(7-methoxyquinolin-4-yl)oxy]ethyl]phenyl})methyl-$\lambda^6$-sulfanone |
| 179 | 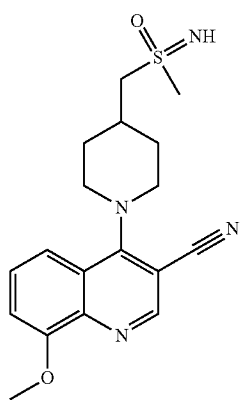 [SMILES: COc1cccc2c(N3CCC(CS(C)(=N)=O)CC3)c(C#N)cnc12] | 4-(4-{[imino(methyl)oxo-$\lambda^6$-sulfanyl]methyl}piperidin-1-yl)-8-methoxyquinoline-3-carbonitrile |
| 179R | 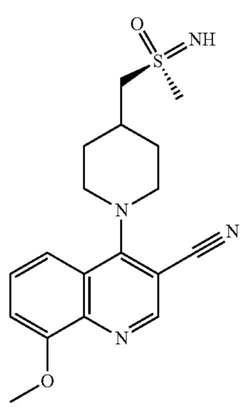 [SMILES: COc1cccc2c(N3CCC(C[S@](C)(=N)=O)CC3)c(C#N)cnc12] | (R)-4-(4-{[imino(methyl)oxo-$\lambda^6$-sulfanyl]methyl}piperidin-1-yl)-8-methoxyquinoline-3-carbonitrile |

TABLE 1-continued

| Compound No. | Structure | Name |
|---|---|---|
| 179S | 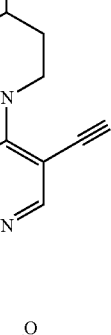 | (S)-4-(4-{[imino(methyl)oxo-$\lambda^6$-sulfanyl]methyl}piperidin-1-yl)-8-methoxyquinoline-3-carbonitrile |
| 180 | 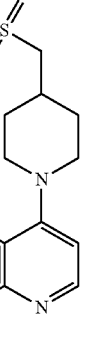 | imino({[1-(8-methoxyquinolin-4-yl)piperidin-4-yl]methyl})methyl-$\lambda^6$-sulfanone |
| 181 | 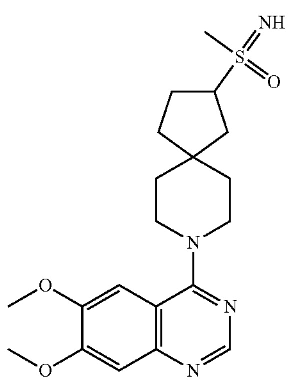 [SMILES: COc1cc2ncnc(N3CCC4(CCC(S(C)(=N)=O)C4)CC3)c2cc1OC] | [8-(6,7-dimethoxyquinazolin-4-yl)-8-azaspiro[4.5]decan-2-yl](imino)methyl-$\lambda^6$-sulfanone |
| 182 | 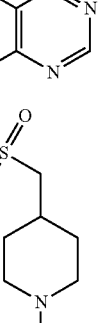 | imino({[1-(8-methoxycinnolin-4-yl)piperidin-4-yl]methyl})methyl-$\lambda^6$-sulfanone |

TABLE 1-continued

| Compound No. | Structure | Name |
|---|---|---|
| 183 | 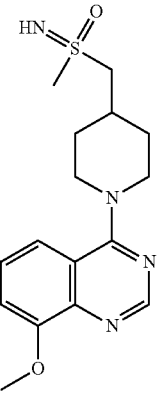 | {[1-(6-fluoro-8-methoxyquinazolin-4-yl)piperidin-4-yl]methyl}(imino)methyl-$\lambda^6$-sulfanone |
| 183R | 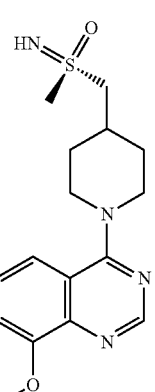 | (R)-{[1-(6-fluoro-8-methoxyquinazolin-4-yl)piperidin-4-yl]methyl}(imino)methyl-$\lambda^6$-sulfanone |
| 183S | 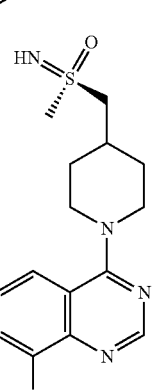 | (S)-{[1-(6-fluoro-8-methoxyquinazolin-4-yl)piperidin-4-yl]methyl}(imino)methyl-$\lambda^6$-sulfanone |
| 184 | 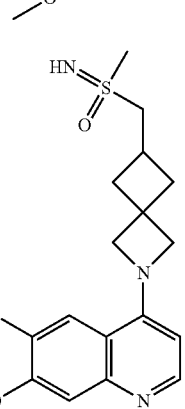 | {[2-(6-fluoro-7-methoxyquinolin-4-yl)-2-azaspiro[3.3]heptan-6-yl]methyl}(imino)methyl-$\lambda^6$-sulfanone |

TABLE 1-continued

| Compound No. | Structure | Name |
|---|---|---|
| 184R | 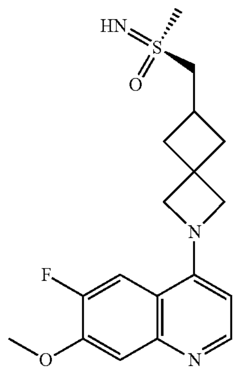 [SMILES: COc1cc2nccc(N3CC4(CC(C[S@](C)(=N)=O)C4)C3)c2cc1F] | (R)-{[2-(6-fluoro-7-methoxyquinolin-4-yl)-2-azaspiro[3.3]heptan-6-yl]methyl}(imino)methyl-$\lambda^6$-sulfanone |
| 184S | 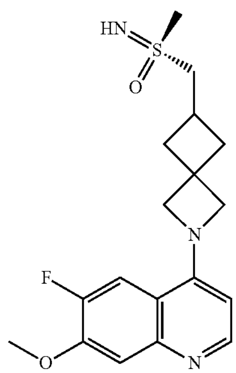 [SMILES: COc1cc2nccc(N3CC4(CC(C[S@@](C)(=N)=O)C4)C3)c2cc1F] | (S)-{[2-(6-fluoro-7-methoxyquinolin-4-yl)-2-azaspiro[3.3]heptan-6-yl]methyl}(imino)methyl-$\lambda^6$-sulfanone |
| 185 | 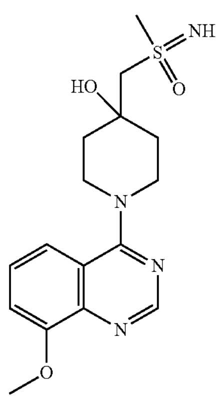 [SMILES: COc1cccc2c(N3CCC(O)(CS(C)(=N)=O)CC3)ncnc12] | {[4-hydroxy-1-(8-methoxyquinazolin-4-yl)piperidin-4-yl]methyl}(imino)methyl-$\lambda^6$-sulfanone |
| 185R | 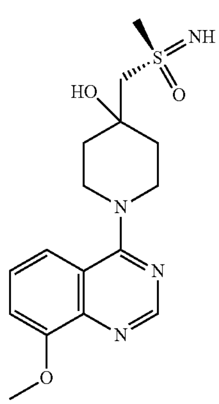 [SMILES: COc1cccc2c(N3CCC(O)(C[S@](C)(=N)=O)CC3)ncnc12] | (R)-{[4-hydroxy-1-(8-methoxyquinazolin-4-yl)piperidin-4-yl]methyl}(imino)methyl-$\lambda^6$-sulfanone |

TABLE 1-continued

| Compound No. | Structure | Name |
| --- | --- | --- |
| 185S | 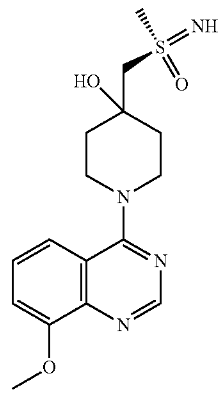 [SMILES: COc1cccc2c(N3CCC(O)(C[S@@](C)(=N)=O)CC3)ncnc12] | (S)-{[4-hydroxy-1-(8-methoxyquinazolin-4-yl)piperidin-4-yl]methyl}(imino)methyl-$\lambda^6$-sulfanone |
| 186 | 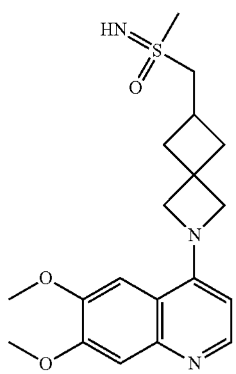 [SMILES: COc1cc2nccc(N3CC4(CC(CS(C)(=N)=O)C4)C3)c2cc1OC] | {[2-(6,7-dimethoxyquinolin-4-yl)-2-azaspiro[3.3]heptan-6-yl]methyl}(imino)methyl-$\lambda^6$-sulfanone |
| 187 | 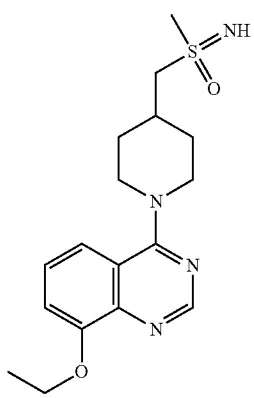 [SMILES: CCOc1cccc2c(N3CCC(CS(C)(=N)=O)CC3)ncnc12] | {[1-(8-ethoxyquinazolin-4-yl)piperidin-4-yl]methyl}(imino)methyl-$\lambda^6$-sulfanone |
| 188 | 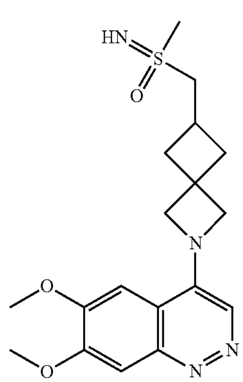 [SMILES: COc1cc2nncc(N3CC4(CC(CS(C)(=N)=O)C4)C3)c2cc1OC] | {[2-(6,7-dimethoxycinnolin-4-yl)-2-azaspiro[3.3]heptan-6-yl]methyl}(imino)methyl-$\lambda^6$-sulfanone |

TABLE 1-continued

| Compound No. | Structure | Name |
|---|---|---|
| 189 | 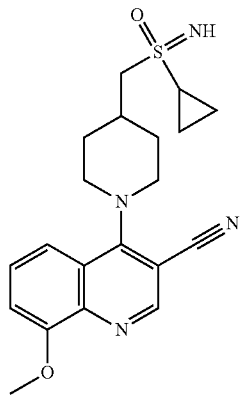 [SMILES: COc1cccc2c(N3CCC(CS(=N)(=O)C4CC4)CC3)c(C#N)cnc12] | 4-(4-{[cyclopropyl(imino)oxo-λ⁶-sulfanyl]methyl}piperidin-1-yl)-8-methoxyquinoline-3-carbonitrile |
| 189R | 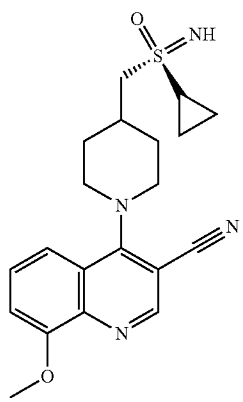 [SMILES: COc1cccc2c(N3CCC(C[S@@](=N)(=O)C4CC4)CC3)c(C#N)cnc12] | (R)-4-(4-{[cyclopropyl(imino)oxo-λ⁶-sulfanyl]methyl}piperidin-1-yl)-8-methoxyquinoline-3-carbonitrile |
| 189S | 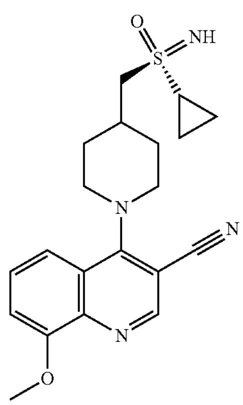 [SMILES: COc1cccc2c(N3CCC(C[S@](=N)(=O)C4CC4)CC3)c(C#N)cnc12] | (S)-4-(4-{[cyclopropyl(imino)oxo-λ⁶-sulfanyl]methyl}piperidin-1-yl)-8-methoxyquinoline-3-carbonitrile |
| 190 | 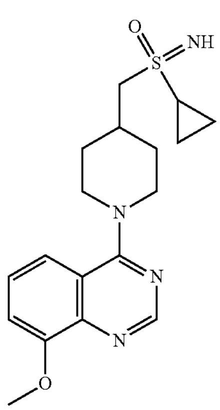 [SMILES: COc1cccc2c(N3CCC(CS(=N)(=O)C4CC4)CC3)ncnc12] | cyclopropyl(imino){[1-(8-methoxyquinazolin-4-yl)piperidin-4-yl]methyl}-λ⁶-sulfanone |

TABLE 1-continued

| Compound No. | Structure | Name |
|---|---|---|
| 191 | 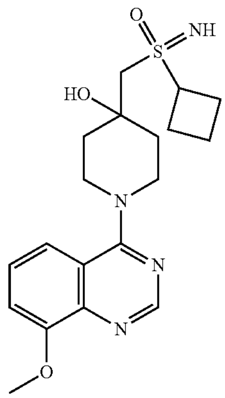 [SMILES: COc1cccc2c(N3CCC(O)(CS(=N)(=O)C4CCC4)CC3)ncnc12] | cyclobutyl(\{[4-hydroxy-1-(8-methoxyquinazolin-4-yl)piperidin-4-yl]methyl\})imino-$\lambda^6$-sulfanone |
| 192 | 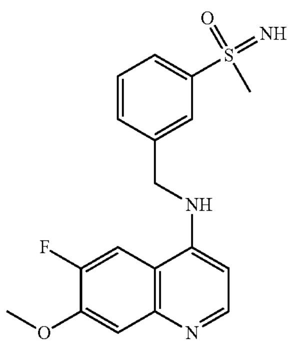 [SMILES: COc1cc2nccc(NCc3cccc(S(C)(=N)=O)c3)c2cc1F] | (3-\{[(6-fluoro-7-methoxyquinolin-4-yl)amino]methyl\}phenyl)(imino)methyl-$\lambda^6$-sulfanone |
| 193 | 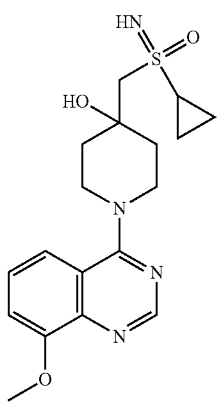 [SMILES: COc1cccc2c(N3CCC(O)(CS(=N)(=O)C4CC4)CC3)ncnc12] | cyclopropyl(\{[4-hydroxy-1-(8-methoxyquinazolin-4-yl)piperidin-4-yl]methyl\})imino-$\lambda^6$-sulfanone |
| 193R | 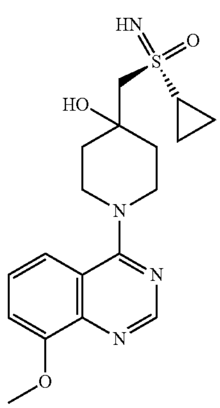 [SMILES: COc1cccc2c(N3CCC(O)(C[S@@](=N)(=O)C4CC4)CC3)ncnc12] | (R)-cyclopropyl(\{[4-hydroxy-1-(8-methoxyquinazolin-4-yl)piperidin-4-yl]methyl\})imino-$\lambda^6$-sulfanone |

TABLE 1-continued

| Compound No. | Structure | Name |
|---|---|---|
| 194S | 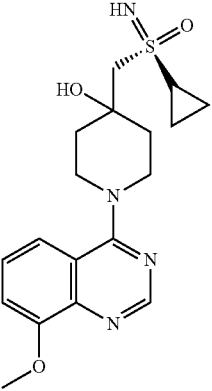 [SMILES: COc1cccc2c(N3CCC(O)(C[S@](=N)(=O)C4CC4)CC3)ncnc12] | (S)-cyclopropyl({[4-hydroxy-1-(8-methoxyquinazolin-4-yl)piperidin-4-yl]methyl})imino-$\lambda^6$-sulfanone |
| 194 | 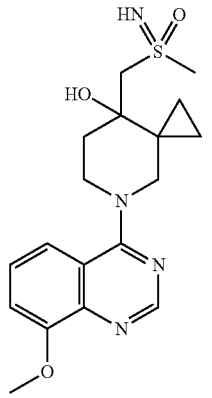 [SMILES: COc1cccc2c(N3CCC(O)(CS(C)(=N)=O)C4(CC4)C3)ncnc12] | {[8-hydroxy-5-(8-methoxyquinazolin-4-yl)-5-azaspiro[2.5]octan-8-yl]methyl}(imino)methyl-$\lambda^6$-sulfanone |
| 195 | 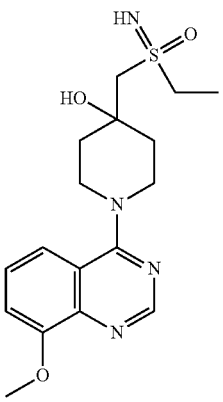 [SMILES: CCS(=N)(=O)CC1(O)CCN(c2ncnc3c(OC)cccc23)CC1] | ethyl({[4-hydroxy-1-(8-methoxyquinazolin-4-yl)piperidin-4-yl]methyl})imino-$\lambda^6$-sulfanone |
| 195R | 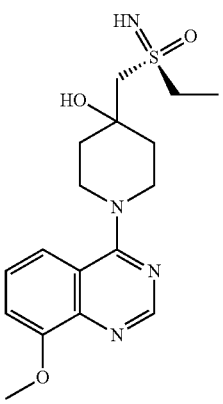 [SMILES: CC[S@@](=N)(=O)CC1(O)CCN(c2ncnc3c(OC)cccc23)CC1] | (R)-ethyl({[4-hydroxy-1-(8-methoxyquinazolin-4-yl)piperidin-4-yl]methyl})imino-$\lambda^6$-sulfanone |

TABLE 1-continued

| Compound No. | Structure | Name |
|---|---|---|
| 195S | 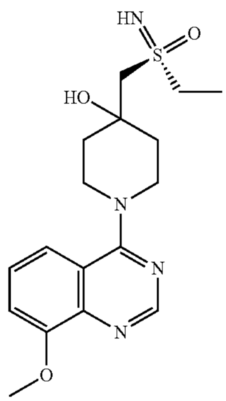 [SMILES: CC[S@](=N)(=O)CC1(O)CCN(c2ncnc3c(OC)cccc23)CC1] | (S)-ethyl({[4-hydroxy-1-(8-methoxyquinazolin-4-yl)piperidin-4-yl]methyl})imino-$\lambda^6$-sulfanone |
| 196 | 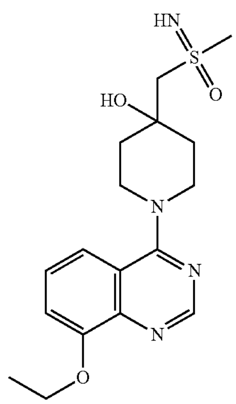 [SMILES: CCOc1cccc2c(N3CCC(O)(CS(C)(=N)=O)CC3)ncnc12] | {[1-(8-ethoxyquinazolin-4-yl)-4-hydroxypiperidin-4-yl]methyl}(imino)methyl-$\lambda^6$-sulfanone |
| 197 | 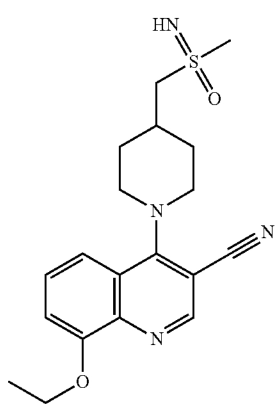 [SMILES: CCOc1cccc2c(N3CCC(CS(C)(=N)=O)CC3)c(C#N)cnc12] | 8-ethoxy-4-(4-{[imino(methyl)oxo-$\lambda^6$-sulfanyl]methyl}piperidin-1-yl)quinoline-3-carbonitrile |

TABLE 1-continued

| Compound No. | Structure | Name |
|---|---|---|
| 198 | 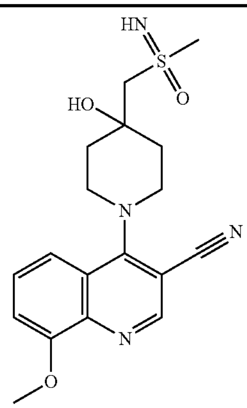 | 4-(4-hydroxy-4-{[imino(methyl)oxo-$\lambda^6$-sulfanyl]methyl}piperidin-1-yl)-8-methoxyquinoline-3-carbonitrile |
| 198R | 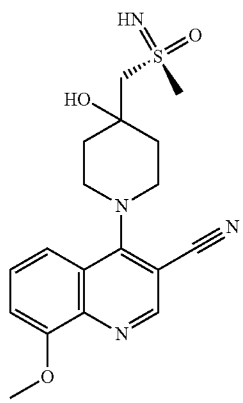 [SMILES: COc1cccc2c(N3CCC(O)(C[S@](C)(=N)=O)CC3)c(C#N)cnc12] | (R)-4-(4-hydroxy-4-{[imino(methyl)oxo-$\lambda^6$-sulfanyl]methyl}piperidin-1-yl)-8-methoxyquinoline-3-carbonitrile |
| 198S | 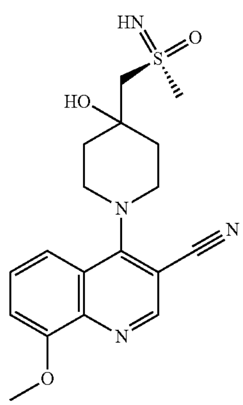 [SMILES: COc1cccc2c(N3CCC(O)(C[S@@](C)(=N)=O)CC3)c(C#N)cnc12] | (S)-4-(4-hydroxy-4-{[imino(methyl)oxo-$\lambda^6$-sulfanyl]methyl}piperidin-1-yl)-8-methoxyquinoline-3-carbonitrile |
| 199 | 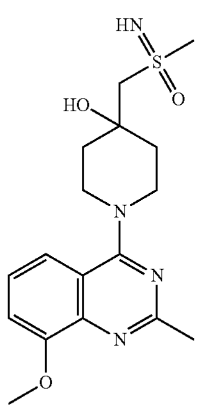 [SMILES: COc1cccc2c(N3CCC(O)(CS(C)(=N)=O)CC3)nc(C)nc12] | {[4-hydroxy-1-(8-methoxy-2-methylquinazolin-4-yl)piperidin-4-yl]methyl}(imino)methyl-$\lambda^6$-sulfanone |

| Compound No. | Structure | Name |
|---|---|---|
| 200 | 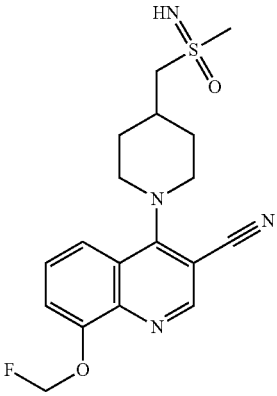 [SMILES: CS(=N)(=O)CC1CCN(c2c(C#N)cnc3c(OCF)cccc23)CC1] | 8-(fluoromethoxy)-4-(4-{[imino(methyl)oxo-λ⁶-sulfanyl]methyl}piperidin-1-yl)quinoline-3-carbonitrile |
| 201 | 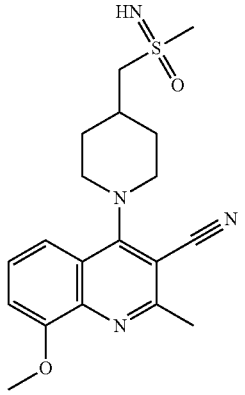 [SMILES: COc1cccc2c(N3CCC(CS(C)(=N)=O)CC3)c(C#N)c(C)nc12] | 4-(4-{[imino(methyl)oxo-λ⁶-sulfanyl]methyl}piperidin-1-yl)-8-methoxy-2-methylquinoline-3-carbonitrile |
| 202 | 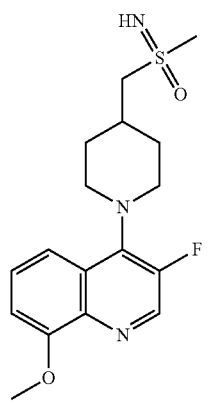 | {[1-(3-fluoro-8-methoxyquinolin-4-yl)piperidin-4-yl]methyl}(imino)methyl-λ⁶-sulfanone |

TABLE 1-continued

| Compound No. | Structure | Name |
| --- | --- | --- |
| 203 | 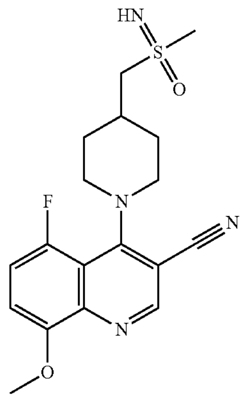 [SMILES: COc1ccc(F)c2c(N3CCC(CS(C)(=N)=O)CC3)c(C#N)cnc12] | 5-fluoro-4-(4-{[imino(methyl)oxo-$\lambda^6$-sulfanyl]methyl}piperidin-1-yl)-8-methoxyquinoline-3-carbonitrile |
| 204 | 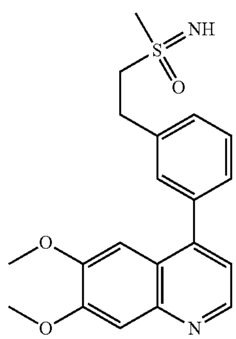 [SMILES: COc1cc2nccc(-c3cccc(CCS(C)(=N)=O)c3)c2cc1OC] | {2-[3-(6,7-dimethoxyquinolin-4-yl)phenyl]ethyl}(imino)methyl-$\lambda^6$-sulfanone |
| 205 | 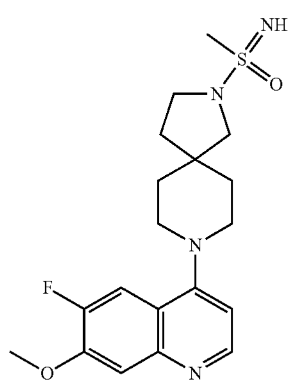 [SMILES: COc1cc2nccc(N3CCC4(CC3)CCN(S(C)(=N)=O)C4)c2cc1F] | [8-(6-fluoro-7-methoxyquinolin-4-yl)-2,8-diazaspiro[4.5]decan-2-yl](imino)methyl-$\lambda^6$-sulfanone |
| 205R | 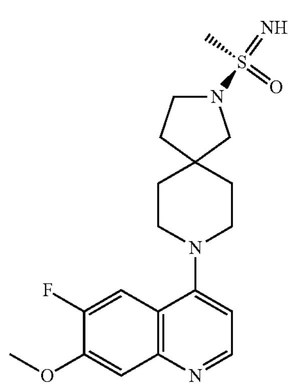 [SMILES: COc1cc2nccc(N3CCC4(CC3)CCN([S@@](C)(=N)=O)C4)c2cc1F] | (R)-[8-(6-fluoro-7-methoxyquinolin-4-yl)-2,8-diazaspiro[4.5]decan-2-yl](imino)methyl-$\lambda^6$-sulfanone |

TABLE 1-continued

| Compound No. | Structure | Name |
| --- | --- | --- |
| 205S | 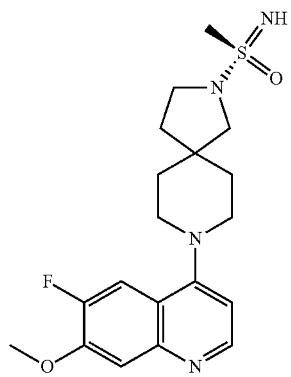 [SMILES: COc1cc2nccc(N3CCC4(CC3)CCN([S@](C)(=N)=O)C4)c2cc1F] | (S)-[8-(6-fluoro-7-methoxyquinolin-4-yl)-2,8-diazaspiro[4.5]decan-2-yl](imino)methyl-$\lambda^6$-sulfanone |
| 206 | 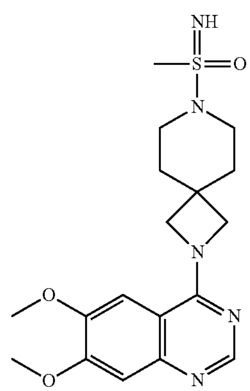 [SMILES: COc1cc2ncnc(N3CC4(CCN(S(C)(=N)=O)CC4)C3)c2cc1OC] | [2-(6,7-dimethoxyquinazolin-4-yl)-2,7-diazaspiro[3.5]nonan-7-yl](imino)methyl-$\lambda^6$-sulfanone |
| 207 | 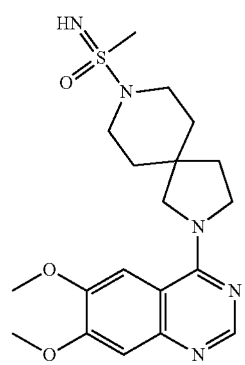 [SMILES: COc1cc2ncnc(N3CCC4(CCN(S(C)(=N)=O)CC4)C3)c2cc1OC] | [2-(6,7-dimethoxyquinazolin-4-yl)-2,8-diazaspiro[4.5]decan-8-yl](imino)methyl-$\lambda^6$-sulfanone |
| 208 | 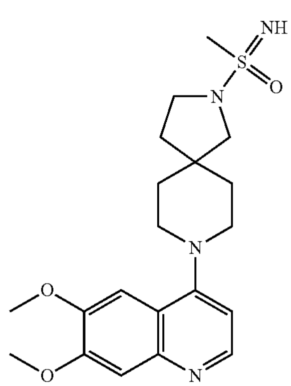 [SMILES: COc1cc2nccc(N3CCC4(CC3)CCN(S(C)(=N)=O)C4)c2cc1OC] | [8-(6,7-dimethoxyquinolin-4-yl)-2,8-diazaspiro[4.5]decan-2-yl](imino)methyl-$\lambda^6$-sulfanone |

TABLE 1-continued

| Compound No. | Structure | Name |
| --- | --- | --- |
| 208R | 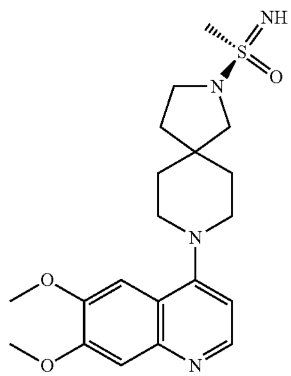 [SMILES: COc1cc2nccc(N3CCC4(CC3)CCN([S@@](C)(=N)=O)C4)c2cc1OC] | (R)-[8-(6,7-dimethoxyquinolin-4-yl)-2,8-diazaspiro[4.5]decan-2-yl](imino)methyl-$\lambda^6$-sulfanone |
| 208S | 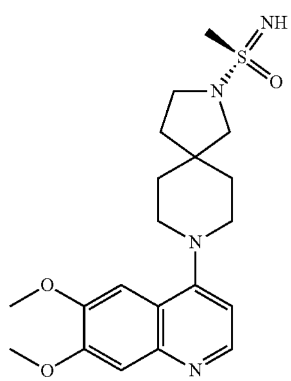 [SMILES: COc1cc2nccc(N3CCC4(CC3)CCN([S@](C)(=N)=O)C4)c2cc1OC] | (S)-[8-(6,7-dimethoxyquinolin-4-yl)-2,8-diazaspiro[4.5]decan-2-yl](imino)methyl-$\lambda^6$-sulfanone |
| 209 | 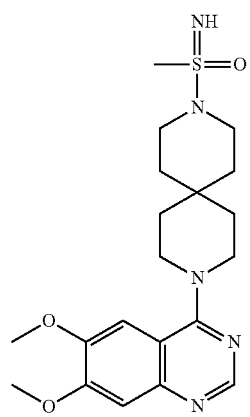 [SMILES: COc1cc2ncnc(N3CCC4(CC3)CCN(S(C)(=N)=O)CC4)c2cc1OC] | [9-(6,7-dimethoxyquinazolin-4-yl)-3,9-diazaspiro[5.5]undecan-3-yl](imino)methyl-$\lambda^6$-sulfanone |
| 210 | 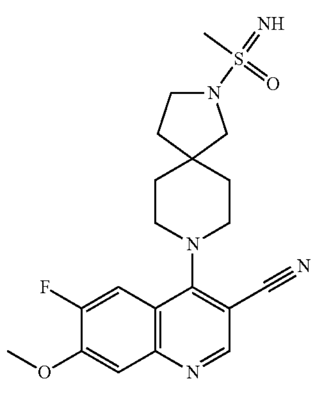 [SMILES: COc1cc2ncc(C#N)c(N3CCC4(CC3)CCN(S(C)(=N)=O)C4)c2cc1F] | 6-fluoro-4-{2-[imino(methyl)oxo-$\lambda^6$-sulfanyl]-2,8-diazaspiro[4.5]decan-8-yl}-7-methoxyquinoline-3-carbonitrile |

TABLE 1-continued

| Compound No. | Structure | Name |
|---|---|---|
| 211 | 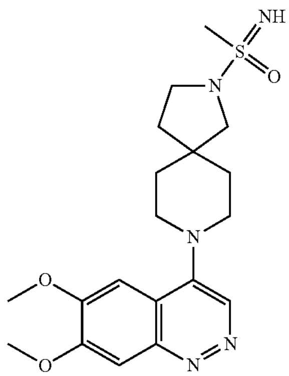 [SMILES: COc1cc2nncc(N3CCC4(CC3)CCN(S(C)(=N)=O)C4)c2cc1OC] | [8-(6,7-dimethoxycinnolin-4-yl)-2,8-diazaspiro[4.5]decan-2-yl](imino)methyl-λ⁶-sulfanone |
| 211R | 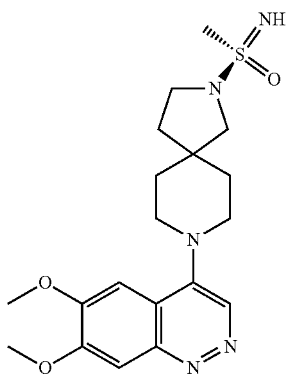 [SMILES: COc1cc2nncc(N3CCC4(CC3)CCN([S@@](C)(=N)=O)C4)c2cc1OC] | (R)-[8-(6,7-dimethoxycinnolin-4-yl)-2,8-diazaspiro[4.5]decan-2-yl](imino)methyl-λ⁶-sulfanone |
| 211S | 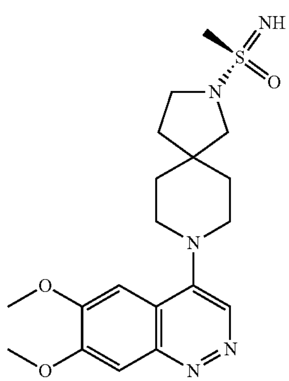 [SMILES: COc1cc2nncc(N3CCC4(CC3)CCN([S@](C)(=N)=O)C4)c2cc1OC] | (S)-[8-(6,7-dimethoxycinnolin-4-yl)-2,8-diazaspiro[4.5]decan-2-yl](imino)methyl-λ⁶-sulfanone |
| 212 | 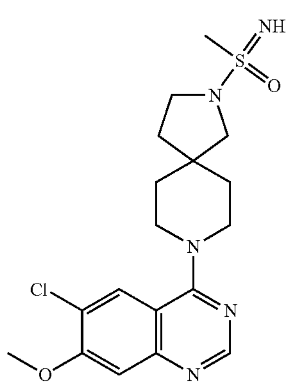 [SMILES: COc1cc2ncnc(N3CCC4(CC3)CCN(S(C)(=N)=O)C4)c2cc1Cl] | [8-(6-chloro-7-methoxyquinazolin-4-yl)-2,8-diazaspiro[4.5]decan-2-yl](imino)methyl-λ⁶-sulfanone |

TABLE 1-continued

| Compound No. | Structure | Name |
|---|---|---|
| 213 | 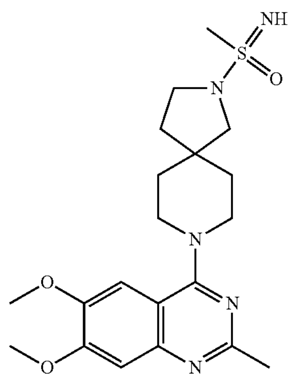 [SMILES: COc1cc2nc(C)nc(N3CCC4(CC3)CCN(S(C)(=N)=O)C4)c2cc1OC] | [8-(6,7-dimethoxy-2-methylquinazolin-4-yl)-2,8-diazaspiro[4.5]decan-2-yl](imino)methyl-$\lambda^6$-sulfanone |
| 214 | 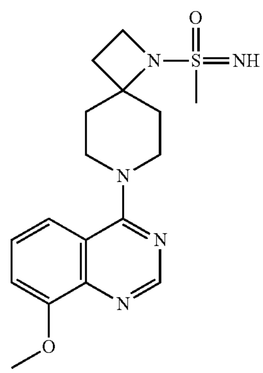 [SMILES: COc1cccc2c(N3CCC4(CC3)CCN4S(C)(=N)=O)ncnc12] | imino[7-(8-methoxyquinazolin-4-yl)-1,7-diazaspiro[3.5]nonan-1-yl]methyl-$\lambda^6$-sulfanone |
| 215 | 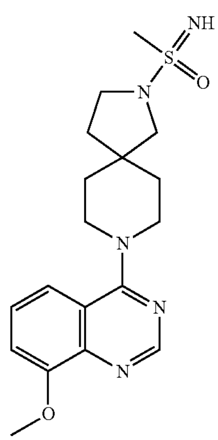 [SMILES: COc1cccc2c(N3CCC4(CC3)CCN(S(C)(=N)=O)C4)ncnc12] | imino[8-(8-methoxyquinazolin-4-yl)-2,8-diazaspiro[4.5]decan-2-yl]methyl-$\lambda^6$-sulfanone |
| 216 | 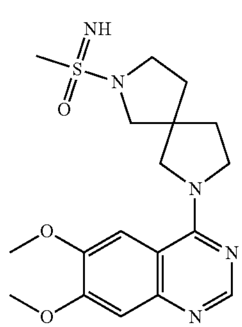 [SMILES: COc1cc2ncnc(N3CCC4(CCN(S(C)(=N)=O)C4)C3)c2cc1OC] | [7-(6,7-dimethoxyquinazolin-4-yl)-2,7-diazaspiro[4.4]nonan-2-yl](imino)methyl-$\lambda^6$-sulfanone |

TABLE 1-continued

| Compound No. | Structure | Name |
| --- | --- | --- |
| 217 | 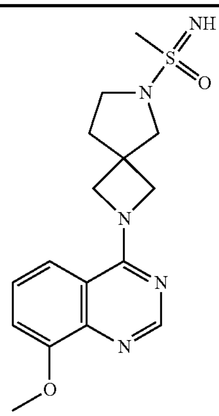 | imino[2-(8-methoxyquinazolin-4-yl)-2,6-diazaspiro[3.4]octan-6-yl]methyl-$\lambda^6$-sulfanone |
| 218 | 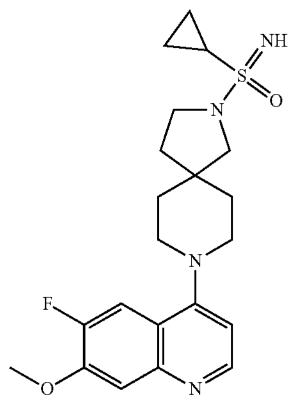 [SMILES: COc1cc2nccc(N3CCC4(CC3)CCN(S(=N)(=O)C3CC3)C4)c2cc1F] | {cyclopropyl[8-(6-fluoro-7-methoxyquinolin-4-yl)-2,8-diazaspiro[4.5]decan-2-yl]imino-$\lambda^6$-sulfanyl}one |
| 218R | 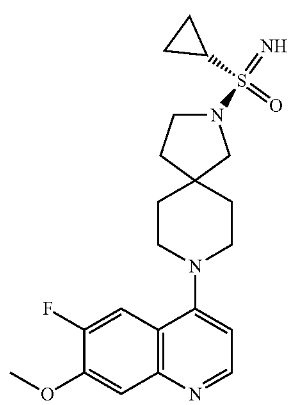 [SMILES: COc1cc2nccc(N3CCC4(CC3)CCN([S@@](=N)(=O)C3CC3)C4)c2cc1F] | (R)-{cyclopropyl[8-(6-fluoro-7-methoxyquinolin-4-yl)-2,8-diazaspiro[4.5]decan-2-yl]imino-$\lambda^6$-sulfanyl}one |
| 218S | 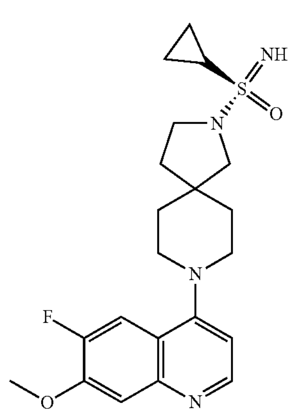 [SMILES: COc1cc2nccc(N3CCC4(CC3)CCN([S@](=N)(=O)C3CC3)C4)c2cc1F] | (S)-{cyclopropyl [8-(6-fluoro-7-methoxyquinolin-4-yl)-2,8-diazaspiro[4.5]decan-2-yl]imino-$\lambda^6$-sulfanyl}one |

TABLE 1-continued

| Compound No. | Structure | Name |
|---|---|---|
| 219 | 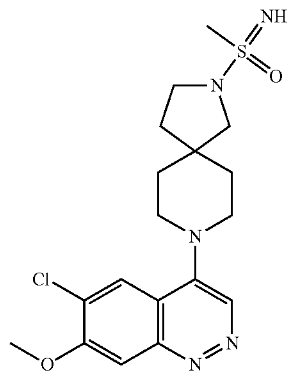 [SMILES: COc1cc2nncc(N3CCC4(CC3)CCN(S(C)(=N)=O)C4)c2cc1Cl] | [8-(6-chloro-7-methoxycinnolin-4-yl)-2,8-diazaspiro[4.5]decan-2-yl](imino)methyl-$\lambda^6$-sulfanone |
| 219R | 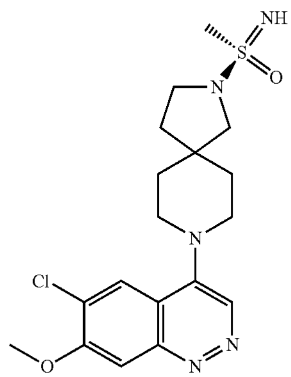 [SMILES: COc1cc2nncc(N3CCC4(CC3)CCN([S@@](C)(=N)=O)C4)c2cc1Cl] | (R)-[8-(6-chloro-7-methoxycinnolin-4-yl)-2,8-diazaspiro[4.5]decan-2-yl](imino)methyl-$\lambda^6$-sulfanone |
| 219S | 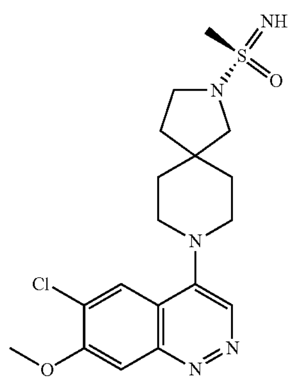 [SMILES: COc1cc2nncc(N3CCC4(CC3)CCN([S@](C)(=N)=O)C4)c2cc1Cl] | (S)-[8-(6-chloro-7-methoxycinnolin-4-yl)-2,8-diazaspiro[4.5]decan-2-yl](imino)methyl-$\lambda^6$-sulfanone |
| 220 | 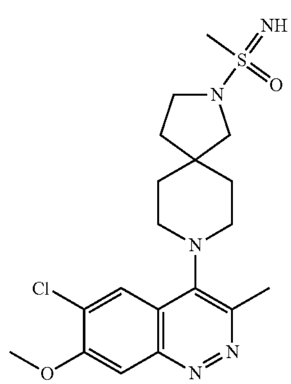 [SMILES: COc1cc2nnc(C)c(N3CCC4(CC3)CCN(S(C)(=N)=O)C4)c2cc1Cl] | [8-(6-chloro-7-methoxy-3-methylcinnolin-4-yl)-2,8-diazaspiro[4.5]decan-2-yl](imino)methyl-$\lambda^6$-sulfanone |

TABLE 1-continued

| Compound No. | Structure | Name |
|---|---|---|
| 221 | 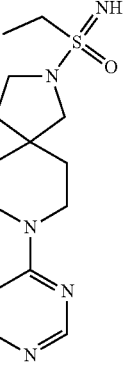 | ethyl[8-(6-fluoro-7-methoxyquinazolin-4-yl)-2,8-diazaspiro[4.5]decan-2-yl]imino-$\lambda^6$-sulfanone |
| 222 | 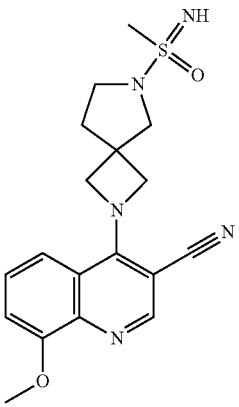 [SMILES: COc1cccc2c(N3CC4(CCN(S(C)(=N)=O)C4)C3)c(C#N)cnc12] | 4-{6-[imino(methyl)oxo-$\lambda^6$-sulfanyl]-2,6-diazaspiro[3.4]octan-2-yl}-8-methoxyquinoline-3-carbonitrile |
| 222R | 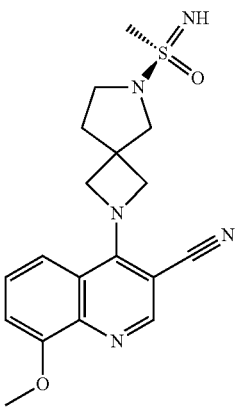 [SMILES: COc1cccc2c(N3CC4(CCN([S@@](C)(=N)=O)C4)C3)c(C#N)cnc12] | (R)-4-{6-[imino(methyl)oxo-$\lambda^6$-sulfanyl]-2,6-diazaspiro[3.4]octan-2-yl}-8-methoxyquinoline-3-carbonitrile |
| 222S | 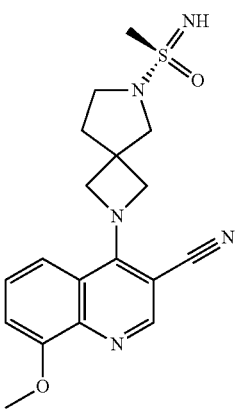 [SMILES: COc1cccc2c(N3CC4(CCN([S@](C)(=N)=O)C4)C3)c(C#N)cnc12] | (S)-4-{6-[imino(methyl)oxo-$\lambda^6$-sulfanyl]-2,6-diazaspiro[3.4]octan-2-yl}-8-methoxyquinoline-3-carbonitrile |

TABLE 1-continued

| Compound No. | Structure | Name |
|---|---|---|
| 223 | 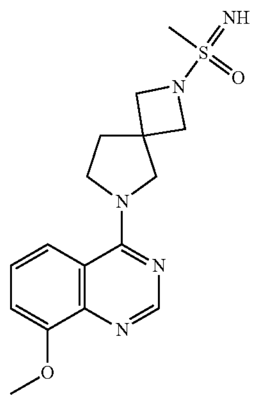 [SMILES: COc1cccc2c(N3CCC4(C3)CN(S(C)(=N)=O)C4)ncnc12] | imino[6-(8-methoxyquinazolin-4-yl)-2,6-diazaspiro[3.4]octan-2-yl]methyl-λ⁶-sulfanone |
| 223R | 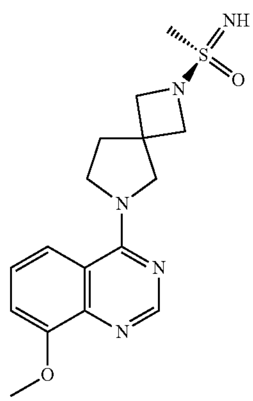 [SMILES: COc1cccc2c(N3CCC4(C3)CN([S@@](C)(=N)=O)C4)ncnc12] | (R)-imino[6-(8-methoxyquinazolin-4-yl)-2,6-diazaspiro[3.4]octan-2-yl]methyl-λ⁶-sulfanone |
| 223S | 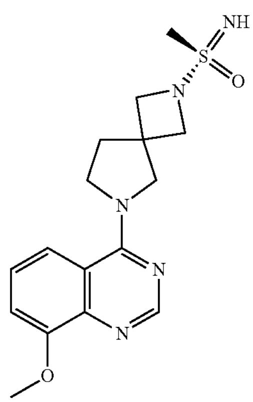 [SMILES: COc1cccc2c(N3CCC4(C3)CN([S@](C)(=N)=O)C4)ncnc12] | (S)-imino[6-(8-methoxyquinazolin-4-yl)-2,6-diazaspiro[3.4]octan-2-yl]methyl-λ⁶-sulfanone |
| 224 | 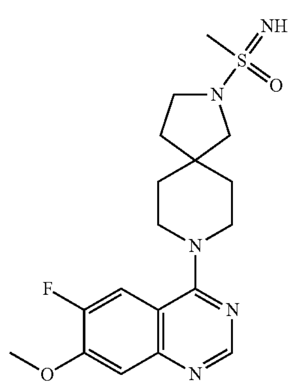 [SMILES: COc1cc2ncnc(N3CCC4(CC3)CCN(S(C)(=N)=O)C4)c2cc1F] | [8-(6-fluoro-7-methoxyquinazolin-4-yl)-2,8-diazaspiro[4.5]decan-2-yl](imino)methyl-λ⁶-sulfanone |

TABLE 1-continued

| Compound No. | Structure | Name |
|---|---|---|
| 225 | 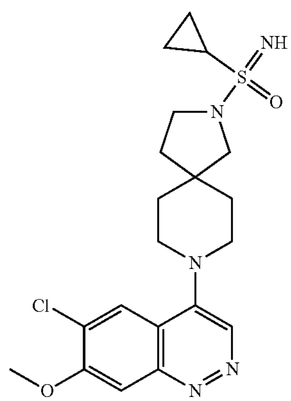 [SMILES: COc1cc2nncc(N3CCC4(CC3)CCN(S(=N)(=O)C3CC3)C4)c2cc1Cl] | {[8-(6-chloro-7-methoxycinnolin-4-yl)-2,8-diazaspiro[4.5]decan-2-yl](cyclopropyl)imino-λ⁶-sulfanyl}one |
| 226 | 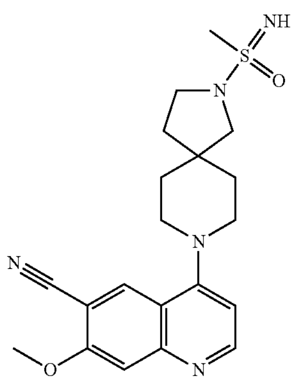 [SMILES: COc1cc2nccc(N3CCC4(CC3)CCN(S(C)(=N)=O)C4)c2cc1C#N] | 4-{2-[imino(methyl)oxo-λ⁶-sulfanyl]-2,8-diazaspiro[4.5]decan-8-yl}-7-methoxyquinoline-6-carbonitrile |
| 227 | 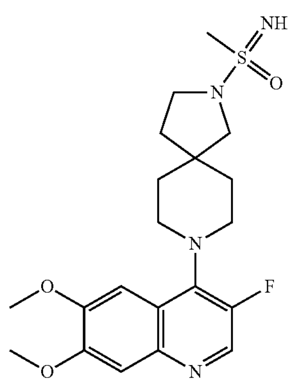 [SMILES: COc1cc2ncc(F)c(N3CCC4(CC3)CCN(S(C)(=N)=O)C4)c2cc1OC] | [8-(3-fluoro-6,7-dimethoxyquinolin-4-yl)-2,8-diazaspiro[4.5]decan-2-yl](imino)methyl-λ⁶-sulfanone |
| 228 | 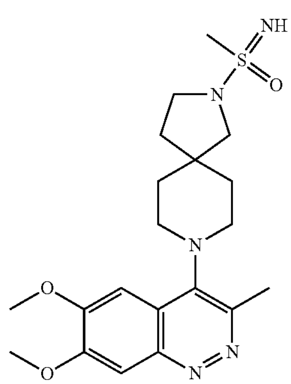 [SMILES: COc1cc2nnc(C)c(N3CCC4(CC3)CCN(S(C)(=N)=O)C4)c2cc1OC] | [8-(6,7-dimethoxy-3-methylcinnolin-4-yl)-2,8-diazaspiro[4.5]decan-2-yl](imino)methyl-λ⁶-sulfanone |

TABLE 1-continued

| Compound No. | Structure | Name |
|---|---|---|
| 229 | 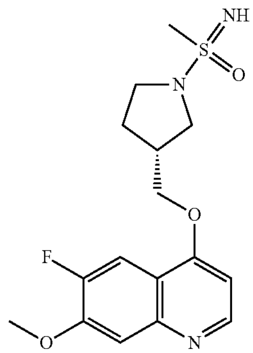 [SMILES: COc1cc2nccc(OC[C@@H]3CCN(S(C)(=N)=O)C3)c2cc1F] | [(3R)-3-{[(6-fluoro-7-methoxyquinolin-4-yl)oxy]methyl}pyrrolidin-1-yl](imino)methyl-$\lambda^6$-sulfanone |
| 229R | 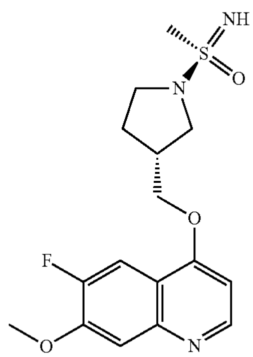 [SMILES: COc1cc2nccc(OC[C@@H]3CCN([S@@](C)(=N)=O)C3)c2cc1F] | (R)-[(3R)-3-{[(6-fluoro-7-methoxyquinolin-4-yl)oxy]methyl}pyrrolidin-1-yl](imino)methyl-$\lambda^6$-sulfanone |
| 229S | 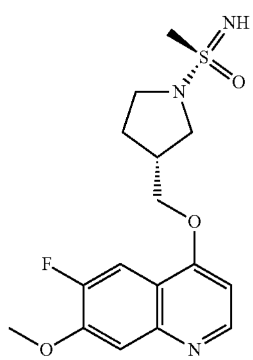 [SMILES: COc1cc2nccc(OC[C@@H]3CCN([S@](C)(=N)=O)C3)c2cc1F] | (S)-[(3R)-3-{[(6-fluoro-7-methoxyquinolin-4-yl)oxy]methyl}pyrrolidin-1-yl](imino)methyl-$\lambda^6$-sulfanone |
| 230 | 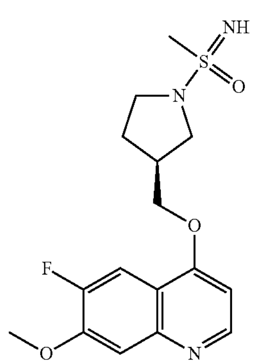 [SMILES: COc1cc2nccc(OC[C@H]3CCN(S(C)(=N)=O)C3)c2cc1F] | [(3S)-3-{[(6-fluoro-7-methoxyquinolin-4-yl)oxy]methyl}pyrrolidin-1-yl](imino)methyl-$\lambda^6$-sulfanone |

TABLE 1-continued

| Compound No. | Structure | Name |
|---|---|---|
| 230R | 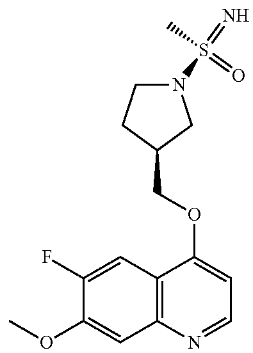 [SMILES: COc1cc2nccc(OC[C@H]3CCN([S@@](C)(=N)=O)C3)c2cc1F] | (R)-[(3S)-3-{[(6-fluoro-7-methoxyquinolin-4-yl)oxy]methyl}pyrrolidin-1-yl](imino)methyl-$\lambda^6$-sulfanone |
| 230S | 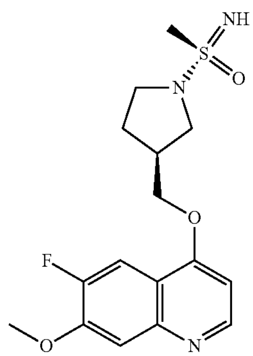 [SMILES: COc1cc2nccc(OC[C@H]3CCN([S@](C)(=N)=O)C3)c2cc1F] | (S)-[(3S)-3-{[(6-fluoro-7-methoxyquinolin-4-yl)oxy]methyl}pyrrolidin-1-yl](imino)methyl-$\lambda^6$-sulfanone |
| 231 | 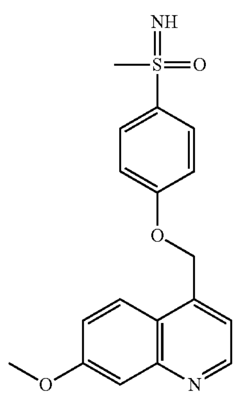 [SMILES: COc1ccc2c(COc3ccc(S(C)(=N)=O)cc3)ccnc2c1] | imino({4-[(7-methoxyquinolin-4-yl)methoxy]phenyl})methyl-$\lambda^6$-sulfanone |
| 232 | 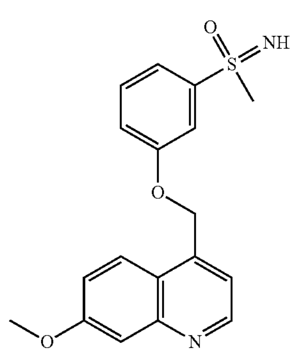 [SMILES: COc1ccc2c(COc3cccc(S(C)(=N)=O)c3)ccnc2c1] | imino({3-[(7-methoxyquinolin-4-yl)methoxy]phenyl})methyl-$\lambda^6$-sulfanone |

TABLE 1-continued
| Compound No. | Structure | Name |
| --- | --- | --- |
| 233 | 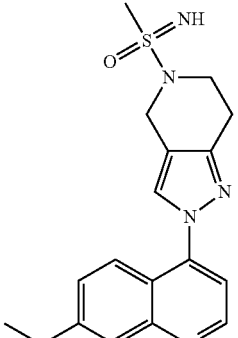 | imino[2-(7-methoxyquinolin-4-yl)-2H,4H,5H,6H,7H-pyrazolo[4,3-c]pyridin-5-yl]methyl-$\lambda^6$-sulfanone |
| 234 | 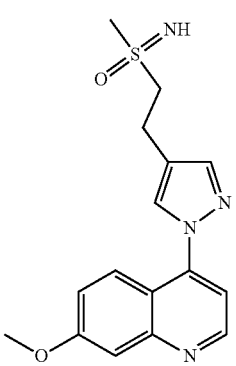 [SMILES: COc1ccc2c(-n3cc(CCS(C)(=N)=O)cn3)ccnc2c1] | imino({2-[1-(7-methoxyquinolin-4-yl)-1H-pyrazol-4-yl]ethyl})methyl-$\lambda^6$-sulfanone |
| 235 | 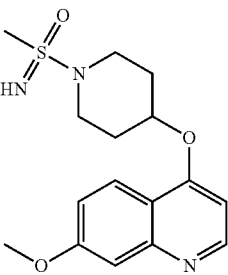 [SMILES: COc1ccc2c(OC3CCN(S(C)(=N)=O)CC3)ccnc2c1] | imino({4-[(7-methoxyquinolin-4-yl)oxy]piperidin-1-yl})methyl-$\lambda^6$-sulfanone |
| 236 | 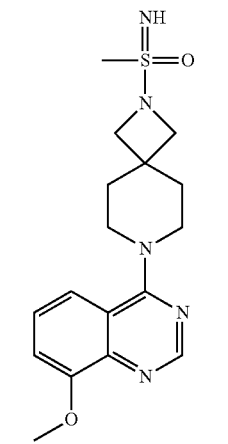 [SMILES: COc1cccc2c(N3CCC4(CC3)CN(S(C)(=N)=O)C4)ncnc12] | imino[7-(8-methoxyquinazolin-4-yl)-2,7-diazaspiro[3.5]nonan-2-yl]methyl-$\lambda^6$-sulfanone |

TABLE 1-continued

| Compound No. | Structure | Name |
|---|---|---|
| 237 | 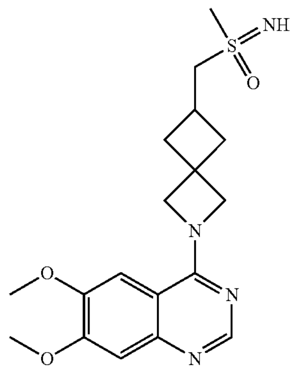 [SMILES: COc1cc2ncnc(N3CC4(CC(CS(C)(=N)=O)C4)C3)c2cc1OC] | {[2-(6,7-dimethoxyquinazolin-4-yl)-2-azaspiro[3.3]heptan-6-yl]methyl}(imino)methyl-$\lambda^6$-sulfanone |
| 237R | 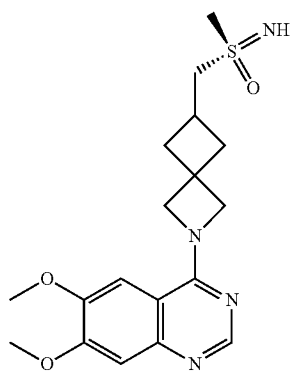 [SMILES: COc1cc2ncnc(N3CC4(CC(C[S@](C)(=N)=O)C4)C3)c2cc1OC] | (R)-{[2-(6,7-dimethoxyquinazolin-4-yl)-2-azaspiro[3.3]heptan-6-yl]methyl}(imino)methyl-$\lambda^6$-sulfanone |
| 237S | 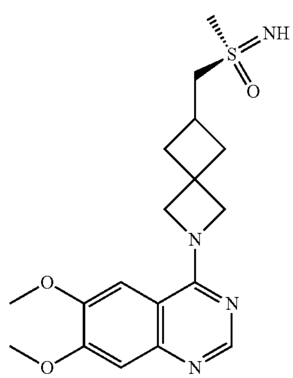 [SMILES: COc1cc2ncnc(N3CC4(CC(C[S@@](C)(=N)=O)C4)C3)c2cc1OC] | (S)-{[2-(6,7-dimethoxyquinazolin-4-yl)-2-azaspiro[3.3]heptan-6-yl]methyl}(imino)methyl-$\lambda^6$-sulfanone |
| 238 | 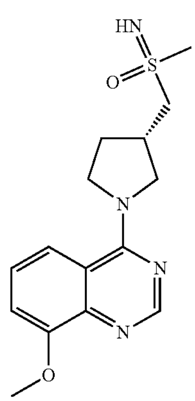 [SMILES: COc1cccc2c(N3CC[C@H](CS(C)(=N)=O)C3)ncnc12] | imino({[(3S)-1-(8-methoxyquinazolin-4-yl)pyrrolidin-3-yl]methyl})methyl-$\lambda^6$-sulfanone |

TABLE 1-continued

| Compound No. | Structure | Name |
|---|---|---|
| 238R | 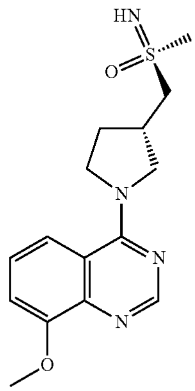 [SMILES: COc1cccc2c(N3CC[C@H](C[S@](C)(=N)=O)C3)ncnc12] | (R)-imino({[(3S)-1-(8-methoxyquinazolin-4-yl)pyrrolidin-3-yl]methyl})methyl-$\lambda^6$-sulfanone |
| 238S | 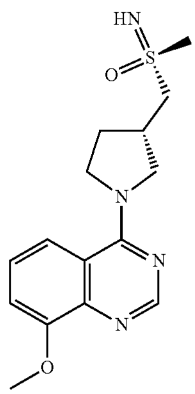 [SMILES: COc1cccc2c(N3CC[C@H](C[S@@](C)(=N)=O)C3)ncnc12] | (S)-imino({[(3S)-1-(8-methoxyquinazolin-4-yl)pyrrolidin-3-yl]methyl})methyl-$\lambda^6$-sulfanone |
| 239 | 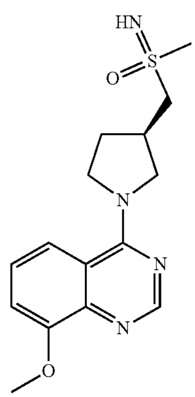 [SMILES: COc1cccc2c(N3CC[C@@H](CS(C)(=N)=O)C3)ncnc12] | imino({[(3R)-1-(8-methoxyquinazolin-4-yl)pyrrolidin-3-yl]methyl})methyl-$\lambda^6$-sulfanone |
| 239R | 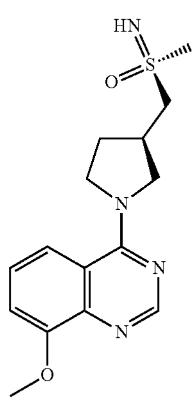 [SMILES: COc1cccc2c(N3CC[C@@H](C[S@](C)(=N)=O)C3)ncnc12] | (R)-imino({[(3R)-1-(8-methoxyquinazolin-4-yl)pyrrolidin-3-yl]methyl})methyl-$\lambda^6$-sulfanone |

TABLE 1-continued

| Compound No. | Structure | Name |
|---|---|---|
| 239S | 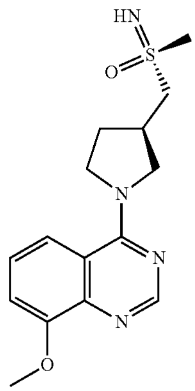 [SMILES: COc1cccc2c(N3CC[C@@H](C[S@@](C)(=N)=O)C3)ncnc12] | (S)-imino({[(3R)-1-(8-methoxyquinazolin-4-yl)pyrrolidin-3-yl]methyl})methyl-λ⁶-sulfanone |
| 240 | 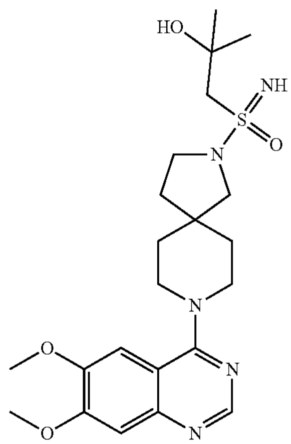 [SMILES: COc1cc2ncnc(N3CCC4(CC3)CCN(S(=N)(=O)CC(C)(C)O)C4)c2cc1OC] | [8-(6,7-dimethoxyquinazolin-4-yl)-2,8-diazaspiro[4.5]decan-2-yl](2-hydroxy-2-methylpropyl)imino-λ⁶-sulfanone |
| 241 | 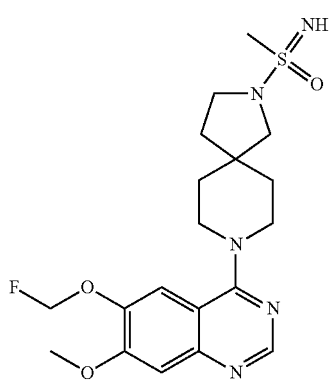 [SMILES: COc1cc2ncnc(N3CCC4(CC3)CCN(S(C)(=N)=O)C4)c2cc1OCF] | {8-[6-(fluoromethoxy)-7-methoxyquinazolin-4-yl]-2,8-diazaspiro[4.5]decan-2-yl}(imino)methyl-λ⁶-sulfanone |
| 242 | 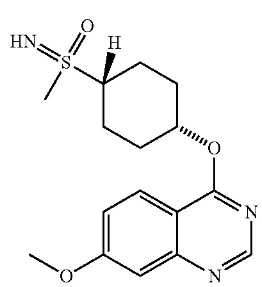 [SMILES: COc1ccc2c(O[C@H]3CC[C@@H](S(C)(=N)=O)CC3)ncnc2c1] | imino(methyl)[(1s,4s)-4-[(7-methoxyquinolin-4-yl)oxy]cyclohexyl]-λ⁶-sulfanone |

TABLE 1-continued

| Compound No. | Structure | Name |
|---|---|---|
| 243 | 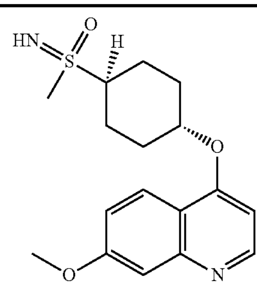 | imino(methyl)[(1r,4r)-4-[(7-methoxyquinolin-4-yl)oxy]cyclohexyl]-$\lambda^6$-sulfanone |
| 244 | 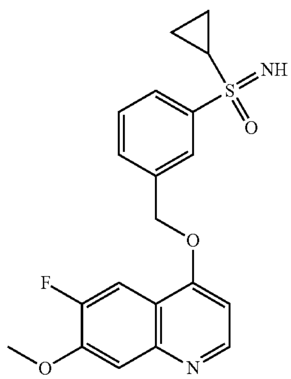 [SMILES: COc1cc2nccc(OCc3cccc(S(=N)(=O)C4CC4)c3)c2cc1F] | [cyclopropyl(3-{[(6-fluoro-7-methoxyquinolin-4-yl)oxy]methyl}phenyl)imino-$\lambda^6$-sulfanyl]one |
| 245 | 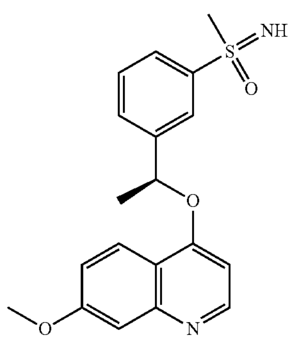 [SMILES: COc1ccc2c(O[C@@H](C)c3cccc(S(C)(=N)=O)c3)ccnc2c1] | imino({3-[(1S)-1-[(7-methoxyquinolin-4-yl)oxy]ethyl]phenyl})methyl-$\lambda^6$-sulfanone |
| 246 | 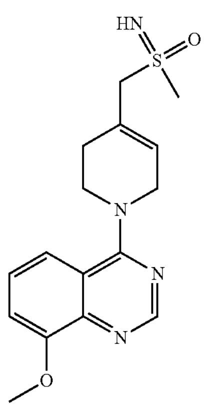 [SMILES: COc1cccc2c(N3CC=C(CS(C)(=N)=O)CC3)ncnc12] | imino({[1-(8-methoxyquinazolin-4-yl)-1,2,3,6-tetrahydropyridin-4-yl]methyl})methyl-$\lambda^6$-sulfanone |

In some variations, any of the compounds described herein, such as a compound of Formula (I), (I-1), (1-2), (1-3), (IA), (1-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (I-1), (I-2), (I-3), (I4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of W, Ring A, $a^1$, $a^2$, $b^1$, $b^2$, $c^1$, $c^2$, $c^3$, $c^4$, $d^1$, $d^2$, $d^3$, $d^4$, $e^1$, $e^2$, Y, $X^1$, $X^2$, $X^3$, $X^4$, $X^5$, $X^6$, $R^{1a}$, $R^{2a}$, $R^{1a1}$, $R^{1b}$, $R^{2b}$, $R^{3b}$, $R^{4b}$, $R^{5b}$, $R^{6b}$, $R^{1c}$, $R^{2c}$, $R^{3c}$, $R^{4c}$, $R^{5c}$, $R^{6c}$, $R^{7c}$, or L provided herein can be combined with every other variation or embodiment of W, Ring A, $a^1$, $a^2$, $b^1$, $b^2$, $c^1$, $c^2$, $c^3$, $c^4$, d, $d^2$, $d^3$, $d^4$, $e^1$, $e^2$, Y, $X^1$, $X^2$, $X^3$, $X^4$, $X^5$, $X^6$, $R^{1a}$, $R^{2a}$, $R^{1a1}$, $R^{1b}$, $R^{2b}$, $R^{3b}$, $R^{4b}$, $R^{5b}$, $R^{6b}$, $R^{1c}$, $R^{2c}$, $R^{3c}$, $R^{4c}$, $R^{5c}$, $R^{6c}$, $R^{7c}$, or L as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of Formula (I-1), (I-2), (I-3), (I4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig).

The compound names provided herein, including in Table 1, are provided by ChemDraw Professional 19.1. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds that are substantially pure.

Also provided are packaged pharmaceutical compositions, comprising a pharmaceutical composition as described herein and instructions for using the composition to treat a patient suffering from a disease or condition described herein.

Methods of Use

As described herein, the compounds of the present disclosure are inhibitors of ENPP1 enzymatic activity. In one aspect, the compounds and pharmaceutical compositions herein may be used to inhibit ENPP1. In another aspect, the compounds and pharmaceutical compositions herein may be used to treat or prevent a disease or condition in an individual.

The inhibitory activity of the compounds described herein against ENPP1 may be determined and measured by methods known in the art including, but not limited to, inhibition of ENPP1 hydrolysis of 2',3'-cGAMP (Cyclic guanosine monophosphate-adenosine monophosphate) (Mardjuki, R. et al. (2020), *Journal of Biological Chemistry*, 295(15), 4881-4892), inhibition of ENPP1 hydrolysis of pNP-TMP (p-nitrophenyl thymidine 5'-monophosphate), or inhibition of ENPP1 hydrolysis of pNP-AMP (p-nitrophenyl adenosine 5'-monophosphate) (Lee, S. et al. (2017), *Frontiers in Pharmacology* 8, 54).

In one aspect, provided herein is a method of inhibiting ENPP1 comprising contacting a cell with an effective amount of a compound or a pharmaceutical composition as described herein. In some embodiments, provided herein are methods of inhibiting ENPP1 comprising contacting a cell with an effective amount of a compound Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) or a compound of Table 1, or a pharmaceutically acceptable salt thereof. In some embodiments, provided herein are methods of inhibiting ENPP1 comprising contacting a cell with an effective amount of a pharmaceutical composition comprising a compound a compound Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) or a compound of Table 1, or a pharmaceutically acceptable salt thereof. In one variations of the aforementioned embodiments, the cell is contacted in vitro. In other variations of the aforementioned embodiments, the cell is contacted in vivo.

In another aspect, the compounds and pharmaceutical compositions herein may be used to treat or prevent a disease or condition in an individual, comprising administering an effective amount of a compound or a pharmaceutical composition as described herein. When used in a prophylactic manner, the compounds disclosed and/or described herein may prevent a disease or disorder from developing in an individual at risk of developing the disease or disorder, or lessen the extent of a disease or disorder that may develop.

In some embodiments, provided herein are methods of treating or preventing a disease or condition in an individual, comprising administering to the subject a therapeutically effective amount of a compound or a pharmaceutical composition as described herein. In some embodiments, provided herein are methods of treating or preventing a disease or condition in an individual, comprising administering to the subject a therapeutically effective amount of a compound Formula (I), (I-1), (I-2), (I-3), (I4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) or a compound of Table 1, or a pharmaceutically acceptable salt thereof. In some embodiments, provided herein are methods of treating or preventing a disease or condition in an individual, comprising administering to the subject a therapeutically effective amount of a pharmaceutical composition comprising a compound a compound Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) or a compound of Table 1, or a pharmaceutically acceptable salt thereof.

In some embodiments, the disease or condition is mediated by ENPP1. In some embodiments, the disease or condition is cancer. In some embodiments, the disease or condition is a bacterial or viral infection. In certain embodiments, the disease or condition is a bacterial infection. In certain other embodiments, the disease or condition is a viral infection. In some embodiments, the disease or condition is insulin resistance. In some embodiments, the disease or condition is type II diabetes. In some embodiments, the disease or condition is chondrocalcinosis. In some embodiments, the disease or condition is osteoarthritis. In some embodiments, the disease or condition is a soft-tissue calcification disorder. In certain embodiments, the disease or condition is cardiac calcification after heart injury. In some embodiments, the disease or condition is calcium pyrophosphate deposition disorder (CPPD). In some embodiments, the disease or condition is hypophosphatasia (HPP).

In some embodiments, provided are methods of treating or preventing cancer in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. In some embodiments, provided are methods of treating or preventing cancer in a subject in need thereof comprising administering to the subject a therapeutically effective amount of at least one chemical entity as described herein. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of a disease in a subject.

In some embodiments, provided herein are methods of treating cancer, comprising administering to an individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of a cancer.

In some embodiments, the provided are methods of treating a bacterial and/or viral infection in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of a bacterial and/or viral infection.

In some embodiments, provided are methods of treating insulin resistance in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of a insulin resistance.

In some embodiments, the provided are methods of treating type II diabetes, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of type II diabetes.

In some embodiments, provided are methods of treating chondrocalcinosis in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of chondrocalcinosis.

In some embodiments, provided are methods of treating osteoarthritis in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of osteoarthritis.

In some embodiments, provided are methods of treating a soft-tissue calcification disorder in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. In certain embodiments, the soft-tissue calcification disorder is cardiac calcification after heart injury. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of a soft-tissue calcification disorder. In certain embodiments, the soft-tissue calcification disorder is cardiac calcification after heart injury.

In some embodiments, provided are methods of treating calcium pyrophosphate deposition disorder (CPPD) in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of calcium pyrophosphate deposition disorder (CPPD).

In some embodiments, provided are methods of treating hypophosphatasia (HPP) in an individual, comprising administering to the individual in need thereof a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof. Also provided herein is the use of a compound of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig), or a compound of Table 1, or a pharmaceutically acceptable salt thereof in the manufacture of a medicament for treatment of hypophosphatasia (HPP).

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium croscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pa.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of any disease or condition described herein in an individual in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders.

The compounds and compositions described and/or disclosed herein may be combined with one or more other therapies to treat the diseases or conditions described herein, including but not limited to cancer, bacterial and/or viral infections, insulin resistance, type II diabetes, chondrocalcinosis, osteoarthritis, calcium pyrophosphate deposition disorder (CPPD), hypophosphatasia, and soft-tissue calcification disorders (such as cardiac calcification after heart injury).

General Synthetic Methods

Compounds of Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-1), (I-2), (I-3), (I-4), (I-5), (Ia), (Ia-1), (Ia-2), (Ia-3), (Ia-4), (Ia-5), (Ia-6), (Ib), (Ic), (Id), (Ie), (Ie-1), (Ie-2), (If), or (Ig) or any variation thereof. Other compounds described herein may be prepared by similar methods.

In some embodiments, compounds provided herein may be synthesized according to Scheme 1, Scheme 2, Scheme 3, and/or Scheme 4.

Scheme 1.

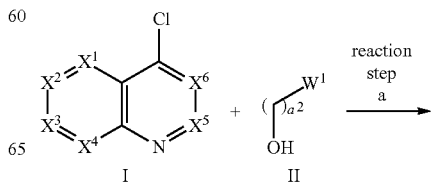

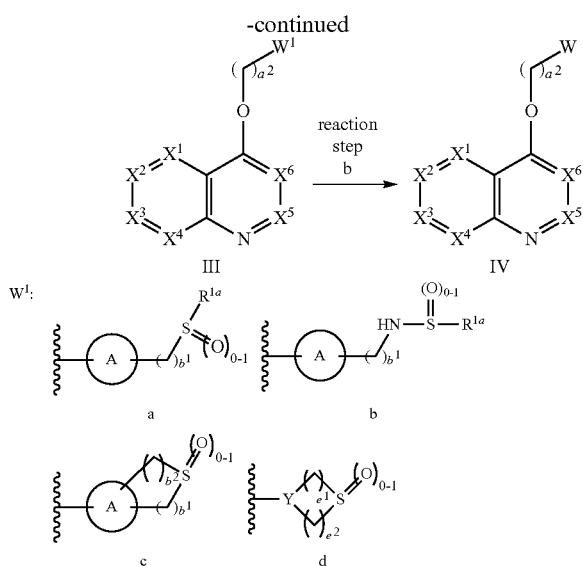

Scheme 1 outlines an exemplary route to the synthesis of compounds of general formula IV wherein the group $W^1$ has structure a, b, c or d. Compounds of general formula III are prepared from heteroaryl chlorides of general formula I and alcohols or phenols of general formula II via an Ullman-type coupling or $S_NAr$ reaction with heat, as either a neat mixture or in a suitable solvent such as isopropanol (reaction step a). Compounds of general formula III are then oxidized with, for example, $PhI(OAc)_2$, in the presence of an ammonia source, such as ammonium acetate, to provide compounds of general formula IV (reaction step b).

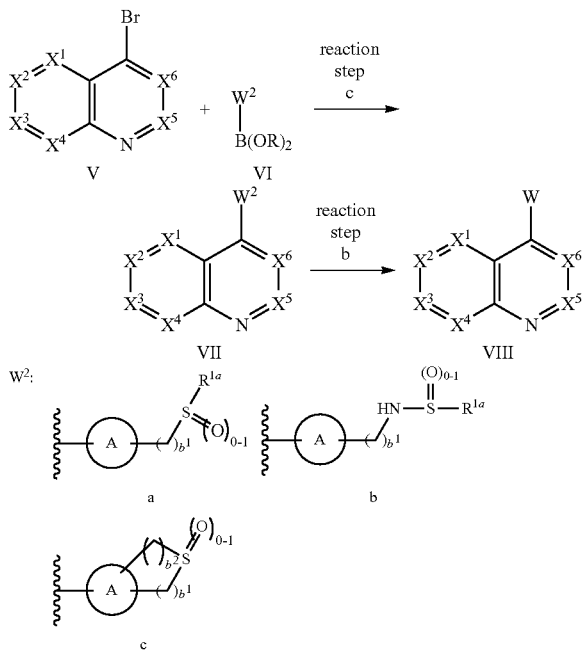

Scheme 2 summarizes an exemplary route toward compounds of general formula VIII where A is an aryl or heteroaryl ring or bicycle. Brominated heteroaryls of general formula V are cross-coupled with boronic acids or boronic esters of general formula VI, wherein the group $W^2$ is a, b or c, by heating in the presence of a palladium catalyst, such as $Pd(PPh_3)_4$ or $Pd(dppf)Cl_2$, and a base, such as $Na_2PO_4$, $Na_2CO_3$ or $CsCO_3$, under with heating, for example between 80 and 120° C. (reaction step c), to yield compounds of general formula VII Sulfoximines of general formula VIII may be prepared from compounds of general formula VII via conditions described in Scheme 1 for the preparation of general formula III (reaction step b).

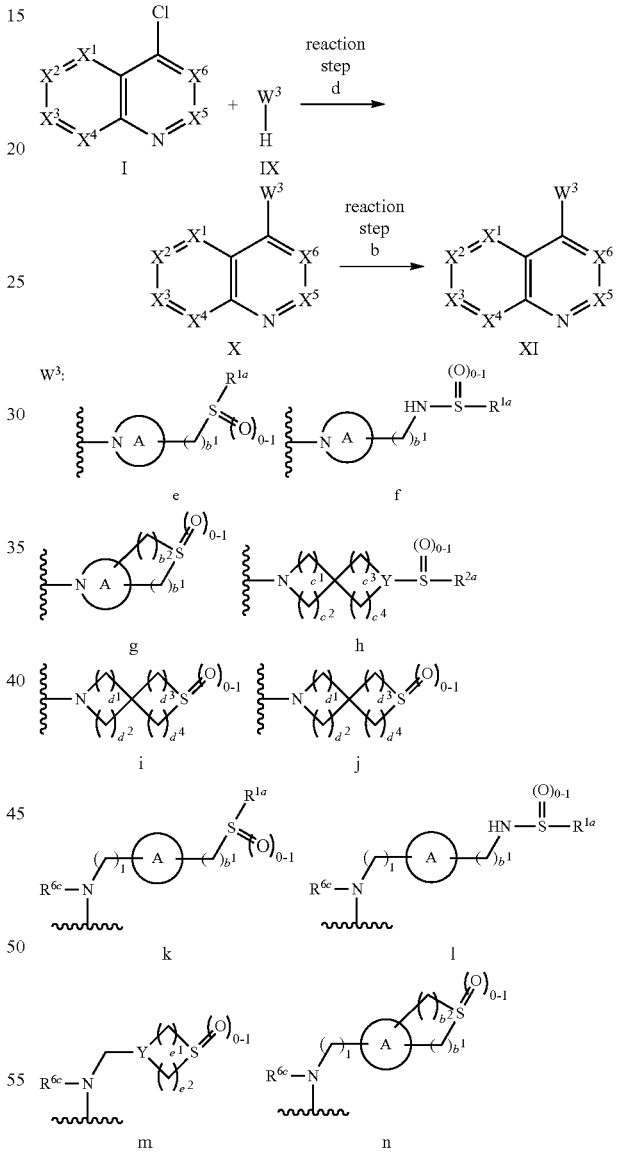

Compounds of the general formula XI may be prepared as outlined in Scheme 3. Heteroaryl chlorides of general formula I are reacted with amines of general formula IX under $S_NAr$ conditions that include heating, for example between 80 C and 100° C. with an appropriate base, such as $K_2CO_3$, $Et_3N$ or $iPr_2NEt$, in a polar solvent such as DMF (reaction step d) to give compounds of general formula X. Sulfoximines of general formula XI may be prepared from the compounds of general formula X via conditions described in Scheme 1 for the preparation of III (reaction step b). A variety of amines may be employed in this route. For example, amines of general formula IX wherein $W^3$ is e-n will provide their respective sulfoximines XIV.

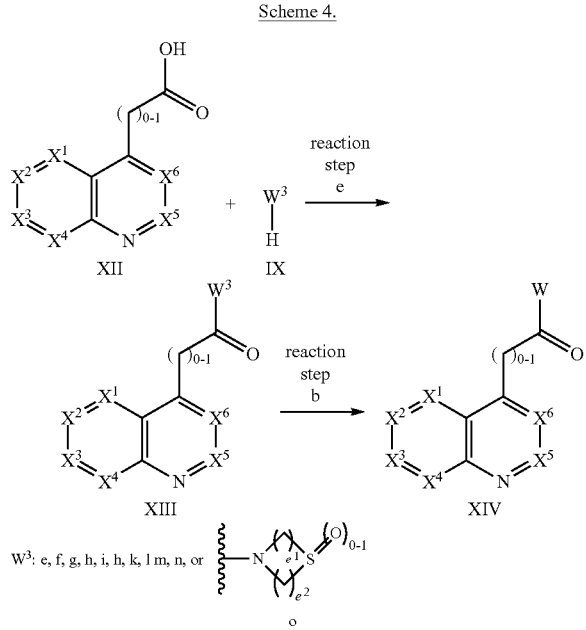

Scheme 4.

Amides of general formula XIV may be prepared from carboxylic acids of general formula XII with amines of general formula IX (wherein $W^3$ is e-o) via intermediate general formula XIII. Various standard condensation reactions may be used (reaction step e). For example, carbodiimide reagents such as DCC or EDC may be employed with an acyl transfer reagent such as HOBt, HOAt, or DMAP. Uronium salts such as HATU or TBTU may also be used with addition of a base, such as iPr$_2$NEt. Sulfoximines general formula XIV may be prepared from the intermediate compounds of general formula XIII via conditions described in Scheme 1 for the preparation of III (reaction step b).

Abbreviations dppf: 1,1'-bis(diphenylphosphino)ferrocene
de: diastereomeric excess (% major diastereomer–% minor diastereomer)
DAST: diethylaminosulfur trifluoride
DCC: dicyclohexyl carbodiimide
DMF-DMA: dimethylformamide dimethylacetal
EDC: 1-Ethyl-3-(3-dimethylaminopropyl)carbodiimide
ee: enantiomeric excess (% major enantiomer–% minor enantiomer)
HOBt: Hydroxybenzotriazole
HOAt: 1-hydroxy-7-azabenzotriazole
DIAD: diisopropyl azodicarboxylate
DMAP: 4-(dimethylamino)pyridine
HATU: (1-[Bis(dimethylamino)methylene]-1H-1,2,3-triazolo[4,5-b]pyridinium 3-oxide hexafluorophosphate
TBDMS: tert-butyl-dimethylsilyl
T-buxphos-Pd-G3: [(2-Di-tert-butylphosphino-2',4',6'-triisopropyl-1,1'-biphenyl)-2-(2'-amino-1,1'-biphenyl)] palladium(II) methanesulfonate
TBTU: 2-(1H-Benzotriazole-1-yl)-1,1,3,3-tetramethylaminium tetrafluoroborate
TFA: trifluoroacetic acid
Xantphos: 4,5-bis(diphenylphosphino)-9,9-dimethylxanthene

ENUMERATED EMBODIMENTS

1. A compound of Formula (I)

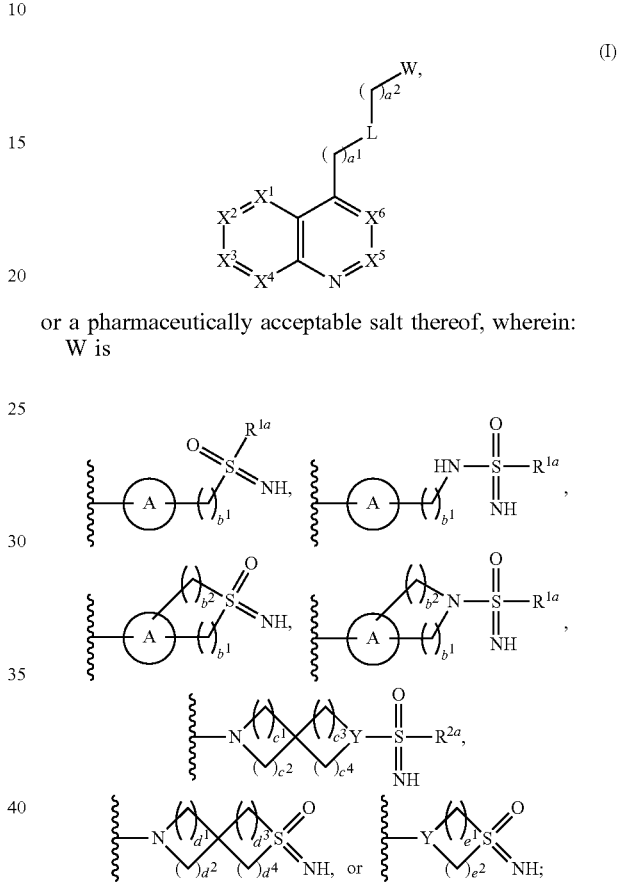

or a pharmaceutically acceptable salt thereof, wherein:
W is ring A is aryl, heteroaryl, cycloalkyl, cycloalkenyl, heterocycloalkyl, or heterocycloalkenyl, each of which is substituted or unsubstituted;
$R^{1a}$ and $R^{2a}$ are each independently hydrogen, $C_{1-6}$ alkyl, $C_{3-6}$ cycloalkyl, 3-6 membered heterocycloalkyl, or $C_{1-6}$ haloalkyl, wherein the $C_{1-6}$ alkyl is optionally substituted by hydroxyl, $C_{1-3}$ alkoxy, or $C_{3-6}$ cycloalkyl;
Y is —N— or —CH—;
$X^1$ is —$CR^{1b}$— or —N—;
$X^2$ is —$CR^{2b}$— or —N—;
$X^3$ is —$CR^{3b}$— or —N—;
$X^4$ is —$CR^{4b}$— or —N—;
$X^5$ is —$CR^{5b}$— or —N—;
$X^6$ is —$CR^{6b}$— or —N—;
$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —NHC(O)$R^{3c}$, or —C(O)$NR^{4c}R^{5c}$;
L is a bond, —O—, —C(O)—, or —$NR^{6c}$—;
$R^{1c}$-$R^{6c}$ are each independently hydrogen or $C_{1-3}$ alkyl;
$a^1$, $a^2$, and $b^1$ are each independently 0, 1, 2, or 3; and
$b^2$, $c^1$-$c^4$, $d^1$-$d^4$, $e^1$, and $e^2$ are each independently 1, 2, or 3.

2. The compound of embodiment 1, or a pharmaceutically acceptable salt thereof, wherein W is

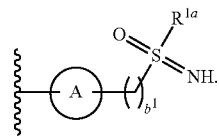

3. The compound of embodiment 1, or a pharmaceutically acceptable salt thereof, wherein W is

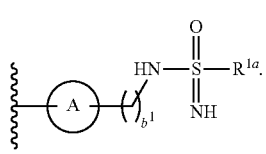

4. The compound of embodiment 1, or a pharmaceutically acceptable salt thereof, wherein W is

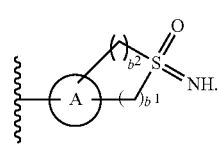

5. The compound of embodiment 1, or a pharmaceutically acceptable salt thereof, wherein W is

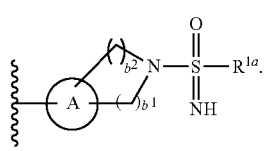

6. The compound of any one of embodiments 2-5, or a pharmaceutically acceptable salt thereof, wherein A is aryl.
7. The compound of any one of embodiments 2-5, or a pharmaceutically acceptable salt thereof, wherein A is heteroaryl.
8. The compound of any one of embodiments 2-5, or a pharmaceutically acceptable salt thereof, wherein A is heterocycloalkyl.
9. The compound of any one of embodiments 2-5, or a pharmaceutically acceptable salt thereof, wherein A is

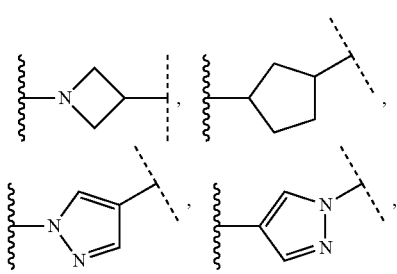

-continued

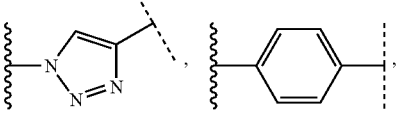

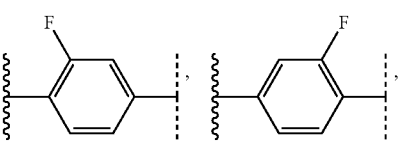

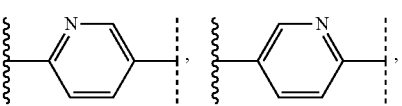

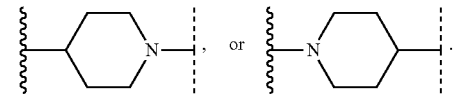

10. The compound of embodiment 3, or a pharmaceutically acceptable salt thereof, wherein A is

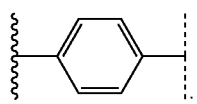

11. The compound of embodiment 5, or a pharmaceutically acceptable salt thereof, wherein A is

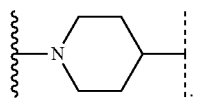

12. The compound of any one of embodiments 2-11, or a pharmaceutically acceptable salt thereof, wherein $R^{1a}$ is $C_{1-6}$ alkyl.
13. The compound of embodiment 12, or a pharmaceutically acceptable salt thereof, wherein $R^{1a}$ is methyl.
14. The compound of any one of embodiments 2-13, or a pharmaceutically acceptable salt thereof, wherein $b^1$ is 0.
15. The compound of any one of embodiments 2-13, or a pharmaceutically acceptable salt thereof, wherein $b^1$ is 2.
16. The compound of embodiment 3, or a pharmaceutically acceptable salt thereof, wherein W is

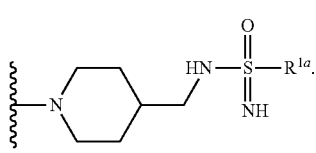

17. The compound of embodiment 4, or a pharmaceutically acceptable salt thereof, wherein W is

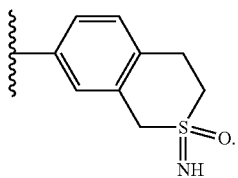 [SMILES: *c1ccc2c(c1)CS(=N)(=O)CC2]

18. The compound of embodiment 5, or a pharmaceutically acceptable salt thereof, wherein W is

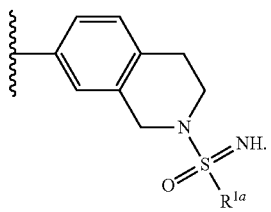

19. The compound of embodiment 1, or a pharmaceutically acceptable salt thereof, wherein W is

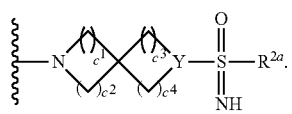

20. The compound of embodiment 19, or a pharmaceutically acceptable salt thereof, wherein W is

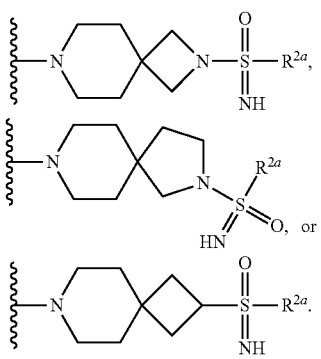

21. The compound of embodiment 19 or 20, or a pharmaceutically acceptable salt thereof, wherein $R^{2a}$ is $C_{1-6}$ alkyl.
22. The compound of embodiment 15, or a pharmaceutically acceptable salt thereof, wherein $R^{2a}$ is methyl.
23. The compound of embodiment 1, or a pharmaceutically acceptable salt thereof, wherein W is

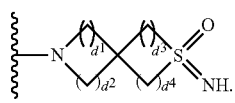

24. The compound of embodiment 23, or a pharmaceutically acceptable salt thereof, wherein W is

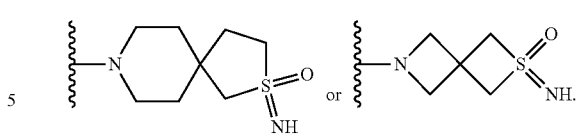

25. The compound of embodiment 1, or a pharmaceutically acceptable salt thereof, wherein W is

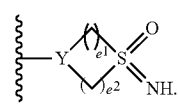

26. The compound of embodiment 25, or a pharmaceutically acceptable salt thereof, wherein W is

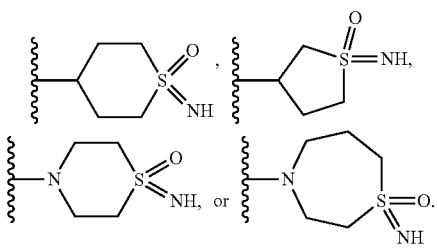

27. The compound of any one of embodiments 1-26, or a pharmaceutically acceptable salt thereof, wherein the

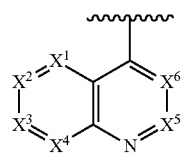

portion of Formula (I) is

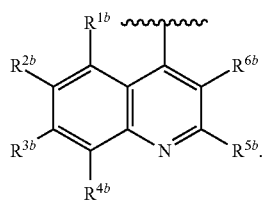

28. The compound of any one of embodiments 1-24, or a pharmaceutically acceptable salt thereof, wherein the

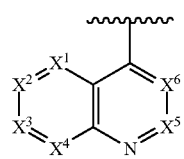

portion of Formula (I) is

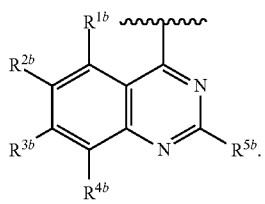

29. The compound of embodiment 27 or 28, or a pharmaceutically acceptable salt thereof, wherein $R^{2b}$ and $R^{3b}$ are methoxy, and $R^{1b}$ and $R^{4b}$ are hydrogen.
30. The compound of embodiment 27 or 28, or a pharmaceutically acceptable salt thereof, wherein $R^{3b}$ is methoxy, and $R^{1b}$, $R^{2b}$, and $R^{4b}$ are hydrogen.
31. The compound of any one of embodiments 1-30, or a pharmaceutically acceptable salt thereof, wherein L is a bond.
32. The compound of any one of embodiments 1-30, or a pharmaceutically acceptable salt thereof, wherein L is —O—.
33. The compound of any one of embodiments 1-30, or a pharmaceutically acceptable salt thereof, wherein L is —C(O)—.
34. The compound of any one of embodiments 1-30, or a pharmaceutically acceptable salt thereof, wherein L is —$NR^{6c}$—.
35. The compound of any one of embodiments 1-30, or a pharmaceutically acceptable salt thereof, wherein L is —NH—.
36. The compound of any one of embodiments 1-35, or a pharmaceutically acceptable salt thereof, wherein $a^1$ is 0.
37. The compound of any one of embodiments 1-35, or a pharmaceutically acceptable salt thereof, wherein $a^1$ is 1.
38. The compound of any one of embodiments 1-37, or a pharmaceutically acceptable salt thereof, wherein $a^2$ is 0.
39. The compound of embodiment 1, or a pharmaceutically acceptable salt thereof, wherein the compound is selected from the group consisting of compounds of Table 1.
40. A pharmaceutical composition comprising a compound of any one of embodiments 1-39, or a pharmaceutically acceptable salt thereof, and a pharmaceutically acceptable carrier or excipient.
41. A method of inhibiting ENPP1 comprising contacting a cell with an effective amount of a compound of any one of embodiments 1-39, or a pharmaceutically acceptable salt thereof.
42. A method of treating cancer in a subject in need thereof, comprising administering to the subject a therapeutically effective amount of a compound of any one of embodiments 1-39, or a pharmaceutically acceptable salt thereof.
43. A method of treating a bacterial and/or viral infection in a subject in need thereof, comprising administering to the subject a therapeutically effective amount of a compound of any one of embodiments 1-39, or a pharmaceutically acceptable salt thereof.
44. A method of treating insulin resistance in a subject in need thereof, comprising administering to the subject a therapeutically effective amount of a compound of any one of embodiments 1-39, or a pharmaceutically acceptable salt thereof.
45. A method of treating type II diabetes in a subject in need thereof, comprising administering to the subject a therapeutically effective amount of a compound of any one of embodiments 1-39, or a pharmaceutically acceptable salt thereof.
46. A method of treating chondrocalcinosis in a subject in need thereof, comprising administering to the subject a therapeutically effective amount of a compound of any one of embodiments 1-39, or a pharmaceutically acceptable salt thereof.
47. A method of treating osteoarthritis in a subject in need thereof, comprising administering to the subject a therapeutically effective amount of a compound of any one of embodiments 1-39, or a pharmaceutically acceptable salt thereof.
48. A method of treating a soft-tissue calcification disorder in a subject in need thereof, comprising administering to the subject a therapeutically effective amount of a compound of any one of embodiments 1-39, or a pharmaceutically acceptable salt thereof.
49. The method of embodiment 48, wherein the soft-tissue calcification disorder is cardiac calcification after heart injury.
50. A method of treating calcium pyrophosphate deposition disorder in a subject in need thereof, comprising administering to the subject a therapeutically effective amount of a compound of any one of embodiments 1-39, or a pharmaceutically acceptable salt thereof.
51. A method of treating hypophosphatasia in a subject in need thereof, comprising administering to the subject a therapeutically effective amount of a compound of any one of embodiments 1-39, or a pharmaceutically acceptable salt thereof.

Particular non-limiting examples are provided in the Example section below.

EXAMPLES

The following examples are offered to illustrate but not to limit the compositions, uses, and methods provided herein. The compounds are prepared using the general methods described above.

Synthesis of Intermediates

Synthesis of Intermediate 4-chloro-6-fluoro-7-methoxy-quinoline

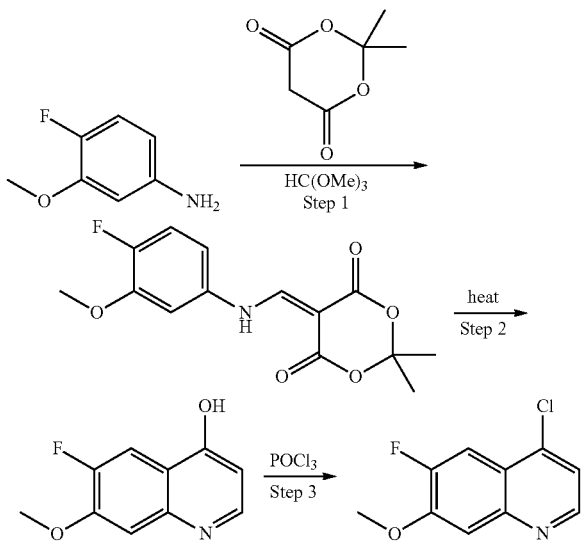

Step 1: A mixture of 4-fluoro-3-methoxyaniline (10 g, 71 mmol), 2,2-dimethyl-1,3-dioxane-4,6-dione (13 g, 92 mmol), trimethoxymethane (11 g, 99 mmol), and MeCN (150 mL) was degassed and purged with $N_2$, and then stirred at 80° C. for 16 h under an $N_2$ atmosphere. The mixture was concentrated, and the residue was triturated with petroleum ether at 25° C. for 30 min. The mixture was filtered and dried to provide 5-[(4-fluoro-3-methoxy-anilino)methylene]-2,2-dimethyl-1,3-dioxane-4,6-dione (16 g).

Step 2: A mixture of 5-[(4-fluoro-3-methoxy-anilino)methylene]-2,2-dimethyl-1,3-dioxane-4,6-dione (16 g, 53 mmol) and Dowtherm® A (80 mL) was degassed and purged with $N_2$, and then the mixture was stirred at 220° C. for 3 h under $N_2$ atmosphere. The mixture was triturated with petroleum ether at 25° C. for 30 min and the solid mixture was filtrated and dried to provide 6-fluoro-7-methoxy-quinolin-4-ol (10 g).

Step 3: To a mixture of 6-fluoro-7-methoxy-quinolin-4-ol (9.2 g, 48 mmol) and $iPr_2NEt$ (20 mL, 115 mmol) in MeCN (100 mL) was added $POCl_3$ (60 mL, 644 mmol). Then the mixture was degassed and purged with $N_2$ and stirred at 80° C. for 12 hours under an $N_2$ atmosphere. The reaction mixture was cooled and concentrated. The residue was dissolved into ethyl acetate (200 ml) and was washed with saturated aqueous $NaHCO_3$ (200 ml). The organic phase was washed with brine (150 mL), dried with $Na_2SO_4$, filtered, concentrated to provide 4-chloro-6-fluoro-7-methoxy-quinoline (9.8 g).

Synthesis of
4-chloro-7-methoxy-quinoline-6-carbonitrile

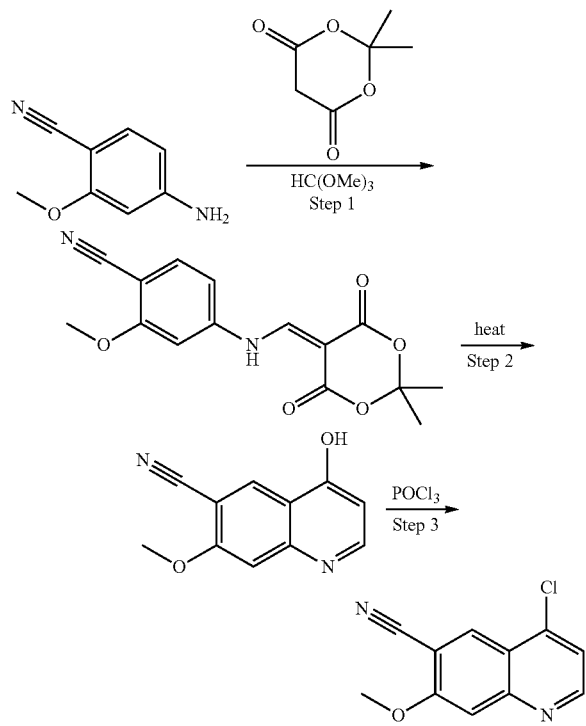

4-Chloro-7-methoxy-quinoline-6-carbonitrile was prepared in three steps from 4-amino-2-methoxy-benzonitrile in the manner described for the synthesis of intermediate 4-chloro-6-fluoro-7-methoxy-quinoline.

Synthesis of Intermediate
4-chloro-6-fluoro-7-methoxyquinazoline
hydrochloride

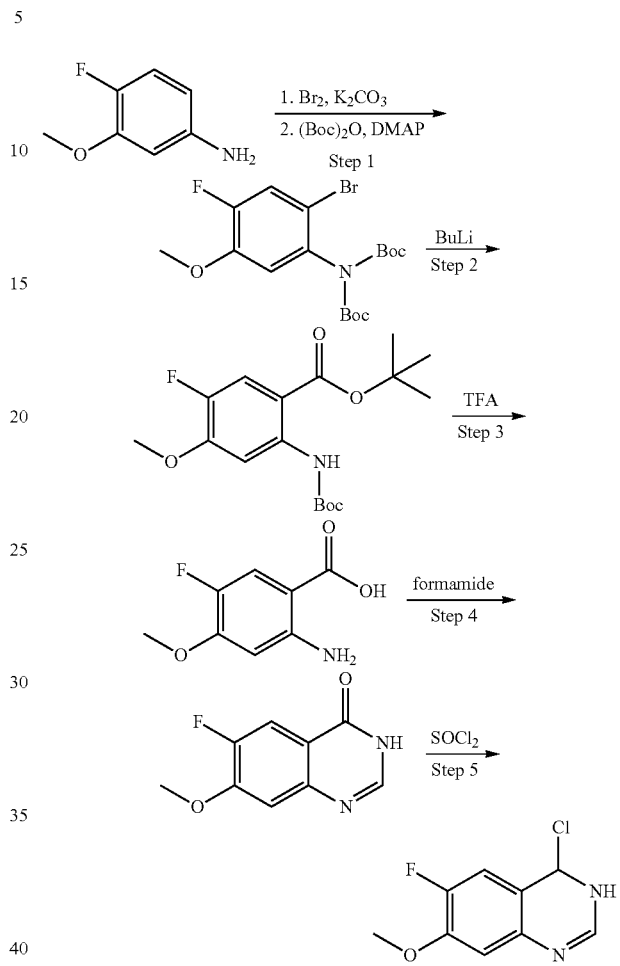

Step 1: To a −15° C. mixture of 4-fluoro-3-methoxy-aniline (15 g, 110 mmol), $CH_2Cl_2$ (240 mL), and $K_2CO_3$ (15 g, 110 mmol), $Br_2$ (5.5 mL, 110 mmol) was added slowly. After stirring for 1 h, the mixture was diluted with $H_2O$ (150 mL) and extracted with $CH_2Cl_2$ (100 mL×2). The organic phases were combined, extracted with brine (50 mL), dried over $Na_2SO_4$, filtered, concentrated, and triturated with $CH_2Cl_2$ (40 mL) and hexane (50 mL) at 20° C. for 30 min to provide 2-bromo-4-fluoro-5-methoxy-aniline (19 g).

A mixture of 2-bromo-4-fluoro-5-methoxy-aniline (24 g, 110 mmol), THF (250 mL) was added $(Boc)_2O$ (57 g, 260 mmol), and DMAP (2.7 g, 22 mmol) was stirred at 20° C. for 12 h. The mixture was concentrated, diluted with $H_2O$ (100 mL), and extracted with EtOAc (80 mL×2). The extracts were combined, washed with brine (50 mL), dried over $Na_2SO_4$, filtered, and purified by chromatography (10-50% EtOAc in petroleum ether) to provide tert-butyl N-(2-bromo-4-fluoro-5-methoxy-phenyl)-N-tert-butoxycarbonyl-carbamate (41 g).

Step 2: To a −78° C. mixture of tert-butyl N-(2-bromo-4-fluoro-5-methoxy-phenyl)-N-tert-butoxycarbonyl-carbamate (20 g, 48 mmol) and THF (150 mL) was added n-BuLi (2.5 M in hexanes, 29 mL) and the mixture was stirred at −78° C. for 1 h. Saturated aqueous $NH_4Cl$ (5.0 mL) was added at 0° C., followed by $H_2O$ (100 mL). The mixture was extracted with EtOAc (70 mL×2), and the extracts were combined, washed with brine (40 mL), dried over Na$_2$SO$_4$, filtered, concentrated, and purified by silica chromatography (10-50% EtOAc in petroleum ether to provide tert-butyl 2-((tert-butoxycarbonyl)amino)-5-fluoro-4-methoxybenzoate (16 g).

Step 3: To a mixture of tert-butyl 2-(tert-butoxycarbonylamino)-5-fluoro-4-methoxybenzoate (9.0 g, 26 mmol), and CH$_2$Cl$_2$ (50 mL) was added TFA (21 mL, 280 mmol). The mixture was stirred at 20° C. for 2 h, concentrated, diluted with H$_2$O (40 mL), and extracted with EtOAc (30 mL×2). The combined extracts were washed with brine (20 mL), dried over Na$_2$SO$_4$, filtered, concentrated, and purified by silica chromatography (10-100% EtOAc in petroleum ether) to provide 2-amino-5-fluoro-4-methoxybenzoic acid (3.1 g).

Step 4: A mixture of 2-amino-5-fluoro-4-methoxy-benzoic acid (1.0 g, 5.4 mmol) and formamide (9.1 mL, 230 mmol) was stirred at 160° C. for 5 h. The mixture was combined with H$_2$O (20 mL). The resulting precipitate was filtered and triturated with MeOH (8.0 mL) at 20° C. for 30 min to provide 6-fluoro-7-methoxyquinazolin-4-ol (0.42 g).

Step 5: A mixture of 6-fluoro-7-methoxy-quinazolin-4-ol (0.40 g, 2.1 mmol) in SOCl$_2$ (8.0 mL) and DMF (15 mg) was stirred at 80° C. for 12 h. The mixture was concentrated to provide 4-chloro-6-fluoro-7-methoxyquinazoline hydrochloride (0.55 g).

Synthesis of Intermediate
4-chloro-3-fluoro-6,7-dimethoxyquinoline to 0° C., and the resulting precipitate filtered and washed with hexane. The solids were triturated with a mixture of 1:5 MeOH/MTBE (300 mL) at 20° C. for 30 min to afford 6,7-dimethoxy-3-nitroquinolin-4-ol (22 g).

Step 2: A mixture of 6,7-dimethoxy-3-nitroquinolin-4-ol (11 g, 44 mmol), SOCl$_2$ (100 mL), and DMF (0.32 g, 4.4 mmol) was stirred at 90° C. for 12 h, then was concentrated to provide 4-chloro-6,7-dimethoxy-3-nitroquinoline hydrochloride (13 g).

Step 3: SnCl$_2$·2H$_2$O (67 g, 300 mmol) was added to a mixture of 4-chloro-6,7-dimethoxy-3-nitroquinoline hydrochloride (13 g, 43 mmol), AcOH (29 mL), and EtOH (230 mL). The mixture was stirred at 80° C. for 12 h, then was concentrated, and combined with CH$_2$Cl$_2$ (400 mL) and NaOH (4M, 80 mL). The mixture was filtered through diatomaceous earth, and concentrated to provide 4-chloro-6,7-dimethoxy-quinolin-3-amine (10 g).

Step 4: To a 0° C. mixture of 4-chloro-6,7-dimethoxy-quinolin-3-amine (5.0 g, 21 mmol) and THF (50 mL) was added dropwise HBF$_4$ (40%, 9.8 mL, 63 mmol). The mixture was stirred for 30 min, and NaNO$_2$ (1.6 g, 23 mmol) in H$_2$O (6.3 mL) was added dropwise at 0° C. The resulting mixture was stirred at 0° C. for 30 min, then it was filtered and the filtrate was stirred at 170° C. for 1 h. The reaction was concentrated and purified by silica chromatography (0-50% MeOH in CH$_2$Cl$_2$) to afford 4-chloro-3-fluoro-6,7-dimethoxyquinoline (0.24 g).

Synthesis of Intermediate
4-chloro-8-ethoxyquinazoline

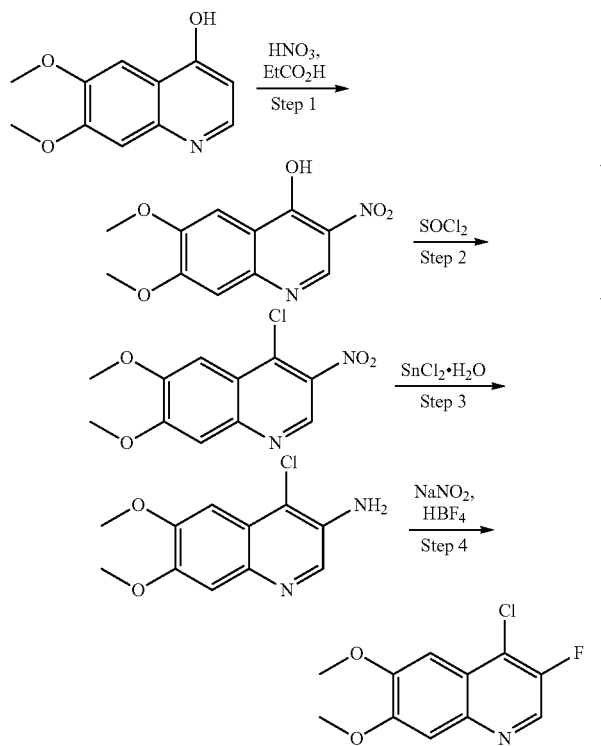

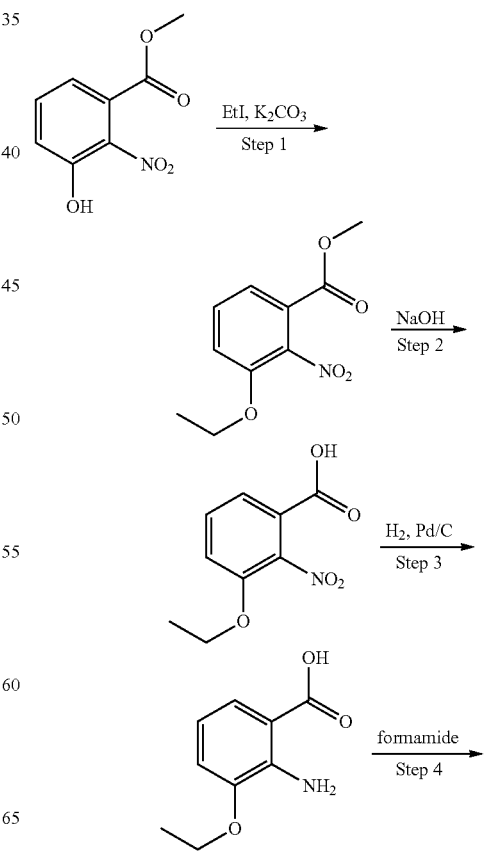

Step 1: Fuming nitric acid (98%, 7.5 mL, 210 mmol) was added slowly to a stirring mixture of 6,7-dimethoxyquinolin-4-ol (20 g, 97 mmol) and propionic acid (450 mL) at 20° C. The mixture was stirred at 100° C. for 6 h, then cooled

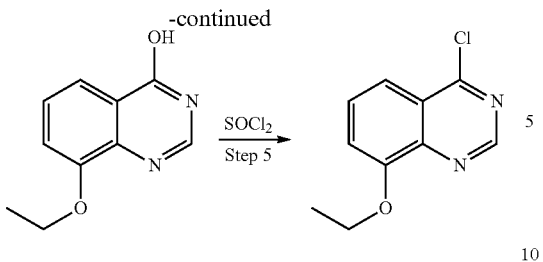

Step 1: A degassed mixture of methyl 3-hydroxy-2-nitrobenzoate (15 g, 76 mmol), iodoethane (24 g, 152 mmol), K₂CO₃ (21 g, 152 mmol) and DMF (75 mL) was stirred at 20° C. for 12 h under an N₂ atmosphere. The mixture was poured into water (150 mL) and extracted with EtOAc (2×80 mL). The extracts were washed with brine (50 mL), dried over Na₂SO₄, and concentrated to provide methyl 3-ethoxy-2-nitrobenzoate (17 g).

Step 2: A degassed mixture of methyl 3-ethoxy-2-nitrobenzoate (6.0 g, 27 mmol), NaOH (3.2 g, 80 mmol), H₂O (30 mL), and THF (30 mL) was stirred at 70° C. for 1 h, then was concentrated to remove THF. The mixture was extracted with EtOAc (30 mL), then the aqueous phase was acidified with HCl (4 N) to pH 2 and extracted with EtOAc (2×50 mL). The extracts were washed with brine (30 mL), dried over anhydrous Na₂SO₄, and concentrated to provide 3-ethoxy-2-nitro-benzoic acid (5.0 g).

Step 3: A degassed mixture of 3-ethoxy-2-nitrobenzoic acid (5.0 g, 24 mmol), MeOH (50 mL), and 10% Pd/C (2.0 g, 4.7 mmol) was stirred under H₂ (15 psi) at 20° C. for 12 h. The mixture was filtered and the filtrate was concentrated to provide compound 2-amino-3-ethoxy-benzoic acid (2.8 g).

Step 4: A mixture of 2-amino-3-ethoxy-benzoic acid (2.8 g, 15 mmol) and formamide (2.8 g, 62 mmol) was stirred at 165° C. for 4 h. The reaction was poured into water (30 mL) and the resulting precipitate was filtered, washed with water (10 mL×2), and dried to provide 8-ethoxyquinazolin-4-ol (1.5 g).

Step 5: A mixture of 8-ethoxyquinazolin-4-ol (0.29 g, 1.5 mmol), SOCl₂ (5 mL, 69 mmol) and DMF (11 mg, 150 μmol) was stirred at 80° C. for 12 hours. The mixture was concentrated to provide compound 4-chloro-8-ethoxyquinazoline (0.29 g).

Synthesis of Intermediate
4-chloro-8-ethoxyquinoline-3-carbonitrile

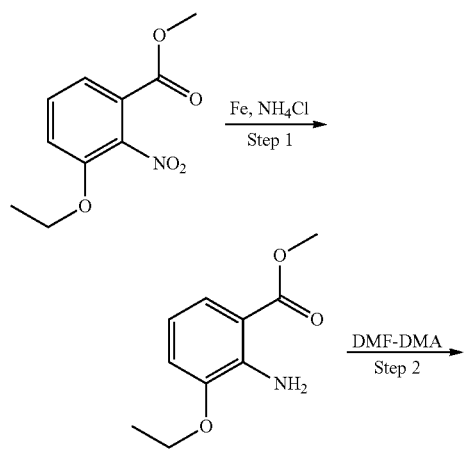

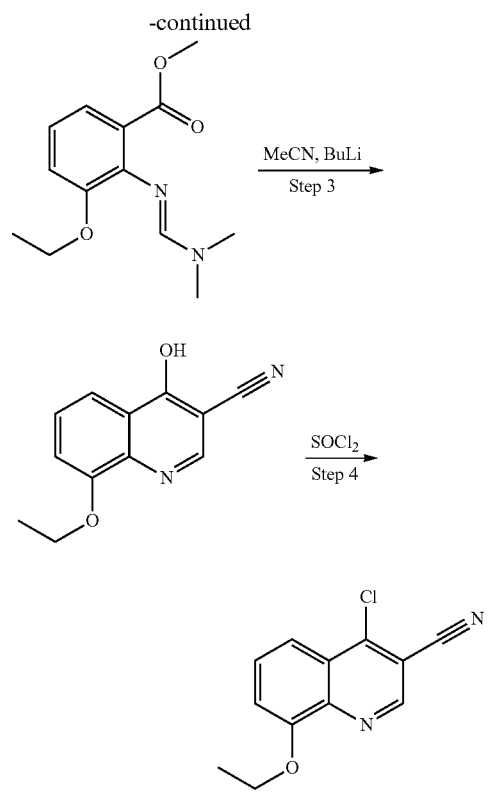

Step 1: To a mixture of methyl 3-ethoxy-2-nitrobenzoate (7.5 g, 33 mmol) in EtOH (50 mL) were added Fe (19 g, 0.33 mol) and NH₄Cl (14 g, 0.27 mol). The mixture was stirred at 70° C. for 12 h, then was filtered and the filtrate was concentrated. The residue was combined with water (50 mL) and extracted with EtOAc (2×50 mL). The combined extracts were washed with brine (30 mL), dried over Na₂SO₄, filtered, concentrated, and purified by silica chromatography (9%-17% EtOAc in petroleum ether) to provide methyl 2-amino-3-ethoxy-benzoate (6.0 g).

Step 2: A degassed mixture of methyl 2-amino-3-ethoxy-benzoate (5.0 g, 26 mmol) and DMF-DMA (3.4 mL, 26 mmol) was stirred at 110° C. for 12 h under an N₂ atmosphere. The mixture was concentrated to provide methyl 2-[(E)-dimethylaminomethyleneamino]-3-ethoxy-benzoate (4.5 g).

Step 3: To a mixture of CH₃CN (1.7 mL, 32 mmol) and THF (25 mL) was added BuLi (2.5 M, 13) at −70° C. After stirring for 0.5 h, methyl 2-[(E)-dimethylaminomethyleneamino]-3-ethoxy-benzoate (4.0 g, 16 mmol) in THF (30 mL) was added and the mixture and stirred at −70 for 1.5 h. HOAc (3.7 mL, 64 mmol) was added, and the mixture was poured into water (30 mL) and the resulting mixture was extracted with EtOAc (2×30 mL). The combined extracts were washed with brine (10 mL), dried over Na₂SO₄, filtered, and concentrated to provide 8-ethoxy-4-hydroxy-quinoline-3-carbonitrile (2.1 g).

Step 4: A degassed mixture of 8-ethoxy-4-hydroxy-quinoline-3-carbonitrile (0.25 g, 1.2 mmol), SOCl₂ (5 mL, 69 mmol) and DMF (20 μL, 0.26 mmol) was stirred at 90° C. for 2 h under an N₂ atmosphere. The mixture was concentrated to provide 4-chloro-8-ethoxyquinoline-3-carbonitrile (0.40 g).

Synthesis of Intermediate 4-chloro-8-(fluoromethoxy)quinoline-3-carbonitrile

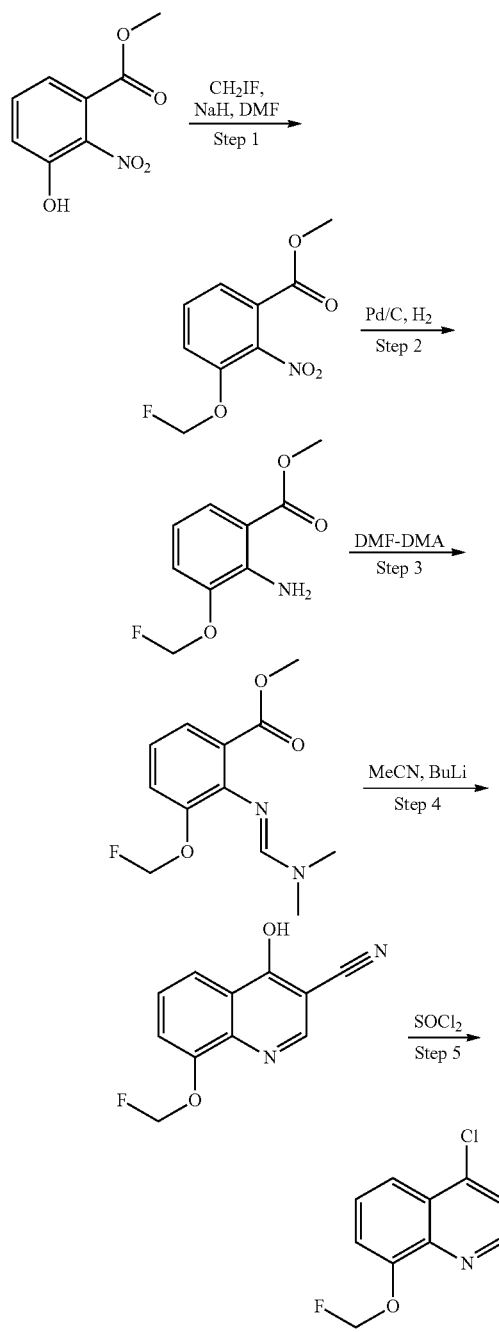

Step 1: To a mixture of methyl 3-hydroxy-2-nitro-benzoate (3.0 g, 15 mmol) and DMF (30 mL) was added 65% NaH (1.4 g, 38 mmol), which was stirred at 0° C. for 0.5 h. Fluoro(iodo)methane (2.9 g, 18 mmol) was added at 25° C. and the mixture stirred for 12 h. Saturated aqueous NH$_4$Cl (20 ml) was added slowly, and the mixture was filtered, concentrated, and combined with EtOAc (50 mL) and washed with H$_2$O (30 ml×3). The extracts were combined, washed with brine (20 mL), dried over Na$_2$SO$_4$, filtered, and concentrated to provide methyl 3-(fluoromethoxy)-2-nitro-benzoate (3.3 g).

Step 2: Pd/C (1.0 g, 10%) was added to methyl 3-(fluoromethoxy)-2-nitro-benzoate (4.9 g, 21 mmol) and EtOH (50 mL) under an N$_2$ atmosphere. The suspension was degassed then stirred under an H$_2$ (15 psi) at 20° C. for 8 h. The mixture was filtered and the filtrate was concentrated to provide methyl 2-amino-3-(fluoromethoxy)benzoate (3.50 g).

Steps 3-5 were run from 2-amino-3-(fluoromethoxy)benzoate in the manner described in Steps 2-4 of the synthesis of Intermediate 4-chloro-8-ethoxyquinoline-3-carbonitrile to provide 4-chloro-8-(fluoromethoxy)quinoline-3-carbonitrile.

Synthesis of Intermediate 4-chloro-5-fluoro-8-methoxyquinoline-3-carbonitrile

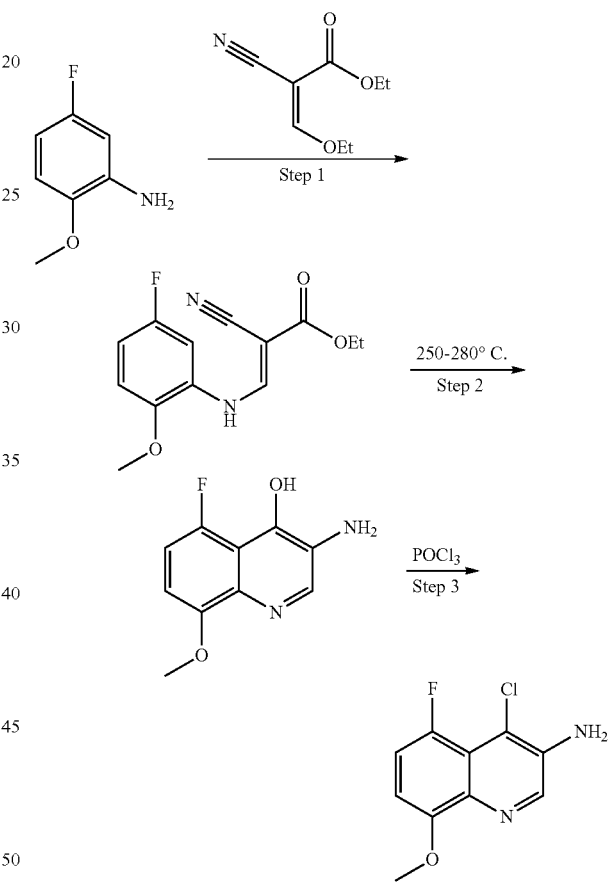

Step 1: A mixture of 5-fluoro-2-methoxy-aniline (4.0 g, 28 mmol) and ethyl (Z)-2-cyano-3-ethoxy-prop-2-enoate (4.8 g, 28 mmol) was stirred at 150° C. for 2 h. The resulting solid was cooled and triturated with petroleum ether (15 mL) at 20° C. for 30 min to give (E)-ethyl 2-cyano-3-((5-fluoro-2-methoxyphenyl)amino)acrylate (7.0 g).

Step 2: A mixture of (E)-ethyl 2-cyano-3-((5-fluoro-2-methoxyphenyl)amino)acrylate (1.0 g, 3.8 mmol) and Ph$_2$O (10 mL) was stirred at 250° C. for 6 h, then at 280° C. for 6 h. The mixture was cooled and the resulting precipitate was stirred with petroleum ether (30 mL) at 80° C. for 15 min and cooled to 40° C. The suspension was filtered, and the filter cake was washed with petroleum ether (5 mL×3) to give 5-fluoro-4-hydroxy-8-methoxyquinoline-3-carbonitrile (0.58 mg).

Step 3: A mixture of 5-fluoro-4-hydroxy-8-methoxyquinoline-3-carbonitrile (0.50 g, 2.3 mmol) and POCl₃ (3.0 mL, 32 mmol) was stirred at 120° C. for 12 h. The mixture was concentrated and saturated NaHCO₃ (5 mL) was added to adjust its pH to 8. The solids were isolated by filtration and the filter cake was washed with water (0.5 mL×3) and petroleum ether (3 mL). This solid was triturated with MTBE (8 mL) at 70° C. for 15 min and cooled to 20° C., filtered, washed with MTBE (0.5 mL×3) and petroleum ether (3 mL) to provide 4-chloro-5-fluoro-8-methoxyquinoline-3-carbonitrile (0.47 g).

Synthesis of Intermediate 4-chloro-8-methoxy-2-methylquinoline-3-carbonitrile

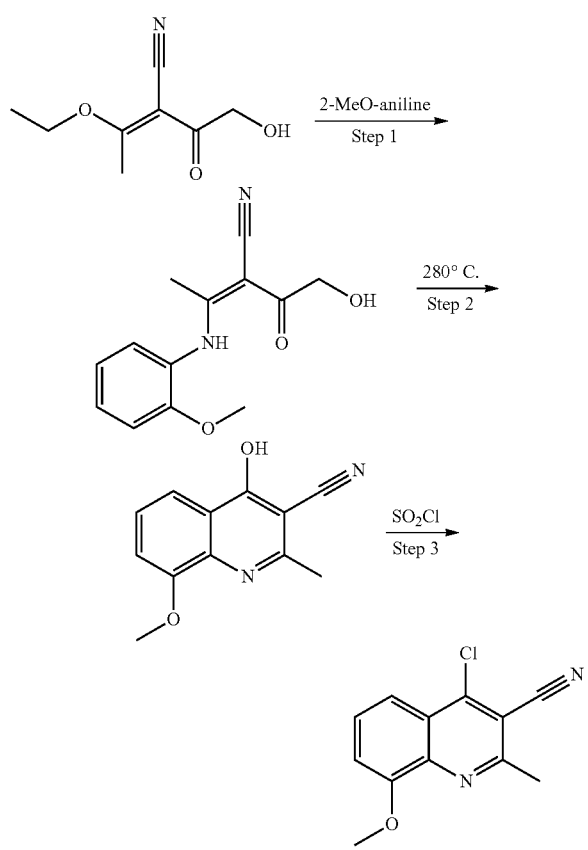

Step 1: A degassed mixture of ethyl (E)-2-cyano-3-ethoxy-but-2-enoate (6.3 g, 34 mmol), 2-methoxyaniline (3.9 mL, 34 mmol), and EtOH (50 mL) was stirred at 90° C. for 4 h under an N₂ atmosphere. The mixture was concentrated and purified by silica chromatography (0-25% EtOAc in petroleum ether) to provide ethyl (Z)-2-cyano-3-(2-methoxyanilino)but-2-enoate (2.7 g).

Step 2: Ethyl (Z)-2-cyano-3-(2-methoxyanilino)but-2-enoate (2.5 g, 9.0 mmol) and DOWTHERM® A (50 mL) were stirred at 280° C. for 10 h. The mixture was triturated with petroleum ether at 20° C. for 30 min to provide 4-hydroxy-8-methoxy-2-methyl-quinoline-3-carbonitrile (1.3 g).

Step 3: A degassed mixture of 4-hydroxy-8-methoxy-2-methyl-quinoline-3-carbonitrile (0.85 g, 3 mmol), DMF (4.3 µL, 55 µmol), and SOCl₂ (10 mL) was stirred at 20° C. for 12 h under an N₂ atmosphere. The mixture was concentrated and purified by silica chromatography (0-100% EtOAc in petroleum ether) to provide 4-chloro-8-methoxy-2-methylquinoline-3-carbonitrile (0.40 g).

Synthesis of Intermediate 4-chloro-6,7-dimethoxy-3-methylcinnoline

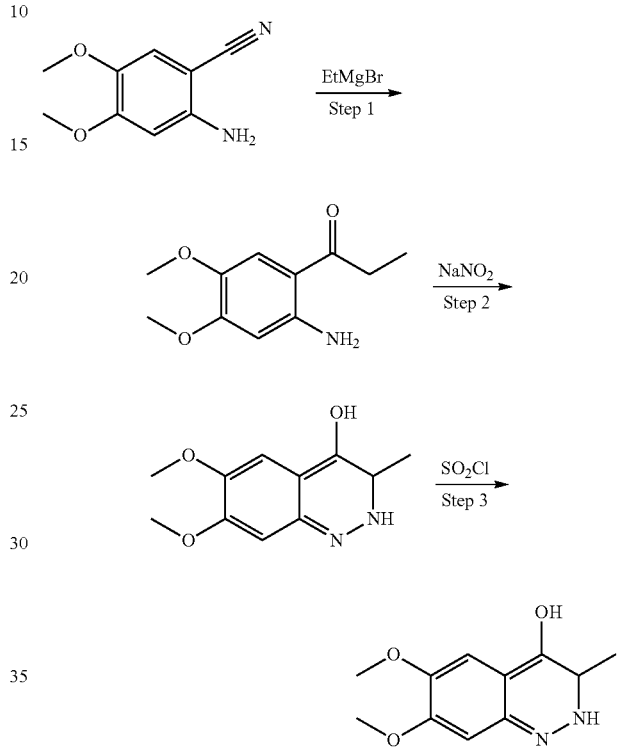

Step 1: To a mixture of 2-amino-4, 5-dimethoxybenzonitrile (7.0 g, 39 mmol) and THF (70 mL) was added EtMgCl (2 M, 79 mL) slowly at 0° C. The mixture was stirred at 50° C. for 2 h, aqueous HCl was added (2 N, 80 mL), and the pH adjusted to 9 by the addition of saturated aqueous NaHCO₃. The resulting mixture was extracted with EtOAc (2×100 mL), extracts were combined, washed with brine (50 mL), dried over Na₂SO₄, concentrated, and purified by silica chromatography (5-100% EtOAc in petroleum ether) to provide 1-(2-amino-4,5-dimethoxy-phenyl)propan-1-one (4.3 g).

Step 2: To a mixture of 1-(2-amino-4, 5-dimethoxy-phenyl) propan-1-one (3.3 g, 16 mmol), conc. HCl (53 mL), and H₂O (6.6 mL) was added NaNO₂ (1.1 g, 16 mmol) in H₂O (6.6 mL) slowly over 10 min at −5° C. The mixture was stirred at −5° C. for 1 h, then at 60° C. for 4 h. The solids were isolated by filtration and washed with H₂O (20.0 mL×3) and dried to provide crude 6,7-dimethoxy-3-methyl-cinnolin-4-ol (4.4 g).

Step 3: A mixture of crude 6,7-dimethoxy-3-methyl-cinnolin-4-ol (4.3 g, 520 mmol), SOCl₂ (30 mL), and DMF (0.15 mL, 2.0 mmol) was stirred at 80° C. for 2 h under an N₂ atmosphere. The mixture was concentrated and purified by preparative HPLC (15-45% MeCN in water, 10 mM NH₄CO₃) to provide 4-chloro-6,7-dimethoxy-3-methylcinnoline (1.5 g).

Synthesis of Intermediate 4-chloro-3-fluoro-8-methoxyquinoline

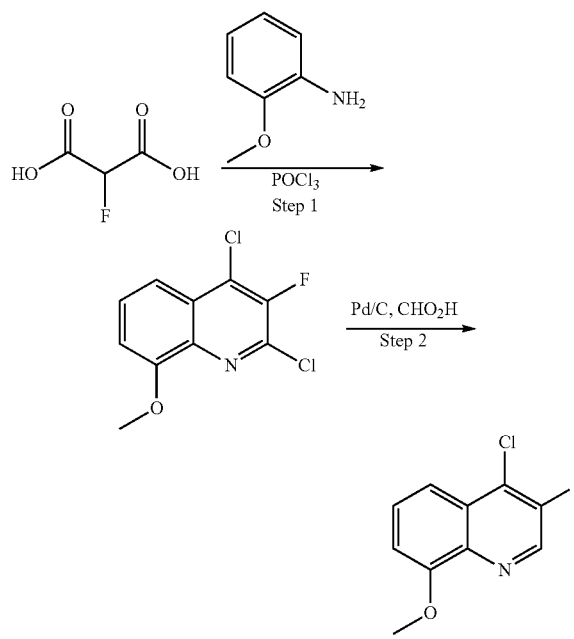

Step 1: To POCl₃ (60 mL) was added 2-fluoropropanedioic acid (1 g, 8.2 mmol) and the mixture was heated to reflux for 30 min then cooled to 60° C. and 2-methoxyaniline (1.0 g, 8.2 mmol) was added slowly. The mixture was heated to 140° C. for 15 h, concentrated, and ice water (5 g) was added. After stirring for 0.5 h, ammonia was added until the pH reached 10. The resulting precipitate was collected by filtration and purified by silica chromatography (0-50% EtOAc in petroleum ether) to provide 2,4-dichloro-3-fluoro-8-methoxy-quinoline (0.38 g).

Step 2: A mixture of 2,4-dichloro-3-fluoro-8-methoxyquinoline (0.38 g, 1.54 mmol), H₂O (2.5 mL), dioxane (5 mL), 10% Pd/C (0.2 g), Et₃N (3.9 mL, 28 mmol), and formic acid (0.23 µL, 6.2 mmol) was stirred at 90° C. for 16 h. The mixture was filtered, and the filtrate was concentrated and purified by silica chromatography (0-50% EtOAc in petroleum ether) to provide 4-chloro-3-fluoro-8-methoxyquinoline (0.12 g).

Synthesis of Intermediate 4,6-dichloro-7-methoxycinnoline hydrochloride

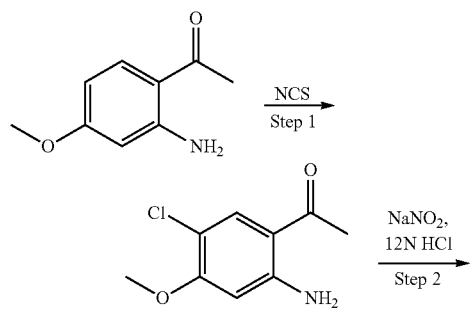

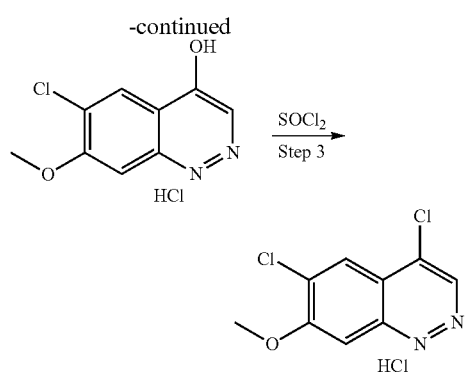

Step 1: To a mixture of 1-(2-amino-4-methoxy-phenyl)ethanone (3.5 g, 21 mmol) and THF (60 mL) was added NCS (3.1 g, 23 mmol). The mixture was stirred at 60° C. for 2 h, poured into H₂O (60 mL) and extracted with EtOAc (2×40 mL). The combined extracts were washed with brine (10 mL), dried over Na₂SO₄, concentrated, and triturated with CH₂Cl₂/petroleum ether (5 mL) at 20° C. for 10 min to provide compound 1-(2-amino-5-chloro-4-methoxy-phenyl)ethanone (2.8 g).

Step 2: A solution of NaNO₂ (0.97 g, 14 mmol) in H₂O (7.5 mL) was added slowly to 1-(2-amino-5-chloro-4-methoxy-phenyl)ethanone (2.8 g, 14 mmol) in 12 N HCl (60 mL) at −5° C. The mixture was stirred for 1 h, then stirred at 60° C. for 4 hours. The resulting precipitate was filtered and washed with water (20 mL×2) to provide 6-chloro-7-methoxy-cinnolin-4-ol hydrochloride (1.8 g).

Step 3: A degassed mixture of 6-chloro-7-methoxy-cinnolin-4-ol hydrochloride (1.8 g, 8.5 mmol), DMF (62 mg, 0.85 mmol), and SOCl₂ (49 g, 410 mmol) was stirred at 90° C. for 2 h. The mixture was concentrated provide compound 4,6-dichloro-7-methoxycinnoline hydrochloride (2.2 g).

Synthesis of Intermediate 4,6-dichloro-7-methoxy-3-methylcinnoline hydrochloride

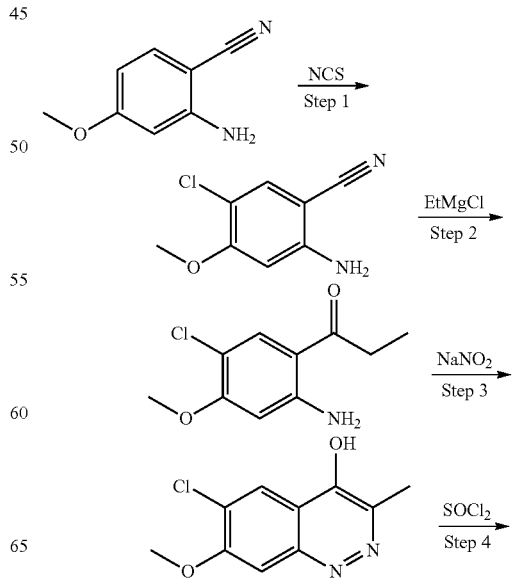

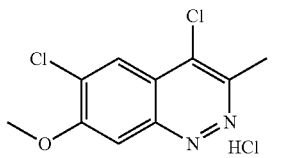

Step 1: A degassed mixture of 2-amino-4-methoxy-benzonitrile (10 g, 67 mmol), NCS (9.9 g, 74 mmol), and THF (150 mL) was stirred at 60° C. for 12 h under an $N_2$ atmosphere. The mixture was poured into saturated aqueous $NaHCO_3$ (100 mL) extracted with EtOAc (2×100 mL). The extracts were washed with brine (50 mL), dried over $Na_2SO_4$, concentrated, and purified by silica chromatography (5-25% EtOAc in petroleum ether) to provide 2-amino-5-chloro-4-methoxy-benzonitrile (7.2 g).

Step 2: To a mixture of 2-amino-5-chloro-4-methoxy-benzonitrile (4.7 g, 26 mmol) and THF (20 mL) was added EtMgCl (2 M in THF, 52 mL). The mixture was stirred at 50° C. for 12 h, and 50 mL of 2M HCl was added slowly. Saturated aqueous $NaHCO_3$ was added to adjust the pH to 9, and the resulting mixture was extracted with EtOAc (2×80 mL). The extracts were washed with brine (10 mL), dried over $Na_2SO_4$, concentrated, and purified by silica chromatography (5-17% EtOAc in petroleum ether) to provide 1-(2-amino-5-chloro-4-methoxy-phenyl)propan-1-one (3.2 g).

Step 3: A solution of $NaNO_2$ (1.0 g, 15 mmol) in 10 mL of $H_2O$ was added slowly to a mixture of 1-(2-amino-5-chloro-4-methoxy-phenyl)propan-1-one (3.2 g, 15 mmol), $H_2O$ (6 mL), and conc. HCl (45 mL) at −5° C. After addition, the mixture was stirred for 1 h and then at 50° C. for 3 h. The resulting precipitate was filtered and washed with water (50 mL×2) to provide 6-chloro-7-methoxy-3-methyl-cinnolin-4-ol (2.5 g).

Step 4: A mixture of 6-chloro-7-methoxy-3-methyl-cinnolin-4-ol (2.5 g, 11 mmol), $SOCl_2$ (25 mL, 0.35 mol), DMF (40 mg, 0.55 mol) was stirred at 80° C. for 2 h, then was concentrated to provide 4,6-dichloro-7-methoxy-3-methyl-cinnoline hydrochloride (3.2 g).

Synthesis of Intermediate 1-(3-((4-hydroxyphenyl)thio)azetidin-1-yl)ethan-1-one

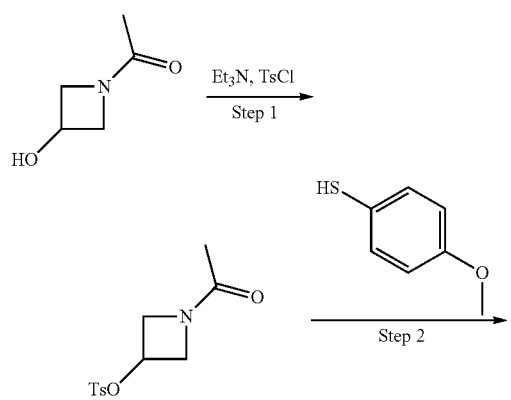

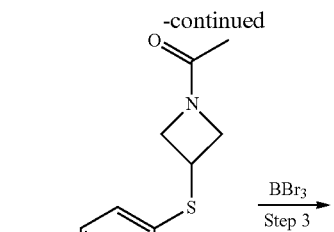

Step 1: To a 0° C. mixture of 1-(3-hydroxyazetidin-1-yl)ethanone (2.0 g, 17 mmol), $CH_2Cl_2$ (20 mL) was added $Et_3N$ (7.3 mL, 52 mmol) and toluene sulfonyl chloride (5.0 g, 26 mmol). The mixture was stirred at 20° C. for 2 h, then was poured into water (30.0 mL) and extracted with EtOAc (2×30 mL). The combined extracts were washed with brine (10.0 mL), dried over $Na_2SO_4$, concentrated and purified by silica chromatography (0-100% EtOAc/petroleum ether) to provide (1-acetylazetidin-3-yl) 4-methylbenzenesulfonate (4.35 g).

Step 2: A degassed mixture of (1-acetylazetidin-3-yl) 4-methylbenzenesulfonate (2.0 g, 7.4 mmol), DMSO (20 mL), $Cs_2CO_3$ (4.8 g, 15 mmol) and 4-methoxybenzenethiol (1.8 mL, 15 mmol) was stirred at 60° C. for 12 h under an $N_2$ atmosphere. The mixture was poured into water (30.0 mL) and extracted with EtOAc (30.0 mL×2). The combined extracts were washed with brine (20.0 mL×2), dried over $Na_2SO_4$, filtered, concentrated, and purified by silica chromatography (0-100% EtOAc/petroleum ether) to provide 1-[3-(4-methoxyphenyl)sulfanylazetidin-1-yl]ethanone (1.5 g).

Step 3: To a degassed −78° C. mixture of 1-[3-(4-methoxyphenyl)sulfanylazetidin-1-yl]ethanone (1.4 g, 6.0 mmol) and $CH_2Cl_2$ (20 mL) was added $BBr_3$ (2.9 mL, 30 mmol). The mixture was stirred at 25° C. for 12 h under an $N_2$ atmosphere, MeOH (5.0 mL) added slowly, and the resulting mixture was concentrated, combined with water (10 mL), and extracted with EtOAc (10.0 mL×2). The combined extracts were washed with aqueous of $NaHCO_3$ (10 mL×2), dried over $Na_2SO_4$, filtered, and concentrated to provide 1-(3-((4-hydroxyphenyl)thio)azetidin-1-yl)ethan-1-one (1.4 g, 78% purity).

Synthesis of Intermediate 6-(methylthio)pyridin-3-ol

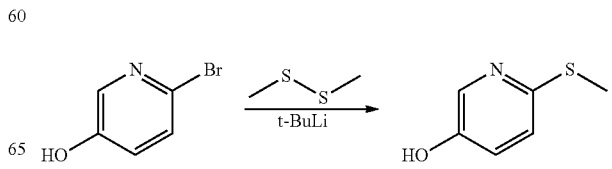

A solution of t-BuLi (1.9 M, 3.2 mL, 6.0 mmol) was added dropwise to 2-bromo-5-hydroxypyridine (0.35 g, 2.0 mmoL) and 10 mL of THF at −78° C. The mixture was stirred for 10 min at −78 C and dimethyldisulfide (0.36 mL, 4.0 mmol) was added slowly. The resulting mixture was stirred for 15 min, then warmed to room temperature and stirred for 2 h. Saturated aqueous NH₄Cl and 2M HCl were added until a pH of 3 was achieved. The phases were separated, and the aqueous phase was extracted with EtOAc (3×). The initial organic phase was combined with the EtOAc extracts, dried over Na₂SO₄, filtered, and concentrated to provide 6-(methylthio)pyridin-3-ol (0.22 g, 1.5 mmol).

Synthesis of Intermediate 4-(cyclopropylthio)phenol

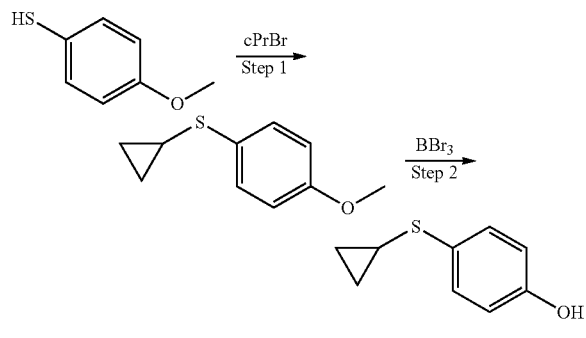

Step 1: A mixture of 4-methoxybenzenethiol (0.37 g, 2.6 mmol), K₂CO₃ (0.54 g, 3.9 mmol), DMF (5 mL), and cyclopropyl bromide (0.27 mL, 3.4 mmol) was heated to 120° C. under and Ar atmosphere overnight. After cooling, cold water and EtOAc were added. The organic phase was separated and washed with cold water (4×) and brine. The organic layer was dried over Na₂SO₄, filtered, concentrated, then purified by chromatography on silica get (1-25% EtOAc in heptane) to obtain 0.38 g of cyclopropyl(4-methoxyphenyl)sulfane.

Step 2: To a mixture of cyclopropyl(4-methoxyphenyl) sulfane (0.36 g, 2.0 mmol) and CH₂Cl₂ (50 mL) at 5° C. was added BBr₃ (1M in CH₂Cl₂, 11 mL, 11 mmol). After stirring for 2 days at room temperature, additional BBr₃ (1M in CH₂Cl₂, 11 mL, 11 mmol) was added and the mixture stirred overnight. Saturated aqueous NaHCO₃ was added (15 mL) followed by water, and the mixture was extracted with CH₂Cl₂ (3×). The combined extracts were dried over Na₂SO₄, filtered and concentrated to provide 0.33 g of 4-(cyclopropylthio)phenol.

Synthesis of Intermediate (3-fluoro-5-(methylthio)phenyl)methanol

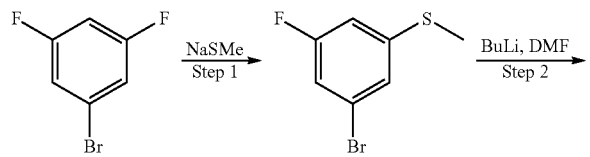

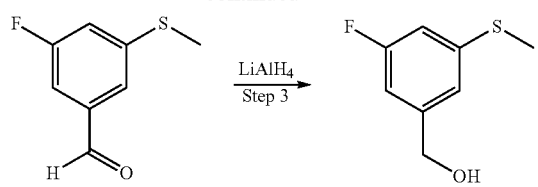

Step 1: A mixture of 1-bromo-3,5-difluoro-benzene (3.0 mL, 26 mmol), DMF (30 mL), and 93% NaSMe (1.8 mL, 26 mmol) was stirred at 20° C. for 12 h. The mixture was poured into saturated aqueous of NH₄Cl (50 mL) and extracted with EtOAc (50 mL×2). The combined extracts were washed with brine (20 mL×2), dried over Na₂SO₄, filtered, concentrated, and purified by silica chromatography (0 ~20% EtOAc/petroleum ether) to provide 1-bromo-3-fluoro-5-methylsulfanylbenzene (2.8 g).

Step 2: BuLi (1.6 M, 5.4 mL) was added to 1-bromo-3-fluoro-5-methylsulfanylbenzene (1.9 g, 8.6 mmol) in THF (10 mL) at −78° C., and the mixture was stirred at −78° C. for 15 min. DMF (0.79 mL, 10 mmol) was added and the mixture was stirred at −78° C. for 0.5 h. Saturated aqueous NH₄Cl (10 mL) was added at −78° C. and then the mixture was stirred at 25° C. for 30 min and was extracted with EtOAc (20 mL×3). The combined extracts were washed with brine (20 mL), dried over Na₂SO₄, filtered, concentrated and purified by silica chromatography (0-35% EtOAc/petroleum ether) to provide 3-fluoro-5-methylsulfanyl-benzaldehyde (0.79 g).

Step 3: LiAlH4 (0.25 g, 6.5 mmol) was added to 3-fluoro-5-methylsulfanyl-benzaldehyde (0.74 g, 4.4 mmol) in THF (20 mL) at 0° C. The mixture was stirred at 20° C. for 2 h, and 0.25 mL of H₂O, aqueous NaOH (15%, 0.25 mL), and an additional 0.25 mL of H₂O were added slowly in sequence. The mixture was stirred at 20° C. for 10 min then extracted with EtOAc (10 mL×2). The combined extracts were dried over Na₂SO₄, filtered, concentrated and purified by silica chromatography (0-70% EtOAc/petroleum ether) to provide (3-fluoro-5-(methylthio)phenyl)methanol (0.47 g).

Synthesis of Intermediate (4-(methylthio)furan-2-yl)methanol

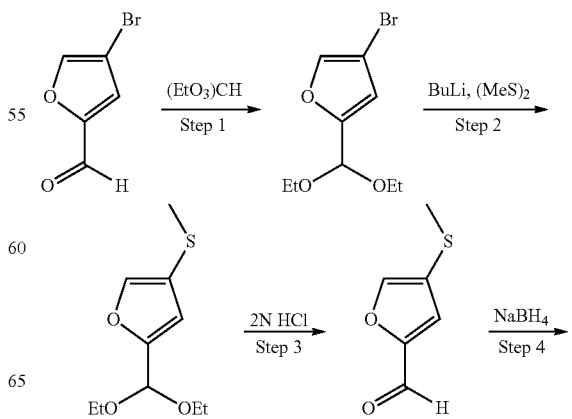

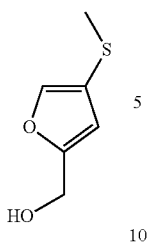

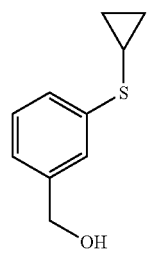

Step 1: A mixture of 4-bromofuran-2-carbaldehyde (5.0 g, 29 mmol), EtOH (9 mL), ethyl orthoformate (6.6 g, 45 mmol), and NH₄Cl (1.5 g, 29 mmol) was stirred at 90° C. for 12 h. The mixture was concentrated, combined with 20 mL of H₂O, and extracted with EtOAc (2×20 mL). The combined extracts were washed with saturated NaHCO₃ (10 mL) and brine (10 mL), dried over Na₂SO₄, filtered, concentrated, and purified by silica chromatography (5-10% EtOAc in petroleum ether) to provide 4-bromo-2-(diethoxymethyl) furan (6.4 g, 26 mmol).

Step 2: A solution of n-BuLi (2.5 M, 3.8 mL, 9.5 mmol) was slowly added to a stirring mixture of 4-bromo-2-(diethoxymethyl)furan (2.0 g, 8.0 mmol) and THF (20 mL) at −70° C. The mixture was stirred at −70° C. for 0.5 h, and (methyldisulfanyl)methane (0.91 g, 9.6 mmol) in THF (2 mL) was added. The mixture was poured to sat NH₄Cl (30 mL) and extracted with EtOAc (2×30 mL). The combined extracts were washed with brine (10 mL), dried over Na₂SO₄, filtered, and concentrated to provide 2-(diethoxymethyl)-4-methylsulfanyl-furan (1.7 g) that was used without further purification.

Step 3: A mixture of 2-(diethoxymethyl)-4-methylsulfanyl-furan (1.7 g, 7.9 mmol), THF (20 mL), and 2M HCl (20 mL, 40 mmol) was stirred at 20° C. for 0.5 h, then was poured into water (30 mL) and extracted with EtOAc (2×30 mL). The combined extracts were washed with brine (10 mL), dried over Na₂SO₄, and concentrated to provide 4-methylsulfanylfuran-2-carbaldehyde (1.1 g) that was used without purification.

Step 4: To a mixture of 4-methylsulfanylfuran-2-carbaldehyde (1.1 g, 7.7 mmol) and MeOH (10 mL) was added NaBH₄ (590 mg, 15 mmol). The mixture was stirred at 25° C. for 1 h, then was concentrated, combined with H₂O (30 mL), and extracted with EtOAc (2×30 mL). The extracts were combined, washed with brine (10 mL), dried over Na₂SO₄, filtered, concentrated, and purified by silica chromatography (10-100% EtOAc in petroleum ether) to provide (4-(methylthio)furan-2-yl)methanol (0.7 g).

Synthesis of Intermediate
(3-cyclopropylsulfanylphenyl) methanol

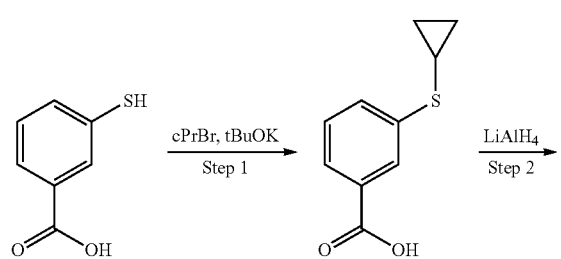

Step 1: A mixture of 3-sulfanylbenzoic acid (2.0 g, 13 mmol), DMSO (20 mL), t-BuOK (3.6 g, 32 mmol) and bromocyclopropane (1.6 mL, 20 mmol) was stirred at 80° C. for 24 h. Aqueous HCl (1 M) was added to bring the pH to 2-3, and the mixture was extracted with EtOAc (20 mL×2). The combined extracts were washed with brine (20 mL), dried over Na₂SO₄, filtered, and concentrated to provide 3-cyclopropylsulfanylbenzoic acid (2.4 g).

Step 2: To LiAlH₄ (0.86 g, 23 mmol) and THF (10 mL) was added slowly 3-cyclopropylsulfanylbenzoic acid (2.2 g, 11 mmol) in THF (20 mL) at 0° C. The mixture was stirred at 20° C. for 12 h and H₂O (1 mL) was added slowly, followed by 15% NaOH (1 mL) and H₂O (3 mL). The mixture was filtered, and the filtrate was concentrated, diluted with EtOAc (20 mL), washed with brine (10 mL), dried over Na₂SO₄, filtered, concentrated, and purified by silica chromatography (33-50% EtOAc in petroleum ether) to provide (3-cyclopropylsulfanylphenyl) methanol (2.0 g).

Synthesis of Intermediate 1
methylthio)phenyl)ethan-1-ol

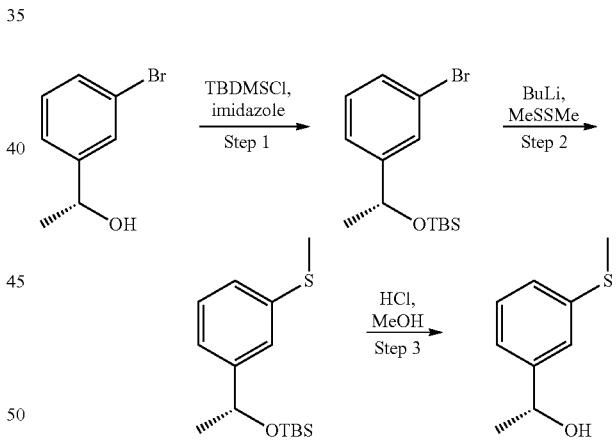

Step 1: A degassed mixture of (1R)-1-(3-bromophenyl) ethanol (5.0 g, 25 mmol), TBDMSCl (4.5 g, 30 mmol), imidazole (2.4 g, 35 mmol), and DMF (50 mL) was stirred at 20° C. for 16 h under an N₂ atmosphere. The reaction was poured into water (60 mL) and extracted with EtOAc (2×60 mL). The organic phase was washed with brine (60 mL), dried over Na₂SO₄, concentrated, and purified by silica chromatography (10-20% EtOAc in Petroleum ether) to provide [(1R)-1-(3-bromophenyl)ethoxy]-tert-butyl-dimethylsilane (7 g).

Step 2: A solution of BuLi (2.5 M, 13 mL) was added slowly to [(1R)-1-(3-bromophenyl)ethoxy]-tert-butyl-dimethyl-silane (7.0 g, 22 mmol) in THF (50 mL) at −78° C. After addition, the mixture was stirred for 30 min and 1,2-dimethyldisulfane (2.2 mL, 24 mmol) was added slowly at −78° C. The resulting mixture was stirred at 20° C. for 2 h, poured into saturated aqueous NH$_4$Cl (50 mL), and extracted with EtOAc (50 mL×2). The combined extracts were washed with brine, dried over Na$_2$SO$_4$, filtered, and concentrated to provide tert-butyl-dimethyl-[(1R)-1-(3-methylsulfanylphenyl)ethoxy]silane (6.5 g).

Step 3: A mixture of tert-butyl-dimethyl-[(1R)-1-(3-methylsulfanylphenyl)ethoxy]silane (6.5 g, 23 mmol), EtOH (50 mL), and HCl (2 M, 50 mL) was stirred at 20° C. for 2 h. The mixture was concentrated and extracted with EtOAc (2×30 mL). The combined extracts were washed with brine (20 mL), dried over Na$_2$SO$_4$, concentrated, and purified by silica chromatography (10-25% EtOAc in petroleum ether) to provide (R)-1-(3-(methylthio)phenyl)ethan-1-ol (2.7 g).

Synthesis of Intermediate (1r,4r)-4-(methylthio)cyclohexan-1-ol

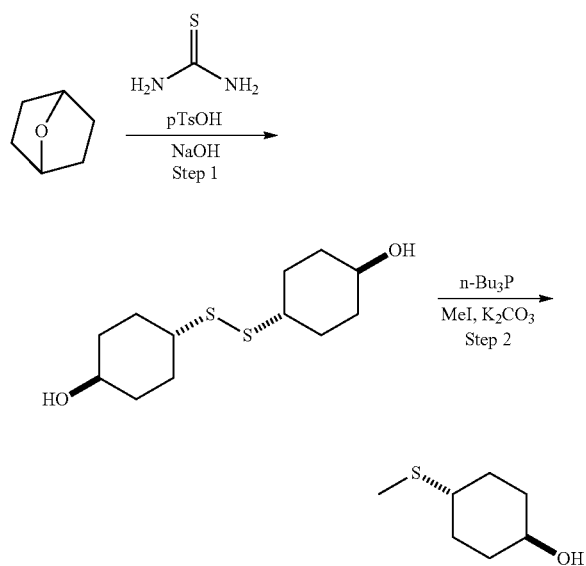

Step 1: A degassed mixture of 7-oxabicyclo[2.2.1]heptane (1.0 g, 10 mmol), thiourea (1.2 g, 15 mmol), p-TsOH (2.9 g, 17 mmol), EtOH (10 mL) was stirred at 90° C. for 12 h. NaOH (1.3 g, 33 mmol) and H$_2$O (3 mL) were added and the mixture was stirred at 90° C. for 2 h, then was concentrated, combined with H$_2$O (20 mL) and extracted with EtOAc (2×20 mL). The extracts were washed with brine (10 mL), dried over Na$_2$SO$_4$, filtered, concentrated, and purified by silica chromatography (20-50% EtOAc in petroleum ether) to provide 4-[(4-hydroxycyclohexyl)disulfanyl]cyclohexanol (0.5 g).

Step 2: To a mixture of 4-[(4-hydroxycyclohexyl)disulfanyl]cyclohexanol (0.4 g, 1.5 mmol), THF (8 mL), and H$_2$O (0.2 mL) was added Bu$_3$P (0.34 g, 1.7 mmol). To the solution was added MeI (0.86 g, 6.1 mmol) and K$_2$CO$_3$ (1.3 g, 9.1 mmol). The mixture was stirred at 25° C. for 12 h, poured into H$_2$O (30 mL) and the resulting mixture was extracted with EtOAc (2×30 mL), washed with brine (10 mL), dried over anhydrous Na$_2$SO$_4$, concentrated, and purified by silica chromatography (20-50% EtOAc in petroleum ether) to afford (1r,4r)-4-(methylthio)cyclohexan-1-ol (0.22 g).

Synthesis of Intermediate (1r,4s)-4-(methylthio)cyclohexan-1-ol

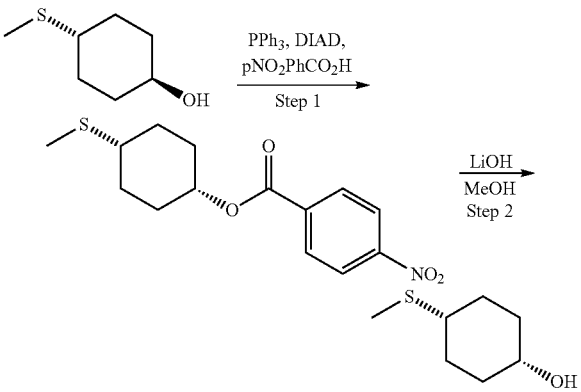

Step 1: To a mixture of (1r,4r)-4-(methylthio)cyclohexan-1-ol (0.70 g, 4.8 mmol), 4-nitrobenzoic acid (1.2 g, 7.2 mmol), PPh$_3$ (2.5 g, 9.6 mmol), and THF (30 mL) was added DIAD (1.9 g, 9.6 mmol). The mixture was stirred at 20° C. for 12 h, poured into H$_2$O (30 mL), and extracted with EtOAc (2×30 mL). The combined extracts were washed with brine (10 mL), dried over Na$_2$SO$_4$, concentrated, and purified by silica chromatography (5-17%, EtOAc in petroleum ether) to provide (1s,4s)-4-(methylthio)cyclohexyl 4-nitrobenzoate (1.1 g).

Step 2: A mixture of (1s,4s)-4-(methylthio)cyclohexyl 4-nitrobenzoate (0.90 g, 3.0 mmol) in THF (9.0 mL), H$_2$O (3.0 mL), and LiOH H$_2$O (0.64 g, 15 mmol) was stirred at 20° C. for 2 h. The mixture was poured into water (30 mL) and extracted with EtOAc (2×30 mL). The combined extracts were washed with brine (10 mL), dried over Na$_2$SO$_4$, concentrated, and purified by silica chromatography (10-50% EtOAc in petroleum ether) to provide (1r,4s)-4-(methylthio)cyclohexanol (0.50 g).

Synthesis of Intermediate 6-((methylthio)methyl)-2-azaspiro[3.3]heptane trifluoroacetate

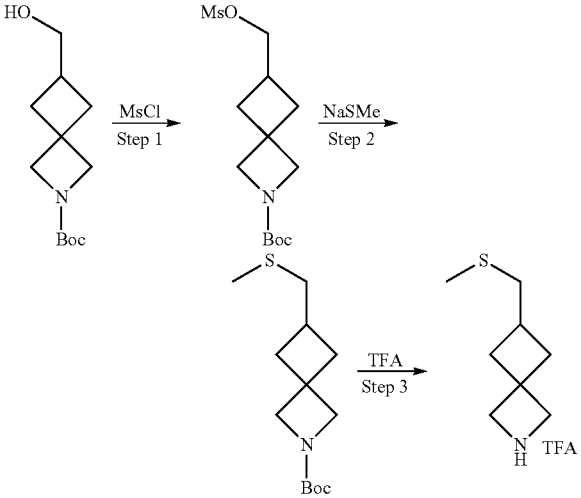

Step 1: To a mixture of tert-butyl 6-(hydroxymethyl)-2-azaspiro[3.3]heptane-2-carboxylate (6.0 g, 26 mmol) and CH$_2$Cl$_2$ (30 mL) was added slowly Et$_3$N (5.3 g, 53 mmol) and MsCl (3.6 g, 32 mmol) at 0° C. The mixture was stirred at 20° C. for 2 h, poured into saturated aqueous NaHCO$_3$ (100 mL), and extracted with EtOAc (2×100 mL). The combined extracts were washed with brine (50 mL), dried over Na$_2$SO$_4$, and concentrated to provide tert-butyl 6-(methylsulfonyloxymethyl)-2-azaspiro[3.3]heptane-2-carboxylate (12 g).

Step 2: To a mixture of tert-butyl 6-(methylsulfonyloxymethyl)-2-azaspiro[3.3]heptane-2-carboxylate (5.0 g, 16 mmol) in EtOH (50 mL) was added 20% aqueous NaSMe (10 mL, 33 mmol). The mixture was stirred at 25° C. for 2 h, then was concentrated, and extracted with EtOAc (2×30 mL). The combined extracts were washed with brine (30 mL), dried over Na$_2$SO$_4$, concentrated, and purified by silica chromatography (17%-50% EtOAc in petroleum ether) to provide tert-butyl 6-(methylsulfanylmethyl)-2-azaspiro[3.3]heptane-2-carboxylate (3.6 g).

Step 3: TFA (14 mL, 190 mmol) was added to a mixture of tert-butyl 6-(methylsulfanylmethyl)-2-azaspiro[3.3]heptane-2-carboxylate (3.6 g, 14 mmol) and CH$_2$Cl$_2$ (20 mL). The mixture was stirred at 20° C. for 12 h and was concentrated to provide 6-((methylthio)methyl)-2-azaspiro[3.3]heptane trifluoroacetate (6.8 g).

Synthesis of Intermediate
2-(methylthio)-8-azaspiro[4.5]decane hydrochloride

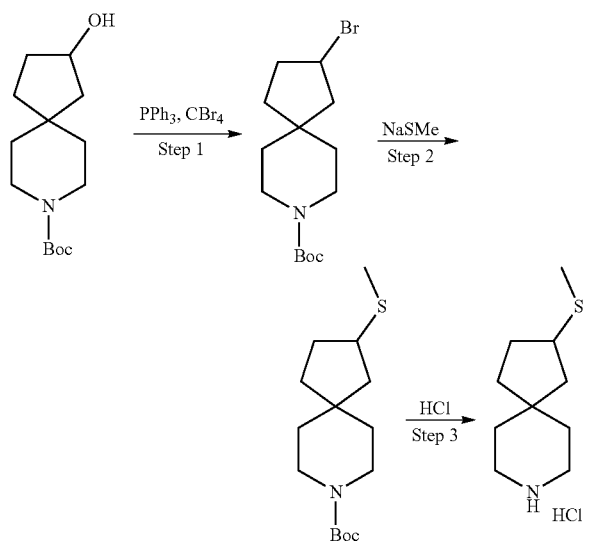

Step 1: To a 0° C. mixture of tert-butyl 3-hydroxy-8-azaspiro[4.5]decane-8-carboxylate (4.0 g, 16 mmol), CBr$_4$ (7.8 g, 24 mmol), and CH$_2$Cl$_2$ (50 mL) was added PPh$_3$ (6.2 g, 24 mmol). The mixture was stirred at 25° C. for 12 h, concentrated, and purified by silica chromatography (10-20% EtOAc in petroleum ether) to afford tert-butyl 3-bromo-8-azaspiro[4.5]decane-8-carboxylate (3.0 g).

Step 2: To a mixture of tert-butyl 3-bromo-8-azaspiro[4.5]decane-8-carboxylate (3.0 g, 9.4 mmol) and EtOH (20 mL) was added 20% sodium methanethiolate in H$_2$O (4.9 g, 14 mmol). The mixture was stirred at 25° C. for 2 h, concentrated to a small volume, poured into H$_2$O (30 mL) and extracted with EtOAc (2×30 mL). The organic phase was washed with brine (10 mL), dried over Na$_2$SO$_4$, filtered, and concentrated to provide tert-butyl 3-methylsulfanyl-8-azaspiro[4.5]decane-8-carboxylate (2.6 g).

Step 3: To a mixture of tert-butyl 3-methylsulfanyl-8-azaspiro[4.5]decane-8-carboxylate (0.26 mg, 0.91 mmol) and EtOAc (5.0 mL) was added HCl/EtOAc (4 M, 5.0 mL). The mixture was stirred at 25° C. for 2 h and concentrated to provide 2-(methylthio)-8-azaspiro[4.5]decane hydrochloride (200 mg).

Synthesis of Intermediate
4-(cyclopropylsulfanylmethyl)piperidine trifluoroacetate

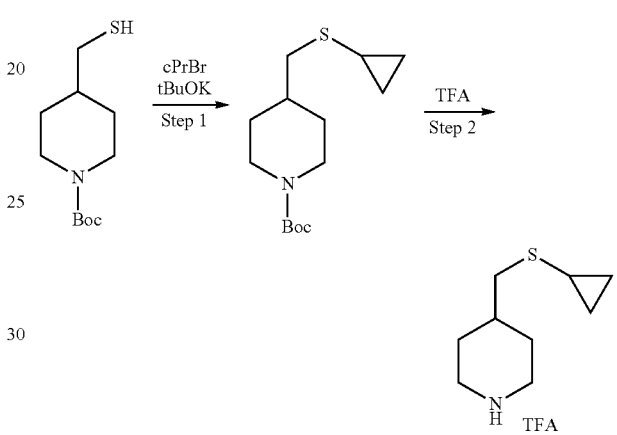

Step 1: A mixture of tert-butyl 4-(sulfanylmethyl)piperidine-1-carboxylate (1.0 g, 4.3 mmol) DMSO (15 mL), t-BuOK (1 M, 4.8 mL), and bromocyclopropane (0.58 g, 4.8 mmol) was stirred at 15° C. for 12 h. EtOAc (10 mL) was added, and the mixture was washed with H$_2$O (5 mL×3) and brine (5 mL), dried over Na$_2$SO$_4$, filtered, concentrated, and purified by silica chromatography (0-50% EtOAc in petroleum ether) to provide tert-butyl 4-(cyclopropylsulfanylmethyl)piperidine-1-carboxylate (0.55 g).

Step 2: To a mixture of tert-butyl 4-(cyclopropylsulfanylmethyl)piperidine-1-carboxylate (0.45 g, 1.7 mmol) and CH$_2$Cl$_2$ (4.5 mL) was added TFA (2.3 g, 20 mmol). The mixture was stirred at 15° C. for 2 h, then was concentrated, combined with toluene (10 mL) and then concentrated again to provide 4-(cyclopropylsulfanylmethyl)piperidine trifluoroacetate (0.45 g).

Synthesis of Intermediate
4-((methylthio)methyl)piperidin-4-ol

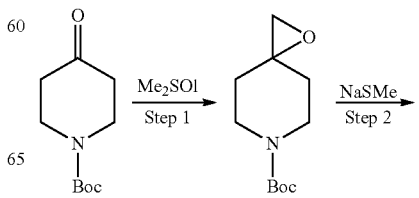

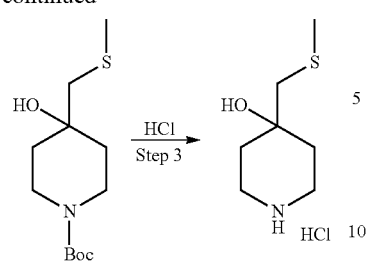

Step 1: To a mixture of 60% NaH (0.40 g, 10 mmol) and DMSO (10 mL) was added trimethyl sulfoxonium iodide (2.2 g, 10 mmol) at 20° C. After addition, the mixture was stirred for 2 h, and tert-butyl 4-oxopiperidine-1-carboxylate (2.0 g, 10 mmol) in DMSO (10 mL) was added slowly. The resulting mixture was stirred at 55° C. for 2 h, diluted with H₂O and extracted with MTBE (30 mL×2). The combined extracts were washed with brine (20 mL×2), dried over Na₂SO₄, filtered, and concentrated to provide tert-butyl 1-oxa-6-azaspiro[2.5]octane-6-carboxylate (2.2 g).

Step 2: To a mixture of tert-butyl 1-oxa-6-azaspiro[2.5]octane-6-carboxylate (1.5 g, 7.0 mmol) and EtOH (10 mL) was added 20% NaSMe in water (3.4 mL, 11 mmol). The mixture was stirred at 20° C. for 2 h, concentrated, diluted with H₂O (30 mL) and extracted with EtOAc (20 mL×2). The combined extracts were washed with brine (20 mL), dried over Na₂SO₄, filtered, and concentrated to provide tert-butyl 4-hydroxy-4-(methylsulfanylmethyl)piperidine-1-carboxylate (1.8 g).

Step 3: To a mixture of tert-butyl 4-hydroxy-4-(methylsulfanylmethyl)piperidine-1-carboxylate (1.8 g, 6.9 mmol) in EtOAc (8.0 mL) was added 4M HCl in EtOAc (4 M, 13 mL). The mixture was stirred at 20° C. for 2 h and concentrated to provide 4-(methylsulfanylmethyl)piperidin-4-ol hydrochloride (1.3 g).

Intermediates in Table 2 were prepared via route described in the synthesis of Intermediate 4-((methylthio)methyl)piperidin-4-ol by using the reagents indicated.

TABLE 2

| Intermediate Name | Structure | Thiol and Base (Step 2) | Acid (Step 3) |
|---|---|---|---|
| 4-((ethylthio)methyl)piperidin-4-ol | 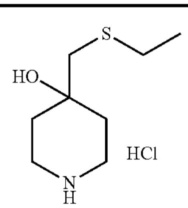 | Ethanethiol, Cs₂CO₃ | HCl/EtOAc |
| 4-((cyclopropylthio)methyl)piperidin-4-ol | 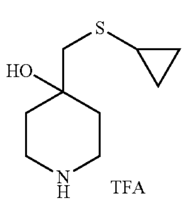 [SMILES: OC1(CSC2CC2)CCNCC1] | Cyclopropylthiol, NaH | TFA |

Synthesis of Intermediate 4-((cyclobutylthio)methy)piperidin-4-ol hydrochloride

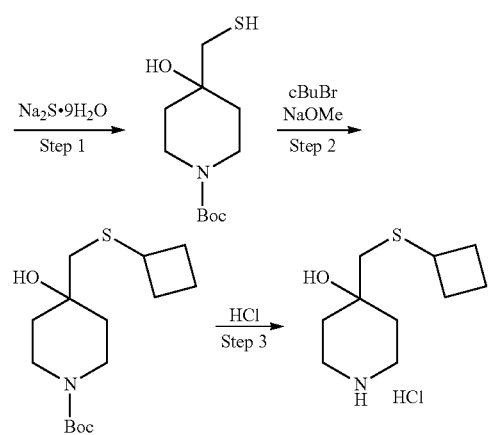

Step 1: A mixture of sodium sulfide nonahydrate (5.6 g, 23 mmol), MeOH (125 mL), TsOH hydrate (7.1 g, 38 mmol) was stirred under N₂ at 0° C. for 15 min. Tert-butyl-1-oxa-6-azaspiro[2.5]octane-6-carboxylate (2.0 g, 9.4 mmol) in MeOH (10 mL) was then added and the mixture was stirred under N₂ at 0° C. for 1 h, then at 20° C. for 1 h. Saturated aqueous NaHCO₃ (40 mL) was added slowly at 0° C. followed by brine (40 mL), The mixture was extracted with EtOAc (50 mL×3), and the extracts were combined, washed with brine (40 mL×2), dried over Na₂SO₄, filtered, concentrated, and purified by silica chromatography (0-40% EtOAc in petroleum ether) to provide tert-butyl 4-hydroxy-4-(mercaptomethyl)piperidine-1-carboxylate (1.53 g).

Step 2: A mixture of tert-butyl 4-hydroxy-4-(mercaptomethyl)piperidine-1-carboxylate (1.2 g, 4.9 mmol), bromocyclobutane (0.60 g, 4.4 mmol), DMF (20 mL) and NaOMe (0.32 g, 5.9 mmol) was stirred at 50° C. for 5 h under an N₂ atmosphere. Saturated aqueous NH₄Cl (40 mL) was added dropwise at 0° C., followed by brine (40 mL). The mixture was extracted with EtOAc (50 mL×3) and the combined extracts were washed with water (40 mL×3) and brine (40 mL×2), dried over Na₂SO₄, filtered, concentrated, and purified by silica chromatography (0-30% EtOAc in petroleum ether) to provide tert-butyl 4-((cyclobutylthio)methyl)-4-hydroxypiperidine-1-carboxylate (0.80 g).

Step 3: To a mixture of tert-butyl 4-((cyclobutylthio)methyl)-4-hydroxypiperidine-1-carboxylate (0.40 g, 1.3 mmol) and MeOH (6 mL) was added HCl/MeOH (4M, 6.9 mL). The mixture was stirred at 20° C. for 5 h, concentrated to give 4-((cyclobutylthio)methyl)piperidin-4-ol hydrochloride (0.28 g).

Synthesis of Intermediate 8-((Methylthio)methyl)-5-azaspiro[2.5]octan-8-ol hydrochloride

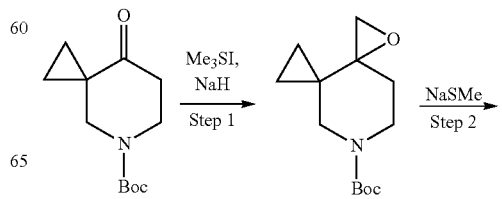

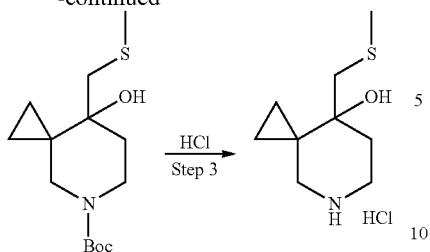

Step 1: A mixture of trimethylsulfonium iodide (2.5 g, 12 mmol), DMSO (25 mL), and 60% NaH (0.60 g, 15 mmol) was stirred at 30° C. for 30 min and tert-butyl 8-oxo-5-azaspiro[2.5]octane-5-carboxylate (0.90 g, 4.0 mmol) in DMSO (5 mL) was added dropwise and the mixture was stirred at 20° C. for 12 h. Saturated aqueous NH₄Cl (5 mL) and water (50 mL) were added. The mixture was extracted with EtOAc (2×50 mL) and the extracts were combined, washed with water (40 mL×3), brine (40 mL×2), dried over Na₂SO₄, filtered, concentrated, and purified by silica chromatography (0-40% EtOAc in petroleum ether) to provide tert-butyl 5-oxa-9-azadispiro[2.0.2⁴.4³]decane-9-carboxylate (0.50 g).

Step 2: A mixture of tert-butyl 5-oxa-9-azadispiro[2.0.2⁴.4³]decane-9-carboxylate (0.50 g, 2.1 mmol), EtOH (20 mL), NaSMe (0.33 g, 4.5 mmol) was stirred at 20° C. for 5 h. Water (10 mL) was added, and the mixture was extracted with EtOAc (2×20 mL), the extracts were combined, washed with water (10 mL) and brine (10 mL), dried over Na₂SO₄, filtered, concentrated, and purified by silica chromatography (0-40% EtOAc in petroleum ether) to provide tert-butyl 8-hydroxy-8-((methylthio)methyl)-5-azaspiro[2.5]octane-5-carboxylate (0.50 g).

Step 3: A 0° C. mixture of tert-butyl 8-hydroxy-8-((methylthio)methyl)-5-azaspiro[2.5]octane-5-carboxylate (0.50 g, 1.7 mmol), MeOH (5 mL), and HCl (4 M in MeOH, 5 mL) was stirred as it warmed to 20° C. over 3 h. The mixture was concentrated to provide 8-((methylthio)methyl)-5-azaspiro[2.5]octan-8-ol hydrochloride (0.39 g).

Synthesis of Intermediate imino(methyl)(2-(piperidin-4-yl)ethyl)-λ⁶-sulfanone hydrochloride

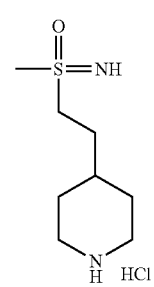

Step 1: PPh₃ (8.6 g, 32.8 mmol) and CBr₄ (10.9 g, 32.9 mmol) were added in portions into a solution of tert-butyl 4-(2-hydroxyethyl)piperidine-1-carboxylate (5.0 g, 21.8 mmol) in CH₂Cl₂ (50 mL). After stirring at 20° C. for 20 h, the mixture was washed with brine (20 mL×3), dried over Na₂SO₄, filtered, concentrated purified by silica gel chromatography (0-80% EtOAc/petroleum ether) to afford the tert-butyl 4-(2-bromoethyl)piperidine-1-carboxylate (6.0 g).

Step 2: To a solution of tert-butyl 4-(2-bromoethyl)piperidine-1-carboxylate (1.0 g, 3.4 mmol) in EtOH (15 mL) at 20° C. was added NaSMe (1.65 g, 4.7 mmol, 20% in water) dropwise and the mixture was stirred at 20° C. for 12 h, concentrated, and dissolved in 30 mL of EtOAc. The solution was washed with brine (10 mL×3) and concentrated and purified by silica gel chromatography (0-30% EtOAc/Petroleum ether) to afford tert-butyl 4-(2-(methylthio)ethyl)piperidine-1-carboxylate (730 mg).

Step 3: To a solution of tert-butyl 4-(2-(methylthio)ethyl)piperidine-1-carboxylate (300 mg, 1.2 mmol) in EtOH (12 mL) at 20° C. was added PhI(OAc)₂ (1.5 g, 4.7 mmol) and NH₄OAc (270 mg, 3.5 mmol). The mixture was stirred at 20° C. for 12 h, then concentrated, and purified by silica gel chromatography (0-100% of 33% of EtOH in EtOAc in petroleum ether) to afford the tert-butyl 4-(2-(methylsulfonimidoyl)ethyl)piperidine-1-carboxylate (310 mg).

Step 4: To a solution of tert-butyl 4-(2-(S-methylsulfonimidoyl)ethyl)piperidine-1-carboxylate (310 mg, 1.1 mmol) in EtOAc (1.5 mL) at 20° C. was added HCl/EtOAc (4 M, 1.24 mL). The mixture was stirred at 20° C. for 2 hours, then was concentrated to give 4-(2-(methylsulfonimidoyl)ethyl)piperidine as a hydrochloride salt (260 mg) that was used without purification.

Intermediates in Table 3 were prepared via the route described for the synthesis of Intermediate imino(methyl)(2-(piperidin-4-yl)ethyl)-λ⁶-sulfanone hydrochloride by using the thiol indicated.

TABLE 3

| Compound Name | Structure | Thiol |
|---|---|---|
| imino(methyl)(3-(piperidin-4-yl)propyl)-λ⁶-sulfanone | 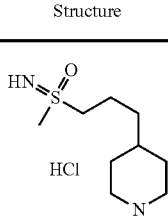 | 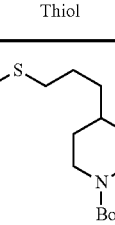 |

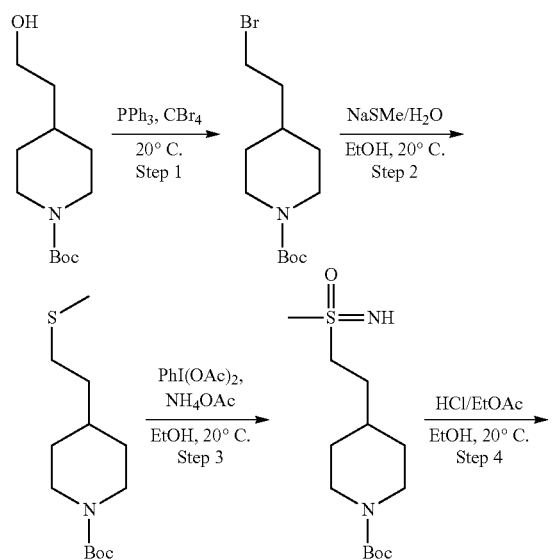

TABLE 3-continued

| Compound Name | Structure | Thiol |
|---|---|---|
| (4-(aminomethyl)phenyl)(imino)(methyl)-λ⁶-sulfanone | ![structure] | ![thiol] |
| ((4-hydroxypiperidin-4-yl)methyl)(imino)(methyl)-λ⁶-sulfanone | ![structure] | ![thiol] |

Synthetic Example S-1

Synthesis of (4-((6,7-dimethoxyquinolin-4-yl)oxy)phenyl)(imino)(methyl)-$\lambda^6$-sulfanone (Compound 1)

Step 1: Synthesis of 6,7-dimethoxy-4-(4-(methylthio)phenoxy)quinoline

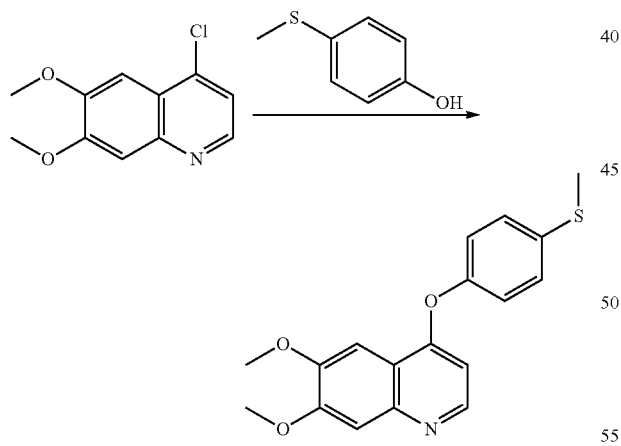

A mixture of 4-chloro-6,7-dimethoxyquinoline (500 mg, 2.24 mmol) and 4-(methylsulfanyl)phenol (942 mg, 3 eq., 6.72 mmol) was heated at 170° C. for 1 hour. The residue was diluted with saturated $Na_2CO_3$ (50 mL)/MeOH (15 mL) and extracted with EtOAc (50 mL×3). The combined organic layers were washed with brine (20 mL), dried over $Na_2SO_4$, filtered and concentrated. Purification by silica gel chromatography (0-50% EtOAc/Petroleum Ether) delivered 6,7-dimethoxy-4-(4-(methylthio)phenoxy)quinoline (400 mg, 1.15 mmol).

Step 2: Synthesis of (4-((6,7-dimethoxyquinolin-4-yl)oxy)phenyl)(imino)(methyl)-$\lambda^6$-sulfanone

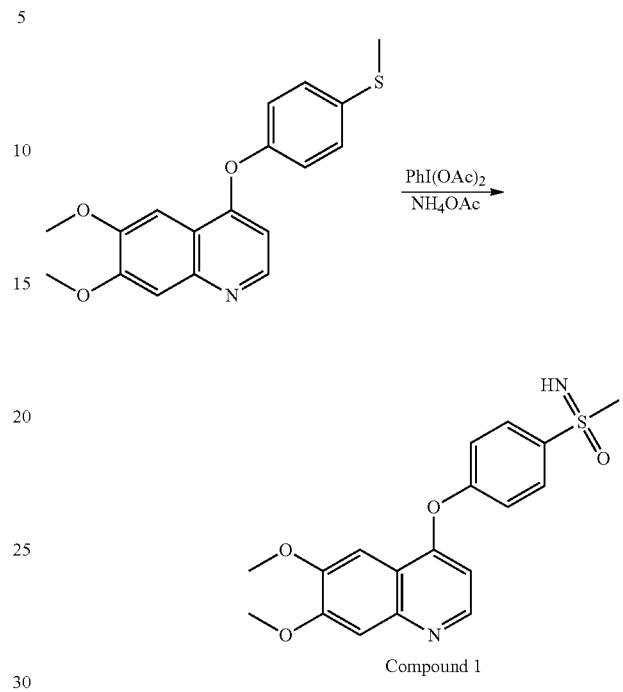

Compound 1

To a solution of 6,7-dimethoxy-4-(4-(methylthio)phenoxy)quinoline (106 mg, 0.31 mmol) in EtOH (2 mL) were added $NH_4OAc$ (94.0 mg, 1.2 mmol) and $PhI(OAc)_2$ (295 mg, 3 eq., 916 μmol). The mixture was stirred at 20° C. for 12 h. The mixture was poured into $H_2O$ (50 mL) and extracted with EtOAc (20 mL×3). The organic phase was washed with brine (50 mL), dried over $Na_2SO_4$, filtered and concentrated. Purification by prep-HPLC (15-35% [10 mM $NH_4HCO_3$] in MeCN in water) afforded of (4-((6,7-dimethoxyquinolin-4-yl)oxy)phenyl)(imino)(methyl)-$\lambda^6$-sulfanone (Compound 1) (60 mg). ESI m/z: 359.1 (M+H). $^1$H NMR (400 MHz, DMSO-d6) δ: 8.56 (d, J=5.1 Hz, 1H), 8.02 (d, J=8.6 Hz, 2H), 7.45-7.40 (m, 4H), 6.69 (d, J=5.1 Hz, 1H), 4.28 (s, 1H), 3.95 (s, 3H), 3.90 (s, 3H), 3.10 (s, 3H).

Synthetic Example S-2

Synthesis of {4-[(6-fluoro-7-methoxyquinolin-4-yl)oxy]phenyl}(imino)methyl-$\lambda^6$-sulfanone (Compound 114)

Step 1: Synthesis of 6-fluoro-7-methoxy-4-(4-(methylthio)phenoxy)quinoline

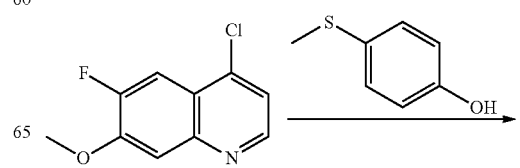

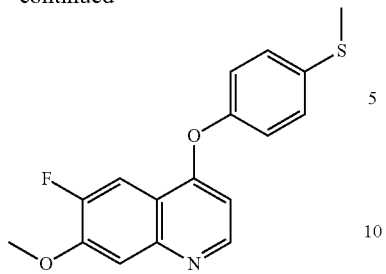

A mixture of 4-chloro-6-fluoro-7-methoxy-quinoline (2.0 g, 9.5 mmol) and 4-methylsulfanylphenol (2.7 g, 19 mmol) was degassed and purged with $N_2$, and then the mixture was stirred at 170° C. for 2 hours under an $N_2$ atmosphere. The mixture was combined with EtOAc (80 mL) and washed with NaOH (1N, 30 mL×4). The organic phase was washed with brine (20 mL×2), dried over $Na_2SO_4$, filtered and concentrated to provide 6-fluoro-7-methoxy-4-(4-methylsulfanylphenoxy)quinoline (2.0 g).

Step 2: Synthesis of {4-[(6-fluoro-7-methoxyquinolin-4-yl)oxy]phenyl}(imino)methyl-$\lambda^6$-sulfanone

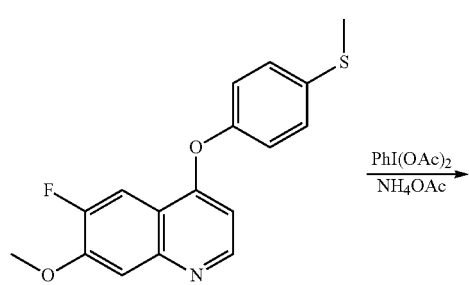

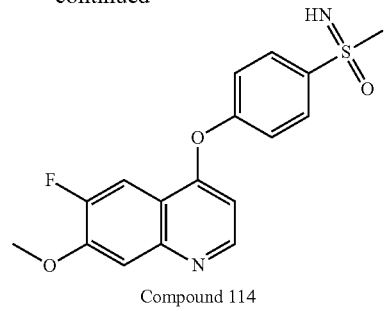

Compound 114

A mixture of 6-fluoro-7-methoxy-4-(4-methylsulfanylphenoxy)quinoline (1.2 g, 3.8 mmol), PhI(OAc)$_2$ (3.7 g, 11 mmol), NH$_4$OAc (1.2 g, 15 mmol), and EtOH (20 mL) was degassed and purged with $N_2$, and the mixture was stirred at 25° C. for 2 hours under an $N_2$ atmosphere. The mixture was concentrated and purified first by silica chromatography and then by preparative HPLC (column: Welch Xtimate C18 250*70 mm #10 um; mobile phase: [water (10 mM NH$_4$HCO$_3$)-ACN]; B %: 18%-48%, 25 min) to afford {4-[(6-fluoro-7-methoxyquinolin-4-yl)oxy]phenyl}(imino)methyl-$\lambda^6$-sulfanone (Compound 114) (0.42 g).

Compounds 10, 12, 18, 44, 75-80, 84, 103, 115-128 and 166-167 were prepared in a similar manner as Compound 1 in Example S-1 and Compound 114 in Example S-2 from the aryl chlorides and phenol derivatives indicated in Table 4.

TABLE 4

| Cmpd | Structure | Aryl Chloride | Alcohol | MS (m/z) |
|---|---|---|---|---|
| 10 | 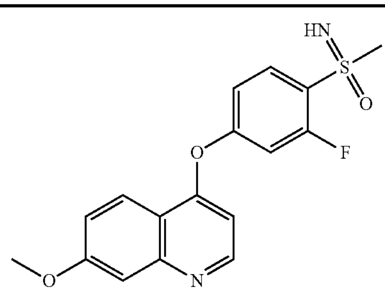 | | | 347.0 (M + H) |
| 12 | 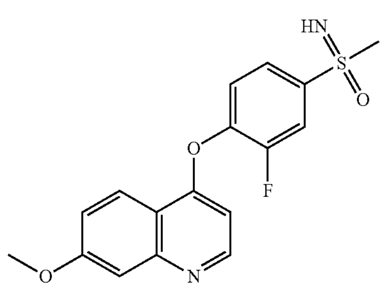 | | | 347.1 (M + H) |

TABLE 4-continued

| Cmpd | Structure | Aryl Chloride | Alcohol | MS (m/z) |
|---|---|---|---|---|
| 18 | 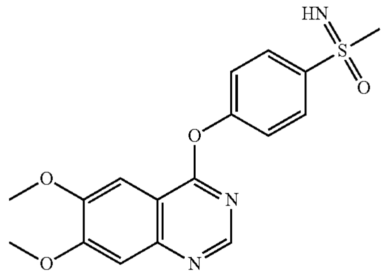 | | | 360.0 (M + H) |
| 44 | 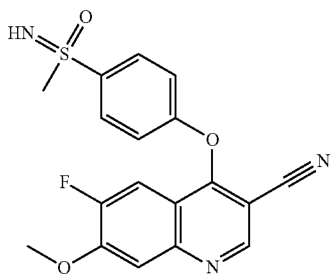 [SMILES: COc1cc2ncc(C#N)c(Oc3ccc(S(C)(=N)=O)cc3)c2cc1F] | | | 372.1 (M + H) |
| 78 | 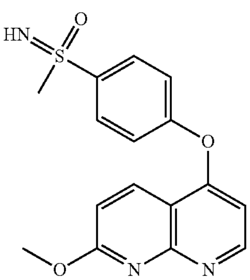 [SMILES: COc1ccc2c(Oc3ccc(S(C)(=N)=O)cc3)ccnc2n1] | | | 330.0 (M + H) |
| 79 | 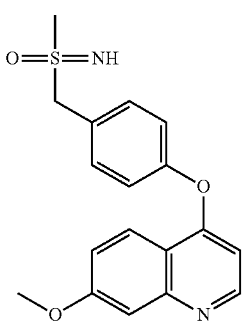 [SMILES: COc1ccc2c(Oc3ccc(CS(C)(=N)=O)cc3)ccnc2c1] | | | 343.0 (M + H) |
| 80 | 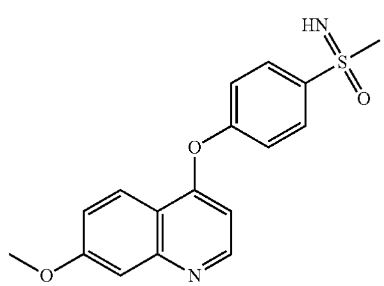 | | | 329.0 (M + H) |

TABLE 4-continued

| Cmpd | Structure | Aryl Chloride | Alcohol | MS (m/z) |
|---|---|---|---|---|
| 84 | 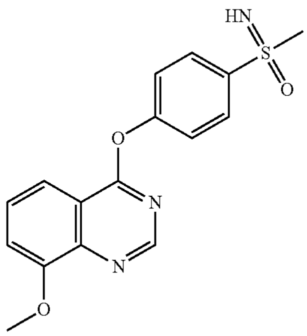 [SMILES: COc1cccc2c(Oc3ccc(S(C)(=N)=O)cc3)ncnc12] | | | 330.0 (M + H) |
| 103 | 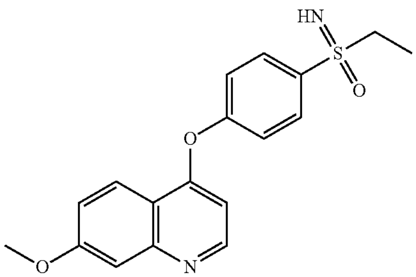 [SMILES: CCS(=N)(=O)c1ccc(Oc2ccnc3cc(OC)ccc23)cc1] | | | 343.0 (M + H) |
| 115 | 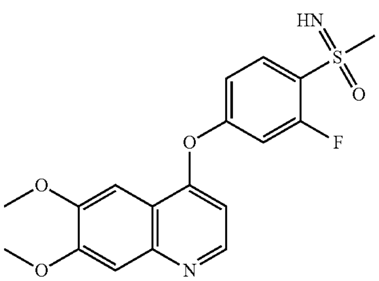 | | | 377.0 (M + H) |
| 116 | 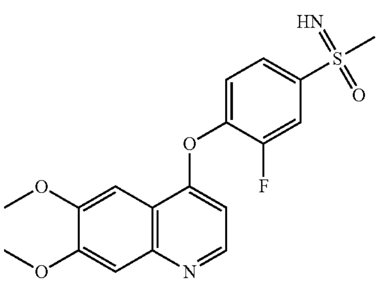 | | | 377.1 (M + H) |
| 117 | 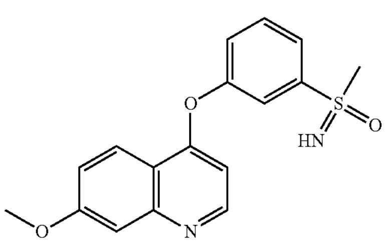 [SMILES: COc1ccc2c(Oc3cccc(S(C)(=N)=O)c3)ccnc2c1] | | | 329.1 (M + H) |

TABLE 4-continued

| Cmpd | Structure | Aryl Chloride | Alcohol | MS (m/z) |
|---|---|---|---|---|
| 118 | 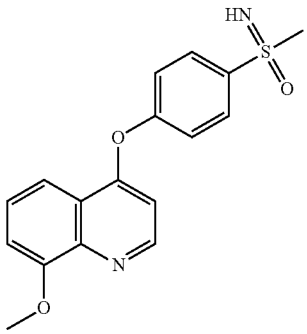 [SMILES: COc1cccc2c(Oc3ccc(S(C)(=N)=O)cc3)ccnc12] | | | 329.0 (M + H) |
| 119 | 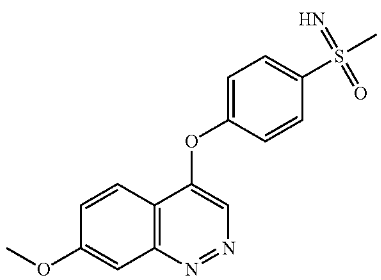 | | | 330.0 (M + H) |
| 120 | 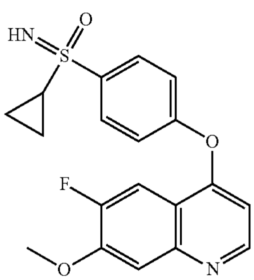 [SMILES: COc1cc2nccc(Oc3ccc(S(=N)(=O)C4CC4)cc3)c2cc1F] | | | 373.0 (M + H) |
| 121 | 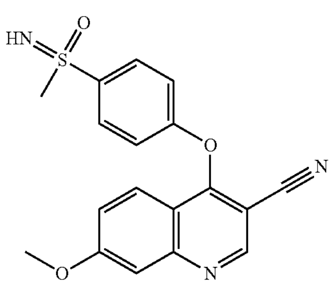 [SMILES: COc1ccc2c(Oc3ccc(S(C)(=N)=O)cc3)c(C#N)cnc2c1] | | | 354.1 (M + H) |
| 122 | 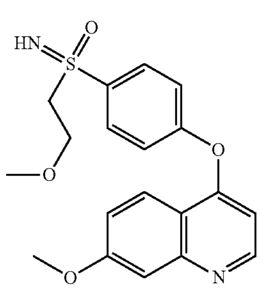 [SMILES: COCCS(=N)(=O)c1ccc(Oc2ccnc3cc(OC)ccc23)cc1] | | | 373.1 (M + H) |

TABLE 4-continued

| Cmpd | Structure | Aryl Chloride | Alcohol | MS (m/z) |
|---|---|---|---|---|
| 123 | 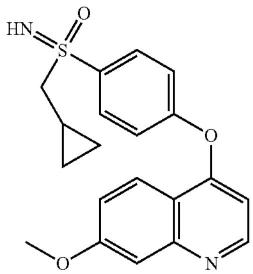 [SMILES: COc1ccc2c(Oc3ccc(S(=N)(=O)CC4CC4)cc3)ccnc2c1] | | | 369.0 (M + H) |
| 124 | 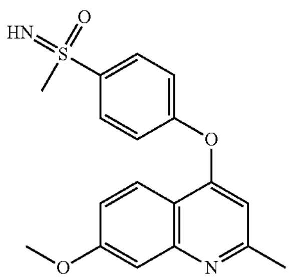 | | | 343.0 (M + H) |
| 125 | 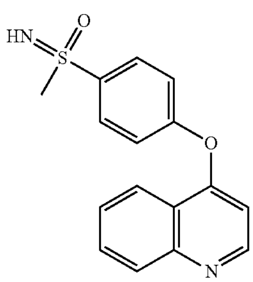 [SMILES: CS(=N)(=O)c1ccc(Oc2ccnc3ccccc23)cc1] | | | 299.0 (M + H) |
| 126 | 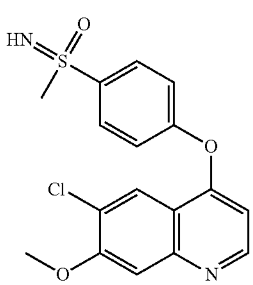 [SMILES: COc1cc2nccc(Oc3ccc(S(C)(=N)=O)cc3)c2cc1Cl] | | | 362.9 (M + H) |
| 127 | 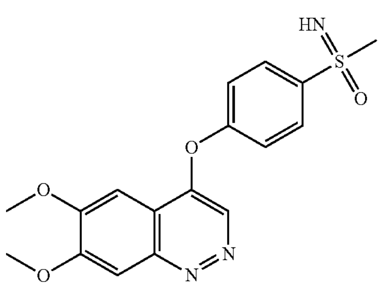 | | | 360.0 (M + H) |

TABLE 4-continued
| Cmpd | Structure | Aryl Chloride | Alcohol | MS (m/z) |
|---|---|---|---|---|
| 128 | 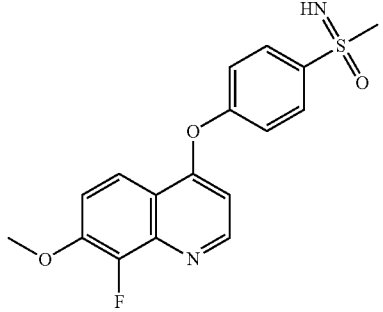 | 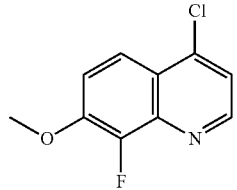 | 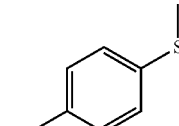 | 347.0 (M + H) |
| 166 | 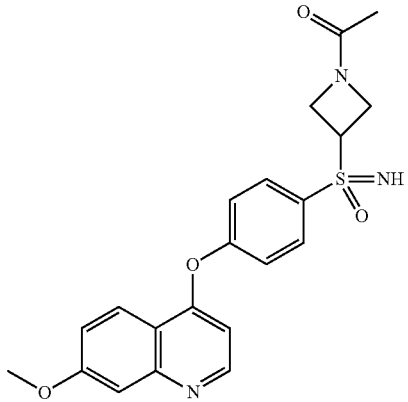 [SMILES: COc1ccc2c(Oc3ccc(S(=N)(=O)C4CN(C(C)=O)C4)cc3)ccnc2c1] | 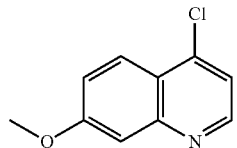 | 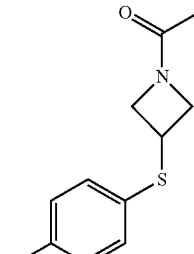 | 412.1 (M + H) |
| 167 | 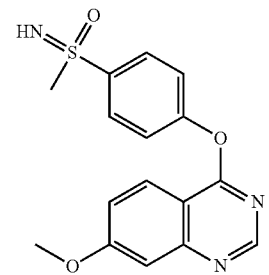 [SMILES: COc1ccc2c(Oc3ccc(S(C)(=N)=O)cc3)ncnc2c1] | 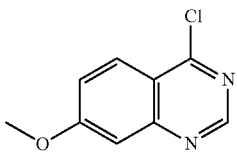 | 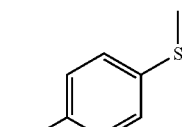 | 330.0 (M + H) |

Synthetic Example S-3

Synthesis of imino({5-[(7-methoxyquinolin-4-yl)oxy]pyridin-2-yl})methyl-$\lambda^6$-sulfanone (Compound 101)

Step 1: Synthesis of 7-methoxy-4-((6-(methylthio)pyridin-3-yl)oxy)quinoline

A mixture of 4-chloro-7-methyoxyquinoline (50 mg, 0.26 mmol), 6-(methylthio)pyridin-3-ol (44 mg, 0.31 mmol), $Cs_2CO_3$ (0.13 g, 0.39 mmol), and 2 mL of DMSO was stirred for 3 h at 100'° C. The mixture was directly purified by reverse phase HPLC (5-100%/MeCN in water (10 mM $NH_4HCO_3$)) to provide 7-methoxy-4-((6-(methylthio)pyridin-3-yl)oxy)quinoline (60 mg, 0.20 mmol).

Step 2: Synthesis of imino({5-[(7-methoxyquinolin-4-yl)oxy]pyridin-2-yl})methyl-$\lambda^6$-sulfanone

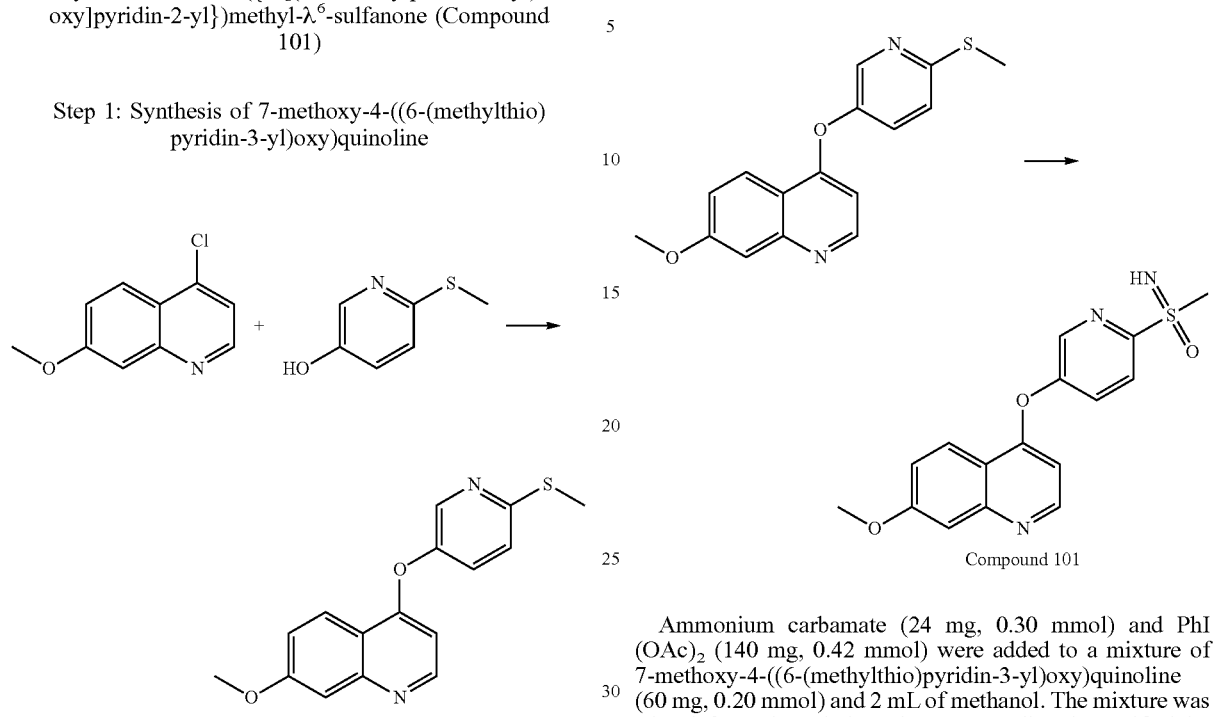

Compound 101

Ammonium carbamate (24 mg, 0.30 mmol) and PhI(OAc)$_2$ (140 mg, 0.42 mmol) were added to a mixture of 7-methoxy-4-((6-(methylthio)pyridin-3-yl)oxy)quinoline (60 mg, 0.20 mmol) and 2 mL of methanol. The mixture was stirred for 1 h and the mixture was directly purified by reverse phase HPLC (5-98% MeCN in water (10 mM $NH_4HCO_3$)) to provide imino({5-[(7-methoxyquinolin-4-yl)oxy]pyridin-2-yl})methyl-$\lambda^6$-sulfanone (Compound 101) (38 mg, 0.12 mmol). ESI MS m/z: 330.1 (M+H).

Compounds 22, 47, 50, 58, 60, 76, 77, 129-132, and 168 were prepared from the aryl chlorides, phenol derivatives, and bases indicated in Table 5 in the manner of steps 1 and 2 of Synthetic Example S-3.

TABLE 5

| Cmpd | Structure | Chloro Compound | Alcohol | Base | MS (m/z) |
|---|---|---|---|---|---|
| 22 | 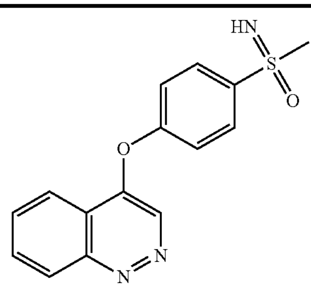 | | | $CsCO_3$ | 300.1 (M + H) |
| 47 | 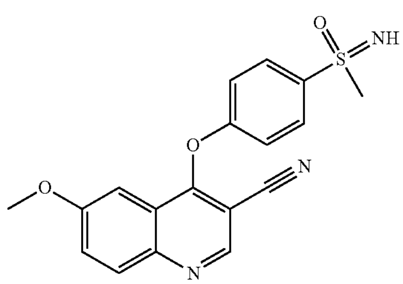 [SMILES: COc1ccc2ncc(C#N)c(Oc3ccc(S(C)(=N)=O)cc3)c2c1] | | | $K_2CO_3$ | 354.1 (M + H) |

TABLE 5-continued

| Cmpd | Structure | Chloro Compound | Alcohol | Base | MS (m/z) |
|---|---|---|---|---|---|
| 50 | 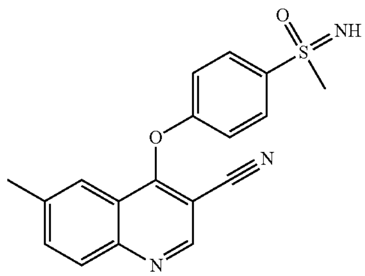 [SMILES: Cc1ccc2ncc(C#N)c(Oc3ccc(S(C)(=N)=O)cc3)c2c1] | | | K$_2$CO$_3$ | 338.1 (M + H) |
| 58 | 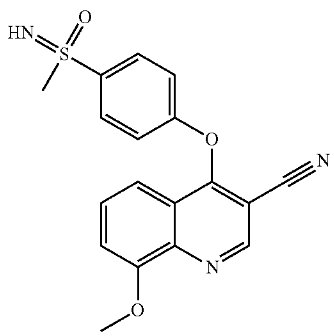 [SMILES: COc1cccc2c(Oc3ccc(S(C)(=N)=O)cc3)c(C#N)cnc12] | | | K$_2$CO$_3$ | 354.1 (M + H) |
| 60 | 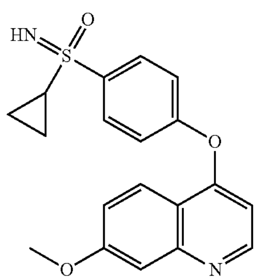 [SMILES: COc1ccc2c(Oc3ccc(S(=N)(=O)C4CC4)cc3)ccnc2c1] | | | CsCO$_3$ | 355.0 (M + H) |
| 76 | 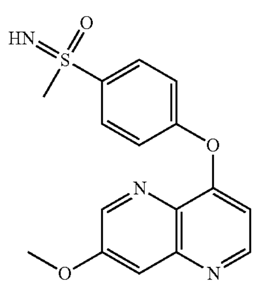 [SMILES: COc1cnc2c(Oc3ccc(S(C)(=N)=O)cc3)ccnc2c1] | | | CsCO$_3$ | 330.1 (M + H) |
| 77 | 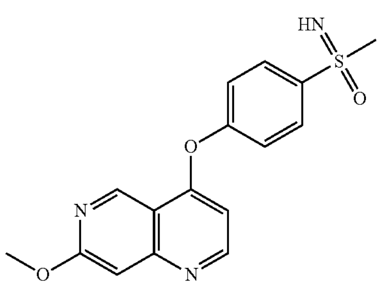 | | | CsCO$_3$ | 330.1 (M + H) |

TABLE 5-continued

| Cmpd | Structure | Chloro Compound | Alcohol | Base | MS (m/z) |
|---|---|---|---|---|---|
| 129 | 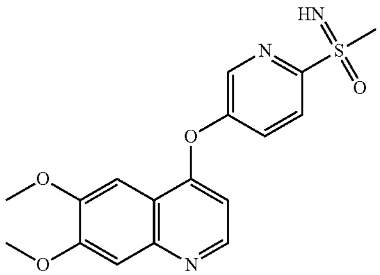 | | | CsCO₃ | 360.1 (M + H) |
| 130 | 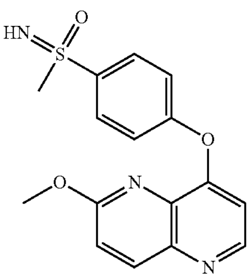 [SMILES: COc1ccc2nccc(Oc3ccc(S(C)(=N)=O)cc3)c2n1] | | | CsCO₃ | 330.1 (M + H) |
| 131 | 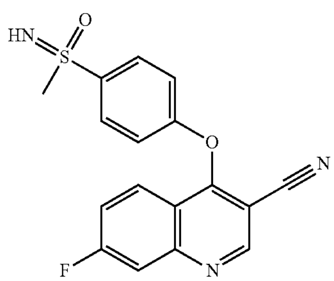 [SMILES: CS(=N)(=O)c1ccc(Oc2c(C#N)cnc3cc(F)ccc23)cc1] | | | CsCO₃ | 342.1 (M + H) |
| 132 | 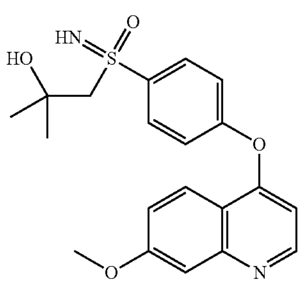 [SMILES: COc1ccc2c(Oc3ccc(S(=N)(=O)CC(C)(C)O)cc3)ccnc2c1] | | | CsCO₃ | 387.0 (M + H) |
| 168 | 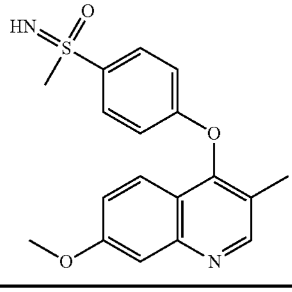 | | | CsCO₃ | 343.1 (M + H) |

Synthetic Example S-4

Synthesis of imino(3-{[(7-methoxyquinolin-4-yl)oxy]methyl}phenyl)methyl-λ⁶-sulfanone (Compound 133)

Step 1: Synthesis of 7-methoxy-4-((3-(methylthio)benzyl)oxy)quinoline

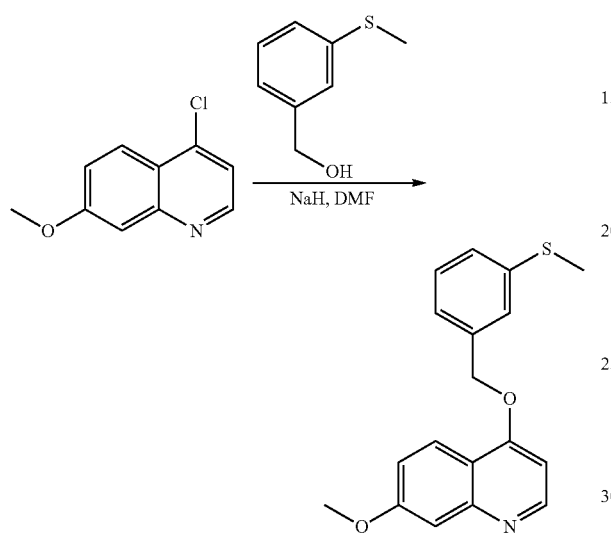

To a mixture of (3-methylsulfanylphenyl)methanol (0.80 g, 5.2 mmol) and DMF (10 mL) was added NaH (0.26 g, 6.5 mmol, 60% in mineral oil). The mixture was stirred at 0° C. for 30 min, and 4-chloro-7-methoxy-quinoline (0.50 g, 2.6 mmol) in DMF (5 mL) was added dropwise. The mixture was stirred at 20° C. for 12 h, water (5 mL) added and the mixture extracted with EtOAc (20 mL×2). The combined extracts were washed with brine (10 mL×2), dried over Na₂SO₄, filtered and concentrated, and purified by chromatography on silica gel (0-100% Ethyl acetate/Petroleum ether gradient) to provide 7-methoxy-4-[(3-methylsulfanylphenyl)methoxy]quinoline (0.44 g).

Step 2: Synthesis of imino(3-{[(7-methoxyquinolin-4-yl)oxy]methyl}phenyl)methyl-λ⁶-sulfanone

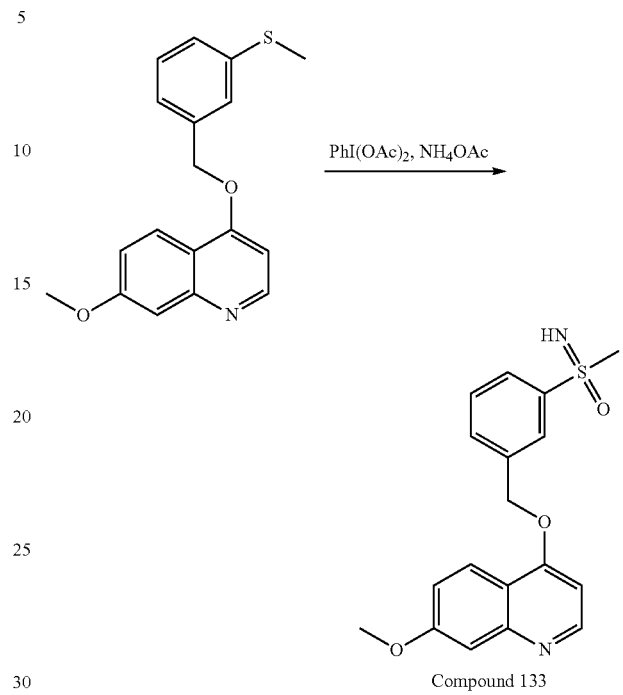

To a mixture of 7-methoxy-4-[(3-methylsulfanylphenyl)methoxy]quinoline (0.39 g, 1.3 mmol) in EtOH (1 mL) was added PhI(OAc)₂ (1.2 g, 3.8 mmol) and NH₄OAc (0.40 mg, 5.0 mmol). The reaction mixture was stirred at 20° C. for 2 hours. The reaction mixture was concentrated and purified by prep-HPLC (Kromasil C18 (250×50 mm×10 um); mobile phase: [water (10 mM NH₄HCO₃)-MeCN]; B %: 15%-45%) to provide imino(3-{[(7-methoxyquinolin-4-yl)oxy]methyl}phenyl)methyl-λ⁶-sulfanone (Compound 133) (101 mg). ESI m/z: 343.0 (M+H).

Compounds 14, 75, 134-138, and 169-178 were prepared from the aryl chlorides, alcohol, and bases indicated in Table 6 in the manner described in Synthetic Example S-4.

TABLE 6

| Cmpd | Structure | Chloro Compound | Alcohol | Solvent | MS (m/z) |
|---|---|---|---|---|---|
| 14 | (NH=S(=O)(Me)-phenyl-CH₂-O-quinazoline with 6,7-dimethoxy) | 4-chloro-6,7-dimethoxyquinazoline | (4-methylthiophenyl)methanol | NaH/DMF | 374.1 (M + H) |

TABLE 6-continued

| Cmpd | Structure | Chloro Compound | Alcohol | Solvent | MS (m/z) |
|---|---|---|---|---|---|
| 75 | 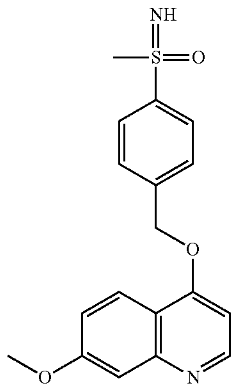 [SMILES: COc1ccc2c(OCc3ccc(S(C)(=N)=O)cc3)ccnc2c1] | | | EtOH | 343.1 (M + H) |
| 107 | 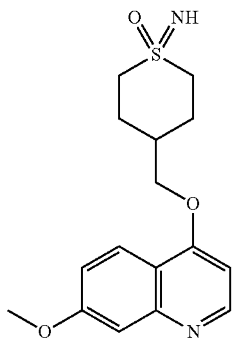 [SMILES: COc1ccc2c(OCC3CCS(=N)(=O)CC3)ccnc2c1] | | | NaH/CH$_2$Cl$_2$ | 321.2 (M + H) |
| 134 | 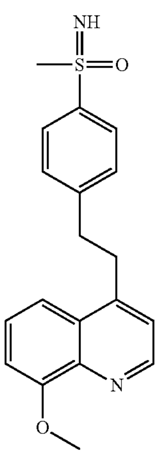 [SMILES: COc1cccc2c(CCc3ccc(S(C)(=N)=O)cc3)ccnc12] | | | EtOH | 343.0 (M + H) |
| 135 | 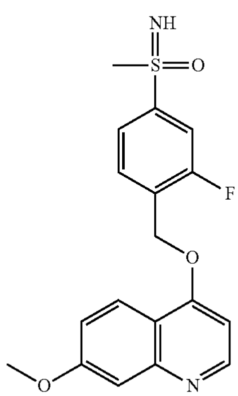 [SMILES: COc1ccc2c(OCc3ccc(S(C)(=N)=O)cc3F)ccnc2c1] | | | NaH/DMF | 361.0 (M + H) |

TABLE 6-continued

| Cmpd | Structure | Chloro Compound | Alcohol | Solvent | MS (m/z) |
|---|---|---|---|---|---|
| 136 | 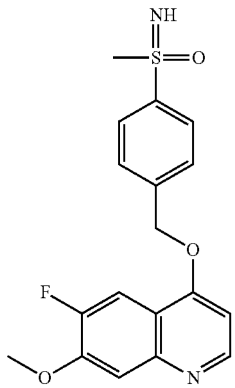 [SMILES: COc1cc2nccc(OCc3ccc(S(C)(=N)=O)cc3)c2cc1F] | | | NaH/DMF | 361.0 (M + H) |
| 137 | 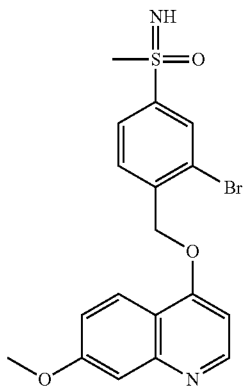 [SMILES: COc1ccc2c(OCc3ccc(S(C)(=N)=O)cc3Br)ccnc2c1] | | | NaH/DMF | 422.9 (M + H) |
| 138 | 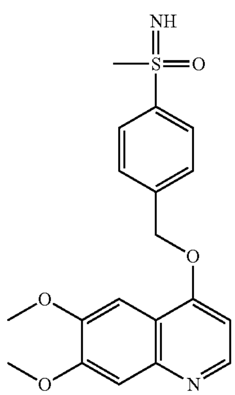 [SMILES: COc1cc2nccc(OCc3ccc(S(C)(=N)=O)cc3)c2cc1OC] | | | NaH/DMF | 373.0 (M + H) |
| 169 | 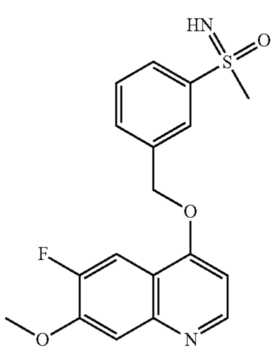 [SMILES: COc1cc2nccc(OCc3cccc(S(C)(=N)=O)c3)c2cc1F] | | | NaH/DMF | 361.1 (M + H) |

/ TABLE 6-continued
| Cmpd | Structure | Chloro Compound | Alcohol | Solvent | MS (m/z) |
|---|---|---|---|---|---|
| 170 | 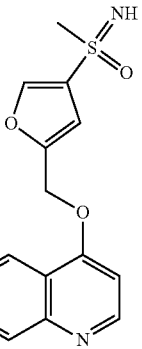 | 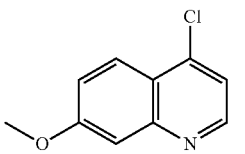 | 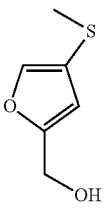 | NaH/DMF | 333.0 (M + H) |
| 171 | 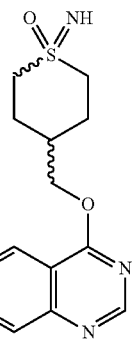 | 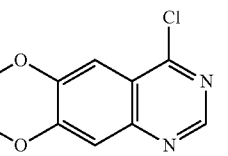 | 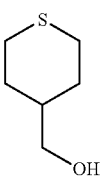 | NaH/DMF | 352.2 (M + H) |
| 172 | 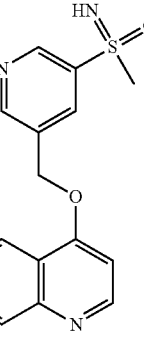 | 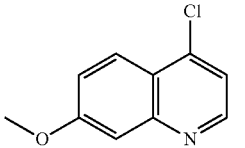 | 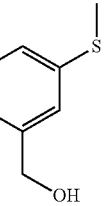 | NaH/DMF | 344.1 (M + H) |
| 173 | 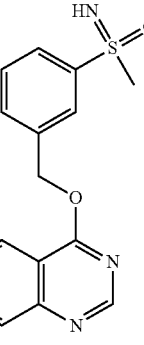 | 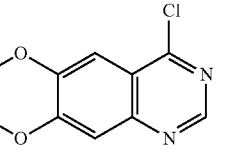 | 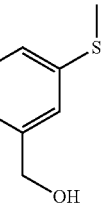 | NaH/DMF | 374.0 (M + H) |

TABLE 6-continued

| Cmpd | Structure | Chloro Compound | Alcohol | Solvent | MS (m/z) |
|---|---|---|---|---|---|
| 174 | 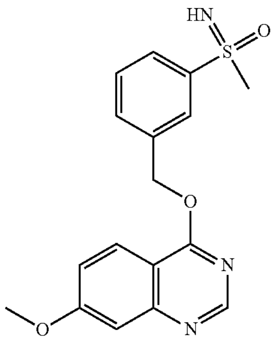 [SMILES: COc1ccc2c(OCc3cccc(S(C)(=N)=O)c3)ncnc2c1] | | | NaH/DMF | 344.1 (M + H) |
| 175 | 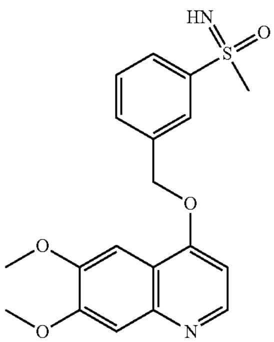 [SMILES: COc1cc2nccc(OCc3cccc(S(C)(=N)=O)c3)c2cc1OC] | | | NaH/DMF | 373.1 (M + H) |
| 176 | 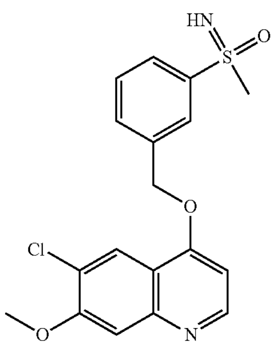 [SMILES: COc1cc2nccc(OCc3cccc(S(C)(=N)=O)c3)c2cc1Cl] | | | NaH/DMF | 377.0 (M + H) |
| 177 | 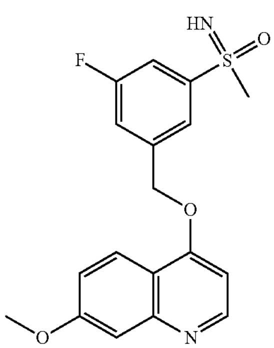 [SMILES: COc1ccc2c(OCc3cc(F)cc(S(C)(=N)=O)c3)ccnc2c1] | | | NaH/DMF | 361.1 (M + H) |

TABLE 6-continued

| Cmpd | Structure | Chloro Compound | Alcohol | Solvent | MS (m/z) |
|---|---|---|---|---|---|
| 178 | 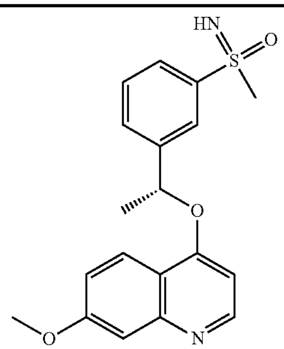 | | | NaH/DMF | 357.2 (M + H) |

Separation of diastereomers of 4-[(1-imino-1-oxido-3, 4, 5, 6-tetrahydro-2H-thiopyran-4-yl)methoxy]-7-methoxy-quinoline (Compound 107)

The diastereomers of 4-[(1-imino-1-oxido-3, 4, 5, 6-tetrahydro-2H-thiopyran-4-yl)methoxy]-7-methoxy-quinoline (Compound 107) were separated by reverse-phase HPLC (Phenomenex Gemini-$_{NX}$ 150×30 mm, 5 um; 15-45% MeCN in H$_2$O (0.1% TFA)) to provide Compound 107a (first eluting) and Compound 107b (second eluting) as TFA salts.

Synthetic Example S-5

Synthesis of imino({2-[1-(8-methoxyquinazolin-4-yl)piperidin-4-yl]ethyl})methyl-$\lambda^6$-sulfanone (Compound 72)

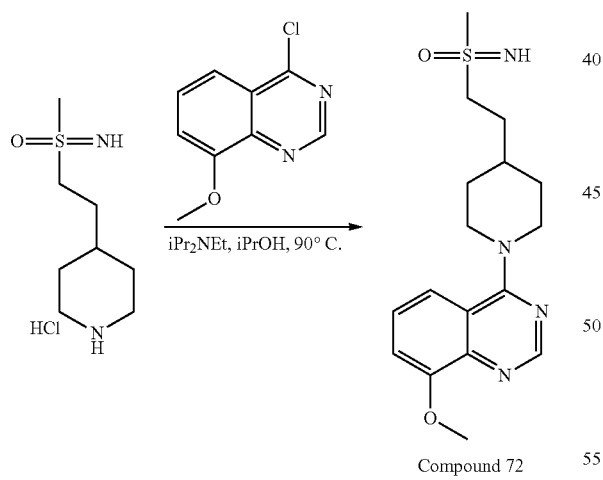

Compound 72

To a mixture of imino-methyl-oxo-[2-(4-piperidyl)ethyl]-λ6-sulfane HCl (130 mg, 573 umol) and 4-chloro-8-methoxy-quinazoline (113 mg, 0.58 mmol) in iPrOH (9 mL) was added iPrNEt$_2$ (363.6 mg, 2.81 mmol). The mixture was stirred at 90° C. for 12 h, then concentrated and purified by prep-HPLC (column: Waters Xbridge BEH C18 100*30 mm*10 um; mobile phase: [water (10 mM NH$_4$HCO$_3$)-ACN]; B %: 8%-38%, 8 min) to afford imino({2-[1-(8-methoxyquinazolin-4-yl)piperidin-4-yl]ethyl})methyl-$\lambda^6$-sulfanone (Compound 72) (26.3 mg). ESI MS m/z: 349.1 (M+H).

Compounds 8, 43, 57, 69, 74, 139-152, 165, and 196-203 were prepared from the aryl chlorides and amines under conditions indicated in Table 7 in the manner of Synthetic Example S-5.

TABLE 7

| Cmpd | Structure | Chloro Compound | Amine | Conditions | MS (m/z) |
|---|---|---|---|---|---|
| 8 | 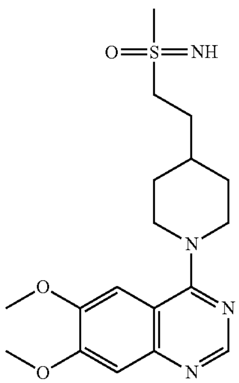 [SMILES: COc1cc2ncnc(N3CCC(CCS(C)(=N)=O)CC3)c2cc1OC] | | | iPrOH | 379.1 (M + H) |
| 43 | 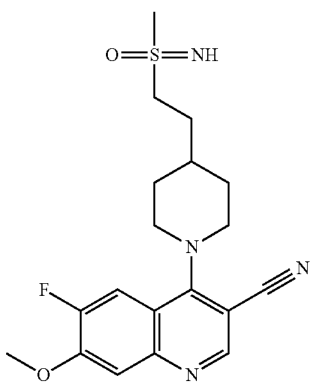 [SMILES: COc1cc2ncc(C#N)c(N3CCC(CCS(C)(=N)=O)CC3)c2cc1F] | | | iPr$_2$NEt, nBuOH 120° C. µW | 391.1 (M + H) |
| 57 | 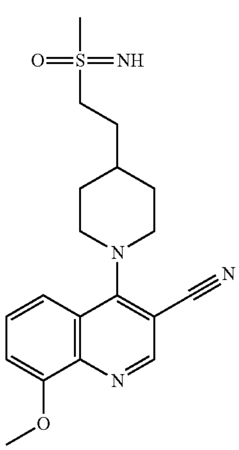 [SMILES: COc1cccc2c(N3CCC(CCS(C)(=N)=O)CC3)c(C#N)cnc12] | | | iPrOH | 373.1 (M + H) |

TABLE 7-continued

| Cmpd | Structure | Chloro Compound | Amine | Conditions | MS (m/z) |
|---|---|---|---|---|---|
| 69 | 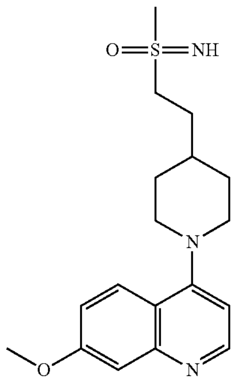 [SMILES: COc1ccc2c(N3CCC(CCS(C)(=N)=O)CC3)ccnc2c1] | | | nBuOH | 348.1 (M + H) |
| 74 | 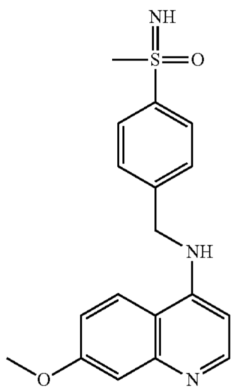 [SMILES: COc1ccc2c(NCc3ccc(S(C)(=N)=O)cc3)ccnc2c1] | | | iPr₂NEt, nBuOH 140° C. | 342.0 (M + H) |
| 139 | 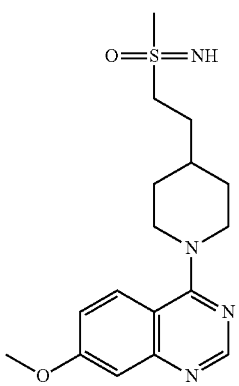 [SMILES: COc1ccc2c(N3CCC(CCS(C)(=N)=O)CC3)ncnc2c1] | | | iPrOH | 349.2 (M + H) |
| 140 | 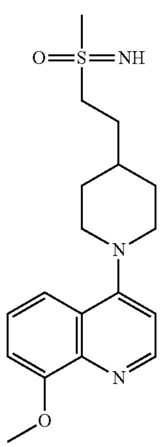 [SMILES: COc1cccc2c(N3CCC(CCS(C)(=N)=O)CC3)ccnc12] | | | nBuOH | 348.1 (M + H) |

TABLE 7-continued

| Cmpd | Structure | Chloro Compound | Amine | Conditions | MS (m/z) |
|---|---|---|---|---|---|
| 141 | 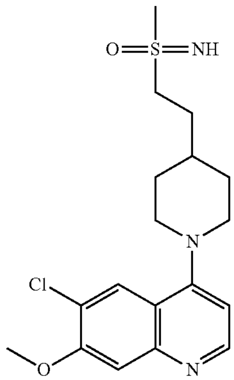 [SMILES: COc1cc2nccc(N3CCC(CCS(C)(=N)=O)CC3)c2cc1Cl] | | | nBuOH | 382.1 (M + H) |
| 142 | 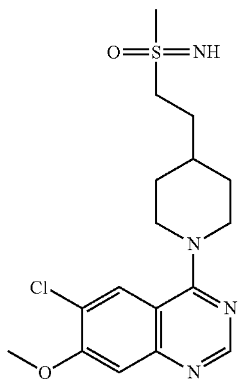 [SMILES: COc1cc2ncnc(N3CCC(CCS(C)(=N)=O)CC3)c2cc1Cl] | | | iPrOH | 383.0 (M + H) |
| 143 | 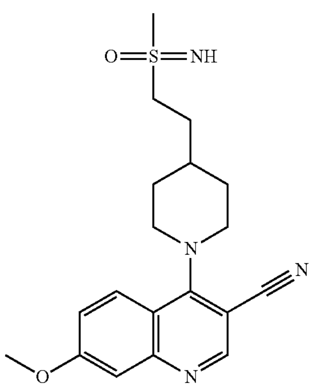 [SMILES: COc1ccc2c(N3CCC(CCS(C)(=N)=O)CC3)c(C#N)cnc2c1] | | | CsCO₃, DMF | 373.1 (M + H) |
| 144 | 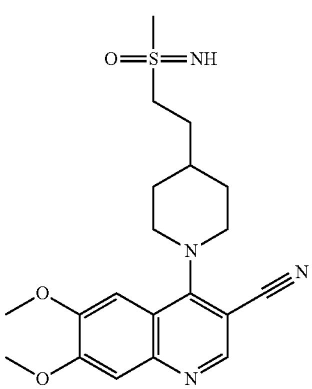 [SMILES: COc1cc2ncc(C#N)c(N3CCC(CCS(C)(=N)=O)CC3)c2cc1OC] | | | iPrOH | 403.1 (M + H) |

TABLE 7-continued

| Cmpd | Structure | Chloro Compound | Amine | Conditions | MS (m/z) |
|---|---|---|---|---|---|
| 145 | 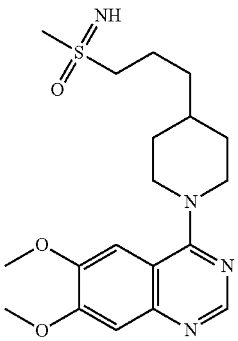 [SMILES: COc1cc2ncnc(N3CCC(CCCS(C)(=N)=O)CC3)c2cc1OC] | | HCl | iPrOH | 393.0 (M + H) |
| 146 | 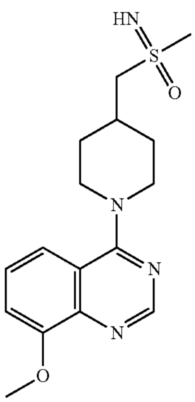 [SMILES: COc1cccc2c(N3CCC(CS(C)(=N)=O)CC3)ncnc12] | | HCl | iPrOH | 335.0 (M + H) |
| 147 | 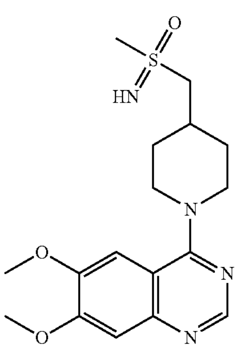 [SMILES: COc1cc2ncnc(N3CCC(CS(C)(=N)=O)CC3)c2cc1OC] | | HCl | iPrOH | 365.10 (M + H) |
| 148 | 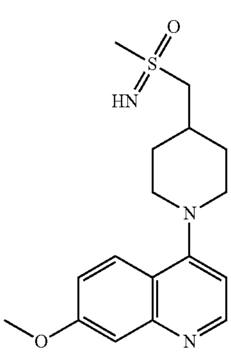 [SMILES: COc1ccc2c(N3CCC(CS(C)(=N)=O)CC3)ccnc2c1] | | HCl | nBuOH | 334.10 (M + H) |

TABLE 7-continued
| Cmpd | Structure | Chloro Compound | Amine | Conditions | MS (m/z) |
|---|---|---|---|---|---|
| 149 | 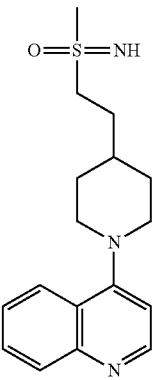 [SMILES: CS(=N)(=O)CCC1CCN(c2ccnc3ccccc23)CC1] | 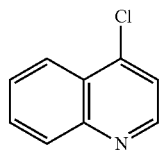 [SMILES: Clc1ccnc2ccccc12] | 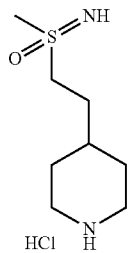 | iPr₂NEt, nBuOH 120° C. μW | 318.1 (M + H) |
| 150 | 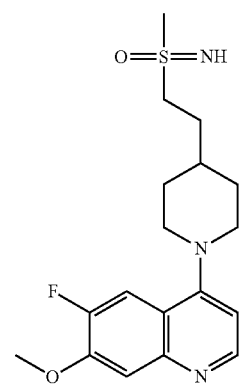 [SMILES: COc1cc2nccc(N3CCC(CCS(C)(=N)=O)CC3)c2cc1F] | 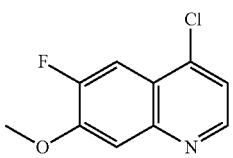 | 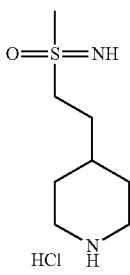 | iPr₂NEt, nBuOH 120° C. μW | 366.1 (M + H) |
| 151 | 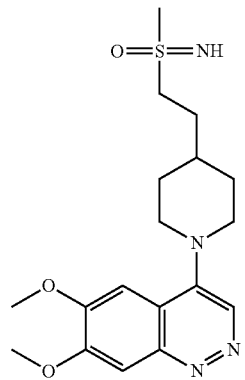 [SMILES: COc1cc2nncc(N3CCC(CCS(C)(=N)=O)CC3)c2cc1OC] | 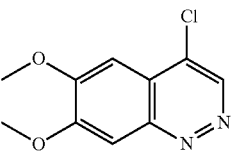 | 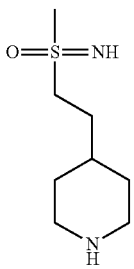 | iPr₂NEt, nBuOH 120° C. | 379.1 (M + H) |
| 152 | 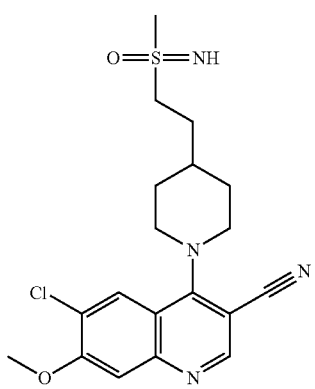 | 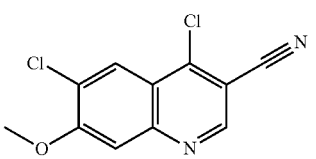 | 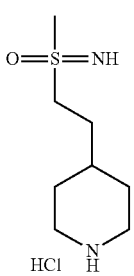 | iPr₂NEt, iPrOH 90° C. μW | 407.0 (M + H) |

TABLE 7-continued

| Cmpd | Structure | Chloro Compound | Amine | Conditions | MS (m/z) |
|---|---|---|---|---|---|
| 165 | 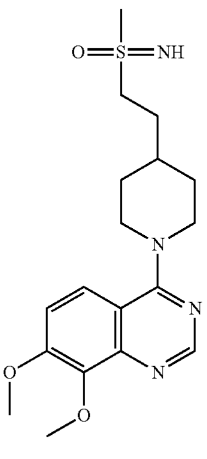 [SMILES: COc1ccc2c(N3CCC(CCS(C)(=N)=O)CC3)ncnc2c1OC] | | | iPrOH | 379.1 (M + H) |
| 196 | 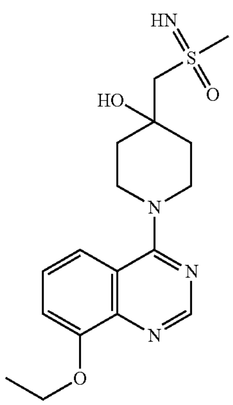 [SMILES: CCOc1cccc2c(N3CCC(O)(CS(C)(=N)=O)CC3)ncnc12] | | | iPr₂NEt, iPrOH 80° C. | 365.0 (M + H) |
| 197 | 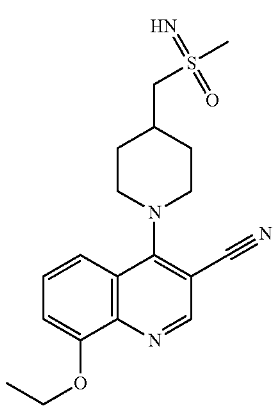 [SMILES: CCOc1cccc2c(N3CCC(CS(C)(=N)=O)CC3)c(C#N)cnc12] | | | iPr₂NEt, iPrOH 90° C. | 373.2 (M + H) |

TABLE 7-continued

| Cmpd | Structure | Chloro Compound | Amine | Conditions | MS (m/z) |
|---|---|---|---|---|---|
| 198 | 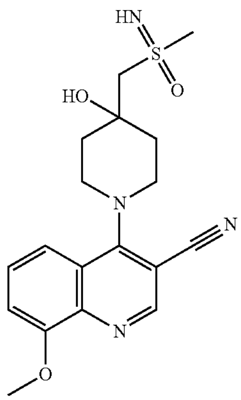 [SMILES: COc1cccc2c(N3CCC(O)(CS(C)(=N)=O)CC3)c(C#N)cnc12] | | | iPr₂NEt, iPrOH 90° C. | 375.2 (M + H) |
| 199 | 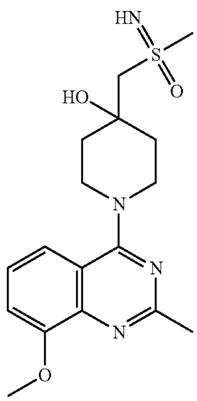 [SMILES: COc1cccc2c(N3CCC(O)(CS(C)(=N)=O)CC3)nc(C)nc12] | | | iPr₂NEt, iPrOH 20° C. | 365.1 (M + H) |
| 200 | 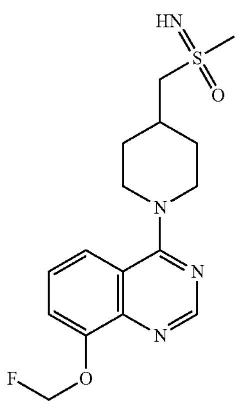 | | | iPr₂NEt, iPrOH 90° C. | 377.1 (M + H) |
| 201 | 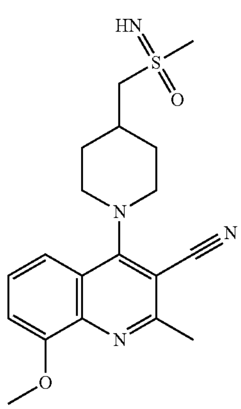 [SMILES: COc1cccc2c(N3CCC(CS(C)(=N)=O)CC3)c(C#N)c(C)nc12] | | | iPr₂NEt, iPrOH 90° C. | 373.1 (M + H) |

TABLE 7-continued

| Cmpd | Structure | Chloro Compound | Amine | Conditions | MS (m/z) |
|---|---|---|---|---|---|
| 202 | 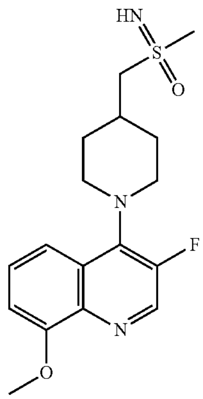 [SMILES: COc1cccc2c(N3CCC(CS(C)(=N)=O)CC3)c(F)cnc12] | | | iPr₂NEt, nBuOH 140° C. | 352.1 (M + H) |
| 203 | 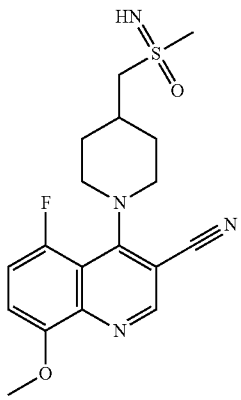 [SMILES: COc1ccc(F)c2c(N3CCC(CS(C)(=N)=O)CC3)c(C#N)cnc12] | | | iPr₂NEt, nBuOH 140° C. | 377.1 (M + H) |

Synthetic Example S-6

Synthesis of {2-[4-(6,7-dimethoxyquinazolin-4-yl)phenyl]ethyl}(imino)methyl-λ⁶-sulfanone (Compound 153)

Step 1: Synthesis of 4-bromophenethyl 4-methylbenzenesulfonate

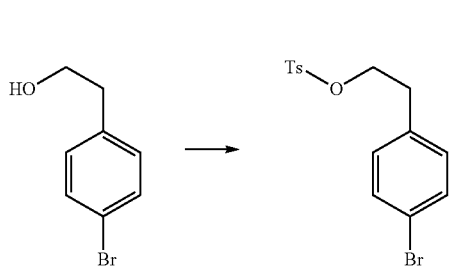 [SMILES: OCCc1ccc(Br)cc1 ; Cc1ccc(S(=O)(=O)OCCc2ccc(Br)cc2)cc1]

To a mixture of 2-(4-bromophenyl)ethanol (1.4 mL, 10 mmol) and 20 mL of CH₂Cl₂ was added pyridine (2.4 mL, 30 mmol) and toluenesulfonyl chloride (2.3 g, 12 mmol) at 0° C. The mixture was stirred at 20° C. for 12 h, poured into 30 mL of water and extracted with CH₂Cl₂ (30.0 mL×2). The extracts were washed with saturated aqueous of NaHCO₃ (20.0 mL×2) and brine (20.0 mL×2), dried over Na₂SO₄, filtered and concentrated and purified by silica gel chromatography (0-52% EtOAc/pet. ether) to afford the compound 2-(4-bromophenyl)ethyl 4-methylbenzenesulfonate (2.4 g).

Step 2: Synthesis of 4-bromophenethyl)(methyl)sulfane

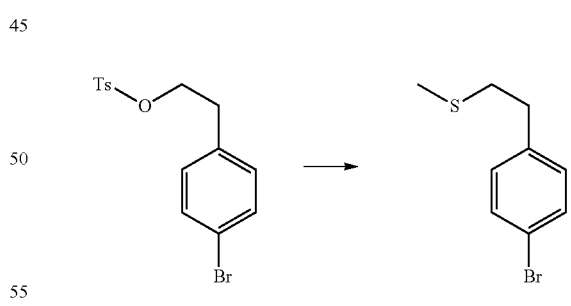

To a mixture of 2-(4-bromophenyl) ethyl 4-methylbenzenesulfonate (0.5 g, 1.4 mmol), NMP (1.5 mL), and THF (2.5 mL) was added NaSMe (20%, 0.67 mL, 2.11 mmol). The mixture was stirred at 20° C. for 12 h, concentrated, diluted with aqueous Na₂CO₃ (20 mL) and extracted with EtOAc (10.0 mL×2). The extracts were washed with brine (10.0 mL×2), dried over Na₂SO₄, filtered and concentrated. Purification by silica gel chromatography (0-100% EtOAc/pet. ether) provided (4-bromophenethyl)(methyl)sulfane (0.3 g).

Step 3: Synthesis of 4,4,5,5-tetramethyl-2-(4-(2-(methylthio)ethyl)phenyl)-1,3,2-dioxaborolane

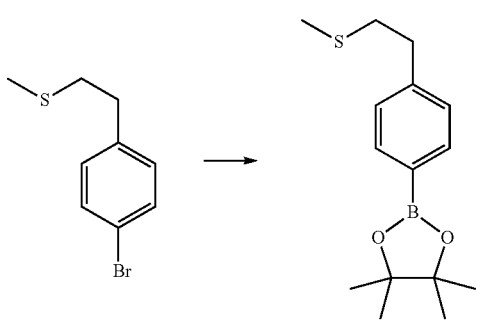

To a mixture of 1-bromo-4-(2-methylsulfanylethyl)benzene (0.25 g, 1.1 mmol) and dioxane (10.0 mL) was added Pd(dppf)Cl$_2$CH$_2$Cl$_2$ (88 mg, 0.11 mmol), KOAc (0.21 g, 2.2 mmol) and bis(pinacolato)diboron (0.33 mg, 1.3 mmol). The mixture was degassed and purged with N$_2$ for 3 times, then stirred at 80° C. for 3 hours under an N$_2$ atmosphere. The mixture was poured into water (10.0 mL) and extracted with EtOAc (10.0 mL×2). The extracts were washed with brine (10.0 mL×2), dried over Na$_2$SO$_4$, filtered, concentrated, and purified by silica gel chromatography (0-35% EtOAc/pet. ether) to afford 4,4,5,5-tetramethyl-2-(4-(2-(methylthio)ethyl)phenyl)-1,3,2-dioxaborolane (0.22 g, 70% purity).

Step 4: Synthesis of 6,7-dimethoxy-4-(4-(2-(methylthio)ethyl)phenyl)quinazoline

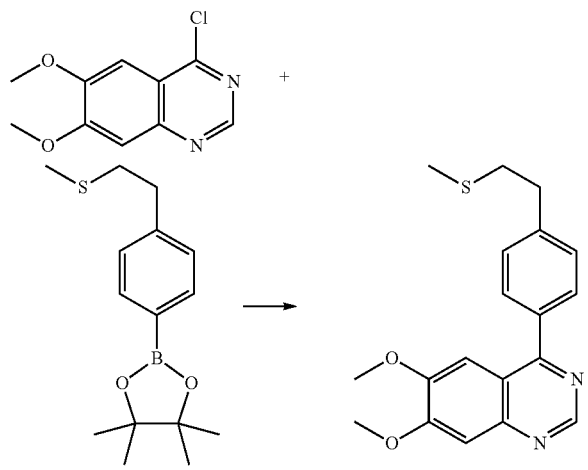

To a mixture of 4-chloro-6,7-dimethoxy-quinazoline (0.15 g, 0.668 mmol), dioxane (8.0 mL), and H$_2$O (1.6 mL) was added Pd(dppf)Cl$_2$CH$_2$Cl$_2$ (55 mg, 67 μmol), K$_2$CO$_3$ (190 mg, 1.3 mmol) and 4,4,5,5-tetramethyl-2-(4-(2-(methylthio)ethyl)phenyl)-1,3,2-dioxaborolane (180 mg, 0.65 mmol). The mixture was degassed and purged with N$_2$ three times and stirred at 80° C. for 12 h under an N$_2$ atmosphere. The mixture was poured into water (10.0 mL) and extracted with EtOAc (10.0 mL×2). The combined extracts were washed with brine (10.0 mL×2), dried over Na$_2$SO$_4$, filtered, and concentrated to give the crude product 6,7-dimethoxy-4-(4-(2-(methylthio)ethyl)phenyl)quinazoline (0.3 g, 50% purity).

Step 5: Synthesis of {2-[4-(6,7-dimethoxyquinazolin-4-yl)phenyl]ethyl}(imino)methyl-λ$^6$-sulfanone

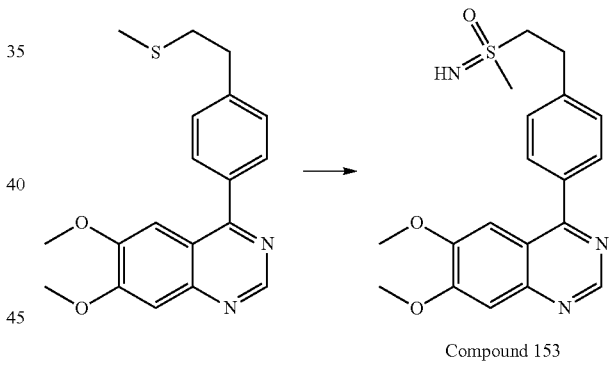

Compound 153

{2-[4-(6,7-dimethoxyquinazolin-4-yl)phenyl]ethyl}(imino)methyl-λ$^6$-sulfanone (Compound 153) was prepared from 6,7-dimethoxy-4-(4-(2-(methylthio)ethyl)phenyl)quinazoline in the manner described for S-1. ESI MS m/z: 372.1 (M+H).

Compounds 88, 98, 154-155, and 204 were prepared from the aryl halide and boronic ester indicated in Table 8 in the manner of steps 4 and 5 in Synthetic Example S-6.

TABLE 8

| Cmpd | Structure | Aryl halide | Boronate | MS (m/z) |
|---|---|---|---|---|
| 88 | 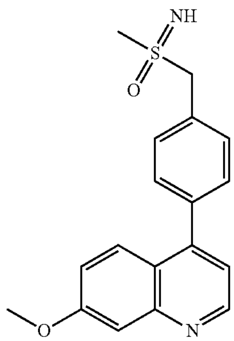 [SMILES: COc1ccc2c(-c3ccc(CS(C)(=N)=O)cc3)ccnc2c1] | | | 327.2 (M + H) |
| 98 | 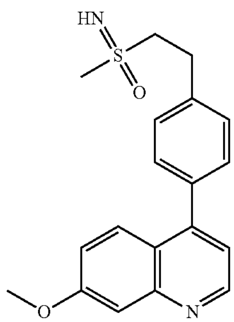 [SMILES: COc1ccc2c(-c3ccc(CCS(C)(=N)=O)cc3)ccnc2c1] | | | 341.1 (M + H) |
| 154 | 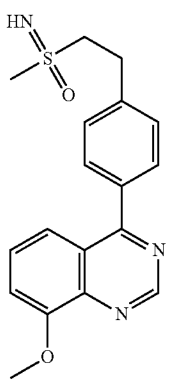 [SMILES: COc1cccc2c(-c3ccc(CCS(C)(=N)=O)cc3)ncnc12] | | | 342.1 (M + H) |
| 155 | 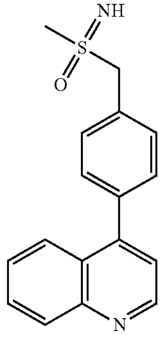 [SMILES: CS(=N)(=O)Cc1ccc(-c2ccnc3ccccc23)cc1] | | | 297.1 (M + H) |

TABLE 8-continued

| Cmpd | Structure | Aryl halide | Boronate | MS (m/z) |
|---|---|---|---|---|
| 204 | 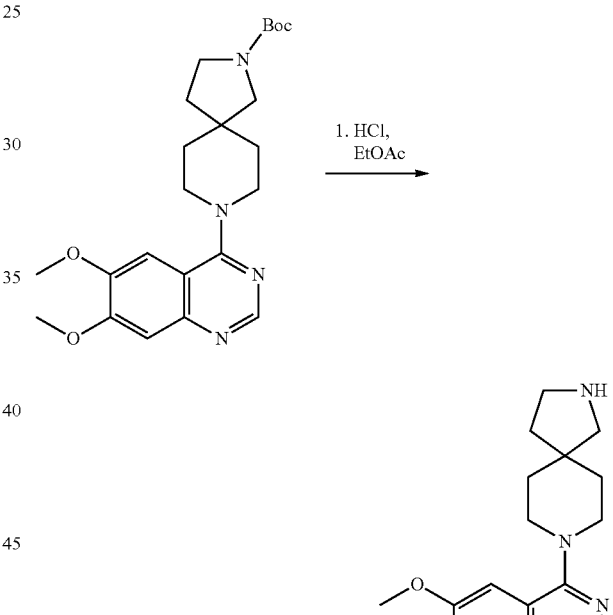 | | | 371.2 (M + H) |

Synthetic Example S-7

Synthesis of [8-(6,7-dimethoxyquinazolin-4-yl)-2,8-diazaspiro[4.5]decan-2-yl](imino)methyl-$\lambda^6$-sulfanone (Compound 54)

Step 1: Synthesis of tert-butyl 8-(6,7-dimethoxyquinazolin-4-yl)-2,8-diazaspiro[4.5]decane-2-carboxylate

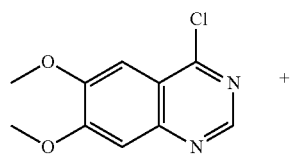

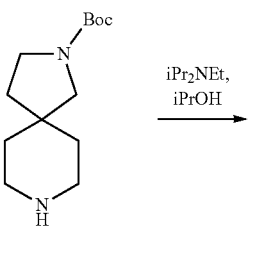

To a mixture of tert-butyl 2,8-diazaspiro[4.5]decane-2-carboxylate (1.0 g, 4.2 mmol) and iPr₂NEt (3.0 mL, 17 mmol), and iPrOH (20 mL) was added 4-chloro-6,7-dimethoxy-quinazoline (0.90 g, 4.0 mmol) and the mixture was stirred at 90° C. for 4 h. The reaction mixture was concentrated and triturated with MTBE/iPrOH/H₂O (3/1/1, 25 mL) at 25° C. for 15 min. The suspension was filtered to afford the compound tert-butyl 8-(6,7-dimethoxyquinazolin-4-yl)-2,8-diazaspiro[4.5]decane-2-carboxylate (2.0 g).

Step 2: Synthesis of 6,7-dimethoxy-4-(2,8-diazaspiro[4.5]decan-8-yl)quinazoline To a mixture of tert-butyl 8-(6,7-dimethoxyquinazolin-4-yl)-2,8-diazaspiro[4.5]decane-2-carboxylate (2.0 g, 4.7 mmol) and THF (10 mL) was added HCl/EtOAc (4 M, 6 mL, 24 mmol) dropwise and the mixture was stirred at 25° C. for 8 h. HCl/MeOH (4 M, 6 mL, 24 mmol) was added and the mixture was stirred at 25° C. for another 12 h. The reaction mixture was concentrated, and the residue dissolved in water (25 mL). Solid NaHCO₃ (about 200 mg) was added to adjust its pH to 8 and NaCl was (about 150 mg) until it reached the saturation point. The mixture was extracted with CH₂Cl₂/iPrOH (3/1, 30 mL×7). The combined organic layers were dried over Na₂SO₄, filtered and concentrated under reduced pressure. The residue was lyophilized to give the compound 6,7-dimethoxy-4-(2,8-diazaspiro[4.5]decan-8-yl)quinazoline (1.2 g).

Step 3: Synthesis of [8-(6,7-dimethoxyquinazolin-4-yl)-2,8-diazaspiro[4.5]decan-2-yl](imino)methyl-λ⁶-sulfanone

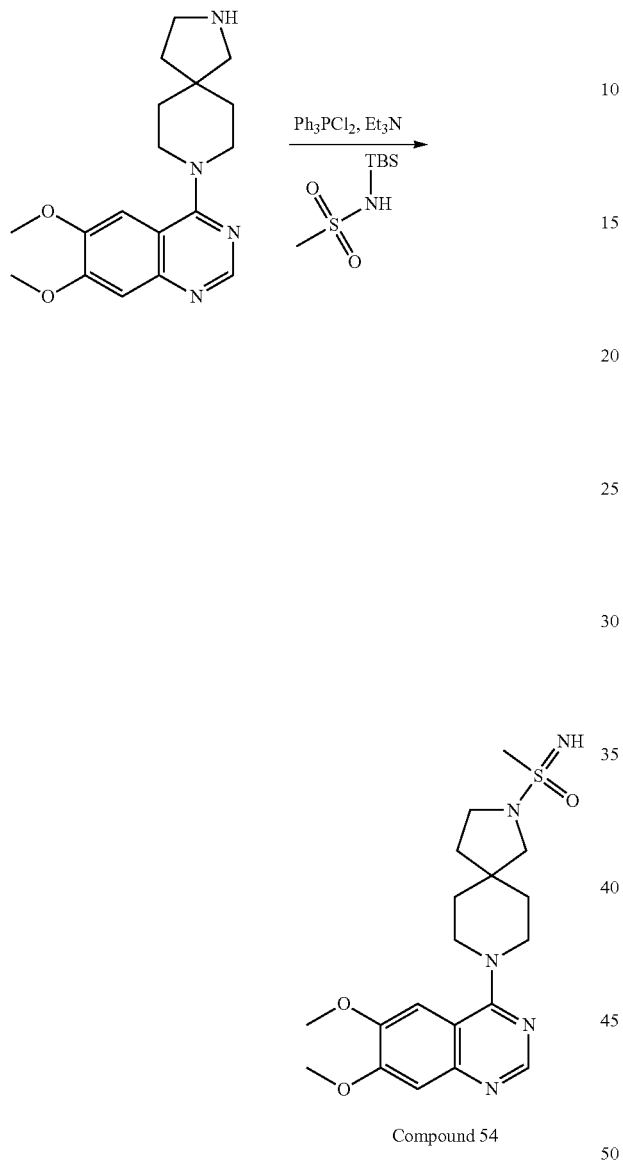

Compound 54

To a mixture of PPh₃Cl₂ (0.36 M, 21 mL) and CHCl₃ (21 mL) was added Et₃N (1.3 mL, 9.0 mmol) under N₂ at 0° C. and the mixture was stirred at 0° C. for 15 min. N-[tert-butyl(dimethyl)silyl]methanesulfonamide (0.67 g, 3.2 mmol) was added and the mixture was stirred at 0° C. for 15 min before being added to a mixture of 6,7-dimethoxy-4-(2,8-diazaspiro[4.5]decan-8-yl)quinazoline (0.70 g, 2.1 mmol), Et₃N (1.4 mL, 10 mmol), and CHCl₃ (21 mL) at 0° C. under N₂. The mixture was stirred at 25° C. for 5 h, then was concentrated, and purified by prep-HPLC (column: Phenomenex Luna C18 200*40 mm*10 um; mobile phase: [water (0.2% FA)-ACN]; B %: 1%-30%, 8 min) to provide [8-(6,7-dimethoxyquinazolin-4-yl)-2,8-diazaspiro[4.5]decan-2-yl](imino)methyl-λ⁶-sulfanone (Compound 54) (0.50 g) as a formic acid salt. ESI MS m/z: 406.1 (M+H).

Synthetic Example S-8

Synthesis of [8-(6-fluoro-7-methoxyquinolin-4-yl)-2,8-diazaspiro[4.5]decan-2-yl](imino)methyl-λ⁶-sulfanone (Compound 205)

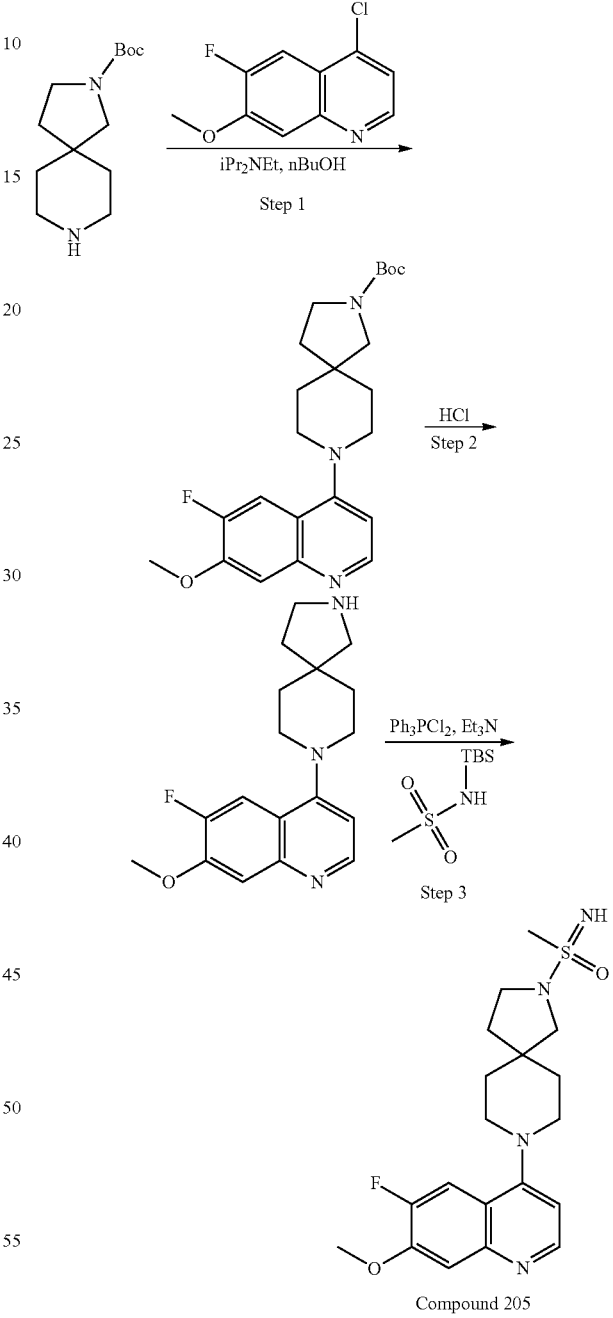

Compound 205

Step 1: A degassed mixture of 4-chloro-6-fluoro-7-methoxy-quinoline (75 g, 0.35 mol), tert-butyl 2,8-diazaspiro[4.5]decane-2-carboxylate (85 g, 0.35 mol), iPr₂NEt (0.19 L, 1.1 mol), n-BuOH (0.75 L) was stirred at 140° C. for 12 h under an N₂ atmosphere. The mixture was concentrated and poured into H₂O (3 L) and extracted with EtOAc (2×1.5 L). The combined extracts were washed with brine (500 mL), dried over Na₂SO₄, and concentrated to provide tert-butyl 8-(6-fluoro-7-methoxy-4-quinolyl)-2,8-diazaspiro[4.5]decane-2-carboxylate (295 g).

Step 2: A solution of 4M HCl in EtOAc (0.75 L) was added slowly to stirring tert-butyl 8-(6-fluoro-7-methoxy-4-quinolyl)-2,8-diazaspiro[4.5]decane-2-carboxylate (150 g, 0.36 mol) and EtOAc (0.4 L) and the mixture was stirred at 20° C. for 12 h. The mixture was concentrated, then mixed with 1 L of MeOH and AmberLyst-21 added until the pH was 9. The mixture was filtered, concentrated, and triturated with petroleum ether/EtOAc (1:1, 1 L) at 20° C. for 0.5 h to afford compound 8-(6-fluoro-7-methoxy-4-quinolyl)-2,8-diazaspiro[4.5]decane (120 g).

Step 3: A mixture of Ph$_3$PCl$_2$ (0.36 M, 0.53 L) and Et$_3$N (29 g, 0.29 mol) was stirred at 0° C. for 0.25 h. N-[tert-butyl(dimethyl)silyl]methanesulfonamide (40 g, 190 mmol) was added at 0° C. and stirred for 0.25 h. The solution was added dropwise to a mixture of 8-(6-fluoro-7-methoxy-4-quinolyl)-2,8-diazaspiro[4.5]decane (30 g, 95 mmol), Et$_3$N (19 g, 190 mmol) and CHCl$_3$ (0.3 L) at 0° C. and stirred at 20° C. for 12 h. The mixture was concentrated and EtOAc was added (2.5 L) followed by aqueous HCl (1 N, 1 L). The aqueous phase was adjusted to pH 8 with saturated NaHCO$_3$. The precipitate was filtered and the filter cake was washed with water (0.5 L×2). The collected solid was dried to provide [8-(6-fluoro-7-methoxyquinolin-4-yl)-2,8-diazaspiro[4.5]decan-2-yl](imino)methyl-λ$^6$-sulfanone (Compound 205) (120 g). ESI MS m/z: 393.2 (M+H).

Compounds 53, 55, 94, 156-160, and 206-226 were prepared from the aryl halides and amines under the conditions indicated in Table 9 in the manner of Synthetic Examples S-7 and S-8.

TABLE 9

| Cmpd | Structure | Aryl Halide | Amine | Cond | MS (m/z) |
|---|---|---|---|---|---|
| 53 | 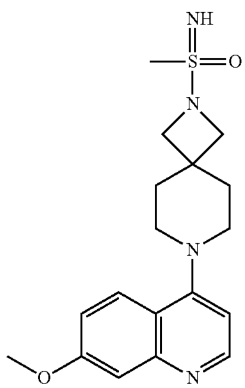 [SMILES: COc1ccc2c(N3CCC4(CC3)CN(S(C)(=N)=O)C4)ccnc2c1] | 4-Cl-7-methoxyquinoline | Boc-2,8-diazaspiro[4.5]decane | TBS, nBuOH | 361.0 (M + H) |
| 54 | 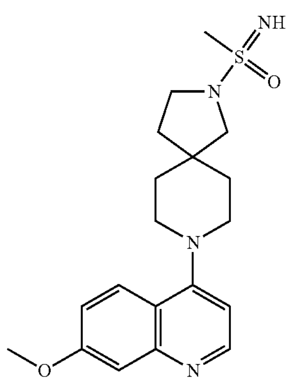 [SMILES: COc1ccc2c(N3CCC4(CC3)CCN(S(C)(=N)=O)C4)ccnc2c1] | 4-Cl-7-methoxyquinoline | Boc-2,8-diazaspiro[4.5]decane | TBS, nBuOH | 375.1 (M + H) |
| 94 | 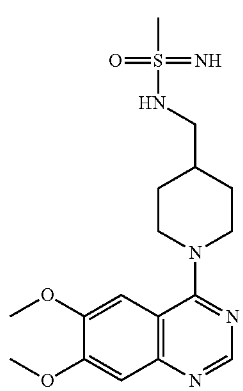 [SMILES: COc1cc2ncnc(N3CCC(CNS(C)(=N)=O)CC3)c2cc1OC] | 4-Cl-6,7-dimethoxyquinazoline | Boc-aminomethylpiperidine | TBS, iPrOH | 380.1 (M + H) |

TABLE 9-continued

| Cmpd | Structure | Aryl Halide | Amine | Cond | MS (m/z) |
|---|---|---|---|---|---|
| 156 | 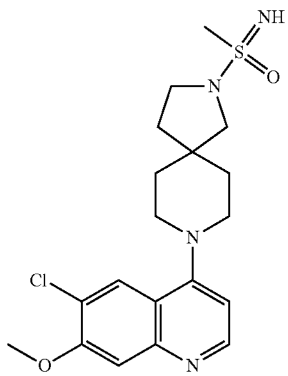 [SMILES: COc1cc2nccc(N3CCC4(CC3)CCN(S(C)(=N)=O)C4)c2cc1Cl] | 6-chloro-7-methoxy-4-chloroquinoline | 2-Boc-2,8-diazaspiro[4.5]decane | methanesulfonamide TBS, nBuOH | 409.0 (M + H) |
| 157 | 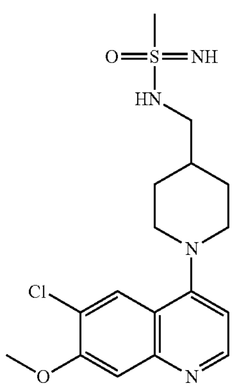 [SMILES: COc1cc2nccc(N3CCC(CNS(C)(=N)=O)CC3)c2cc1Cl] | 6-chloro-7-methoxy-4-chloroquinoline | 4-(Boc-aminomethyl)piperidine | methanesulfonamide TBS, nBuOH | 383.0 (M + H) |
| 158 | 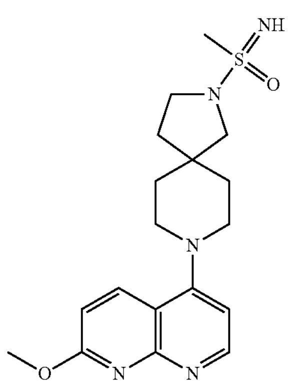 [SMILES: COc1ccc2c(N3CCC4(CC3)CCN(S(C)(=N)=O)C4)ccnc2n1] | 4-chloro-7-methoxy-1,8-naphthyridine | 2-Boc-2,8-diazaspiro[4.5]decane | methanesulfonamide TBS, nBuOH | 376.1 (M + H) |
| 159 | 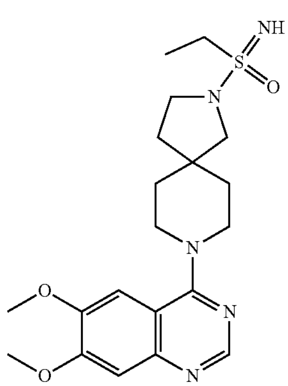 [SMILES: CCS(=N)(=O)N1CCC2(CCN(c3ncnc4cc(OC)c(OC)cc34)CC2)C1] | 4-chloro-6,7-dimethoxyquinazoline | 2-Boc-2,8-diazaspiro[4.5]decane | ethanesulfonamide TBS | 420.1 (M + H) |

TABLE 9-continued

| Cmpd | Structure | Aryl Halide | Amine | Cond | MS (m/z) |
|---|---|---|---|---|---|
| 160 | 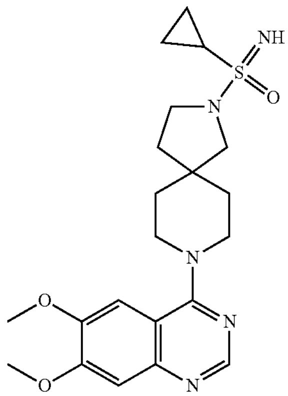 [SMILES: COc1cc2ncnc(N3CCC4(CC3)CCN(S(=N)(=O)C3CC3)C4)c2cc1OC] | | | | 432.1 (M + H) |
| 206 | 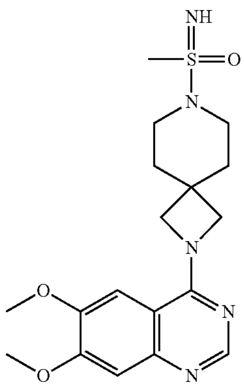 [SMILES: COc1cc2ncnc(N3CC4(CCN(S(C)(=N)=O)CC4)C3)c2cc1OC] | | | Step 3: TBS; CHCl₃ | 392.2 (M + H) |
| 207 | 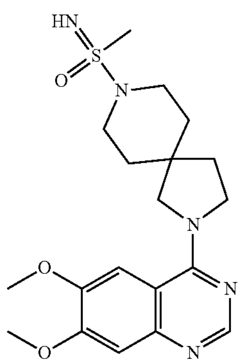 [SMILES: COc1cc2ncnc(N3CCC4(CCN(S(C)(=N)=O)CC4)C3)c2cc1OC] | | | Step 3: TBS; CHCl₃ | 406.2 (M + H) |
| 208 | 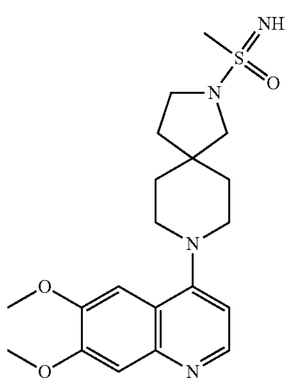 [SMILES: COc1cc2nccc(N3CCC4(CC3)CCN(S(C)(=N)=O)C4)c2cc1OC] | | | Step 1: 140° C., nBuOH Step 3: TBS; CHCl₃ | 405.1 (M + H) |

TABLE 9-continued

| Cmpd | Structure | Aryl Halide | Amine | Cond | MS (m/z) |
|---|---|---|---|---|---|
| 209 | 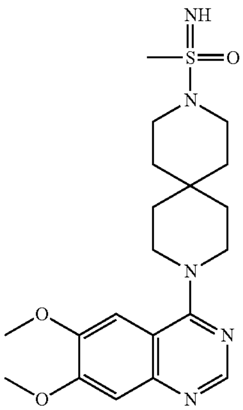 [SMILES: COc1cc2ncnc(N3CCC4(CC3)CCN(S(C)(=N)=O)CC4)c2cc1OC] | | | Step 3: TBS; CHCl₃ | 420.1 (M + H) |
| 210 | 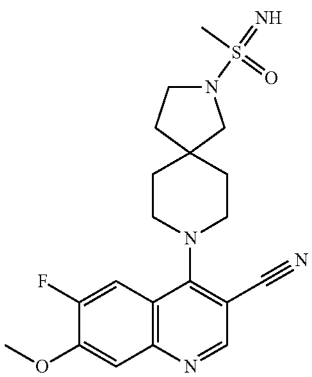 [SMILES: COc1cc2ncc(C#N)c(N3CCC4(CC3)CCN(S(C)(=N)=O)C4)c2cc1F] | | | Step 3: TBS; CHCl₃ | 418.1 (M + H) |
| 211 | 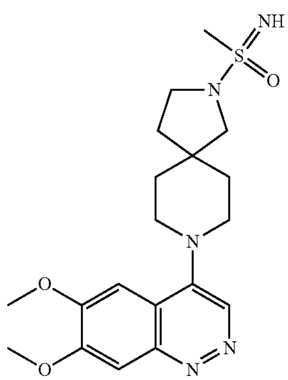 [SMILES: COc1cc2nncc(N3CCC4(CC3)CCN(S(C)(=N)=O)C4)c2cc1OC] | | | Step 3: TBS; CHCl₃ | 406.1 (M + H) |
| 212 | 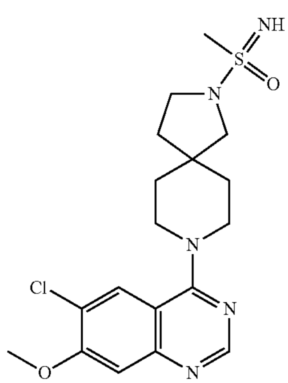 [SMILES: COc1cc2ncnc(N3CCC4(CC3)CCN(S(C)(=N)=O)C4)c2cc1Cl] | | | Step 3: TBS; CHCl₃ | 410.2 (M + H) |

TABLE 9-continued

| Cmpd | Structure | Aryl Halide | Amine | Cond | MS (m/z) |
|---|---|---|---|---|---|
| 213 | 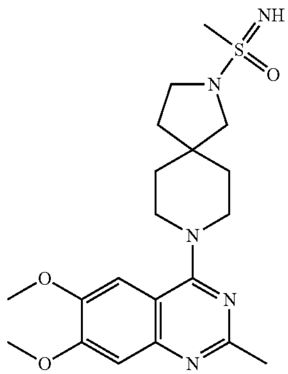 [SMILES: COc1cc2nc(C)nc(N3CCC4(CC3)CCN(S(C)(=N)=O)C4)c2cc1OC] | | | Step 3: TBS; methanesulfonamide CHCl₃ | 420.1 (M + H) |
| 214 | 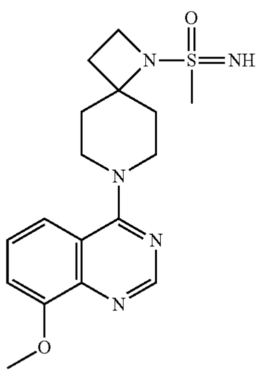 [SMILES: COc1cccc2c(N3CCC4(CC3)CCN4S(C)(=N)=O)ncnc12] | | | Step 3: TBS; methanesulfonamide CHCl₃ | 362.2 (M + H) |
| 215 | 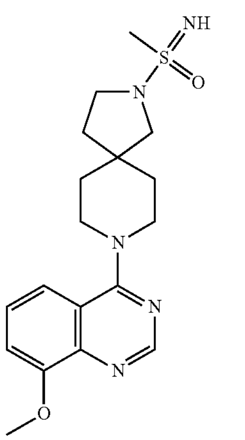 [SMILES: COc1cccc2c(N3CCC4(CC3)CCN(S(C)(=N)=O)C4)ncnc12] | | | Step 3: TBS; methanesulfonamide CHCl₃ | 376.1 (M + H) |
| 216 | 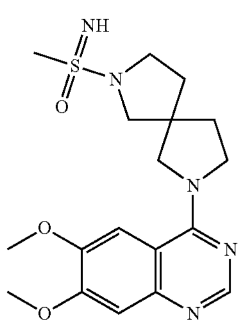 [SMILES: COc1cc2ncnc(N3CCC4(CCN(S(C)(=N)=O)C4)C3)c2cc1OC] | | | Step 3: TBS; methanesulfonamide CHCl₃ | 392.2 (M + H) |

TABLE 9-continued

| Cmpd | Structure | Aryl Halide | Amine | Cond | MS (m/z) |
|---|---|---|---|---|---|
| 217 | 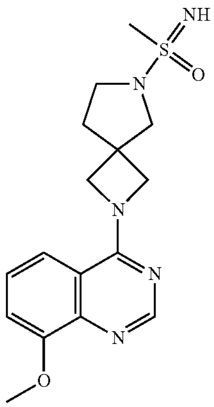 [SMILES: COc1cccc2c(N3CC4(CCN(S(C)(=N)=O)C4)C3)ncnc12] | | | Step 3: TBS; CHCl₃ | 348.2 (M + H) |
| 218 | 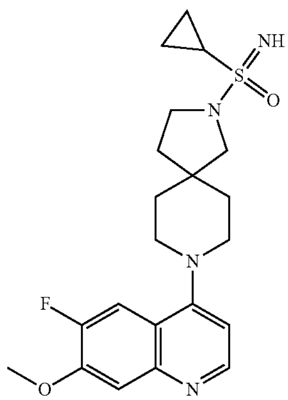 [SMILES: COc1cc2nccc(N3CCC4(CC3)CCN(S(=N)(=O)C3CC3)C4)c2cc1F] | | | Step 3: TBS; CHCl₃ | 419.2 (M + H) |
| 219 | 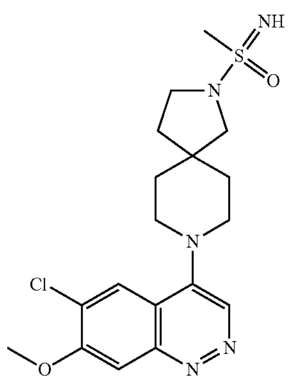 [SMILES: COc1cc2nncc(N3CCC4(CC3)CCN(S(C)(=N)=O)C4)c2cc1Cl] | | | Step 3: TBS; CHCl₃ | 410.0 (M + H) |
| 220 | 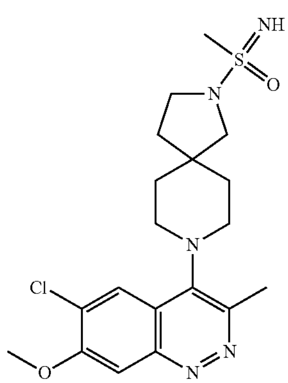 [SMILES: COc1cc2nnc(C)c(N3CCC4(CC3)CCN(S(C)(=N)=O)C4)c2cc1Cl] | | | Step 3: TBS; CHCl₃ | 424.0 (M + H) |

TABLE 9-continued

| Cmpd | Structure | Aryl Halide | Amine | Cond | MS (m/z) |
|---|---|---|---|---|---|
| 221 | 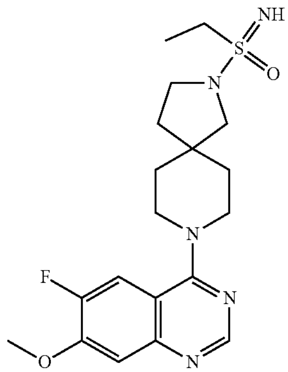 [SMILES: CCS(=N)(=O)N1CCC2(CCN(c3ncnc4cc(OC)c(F)cc34)CC2)C1] | | | Step 3: TBS; CHCl₃ | 408.3 (M + H) |
| 222 | 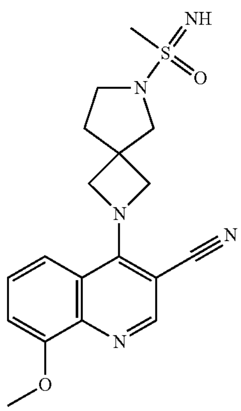 [SMILES: COc1cccc2c(N3CC4(CCN(S(C)(=N)=O)C4)C3)c(C#N)cnc12] | | | Step 3: TBS; CHCl₃ | 372.1 (M + H) |
| 223 | 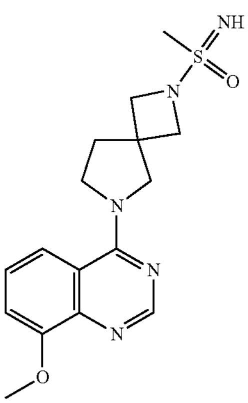 [SMILES: COc1cccc2c(N3CCC4(C3)CN(S(C)(=N)=O)C4)ncnc12] | | | Step 3: TBS; CHCl₃ | 348.2 (M + H) |
| 224 | 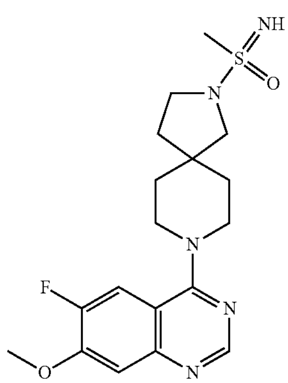 [SMILES: COc1cc2ncnc(N3CCC4(CC3)CCN(S(C)(=N)=O)C4)c2cc1F] | | | Step 3: TBS; CHCl₃ | 394.1 (M + H) |

TABLE 9-continued

| Cmpd | Structure | Aryl Halide | Amine | Cond | MS (m/z) |
|---|---|---|---|---|---|
| 225 | 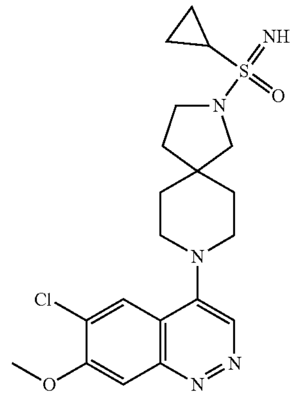 [SMILES: COc1cc2nncc(N3CCC4(CC3)CCN(S(=N)(=O)C3CC3)C4)c2cc1Cl] | | | Step 3: TBS; CHCl₃ | 436.1 (M + H) |
| 226 | 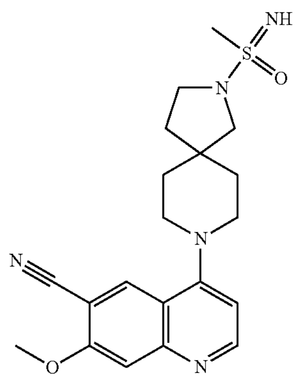 [SMILES: COc1cc2nccc(N3CCC4(CC3)CCN(S(C)(=N)=O)C4)c2cc1C#N] | | | Step 3: TBS; CHCl₃ | 400.1 (M + H) |

Synthetic Example S-9

Synthesis of [7-(6,7-dimethoxyquinolin-4-yl)-1,2,3,4-tetrahydroisoquinolin-2-yl](imino)methyl-$\lambda^6$-sulfanone (Compound 161)

Step 1: Synthesis of tert-butyl 7-(6,7-dimethoxyquinazolin-4-yl)-3,4-dihydroisoquinoline-2(1H)-carboxylate

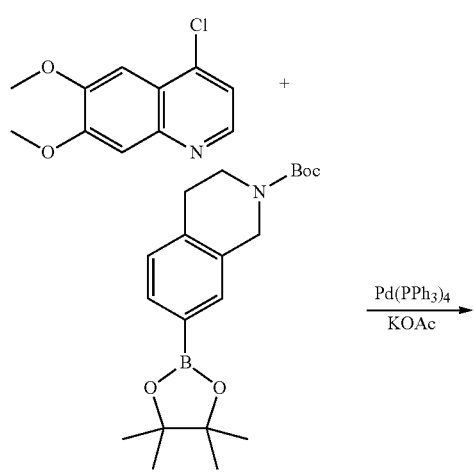

A mixture of 4-chloro-6,7-dimethoxy-quinoline (1.1 g, 4.6 mmol), tert-butyl 7-(4,4,5,5-tetramethyl-1,3,2-dioxaborolan-2-yl)-3,4-dihydro-1H-isoquinoline-2-carboxylate (2.0 g, 5.6 mmol), KOAc (0.91 g, 9.3 mmol), Pd(PPh₃)₄ (0.27 g, 0.23 mmol), dioxane (10 mL), and H₂O (2 mL) was degassed and purged with N₂ and then stirred at 110° C. for 12 hours under a N₂ atmosphere. The residue was diluted with water (50 mL) and extracted with EtOAc (50 mL×2). The combined extracts were washed with brine (30 mL), dried over Na₂SO₄, filtered and concentrated, and purified by silica chromatography (Petroleum ether/EtOAc, 9-100%) to provide tert-butyl 7-(6,7-dimethoxy-4-quinolyl)-3,4-dihydro-1H-isoquinoline-2-carboxylate (1.1 g).

Step 2: Synthesis of [7-(6,7-dimethoxyquinolin-4-yl)-1,2,3,4-tetrahydroisoquinolin-2-yl](imino)methyl-λ⁶-sulfanone

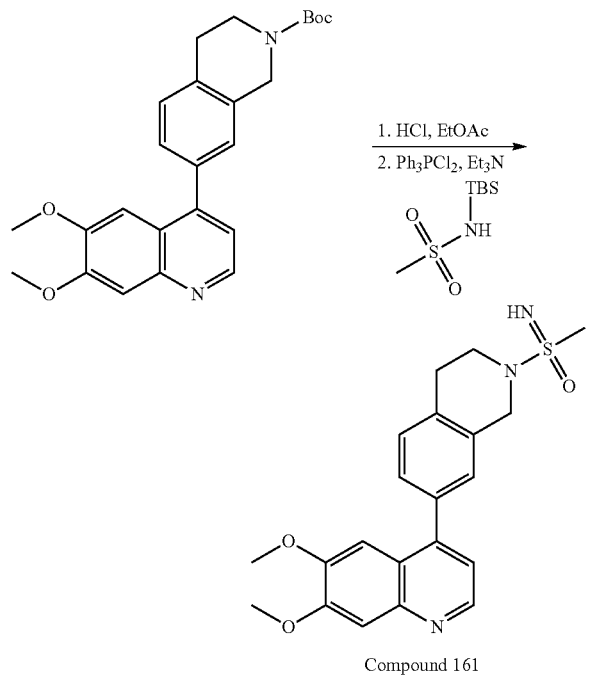

Compound 161

To a mixture of tert-butyl 7-(4,4,5,5-tetramethyl-1,3,2-dioxaborolan-2-yl)-3,4-dihydro-1H-isoquinoline-2-carboxylate (1.1 g, 3.1 mmol) and EtOAc (5 mL) was added 4 M HCl in EtOAc (12.7 mL). The mixture was stirred at 20° C. for 2 h, then was concentrated and 30 mL of saturated aqueous NaHCO₃ was added. The mixture was extracted with EtOAc (20 mL×2) and extracts were combined and washed with brine (20 mL), dried over Na₂SO₄, filtered and concentrated to provide 6,7-dimethoxy-4-(1,2,3,4-tetrahydroisoquinolin-7-yl)quinoline (0.54 g).

To a mixture of Ph₃PCl₂ (0.36 M, 6.5 mL) and CHCl₃ (3 mL) was added dropwise Et₃N (0.33 mL, 2.3 mmol) at 0° C. The mixture was stirred at this temperature for 15 mins, and N-[tert-butyl(dimethyl)silyl]methanesulfonamide (0.49 g, 2.3 mmol) was added and the mixture stirred at 0° C. for 15 mins. 6,7-dimethoxy-4-(1,2,3,4-tetrahydroisoquinolin-7-yl)quinoline (0.5 g, 1.6 mmol) and Et₃N (1.1 mL, 7.8 mmol) was added at 0° C. The resulting mixture was stirred at 20° C. for 1.5 h before being concentrated and purified by prep-HPLC (column: Phenomenex Luna C18 200*40 mm*10 um; mobile phase: [water (0.2% FA)-ACN]; B %: 1%-40%, 8 min) to provide [7-(6,7-dimethoxyquinolin-4-yl)-1,2,3,4-tetrahydroisoquinolin-2-yl](imino)methyl-λ⁶-sulfanone (Compound 161) (71 mg). ESI MS m/z=398.1 (M+H).

Compounds 37, 52, and 162-163 were prepared from the aryl halide and boronic ester indicated in Table 10 in the manner described in Synthetic Example S-9.

TABLE 10

| Cmpd | Structure | Aryl Halide | Boronate | MS (m/z) |
|---|---|---|---|---|
| 37 | 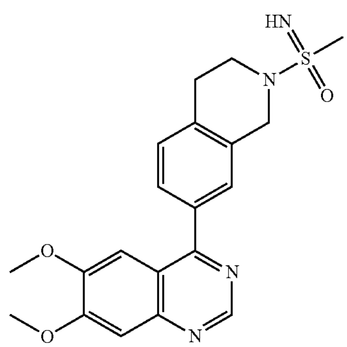 | | | 399.0 (M + H) |
| 52 | 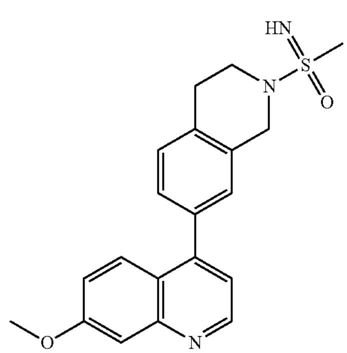 | | | 368.1 (M + H) |

TABLE 10-continued

| Cmpd | Structure | Aryl Halide | Boronate | MS (m/z) |
|---|---|---|---|---|
| 162 | (structure: methoxyquinoline-phenyl-CH₂NH-S(=O)=NH) | 4-chloro-7-methoxyquinoline | Boc-HN-CH₂-phenyl-Bpin | 342.0 (M + H) |
| 163 | (structure: methoxy-1,8-naphthyridine-tetrahydroisoquinoline-N-S(=O)Me with HN=) | 4-chloro-2-methoxy-1,8-naphthyridine | Boc-N-tetrahydroisoquinoline-Bpin | 369.1 (M + H) |

Synthetic Example S-10

Synthesis of 1-imino-4-[2-(7-methoxyquinolin-4-yl)acetyl]-1λ⁶-thiomorpholin-1-one (Compound 26)

Step 1. Synthesis of methyl 2-(7-methoxyquinolin-4-yl)acetate

To a stirring mixture of 7-methoxy-4-methylquinoline (0.52 g, 3.0 mmol), dimethyl carbonate (0.33 mL, 3.9 mmol), and THF (6.0 mL) at 0° C. was added 1M LiHMDS in THF (12 mL, 12 mmol). The mixture warmed to ambient temperature and was stirred for 1 h. Saturated aqueous NH₄Cl (10 mL) was added and the mixture stirred overnight. Water was added and the mixture extracted with CH₂Cl₂. The extracts were dried over Na₂SO₄, filtered, concentrated and purified by silica chromatography (10%-70% EtOAc in heptane) to provide 0.66 g of methyl 2-(7-methoxyquinolin-4-yl)acetate.

Step 2. Synthesis of 2-(7-methoxyquinolin-4-yl)-1-thiomorpholinoethan-1-one

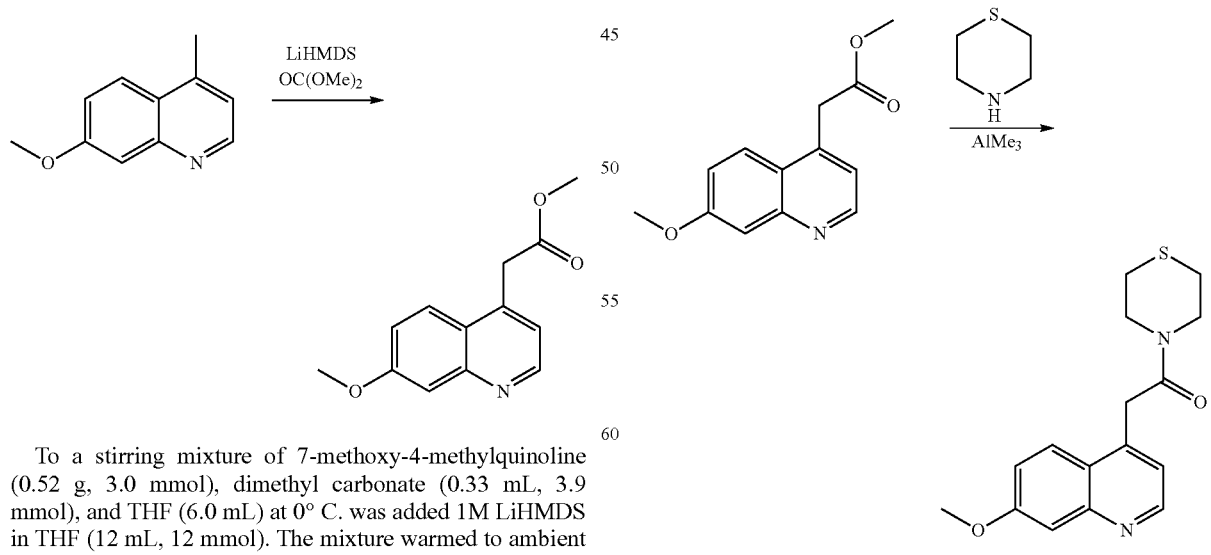

Trimethylaluminum (2M in toluene; 0.12 mL, 0.24 mmol) was added to a stirring mixture of thiomorpholine (0.023 mL, 0.24 mmol) and toluene (3.0 mL). After stirring 30 min, methyl 2-(7-methoxyquinoline-4-yl)acetate (0.046 g, 0.20 mmol) was added. The mixture was heated at 80° C. for 18 h, cooled to ambient temperature, and 10 drops of 1N aqueous HCl was added. Water was then added, the pH adjusted to ~4 with aqueous saturated NaHCO$_3$, and the mixture was extracted with CH$_2$Cl$_2$. The extracts were dried over Na$_2$SO$_4$, filtered, concentrated, and purified by reverse phase preparative HPLC (5-50% MeCN in water, 0.1% NH$_4$HCO$_3$) to provide 54 mg of 2-(7-methoxyquinolin-4-yl)-1-thiomorpholinoethan-1-one.

Step 3. Synthesis of 1-imino-4-[2-(7-methoxyquinolin-4-yl)acetyl]-1λ$^6$-thiomorpholin-1-one

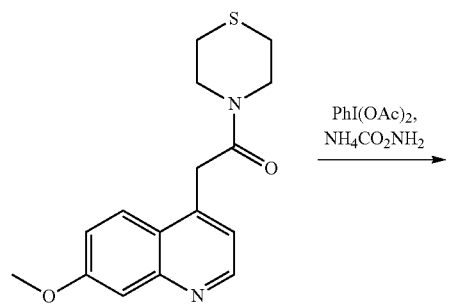

A mixture of 2-(7-methoxyquinolin-4-yl)-1-thiomorpholinoethan-1-one (54 mg, 0.18 mmol), methanol (3.5 mL), ammonium carbamate (20 mg, 0.26 mmol) and PhI(OAc)$_2$ (0.11 g, 0.35 mmol) was stirred 3 hours. Additional ammonium carbamate (10 mg, 0.13 mmol) and PhI(OAc)$_2$ (56 mg, 0.18 mmol) were added and the mixture stirred for 1 h. After concentration, the mixture was purified by silica chromatography (0-3% MeOH in CH$_2$Cl$_2$) to provide 18 mg of 1-imino-4-[2-(7-methoxyquinolin-4-yl)acetyl]-1λ$^6$-thiomorpholin-1-one (Compound 26). ESI MS m/z: 334.1 (M+H).

Synthetic Example S-11

Synthesis of 1-imino-4-(7-methoxyquinoline-4-carbonyl)-1λ$^6$-thiomorpholin-1-one (Compound 6)

Step 1: Synthesis of (7-methoxyquinolin-4-yl)(thiomorpholino)methanone

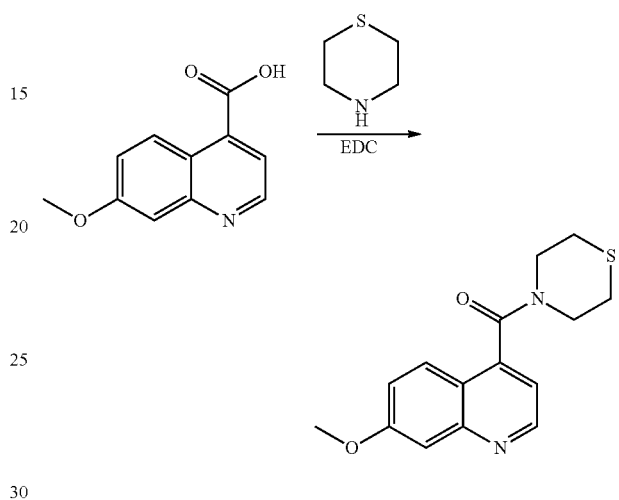

To a stirring mixture of 7-methoxyquinoline-4-carboxylic acid (41 mg, 0.20 mmol), EDC (42 mg, 0.22 mmol), ethyl cyano(hydroxyamino)acetate (2.8 mg, 0.020 mmol) and DMF (3.0 mL) was added thiomorpholine (25 mg, 0.24 mmol). After stirring for 3 h, the mixture was directly purified by reverse phase preparative HPLC (ReproSil column (5-40); 5-40% MeCN in water, 0.1% NH$_4$HCO$_3$) provided 52 mg of (7-methoxyquinolin-4-yl)(thiomorpholino)methanone.

Step 2: Synthesis of 1-imino-4-(7-methoxyquinoline-4-carbonyl)-1λ$^6$-thiomorpholin-1-one

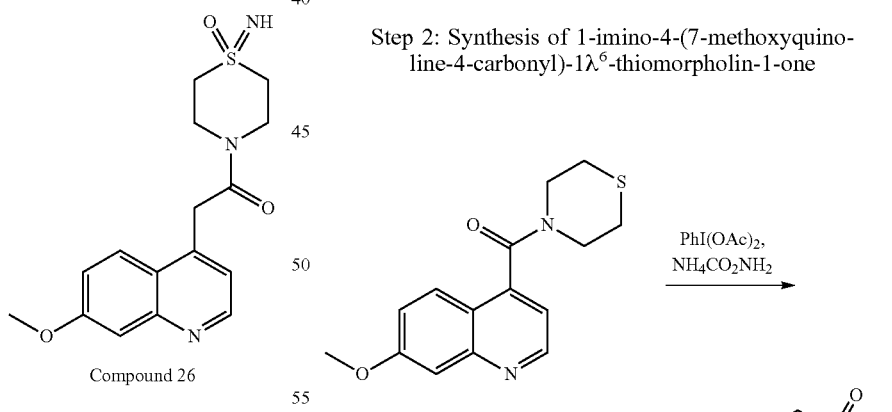

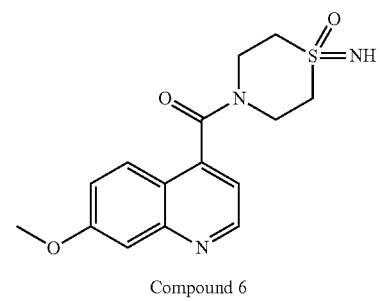

Compound 6

337

1-imino-4-(7-methoxyquinoline-4-carbonyl)-1λ⁶-thiomorpholin-1-one (Compound 6) was prepared from (7-methoxyquinolin-4-yl)(thiomorpholino)methanone in the manner described for Step 3 in the synthesis of Compound 26 (Synthetic Example S-10). ESI MS m/z: 320.1 (M+H).

Synthetic Example S-12

Synthesis of (4-{[(6,7-dimethoxyquinazolin-4-yl)oxy]methyl}piperidin-1-yl)(imino)methyl-λ⁶-sulfanone (Compound 164)

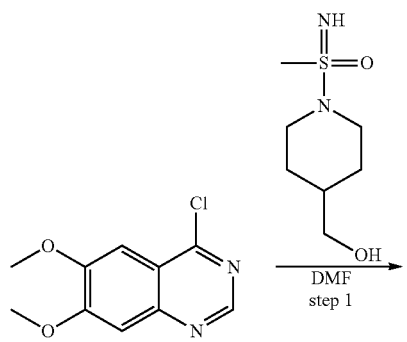

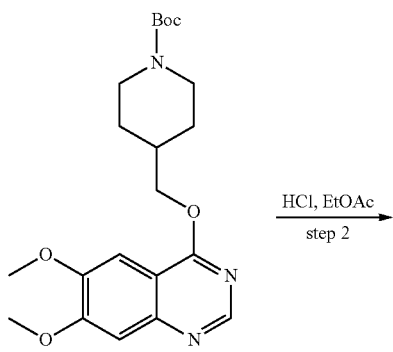

338

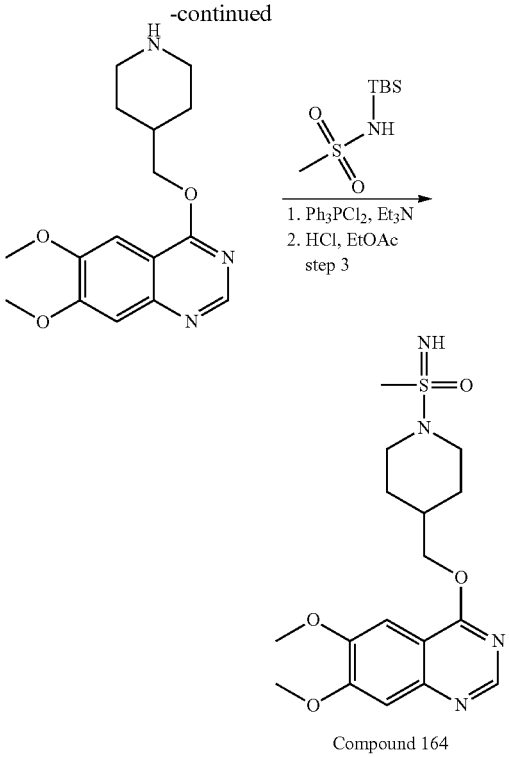

(4-{[(6,7-dimethoxyquinazolin-4-yl)oxy]methyl}piperidin-1-yl)(imino)methyl-λ⁶-sulfanone was prepared in three steps. In step 1, tert-butyl 4-(((6,7-dimethoxyquinazolin-4-yl)oxy)methyl)piperidine-1-carboxylate was prepared from 4-chloro-6,7-dimethoxyquinazoline in the manner described to Step 1 in the synthesis of Compound 133 (Synthetic Example S-4), except DMF was used as solvent instead of EtOH. (4-{[(6,7-dimethoxyquinazolin-4-yl)oxy]methyl}piperidin-1-yl)(imino)methyl-λ⁶-sulfanone (Compound 164) was prepared in two steps from tert-butyl 4-(((6,7-dimethoxyquinazolin-4-yl)oxy)methyl)piperidine-1-carboxylate in the same manner as Steps 2 and 3 of the synthesis of Compound 54 (Synthetic Example S-7). ESI MS m/z: 381.1 (M+H).

Compounds 229-230 were prepared from the aryl halide and alcohol indicated in Table 11 in the manner described in Synthetic Example S-12.

TABLE 11

| Cmpd | Structure | Aryl Halide | Alcohol | MS (m/z) |
|---|---|---|---|---|
| 229 | 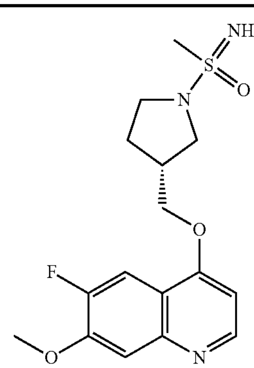 | | | 354.1 (M + H) |

TABLE 11-continued

| Cmpd | Structure | Aryl Halide | Alcohol | MS (m/z) |
|---|---|---|---|---|
| 230 | 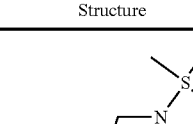 | 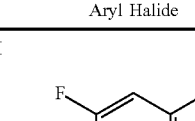 | 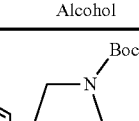 | 354.1 (M + H) |

Synthetic Example S-13

Synthesis of 4-(4-{[imino(methyl)oxo-λ⁶-sulfanyl]methyl}piperidin-1-yl)-8-methoxyquinoline-3-carbonitrile (Compound 179)

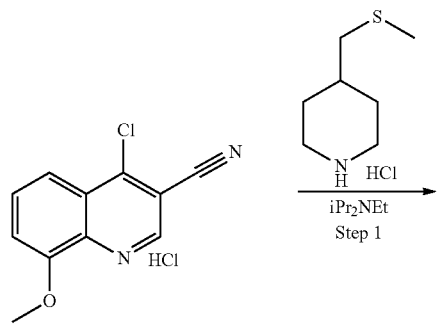

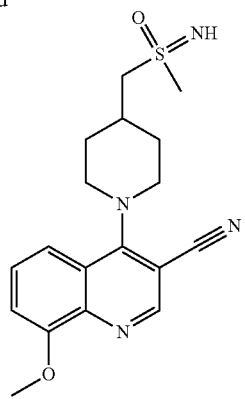

Compound 179

Step 1: To a mixture of 4-chloro-8-methoxy-quinoline-3-carbonitrile hydrochloride (4.1 g, 16 mmol) and iPrOH (80 mL) was added iPr₂NEt (14 mL, 80 mmol) and 4-(methylsulfanylmethyl)piperidine hydrochloride (2.9 g, 16 mmol). The mixture was stirred at 90° C. for 4 h, cooled, concentrated, and triturated with H₂O (20 mL) for 30 min and MTBE (20 mL) for 30 minutes to provide 8-methoxy-4-[4-(methylsulfanylmethyl)-1-piperidyl]quinoline-3-carbonitrile (5.4 g).

Step 2: A mixture of 8-methoxy-4-[4-(methylsulfanylmethyl)-1-piperidyl]quinoline-3-carbonitrile (5.9 g, 18 mmol), EtOH (50 mL), PhI(OAc)₂ (17 g, 54 mmol) and NH₄OAc (5.6 g, 72 mmol). The mixture was stirred at 20° C. for 2 h, concentrated and triturated with 1120 (30 mL) for 30 min, and purified by preparative HPLC (2-25% MeCN/water (0.23% formic acid)) to afford 8-methoxy-4-[4-[(methylsulfonimidoyl)methyl]-1-piperidyl]quinoline-3-carbonitrile (2.7 g). ESI MS m/z: 359.1 (M+H).

Compounds 180-195 were prepared from aryl chlorides and amines under conditions indicated in Table 12 in the manner described in Synthetic Example S-13.

TABLE 12

| Cmpd | Structure | Chloro Compound | Amine | Conditions | MS (m/z) |
|---|---|---|---|---|---|
| 180 | 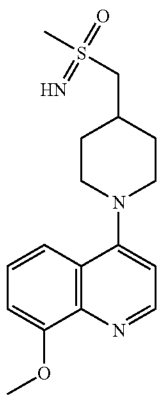 [SMILES: COc1cccc2c(N3CCC(CS(C)(=N)=O)CC3)ccnc12] | | | iPr₂NEt, nBuOH 140° C. | 334.1 (M + H) |
| 181 | 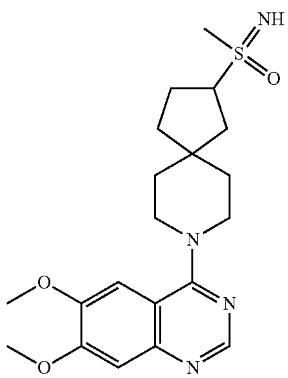 [SMILES: COc1cc2ncnc(N3CCC4(CCC(S(C)(=N)=O)C4)CC3)c2cc1OC] | | | iPr₂NEt, nBuOH 90° C. | 405.1 (M + H) |
| 182 | 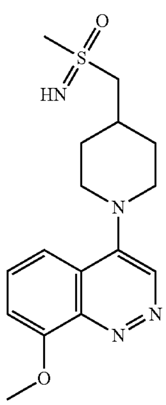 [SMILES: COc1cccc2c(N3CCC(CS(C)(=N)=O)CC3)cnnc12] | | | Cs₂CO₃, DMSO, 80° C. | 335.1 (M + H) |
| 183 | 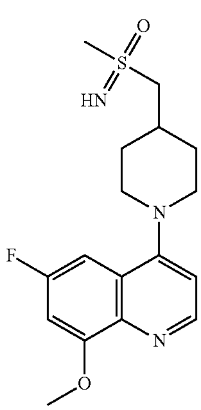 [SMILES: COc1cc(F)cc2c(N3CCC(CS(C)(=N)=O)CC3)ccnc12] | | | iPr₂NEt, nBuOH 20° C. | 353.2 (M + H) |

TABLE 12-continued

| Cmpd | Structure | Chloro Compound | Amine | Conditions | MS (m/z) |
|---|---|---|---|---|---|
| 184 | 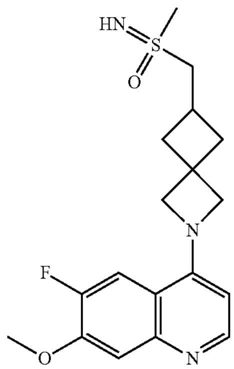 [SMILES: COc1cc2nccc(N3CC4(CC(CS(C)(=N)=O)C4)C3)c2cc1F] | | | iPr₂NEt, nBuOH 140° C. | 364.2 (M + H) |
| 185 | 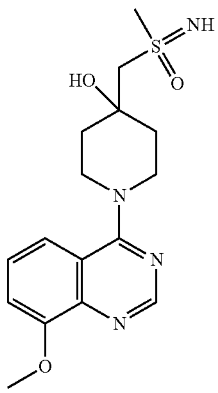 | | | iPr₂NEt, iPrOH 20° C. | 351.2 (M + H) |
| 186 | 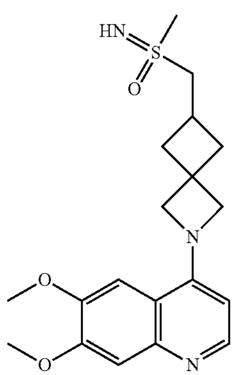 [SMILES: COc1cc2nccc(N3CC4(CC(CS(C)(=N)=O)C4)C3)c2cc1OC] | | | iPr₂NEt, nBuOH 140° C. | 376.1 (M + H) |
| 187 | 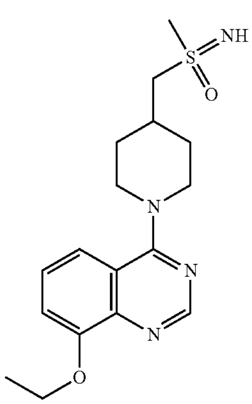 [SMILES: CCOc1cccc2c(N3CCC(CS(C)(=N)=O)CC3)ncnc12] | | | iPr₂NEt, iPrOH 15° C. | 349.1 (M + H) |

TABLE 12-continued

| Cmpd | Structure | Chloro Compound | Amine | Conditions | MS (m/z) |
|---|---|---|---|---|---|
| 188 | 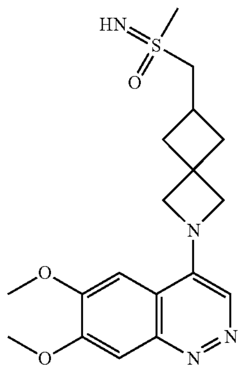 [SMILES: COc1cc2nncc(N3CC4(CC(CS(C)(=N)=O)C4)C3)c2cc1OC] | | | iPr₂NEt, iPrOH 120° C. | 377.2 (M + H) |
| 189 | 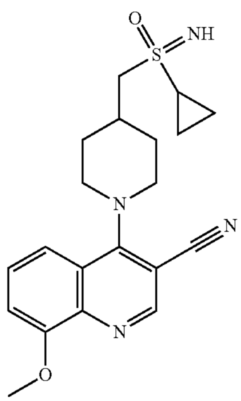 [SMILES: COc1cccc2c(N3CCC(CS(=N)(=O)C4CC4)CC3)c(C#N)cnc12] | | | iPr₂NEt, iPrOH 120° C. | 385.1 (M + H) |
| 190 | 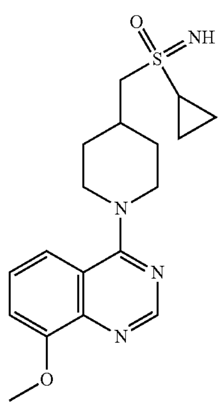 [SMILES: COc1cccc2c(N3CCC(CS(=N)(=O)C4CC4)CC3)ncnc12] | | | iPr₂NEt, iPrOH 90° C. | 361.2 (M + H) |
| 191 | 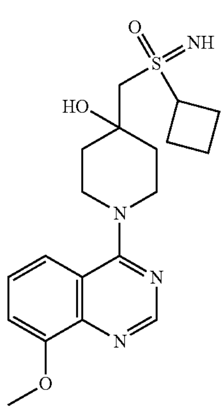 [SMILES: COc1cccc2c(N3CCC(O)(CS(=N)(=O)C4CCC4)CC3)ncnc12] | | | iPr₂NEt, iPrOH 40° C. | 391.1 (M + H) |

TABLE 12-continued

| Cmpd | Structure | Chloro Compound | Amine | Conditions | MS (m/z) |
|---|---|---|---|---|---|
| 192 | 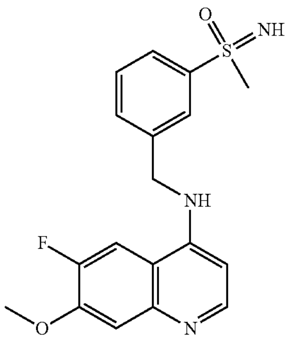 [SMILES: COc1cc2nccc(NCc3cccc(S(C)(=N)=O)c3)c2cc1F] | | | iPr₂NEt, nBuOH 160° C. | 360.1 (M + H) |
| 193 | 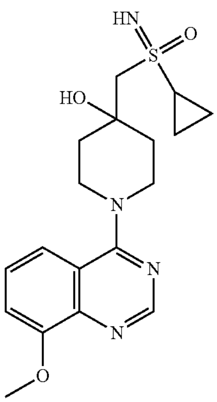 [SMILES: COc1cccc2c(N3CCC(O)(CS(=N)(=O)C4CC4)CC3)ncnc12] | | | iPr₂NEt, iPrOH 40° C. | 377.2 (M + H) |
| 194 | 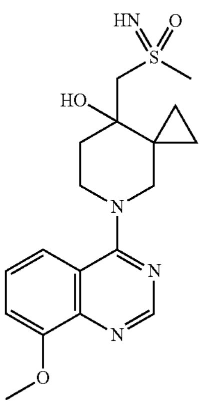 [SMILES: COc1cccc2c(N3CCC(O)(CS(C)(=N)=O)C4(CC4)C3)ncnc12] | | | iPr₂NEt, iPrOH, 20° C. | 377.1 (M + H) |
| 195 | 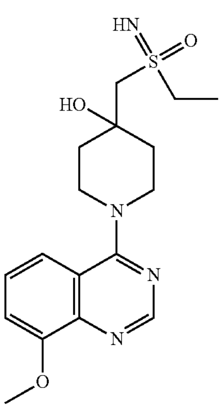 [SMILES: CCS(=N)(=O)CC1(O)CCN(c2ncnc3c(OC)cccc23)CC1] | | | iPr₂NEt, iPrOH, 20° C. | 365.1 (M + H) |

Synthetic Example S-14

Synthesis of [8-(3-fluoro-6,7-dimethoxyquinolin-4-yl)-2,8-diazaspiro[4.5]decan-2-yl](imino)methyl-$\lambda^6$-sulfanone (Compound 227)

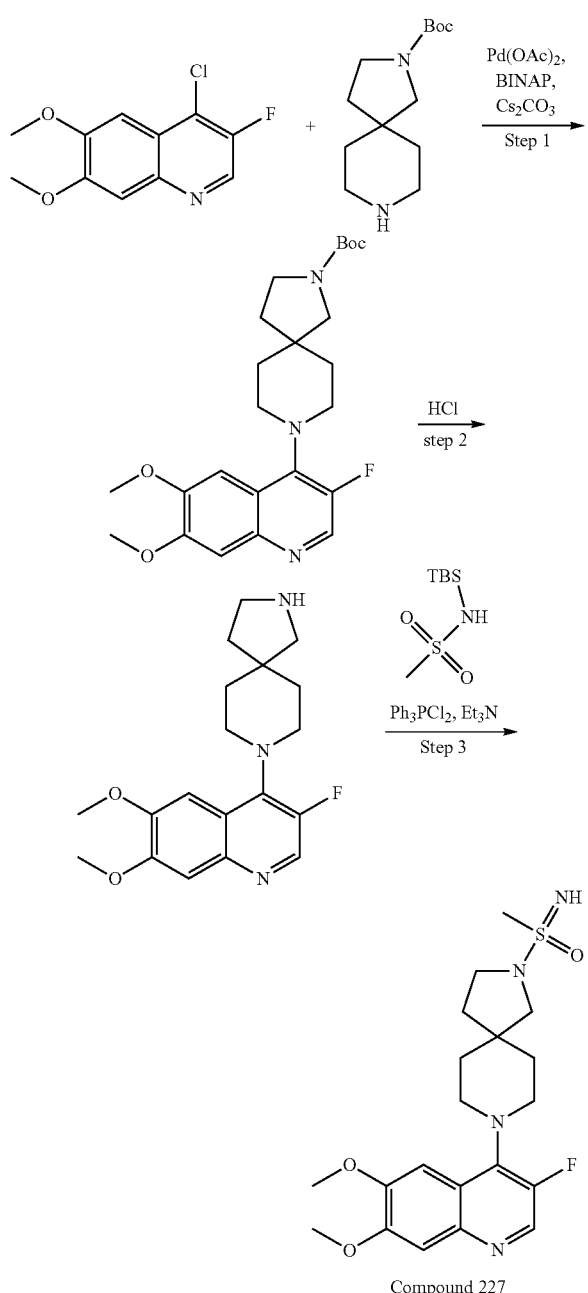

Compound 227

Step 1: A mixture of 4-chloro-3-fluoro-6,7-dimethoxyquinoline (0.21 g, 0.85 mmol), dioxane (1.0 mL), Cs$_2$CO$_3$ (0.57 g, 1.7 mmol), Pd(OAc)$_2$ (19 mg), [1-(2-diphenylphosphanyl-1-naphthyl)-2-naphthyl]-diphenyl-phosphane (54 mg, 87 µmol), and tert-butyl 2,8-diazaspiro[4.5]decane-2-carboxylate hydrochloride (0.24 g, 0.85 mmol) was stirred at 140° C. for 12 h under an N$_2$ atmosphere. The mixture was concentrated, combined with H$_2$O (10 mL) and extracted with EtOAc (10 mL×2). The extracts were combined, washed with brine (10 mL), dried over Na$_2$SO$_4$, filtered, and concentrated, and purified by silica chromatography (10%-100% EtOAc in petroleum ether) to provide tert-butyl 8-(3-fluoro-6,7-dimethoxyquinolin-4-yl)-2,8-diazaspiro[4.5]decane-2-carboxylate hydrochloride (0.36 g).

Step 2: A mixture of tert-butyl 8-(3-fluoro-6,7-dimethoxy-4-quinolyl)-2,8-diazaspiro[4.5]decane-2-carboxylate (0.36 g, 0.81 mmol), EtOAc (7.0 mL), and HCl/EtOAc (4 M, 3.6 mL) was stirred at 20° C. for 2 h, then was concentrated to provide 3-fluoro-6,7-dimethoxy-4-(2,8-diazaspiro[4.5]decan-8-yl)quinoline (0.30 g).

Step 3: A mixture of Ph$_3$PCl$_2$ (0.36 M in CHCl$_3$, 3.6 mL), CHCl$_3$ (8.0 mL), and Et$_3$N (0.27 mg, 2.6 mmol) was stirred at 0° C. for 0.5 h. 8-(3-fluoro-6,7-dimethoxy-4-quinolyl)-2,8-diazaspiro[4.5]decane hydrochloride (0.25 mg, 0.66 mmol) was added at 0° C. and it was stirred for 0.5 h. N-[tert-butyl(dimethyl)silyl]methanesulfonamide (0.27 g, 1.3 mmol) and Et$_3$N (0.27 g, 2.6 mmol) were added at 20° C. After stirring for 1 h, the mixture was concentrated, and 1M HCl (5.0 mL) was added to adjust the pH to 3, and H$_2$O (5.0 mL) was added. The mixture was extracted with EtOAc (15 mL), and the pH of the aqueous phase was adjusted to pH 7 with saturated NaHCO$_3$ (5.0 mL). The solution was purified directly by preparative HPLC (1-30% MeCN in H$_2$O (0.2% formic acid)) to provide 3-fluoro-6,7-dimethoxy-4-(2-(S-methylsulfonimidoyl)-2,8-diazaspiro[4.5]decan-8-yl)quinoline (Compound 227) (69 mg). ESI MS m/z: 423.2 (M+H).

Synthetic Example S-15

Synthesis of [8-(6,7-dimethoxy-3-methylcinnolin-4-yl)-2,8-diazaspiro[4.5]decan-2-yl](imino)methyl-$\lambda^6$-sulfanone (Compound 228)

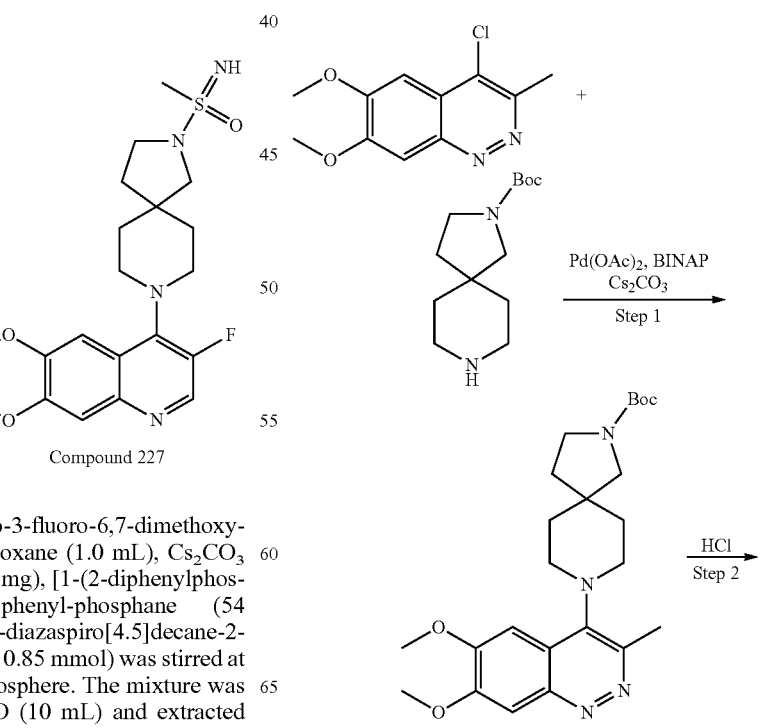

353

-continued

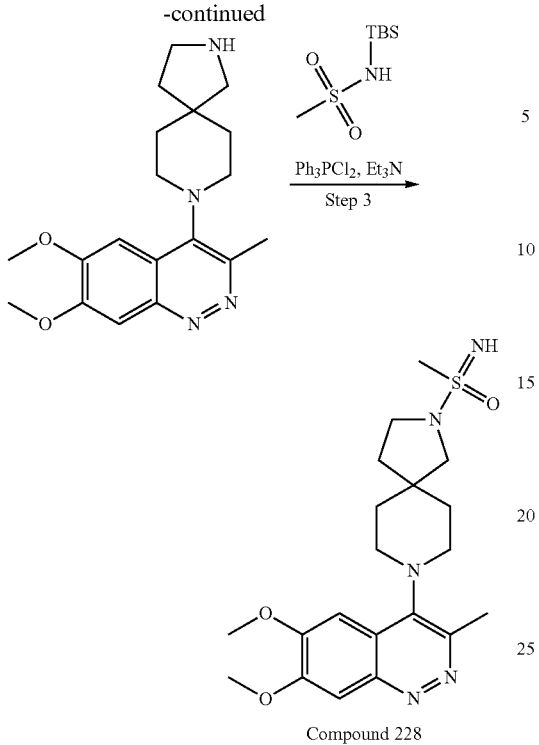

Compound 228

Compound 228 was prepared in the same manner as Compound 227 in Synthetic Example S-14 with 4-chloro-6,7-dimethoxy-3-methyl-cinnoline in place of 4-chloro-3-fluoro-6,7-dimethoxy-quinoline in step 1. ESI MS m/z: 420.3 (M+H).

Synthetic Example S-16

Synthesis of imino({4-[(7-methoxyquinolin-4-yl)methoxy]phenyl})methyl-$\lambda^6$-sulfanone (Compound 231)

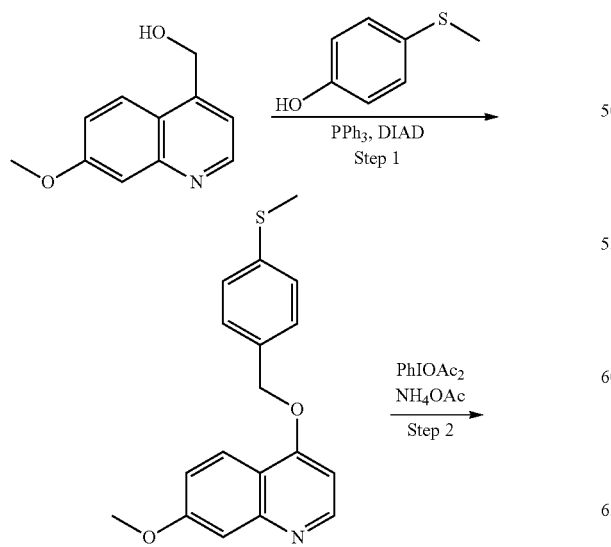

354

-continued

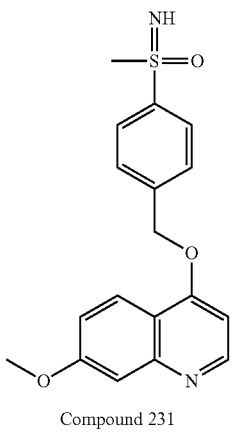

Compound 231

Step 1: To a 0° C. mixture of (7-methoxy-4-quinolyl)methanol (50 mg, 0.26 mmol) and 4-methylsulfanylphenol (44 mg, 0.31 mmol), and THF (2.0 mL) was added PPh$_3$ (140 mg, 0.53 mmol) followed by dropwise addition of DIAD (110 mg, 0.52 mmol) in THF (0.5 mL). The resulting mixture was stirred at 25° C. for 12 h, H$_2$O (5 mL) was added and the mixture was extracted with 15 mL of EtOAc and the extract was washed with 10 mL of brine, dried over Na$_2$SO$_4$, filtered, concentrated, and purified by chromatography over silica (10-100%/EtOAc in hexanes) to provide 7-methoxy-4-[(4-methylsulfanylphenoxy)methyl]quinoline (40 mg).

Step 2: A mixture of 7-methoxy-4-[(4-methylsulfanylphenoxy)methyl]quinoline (40 mg, 0.13 mmol), EtOH (1.00 mL), PhIOAc$_2$ (124 mg, 0.41 mmol), and NH$_4$OAc (39 mg, 0.51 mmol) was stirred at 25° C. for 2 h. The reaction mixture was concentrated and purified by preparative HPLC (20-40% MeCN in water, 0.1%) to provide imino({4-[(7-methoxyquinolin-4-yl)methoxy]phenyl})methyl-$\lambda^6$-sulfanone (Compound 231) (2.3 mg). ESI MS m/z: 343.0 (M+H).

Synthetic Example S-17

Synthesis of imino({3-[(7-methoxyquinolin-4-yl)methoxy]phenyl})methyl-$\lambda^6$-sulfanone (Compound 232)

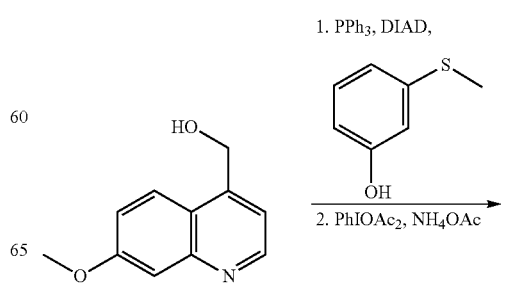

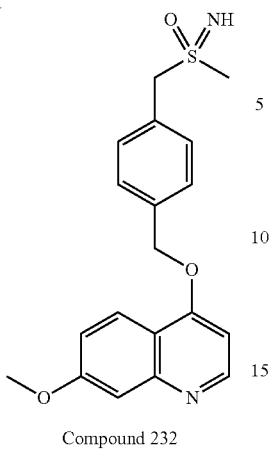

Compound 232

Imino({3-[(7-methoxyquinolin-4-yl)methoxy]phenyl})methyl-λ⁶-sulfanone (Compound 232) was prepared in two steps from (7-methoxy-4-quinolyl)methanol and 4-methyl-sulfanylphenol in manner described in Synthetic Example S-16. ESI MS m/z: 343.0 (M+H).

Synthetic Example S-18

Synthesis of imino[2-(7-methoxyquinolin-4-yl)-2H, 4H,5H,6H,7H-pyrazolo[4,3-c]pyridin-5-yl]methyl-λ⁶-sulfanone (Compound 233)

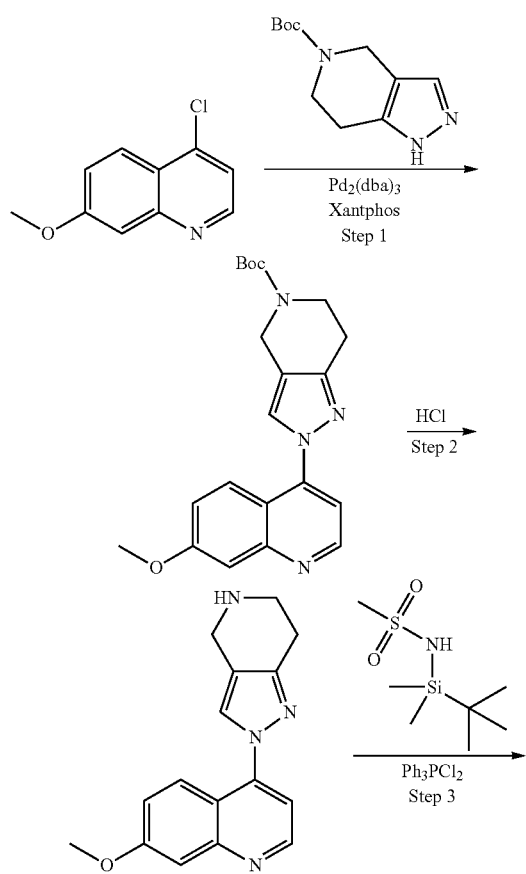

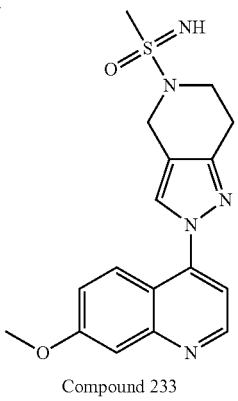

Compound 233

Step 1: A mixture of 4-chloro-7-methoxyquinoline (0.5 g, 2.6 mmol), tert-butyl-1,4,6,7-tetrahydropyrazolo[4,3-c]pyridine-5-carboxylate (0.63 g, 2.8 mmol), Xantphos (0.3 g, 0.52 mmol), K₃PO₄ (1.1 g, 5.2 mmol), Pd₂(dba)₃ (0.24 g, 0.26 mmol), and dioxane (10 ml) was heated at 140° C. for 2 h in a microwave reactor. The mixture was poured into H₂O (20 mL), extracted with EtOAc (20.0 mL×2). The combined extracts were washed with brine (20 mL×2), dried over Na₂SO₄, filtered, concentrated, and purified by silica chromatography (0-100% EtOAc in petroleum ether) to provide tert-butyl 2-(7-methoxy-4-quinolyl)-6,7-dihydro-4H-pyrazolo[4,3-c]pyridine-5-carboxylate (1.3 g with 85% purity).

Step 2: To a mixture of tert-butyl 2-(7-methoxy-4-quinolyl)-6, 7-dihydro-4H-pyrazolo[4, 3-c]pyridine-5-carboxylate (1.5 g, 3.9 mmol) and EtOAc (2.0 mL) was added HCl/EtOAc (4 M, 7.4 mL) and the mixture was stirred at 25° C. for 2 h. The mixture was concentrated, combined MeOH (20 mL) and amberlyst-21 (2.0 g) was added. The mixture was filtered and concentrated to provide 7-methoxy-4-(4, 5, 6, 7-tetrahydropyrazolo[4, 3-c]pyridin-2-yl)quinoline (1.0 g).

Step 3: To Ph₃PCl₂ (0.36 M, 5.0 mL) in CHCl₃ (2.0 mL) was added Et₃N (0.37 mL, 2.7 mmol) and the mixture was stirred at 0° C. for 10 min. N-[tert-butyl(dimethyl)silyl]methanesulfonamide (0.37 g, 1.8 mmol) was added and the mixture was stirred at 0° C. for 20 min, then 7-methoxy-4-(4,5,6,7-tetrahydropyrazolo[4, 3-c]pyridin-2-yl)quinoline (0.5 g, 1.8 mmol) and Et₃N (0.75 mL, 5.4 mmol) in CHCl₃ (3 mL) was added at 0 TC. The mixture was stirred at 25° C. for 90 min and was concentrated. The residue was combined with MeOH (1.0 mL) and 1M aqueous HCl (40.0 mL, 40 mmol) was added. The mixture was stirred at 20° C. for 10 min, the mixture was concentrated and purified by reverse-phase HPLC (1-40%/MeCN/water (0.2% formic acid)] to provide imino[2-(7-methoxyquinolin-4-yl)-2H,4H, 5H,6H,7H-pyrazolo[4,3-c]pyridin-5-yl]methyl-λ⁶-sulfanone (Compound 233) (89 mg). ESI MS m/z: 358.1 (M+H).

Synthetic Example S-19

Synthesis of imino({2-[1-(7-methoxyquinolin-4-yl)-1H-pyrazol-4-yl]ethyl})methyl-λ⁶-sulfanone (Compound 234)

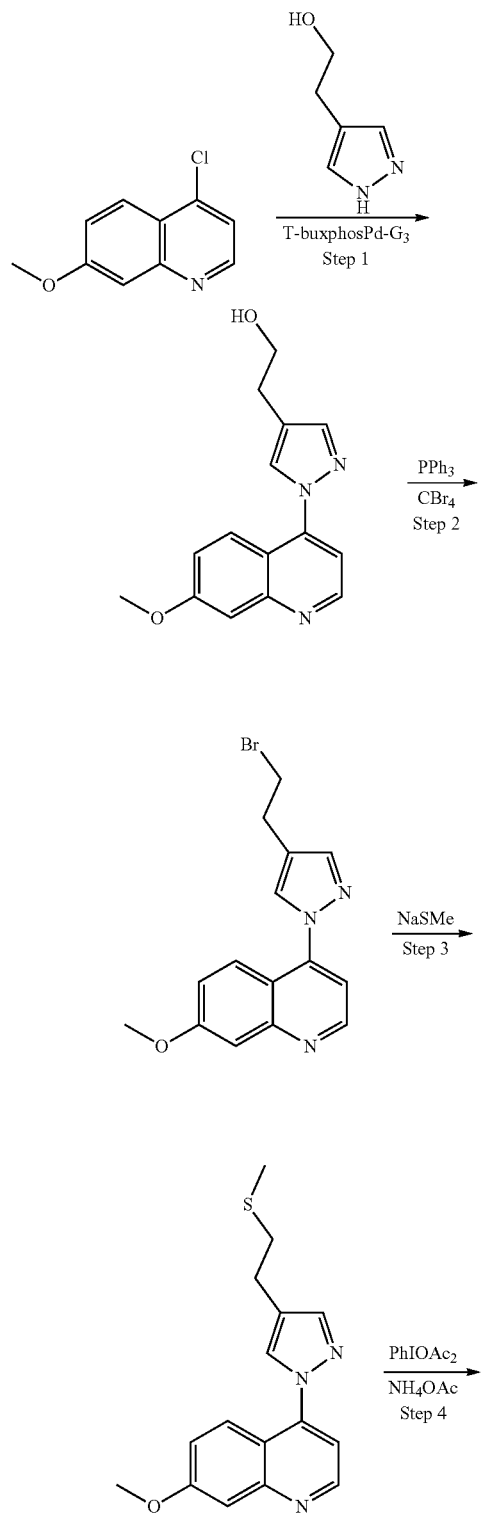

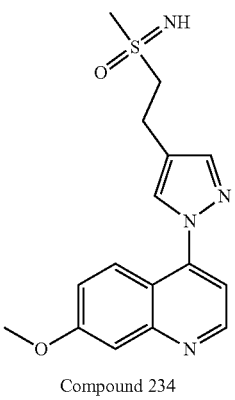

Compound 234

Step 1: A mixture of 2-(1H-pyrazol-4-yl) ethanol (0.64 g, 5.7 mmol), 4-chloro-7-methoxy-quinoline (1.0 g, 5.2 mmol), tBuONa (1.5 g, 16 mmol), T-buxphosPh-G₃ (0.41 g, 0.52 mmol), and THF (10 mL) was degassed with bubbling N₂, then was stirred at 110° C. for 12 h under an N₂ atmosphere. The mixture was poured into H₂O (10 mL) and extracted with EtOAc (10.0 mL×2). The combined extracts were washed with brine (10 mL×2), dried over Na₂SO₄, filtered, concentrated, and purified by silica chromatography (0-100% EtOAc/petroleum ether to provide 2-[1-(7-methoxy-4-quinolyl)pyrazol-4-yl]ethanol (0.27 g).

Step 2: To a 0° C. mixture of 2-[1-(7-methoxy-4-quinolyl)pyrazol-4-yl]ethanol (0.22 g, 0.82 mmol) and CH₂Cl₂ (5.0 mL) were added PPh₃ (0.32 g, 1.2 mmol) and CBr₄ (0.41 g, 1.2 mmol). The mixture was stirred at 20° C. for 12 h, then was concentrated, poured into water (10 mL), and extracted with EtOAc (10.0 mL×2). The combined extracts were washed with brine (10.0 mL×2), dried over Na₂SO₄, filtered, and concentrated to provide 4-[4-(2-bromoethyl) pyrazol-1-yl]-7-methoxy-quinoline (0.27 g) that was used without purification.

Step 3: A mixture of 4-[4-(2-bromoethyl)pyrazol-1-yl]-7-methoxy-quinoline (0.25 g, 0.75 mmol), EtOH (5 mL), aqueous NaSMe (20%, 0.48 mL, 1.5 mmol) was stirred at 20° C. for 12 h under N₂. The mixture was poured into H₂O (10 mL) and extracted with EtOAc (10 mL×2). The combined extracts were washed with brine (10 mL×2), dried over Na₂SO₄, filtered, concentrated, and purified by preparative TLC (SiO₂, 10:1:1 CH₂Cl₂/MeOH/EtOAc, then 4:1:1 petroleum ether/EtOAc/THF) to provide 7-methoxy-4-[4-(2-methylsulfanylethyl)pyrazol-1-yl]quinoline (0.12 g).

Step 4: A mixture of 7-methoxy-4-[4-(2-methylsulfanylethyl)pyrazol-1-yl]quinoline (0.10 g, 0.33 mmol), EtOH (2 mL), PhI(OAc)₂ (0.32 g, 1.0 mmol), and NH₄OAc (0.10 g, 1.3 mmol) was stirred at 20° C. for 1 h. The mixture was concentrated and purified by preparative TLC (SiO₂, 10:1 CH₂Cl₂/MeOH) to provide 7-methoxy-4-(4-(2-(S-methylsulfonimidoyl)ethyl)-1H-pyrazol-1-yl)quinoline (Compound 234) (15 mg). ESI MS m/z: 331.2 (M+H)

Synthetic Example S-20

Synthesis of imino({4-[(7-methoxyquinolin-4-yl)oxy]piperidin-1-yl})methyl-$\lambda^6$-sulfanone (Compound 235)

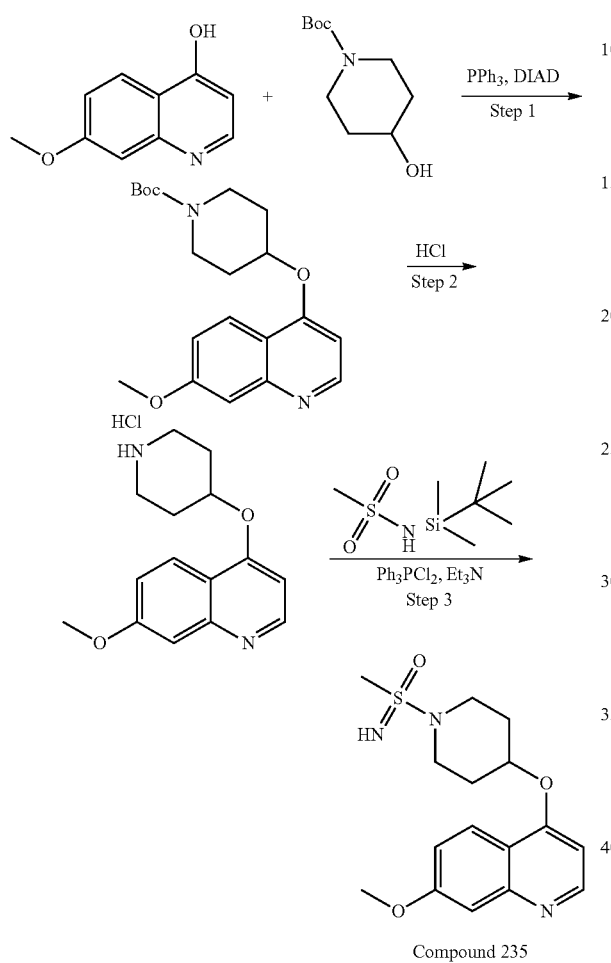

Compound 235

Step 1: To a mixture of 7-methoxyquinolin-4-ol (1.0 g, 5.7 mmol) and tert-butyl 4-hydroxypiperidine-1-carboxylate (1.2 g, 5.7 mmol) in THF (25 mL) was added PPh$_3$ (3.0 g, 11 mmol) followed by the dropwise addition of DIAD (2.2 mL, 11 mmol) in THF (5 mL) at 0° C. The resulting mixture was stirred at 25° C. for 12 h, then was concentrated, combined with H$_2$O (20 mL) and extracted with EtOAc (20.00 mL×2). The combined extracts were washed with brine (20 mL), dried over Na$_2$SO$_4$, filtered, concentrated, and purified by silica chromatography (10-100% petroleum ether/EtOAc) to afford tert-butyl 4-[(7-methoxy-4-quinolyl)oxy]piperidine-1-carboxylate (2.2 g).

Step 2: A mixture of tert-butyl 4-[(7-methoxy-4-quinolyl)oxy]piperidine-1-carboxylate (2.0 g, 5.6 mmol), EtOAc (3 mL), and 4 M HCl in EtOAc (30 mL, 120 mmol) was stirred at 25° C. for 2 h. The mixture was concentrated to provide 7-methoxy-4-(4-piperidyloxy)quinoline hydrochloride (1.9 g).

Step 3: To a mixture of Ph$_3$PCl$_2$ (0.36 M, 27 mL, 9.7 mmol) in CHCl$_3$ (10 mL) was added Et$_3$N (1.4 mL, 9.6 mmol) at 0° C. The mixture was stirred for 15 min, then N-[tert-butyl(dimethyl)silyl]methanesulfonamide (2.0 g, 9.7 mmol) was added and stirred at 0° C. for 15 min. 7-methoxy-4-(4-piperidyloxy)quinoline (1.0 g, 3.9 mmol) and Et$_3$N (1.35 mL, 9.7 mmol) was added at 0° C. and the resulting mixture was stirred at 20° C. for 1.5 h. The mixture was concentrated to afford tert-butyl-[[[4-[(7-methoxy-4-quinolyl)oxy]-1-piperidyl]-methyl-oxo-$\lambda^6$-sulfanylidene]amino]-dimethyl-silane (1.8 g, crude), a portion of which (1.60 g, 3.5 mmol) was combined with MeOH (10.00 mL) and aqueous HCl (1 M, 8.0 mL, 8 mmol). The mixture was stirred at 25° C. for 30 min, and saturated aqueous NaHCO$_3$ (15 mL) was added. The mixture was extracted with EtOAc (20 mL) and the extract was washed with brine (10 mL), dried over Na$_2$SO$_4$, filtered, concentrated, and purified by reverse-phase HPLC (10-30% MeCN in H$_2$O (0.2% formic acid)) to afford imino({4-[(7-methoxyquinolin-4-yl)oxy]piperidin-1-yl})methyl-$\lambda^6$-sulfanone (Compound 235) (310 mg). ESI MS m/z: 336.0 (M+H).

Synthetic Example S-21

Synthesis of imino[7-(8-methoxyquinazolin-4-yl)-2,7-diazaspiro[3.5]nonan-2-yl]methyl-$\lambda^6$-sulfanone (Compound 236)

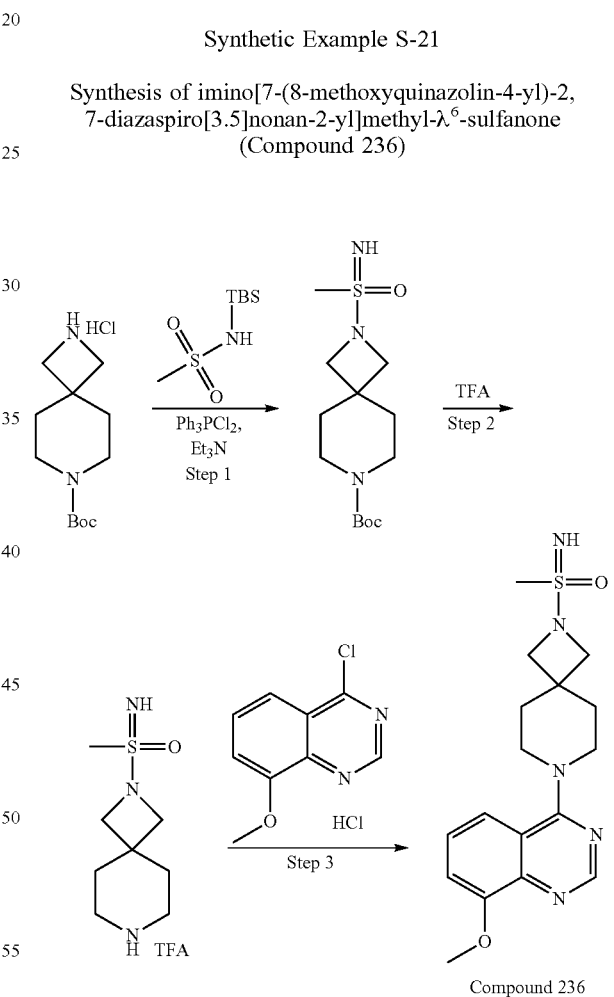

Compound 236

Step 1: To a 0° C. mixture of PPh$_3$OCl$_2$ (0.36 M, 26 mL) and CHCl$_3$ (26 mL) under nitrogen was added Et$_3$N (1.7 mL, 12 mmol) and the mixture was stirred at 0° C. for 15 min. N-[tert-butyl(dimethyl)silyl]methanesulfonamide (0.9 g, 4.3 mmol) was added and the mixture was stirred at 0° C. for 15 min. This mixture was added into a solution of tert-butyl 2,7-diazaspiro[3.5]nonane-7-carboxylate hydrochloride (0.75 g, 2.9 mmol) and Et$_3$N (1.7 mL, 12 mmol) in CHCl$_3$ (25 mL) at 0° C. and the mixture was stirred at 0° C. for 0.5 hour and then at 25° C. for 1.5 hours. The reaction mixture was concentrated and purified by silica gel chromatography (0-90% THF in (1:1 EtOAc/petroleum ether)) to provide tert-butyl 2-(S-methylsulfonimidoyl)-2,7-diazaspiro[3.5]nonane-7-carboxylate (0.54 g).

Step 2: To a mixture of tert-butyl 2-(S-methylsulfonimidoyl)-2,7-diazaspiro[3.5]nonane-7-carboxylate (0.49 g, 1.6 mmol) in CH$_2$Cl$_2$ (20 mL) at 0° C. was added TFA (1 mL, 14 mmol). The mixture was stirred at 25° C. for 4 h, then was concentrated under to give 2-(S-methylsulfonimidoyl)-2,7-diazaspiro[3.5]nonane trifluoroacetate (0.58 mg).

Step 3: To a mixture of 2-(S-methylsulfonimidoyl)-2,7-diazaspiro[3.5]nonane trifluoroacetate (0.33 g, 1.0 mmol) and 4-chloro-8-methoxy-quinazoline hydrochloride (0.2 g, 0.86 mmol) in isopropanol (10 mL) was added iPr$_2$NEt (1.3 mL, 7.6 mmol) and the mixture was stirred at 20° C. for 12 h. The mixture was concentrated and purified by reverse-phase HPLC (15-35% MeCN in H$_2$O (10 mM NH$_4$HCO$_3$)) to afford imino[7-(8-methoxyquinazolin-4-yl)-2,7-diazaspiro[3.5]nonan-2-yl]methyl-λ$^6$-sulfanone (Compound 236) (145 mg). ESI MS m/z: 362.2 (M+H).

Synthetic Example S-22

Synthesis of [8-(6,7-dimethoxyquinazolin-4-yl)-8-azaspiro[4.5]decan-2-yl](imino)methyl-λ$^6$-sulfanone (Compound 237)

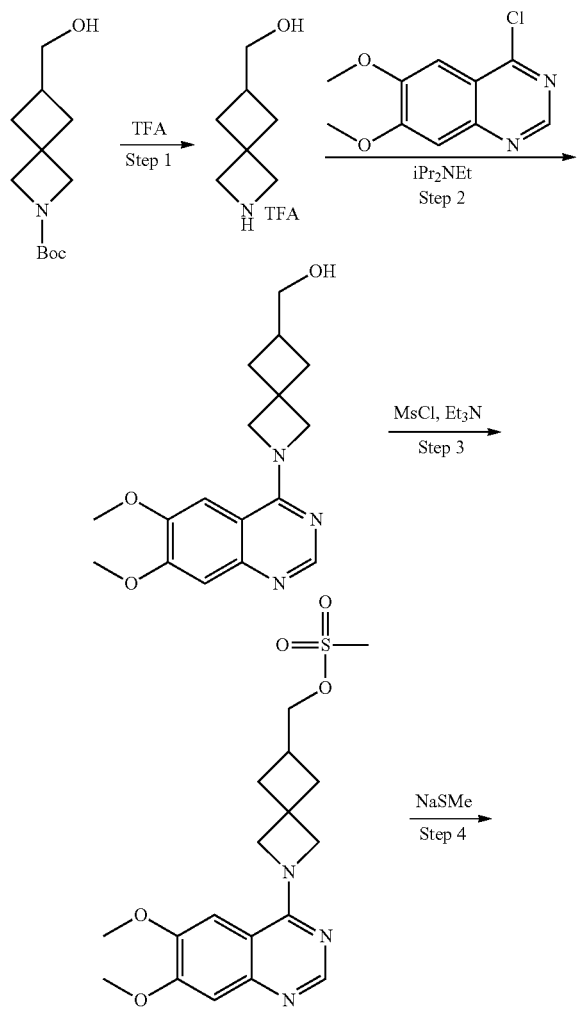

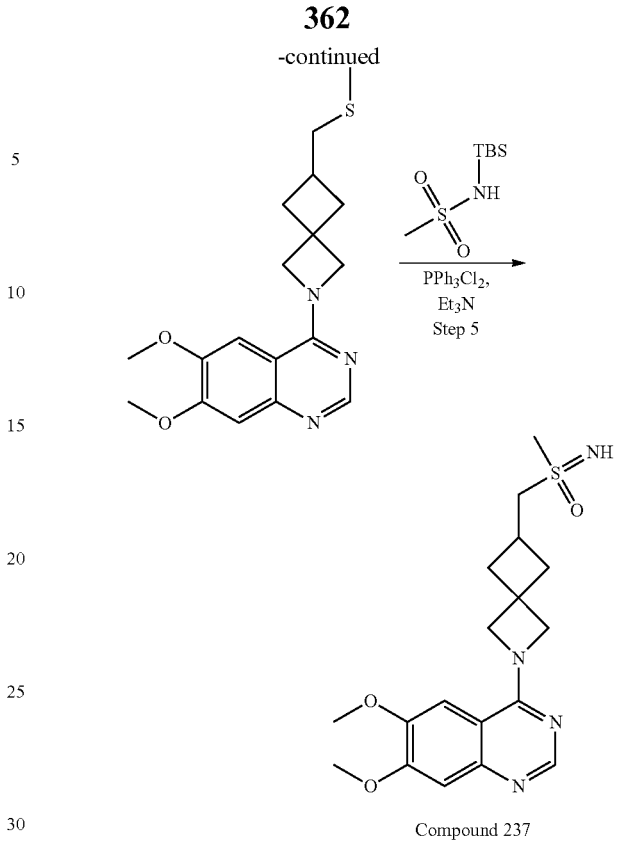

Compound 237

Steps 1 & 2: A mixture of tert-butyl 6-(hydroxymethyl)-2-azaspiro[3.3]heptane-2-carboxylate (0.90 g, 3.9 mmol), CH$_2$Cl$_2$ (15 mL) and TFA (4.5 mL, 61 mmol) was stirred at 25° C. for 2 h, then was concentrated. The resulting residue, iPrOH (25 mL), iPr$_2$NEt (6.1 mL, 35 mmol), and 4-chloro-6,7-dimethoxy-quinazoline (1.6 g, 7.0 mmol) were stirred together at 80° C. for 2 h. The mixture was concentrated and purified by reversed-phase HPLC (basic condition) to provide [2-(6,7-dimethoxyquinazolin-4-yl)-2-azaspiro[3.3]heptan-6-yl]methanol (110 mg, 92% purity) in two batches (110 mg, 92% purity; 500 mg, 42% purity).

Step 2: A mixture of [2-(6,7-dimethoxyquinazolin-4-yl)-2-azaspiro[3.3]heptan-6-yl]methanol (0.41 g, 1.3 mmol), CH$_2$Cl$_2$ (10 mL), Et$_3$N (0.40 g, 3.9 mmol), and MsCl (0.30 g, 2.6 mmol) was stirred at 25° C. for 12 h, then was concentration and combined with H$_2$O (15 mL) and extracted with EtOAc (15 mL×2). The combined extracts were washed with brine (10 mL), dried over Na$_2$SO$_4$, filtered, and concentrated to give [2-(6,7-dimethoxyquinazolin-4-yl)-2-azaspiro[3.3]heptan-6-yl]methylmethanesulfonate (130 mg).

Step 4: A mixture of [2-(6,7-dimethoxyquinazolin-4-yl)-2-azaspiro[3.3]heptan-6-yl]methyl methanesulfonate (0.11 g, 1.0 eq), EtOH (5 mL), and 20% aqueous NaSMe (0.15 mL) was stirred at 25° C. for 2 h, then was concentrated, diluted with H$_2$O (10 mL), and extracted with EtOAc (10 mL×2). The combined extracts were washed with brine (10 mL), dried over Na$_2$SO$_4$, filtered, and concentrated to provide 6,7-dimethoxy-4-[6-(methylsulfanylmethyl)-2-azaspiro[3.3]heptan-2-yl]quinazoline (100 mg).

Step 5: A mixture of 6,7-dimethoxy-4-[6-(methylsulfanylmethyl)-2-azaspiro[3.3]heptan-2-yl]quinazoline (90 mg, 0.26 mmol) in EtOH (5 mL) was added DIB (251 mg, 0.78 mmol) and NH$_4$OAc (80 mg, 1.0 mmol) was stirred at 20° C. for 2 h, then was concentrated and purified by preparative HPLC (1-30% MeCN in $H_2O$ (10 mM $NH_4HCO_3$)) to provide 8-(6,7-dimethoxyquinazolin-4-yl)-8-azaspiro[4.5]decan-2-yl](imino)methyl-X-sulfanone (Compound 237) (24 mg). ESI MS m/z: 377.2 (M+H).

Compounds 238-239 were prepared from aryl halide and alcohol under conditions indicated in Table 13 in the manner described in Synthetic Example S-22.

TABLE 13

| Cmpd | Structure | Aryl Halide | Alcohol | MS (m/z) |
|---|---|---|---|---|
| 238 | 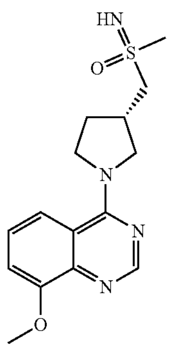 [SMILES: COc1cccc2c(N3CC[C@H](CS(C)(=N)=O)C3)ncnc12] | | | 321.0 (M + H) |
| 239 | 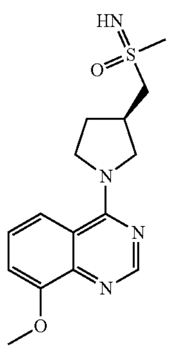 [SMILES: COc1cccc2c(N3CC[C@@H](CS(C)(=N)=O)C3)ncnc12] | | | 321.1 (M + H) |

Synthetic Example S-23

Synthesis of [8-(6,7-dimethoxyquinazolin-4-yl)-2,8-diazaspiro[4.5]decan-2-yl](2-hydroxy-2-methylpropyl)imino-$\lambda^6$-sulfanone (Compound 240)

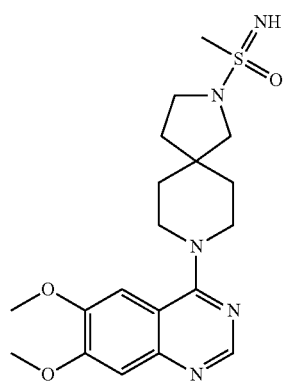

BuLi, acetone
→

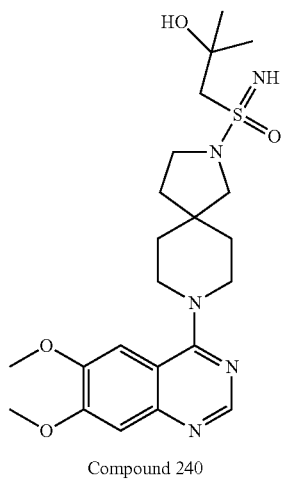

Compound 240

A solution of BuLi (2.5 M, 2.0 mL) was added slowly to a −78° C. stirring mixture of 6,7-dimethoxy-4-(2-(S-methylsulfonimidoyl)-2,8-diazaspiro[4.5]decan-8-yl)quinazoline (0.04 g, 0.99 mmol) and THF (5 mL). After stirring for 30 min, acetone (0.29 mL, 4.0 mmol) was added slowly at −78° C. The reaction mixture was warmed up to 25° C., stirred for 1 h, concentrated, and purified by preparative HPLC (20-40%/MeCN/$H_2O$ (10 mM $NH_4HCO_3$)) to provide 1-[[8-(6,7-dimethoxyquinazolin-4-yl)-2,8-diazaspiro[4.5]decan-2-yl]sulfonimidoyl]-2-methyl-propan-2-ol (Compound 240) (8.5 mg). ESI MS m/z: 464.3 (M+H).

Synthetic Example S-24

Synthesis of {8-[6-(fluoromethoxy)-7-methoxyquinazolin-4-yl]-2,8-diazaspiro[4.5]decan-2-yl}(imino)methyl-$\lambda^6$-sulfanone (Compound 241)

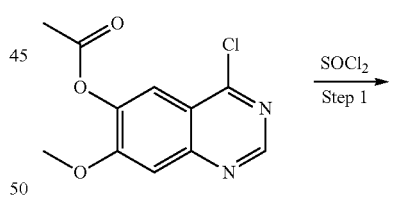
SOCl₂
Step 1

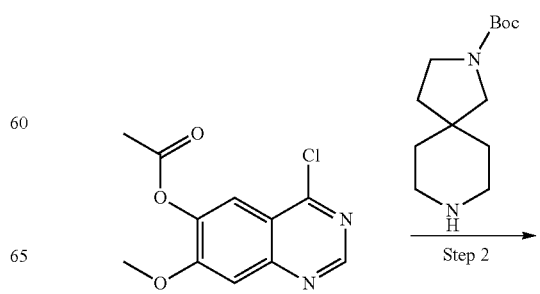
Step 2

-continued

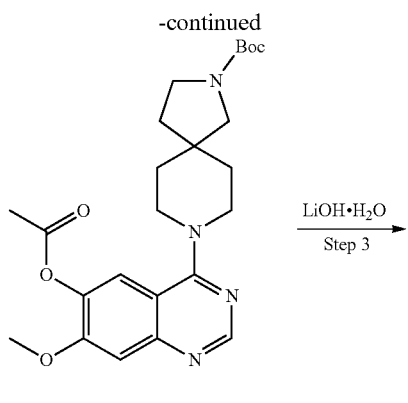

LiOH·H₂O
Step 3

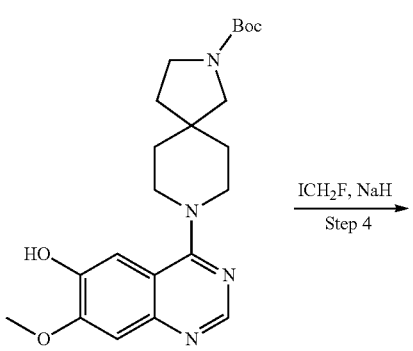

ICH₂F, NaH
Step 4

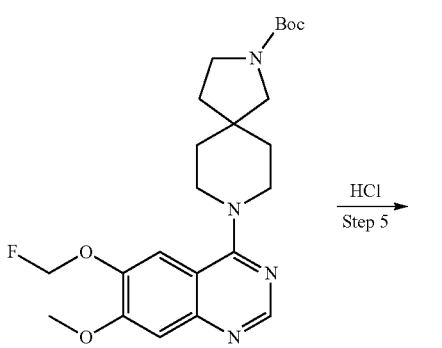

HCl
Step 5

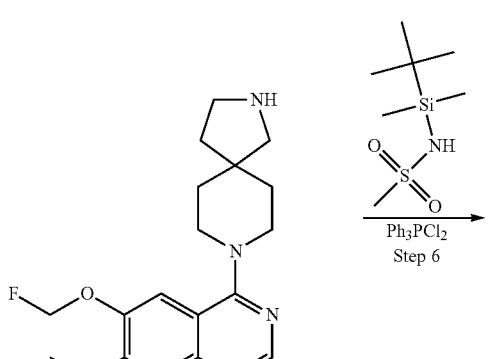

Ph₃PCl₂
Step 6

Compound 241

-continued

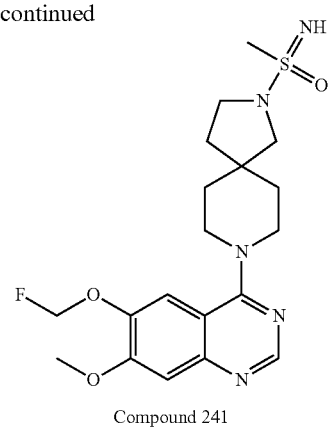

Compound 241

Step 1: A degassed mixture of (4-hydroxy-7-methoxy-quinazolin-6-yl) acetate (5.0 g, 21 mmol), SOCl₂ (50 mL, 690 mmol), and DMF (0.5 mL) was stirred at 85° C. for 12 h under an N₂ atmosphere. The reaction was concentrated to provide (4-chloro-7-methoxy-quinazolin-6-yl) acetate (5.1 g).

Step 2: A degassed mixture of (4-chloro-7-methoxy-quinazolin-6-yl) acetate (2.4 g, 9.5 mmol), tert-butyl 2,8-diazaspiro[4.5]decane-2-carboxylate (1.9 g, 7.9 mmol), Et₃N (6.6 mL, 47 mmol), and CHCl₃ (30 mL) was stirred at 20° C. for 12 h under an N₂ atmosphere. The crude product stirred with a mixture of petroleum ether and ethyl acetate (7:1) at 20° C. for 30 min. Solids were filtered away, and the filtrate was concentrated, and purified by silica chromatography (1:0:0:0 to 0:20:4:1 petroleum ether/EtOAc:CH₂Cl₂: MeOH) to provide tert-butyl 8-(6-acetoxy-7-methoxy-quinazolin-4-yl)-2,8-diazaspiro[4.5]decane-2-carboxylate (2.6 g).

Step 3: A degassed mixture of tert-butyl 8-(6-acetoxy-7-methoxy-quinazolin-4-yl)-2,8-diazaspiro[4.5]decane-2-carboxylate (2.3 g, 5.1 mmol), LiOH H₂O (0.65 g, 15 mmol), MeOH (94 mL), and H₂O (47 mL) was stirred at 20° C. for 12 h under an N₂ atmosphere. The mixture was concentrated and extracted with EtOAc (25 mL×10), dried over Na₂SO₄, filtered and concentrated tert-butyl 8-(6-hydroxy-7-methoxy-quinazolin-4-yl)-2,8-diazaspiro[4.5]decane-2-carboxylate (1.7 g).

Step 4: A 0° C. mixture of tert-butyl 8-(6-hydroxy-7-methoxy-quinazolin-4-yl)-2,8-diazaspiro[4.5]decane-2-carboxylate (1.6 g, 3.9 mmol), DMF (20 mL), and 60% NaH (0.44 g, 11 mmol) was stirred for 0.5 h. Fluoroiodomethane (0.69 g, 4.3 mmol) was added and the mixture was stirred at 20° C. 12 h. Saturated aqueous NH₄Cl (20 ml) was added, then the mixture was filtered, and the filtrate concentrated and purified by silica chromatography (0-100% EtOAc in petroleum ether) to provide tert-butyl 8-[6-(fluoromethoxy)-7-methoxy-quinazolin-4-yl]-2,8-diazaspiro[4.5]decane-2-carboxylate (1.37 g).

Step 5: A mixture of tert-butyl 8-[6-(fluoromethoxy)-7-methoxy-quinazolin-4-yl]-2,8-diazaspiro[4.5]decane-2-carboxylate (1.3 g, 2.8 mmol), EtOAc (6 mL), and HCl (6 M in EtOAc, 15 mL) was stirred at 20° C. for 12 h. The mixture was concentrated to provide 4-(2,8-diazaspiro[4.5]decan-8-yl)-6-(fluoromethoxy)-7-methoxy-quinazoline hydrochloride (1.0 g).

Step 6: N-[tert-butyl(dimethyl)silyl]methanesulfonamide (1.1 g, 5.2 mmol) was added into Ph₃PCl₂ (0.36 M in CHCl₃, 14 mL) at 0° C. After stirring for 0.5 h, a mixture of 4-(2,8-diazaspiro[4.5]decan-8-yl)-6-(fluoromethoxy)-7-methoxy-quinazoline (0.60 g, 1.7 mmol), CH3Cl (5 mL), Et₃N (1.5 mL, 10 mmol) was added and the mixture was stirred at 20° C. for 12 h. The mixture was concentrated and purified by preparative HPLC (1-20% MeCN in H₂O (0.2% formic acid)) to provide {8-[6-(fluoromethoxy)-7-methoxy-quinazolin-4-yl]-2,8-diazaspiro[4.5]decan-2-yl}(imino)methyl-λ⁶-sulfanone (Compound 241) (75 mg). ESI MS m/z: 424.1 (M+H).

Synthetic Example S-25

Synthesis of imino(methyl)[(1s,4s)-4-[(7-methoxy-quinolin-4-yl)oxy]cyclohexyl]-λ⁶-sulfanone (Compound 242)

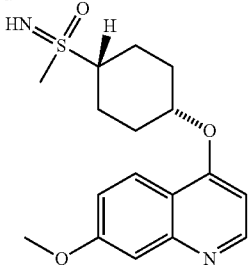

Compound 242

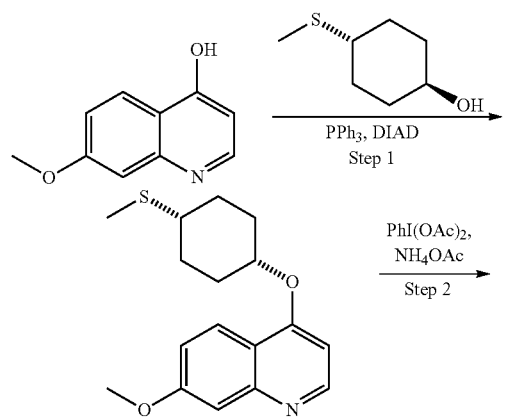

Step 1: To a mixture of (1r,4r)-4-(methylthio)cyclohexan-1-ol (0.17 g, 1.2 mmol), 7-methoxyquinolin-4-ol (0.24 g, 1.4 mmol), PPh₃ (0.61 g, 2.3 mmol), THF (7 mL) was added DIAD (470 mg, 2.32 mmol, 2.0 eq). The mixture was stirred at 20° C. for 12 h, concentrated, and purified by silica chromatography (50-100% EtOAc in petroleum ether) to provide 7-methoxy-4-(4-methylsulfanylcyclohexoxy)quinoline (0.15 g).

Step 2: A mixture of 7-methoxy-4-(4-methylsulfanylcyclohexoxy)quinoline (0.15 mg, 0.49 mmol), EtOH (3 mL), PhI(OAc)₂ (0.48 mg, 1.5 mmol), and NH₄OAc (0.15 mg, 2.0 mmol). The mixture was stirred at 20° C. for 1 hour. The reaction mixture was concentrated in and purified by preparative HPLC (1-30% MeCN/water (0.2% formic acid) to provide imino(methyl)[(1s,4s)-4-[(7-methoxyquinolin-4-yl)oxy]cyclohexyl]-λ⁶-sulfanone (Compound 242) (36 mg). ESI MS m/z: 335.1.

Compounds 243-245 in Table 14 were prepared from the aryl hydroxide and alcohol indicated by the procedure described in Synthetic Example S-25.

TABLE 14

| Cmpd | Structure | Aryl Hydroxide | Alcohol | MS (m/z) |
|---|---|---|---|---|
| 243 | ![structure] | ![structure] | ![structure] | 335.0 (M + H) |
| 244 | ![structure] | ![structure] | ![structure] | 387.2 (M + H) |

TABLE 14-continued

| Cmpd | Structure | Aryl Hydroxide | Alcohol | MS (m/z) |
|------|-----------|----------------|---------|----------|
| 245 | (structure shown) | (structure shown) | (structure shown) | 357.1 (M + H) |

Synthetic Example S-26

Synthesis of imino({[1-(8-methoxyquinazolin-4-yl)-1,2,3,6-tetrahydropyridin-4-yl]methyl})methyl-$\lambda^6$-sulfanone (Compound 246)

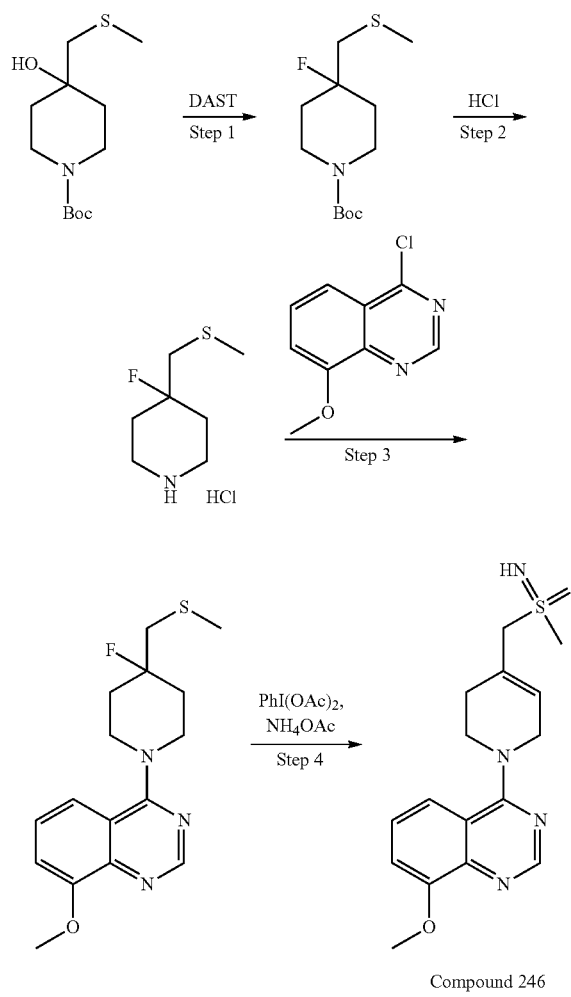

Compound 246

Step 1: A mixture of DAST (1.2 g, 7.6 mmol) and $CH_2Cl_2$ (10 mL) was added slowly to a stirring mixture of tert-butyl 4-hydroxy-4-(methylsulfanylmethyl)piperidine-1-carboxylate (2.0 g, 7.6 mmol) and $CH_2Cl_2$ (5.0 mL) at −70° C. After stirring at −70° C. for 0.5 h, the resulting mixture was stirred at 20° C. for 12 h, then was poured into water (20 mL) and extracted with EtOAc (2×20 mL). The combined extracts were washed with brine (20 mL), dried over $Na_2SO_4$, concentrated, and purified by silica chromatography (0-50% EtOAc in petroleum ether) to provide tert-butyl 4-fluoro-4-(methylsulfanylmethyl)piperidine-1-carboxylate (1.0 g).

Step 2: A mixture of tert-butyl 4-fluoro-4-(methylsulfanylmethyl)piperidine-1-carboxylate (0.25 g, 0.95 mmol) and HCl/EtOAc (6 M, 5.0 mL) was stirred at 20° C. for 2 h under an $N_2$ atmosphere. The mixture was concentrated to provide 4-fluoro-4-(methylsulfanylmethyl)piperidine hydrochloride (0.20 g).

Step 3: To a mixture of 4-fluoro-4-(methylsulfanylmethyl)piperidine hydrochloride (0.25 g, 1.2 mmol) and iPrOH (5.0 mL) was added $iPr_2NEt$ (0.81 g, 6.2 mmol) and 4-chloro-8-methoxy-quinazoline (0.29 g, 1.2 mmol) and the resulting mixture was stirred at 20° C. for 2 h, then was concentrated, combined with water (30 mL), and extracted with EtOAc (2×30 mL). The combined extracts were washed with brine (10 mL), dried over $Na_2SO_4$, concentrated, to provide 4-[4-fluoro-4-(methylsulfanylmethyl)-1-piperidyl]-8-methoxy-quinazoline (0.47 g).

Step 4: A mixture of 4-[4-fluoro-4-(methylsulfanylmethyl)-1-piperidyl]-8-methoxy-quinazoline (0.47 g, 1.4 mmol), in EtOH (5.0 mL), $PhI(OAc)_2$ (1.4 g, 4.3 mmol), and $NH_4OAc$ (0.45 g, 5.7 mmol) was stirred for 2 h. The mixture was concentrated and purified by preparative HPLC (1-25% MeCN in $H_2O$, 0.2% formic acid) to provide imino({[1-(8-methoxyquinazolin-4-yl)-1,2,3,6-tetrahydropyridin-4-yl]methyl})methyl-$\lambda^6$-sulfanone (Compound 246) (20 mg). ESI MS m/z: 333.1 (M+H).

Table 15 describes chiral separation conditions for specific examples where supercritical $CO_2$ is the non-polar co-solvent.

TABLE 15

| | SFC Separation Conditions | | | | |
|---|---|---|---|---|---|
| Compound | Conditions (column & polar co-solvent system) | First | ee % | Second | ee % |
| 1 | Phenomenex-Cellulose-2 (250 mm*30 mm,10 μm) 55% [0.1% NH$_3$/H$_2$O in MeOH] | 1S | >99 | 1R | >99 |
| 44 | Chiralpak (250 × 30 mm, 5 μm) 40% [0.1% NH$_3$/H$_2$O in EtOH] | 44a | >99 | 44b | >99 |
| 54 | Chiralpak AS (250 × 30 mm, 10 μm) 40% [0.1% NH$_3$/H$_2$O in EtOH] | 54a | >99 | 54b | 99 |
| 55 | Chiralpak IC (250 × 30 mm, 10 μm) 57% [0.1% NH$_3$/H$_2$O in MeOH] | 55a | 99 | 55b | 98 |
| 60 | Chiralpak IC (250 × 20 mm, 5 μm) 50% [20 mM NH$_3$ in MeOH] | 60a | >99 | 60b | 99 |
| 75 | Chiralpak AS-3 (50 × 4.6 mm, 3 μm) 35% [0.1% NH$_3$/H$_2$O in EtOH] | 75a | >99 | 75b | 99 |
| 80 | Phenomenex-Cellulose-2 (250 mm*50 mm,10 μm) 55% [0.1% NH$_3$/H$_2$O in MeOH] | 80a | >99 | 80b | 99 |
| 103 | Chiralpak OD (250 × 30 mm, 10 μm) 50% (0.1% NH$_3$/H$_2$O in iPrOH) | 103a | >99 | 103b | >99 |
| 114 | Chiralcel OD (250 × 30 mm, 10 μm); 43% [0.1% NH$_3$/H$_2$O iPrOH] | 114a | >99 | 114b | >99 |
| 133 | Chiralpak AS (250 × 30 mm, 10 μm) 45% [0.1% NH$_3$/H$_2$O in iPrOH] | 133a | >99 | 133b | 95 |
| 141 | Chiralpak IC (250 × 30 mm, 10 μm) 60% [0.1% NH$_3$/H$_2$O in iPrOH] | 141a | 98 | 141b | 99 |
| 146 | Chiralpak AD (250 × 30 mm, 10 μm); 60% [0.1% NH$_3$/H$_2$O in MeOH] | 146a | >99 | 146b | >99 |
| 160 | Regis (S,S) Whelk-O1 (250 × 30 mm, 5 μm) 62.5% [0.1% NH$_3$/H$_2$O in EtOH] | 160a | >99 | 160b | 98.5 |
| 161 | Regis (S,S) Whelk-O1 (250 × 30 mm, 5 μm) 45% [0.1% NH$_3$/H$_2$O in MeOH] | 161a | 83 | 161b | 90 |
| 169 | Chiralpak AS (250 × 30 mm, 10 μm) 45% [0.1% NH$_3$/H$_2$O in iPrOH] | 169a | >99 | 169b | >99 |
| 175 | Chiralpak AS (250 × 30 mm, 10 μm) 52% [0.1% in iPrOH] | 175a | >99 | 175b | >99 |
| 177 | Chiralpak AD (250 × 30 mm, 10 μm); 55% [0.1% NH$_3$/H$_2$O in EtOH] | 177a | >99 | 177b | 99.0 |
| 178 | Chiralpak AD (250 × 30 mm, 10 μm); 50% [0.1% NH$_3$/H$_2$O in MeOH] | 178a | >99 | 178b | 98 |
| 179 | Phenomenex-Cellulose-2 (250 mm*50 mm, 10 μm) 60% [0.1% NH$_3$/H$_2$O in MeOH] | 179a | >99 | 179b | >99 |
| 183 | Chiralpak AD (250 × 30 mm, 10 μm); 65% [0.1% NH$_3$/H$_2$O in EtOH] | 183a | >99 | 183b | >99 |
| 184 | Phenomenex-Cellulose-2 (250 mm*50 mm, 10 μm) 60% [0.1% NH$_3$/H$_2$O in MeOH] | 184a | >99 | 184b | 97 |
| 185 | Chiralpak AD (250 × 30 mm, 10 μm); 60% [0.1% NH$_3$/H$_2$O in EtOH] | 185a | >99 | 185b | >99 |
| 189 | Chiralpak AD (250 × 30 mm, 10 μm); 35% EtOH | 189a | >99 | 189b | 98.9 |
| 193 | Phenomenex-Cellulose-2 (250 mm*50 mm,10 μm) 60% EtOH | 193a | >99 | 193b | 98.6 |
| 195 | Chiralpak AD (250 × 30 mm, 10 μm); 63% [0.1% NH$_3$/H$_2$O in EtOH] | 195a | >99 | 195b | 98.7 |
| 198 | Chiralpak AD (250 × 30 mm, 10 μm); 46% [0.1% NH$_3$/H$_2$O in MeOH] | 198a | 99 | 198b | 98 |
| 205 | Chiralpak AS (250 × 30 mm, 10 μm) 25% [0.1% in iPrOH] | 205a | >99 | 205b | >99 |
| 208 | Chiralpak AD (250 × 30 mm, 10 μm); 46% [0.1% NH$_3$/H$_2$O in EtOH] | 208a | >99 | 208b | 97.9 |
| 211 | Chiralpak AS (250 × 30 mm, 10 μm) 40% [0.1% in MeOH] | 211a | >99 | 211b | >99 |
| 218 | Regis (S,S) Whelk-O1 (250 × 30 mm, 5 μm) 50% [0.1% NH$_3$/H$_2$O in EtOH] | 218a | >99 | 218b | >99 |
| 219 | Phenomenex-Cellulose-2 (250 mm*50 mm, 10 μm) 50% [0.1% NH$_3$/H$_2$O in EtOH] | 219a | >99 | 219b | 95.4 |
| 222 | Chiralpak AS (250 × 30 mm, 10 μm) 35% [0.1% NH$_3$/H$_2$O in EtOH] | 222a | >99 | 222b | 96.9 |
| 223 | Chiralpak IG (250 × 30 mm, 10 μm); 60% [0.1% NH$_3$/H$_2$O in EtOH] | 223a | >99 | 223b | >99 |
| 229 | Chiralpak AD (250 × 30 mm, 10 μm); 42% [0.1% NH$_3$/H$_2$O in iPrOH] | 229a | >99 (de) | 229b | >99 (de) |
| 230 | Chiralpak IG (250 × 30 mm, 10 μm); 50% [0.1% NH$_3$/H$_2$O in MeOH] | 230a | >99 | 230b | >99 |

TABLE 15-continued

SFC Separation Conditions

| Compound | Conditions (column & polar co-solvent system) | First | ee % | Second | ee % |
|---|---|---|---|---|---|
| 237 | Chiralpak AD (250 × 30 mm, 10 μm); 55% [0.1% NH$_3$/H$_2$O in EtOH] | 237a | >99 | 237a | >99 |
| 238 | Chiralpak AD (250 × 30 mm, 10 μm); 60% [0.1% NH$_3$/H$_2$O in MeOH] | 238a | >99 | 238b | >99 |
| 239 | Chiralpak IG (250 × 30 mm, 10 μm); 60% [0.1% NH$_3$/H$_2$O in MeOH] | 239a | >99 | 239b | 97.3 |

TABLE 16

$^1$H NMR data for examples at 400 MHz

| Compound | Solvent | δ ppm |
|---|---|---|
| 1 | DMSO-d$^6$ | 8.56 (d, J = 5.1 Hz, 1H), 8.02 (d, J = 8.6 Hz, 2H), 7.45-7.40 (m, 4H), 6.69 (d, J = 5.1 Hz, 1H), 4.28 (s, 1H), 3.95 (s, 3H), 3.90 (s, 3H), 3.10 (s, 3H) |
| 6 | DMSO-d$^6$ | 8.88 (d, J = 4.4 Hz, 1H), 7.80 (dd, J = 33.4, 9.1 Hz, 1H), 7.47 (d, J = 28.7 Hz, 1H), 7.47 (d, J = 2.6 Hz, 1H), 7.31 (dd, J = 9.1, 2.6 Hz, 1H), 4.55-4.14 (m, 1H), 3.94 (s, 3H), 4.07-3.70 (m, 2H), 3.45 (s, 2H), 3.28 (d, J = 19.1 Hz, 2H), 3.18-2.92 (m, 1H), 2.91-2.73 (m, 1H). |
| 8 | CDCl$_3$ | 8.67 (s, 1H), 7.24 (s, 1H), 7.09 (s, 1H), 4.20 (br d, 13.2 Hz, 2H), 4.03 (s, 3H), 4.00 (s, 3H), 3.22-3.13 (m, 2H), 3.12-3.03 (m, 2H), 3.02 (s, 3H), 2.62 (br s, 1H), 2.00-1.86 (m, 4H), 1.77 (br s, 1H), 1.59-1.48 (m, 2H) |
| 10 | CDCl$_3$ | 8.76 (d, J = 5.2 Hz, 1H), 8.07-7.98 (m, 2H), 7.48 (d, J = 2.8 Hz, 1H), 7.26-7.22 (m, 1H), 7.08-7.03 (m, 1H), 7.27-7.21 (m, 1H), 6.73 (d, J = 5.2 Hz, 1H), 3.99 (s, 3H), 3.30 (s, 3H), 3.02 (br s, 1H) |
| 12 | DMSO-d$^6$ | 8.68 (d, J = 5.13 Hz, 1H), 8.19 (d, J = 9.13 Hz, 1H), 8.01 (br d, J = 10.13 Hz, 1H), 7.87 (br d, J = 8.38 Hz, 1H), 7.65 (t, J = 8.07 Hz, 1H), 7.46 (d, J = 2.00 Hz, 1H), 7.33 (dd, J = 9.13, 2.13Hz, 1H), 6.63 (d, J = 5.13 Hz, 1H), 4.45 (br s, 1H), 3.95 (s, 3H), 3.17 (s, 3H) |
| 18 | DMSO-d$^6$ | 8.56 (s, 1 H), 7.99-8.06 (m, 2 H), 7.51-7.57 (m, 3 H), 7.39 (s, 1 H), 4.28 (s, 1 H), 3.97 (d, J = 6.62 Hz, 6 H), 3.12 (s, 3 H) |
| 22 | DMSO-d$^6$ | 8.91 (s, 1H), 8.54 (d, J = 8.6 Hz, 1H), 8.28 (d, J = 8.2 Hz, 1H), 8.10-8.02 (m, 3H), 7.96 (ddd, J = 8.1, 7.0, 1.2 Hz, 1H), 7.58-7.51 (m, 2H), 4.32 (s, 1H), 3.13 (s, 3H) |
| 26 | DMSO-d$^6$ | δ 8.72 (d, J = 4.5 Hz, 1H), 7.95 (d, J = 9.2 Hz, 1H), 7.39 (d, J = 2.6 Hz, 1H), 7.24 (dd, J = 9.3, 2.6 Hz, 1H), 7.21 (d, J = 4.6 Hz, 1H), 4.36-4.23 (m, 2H), 4.13-4.03 (m, 2H), 3.92 (s, 3H), 3.87 (s, 1H), 3.85-3.75 (m, 1H), 3.67-3.56 (m, 1H), 3.28-3.07 (m, 2H), 3.06-2.91 (m, 2H). |
| 43 | CDCl$_3$ | 8.67 (s, 1H), 7.58 (d, J = 12.4 Hz, 1H), 7.47 (d, J = 8.0 Hz, 1H), 4.05 (s, 3H), 3.79 (br d, J = 12.4 Hz, 2H), 3.55-3.40 (m, 2H), 3.24-3.13 (m, 2H), 3.05 (s, 3H), 2.05-1.93 (m, 4H), 1.85-1.75 (m, 2H), 1.67-1.52 (m, 2H) |
| 44 | DMSO-d$^6$ | 9.15 (s, 1H), 7.98-7.93 (m, 2H), 7.85-7.79 (m, 2H), 7.33-7.26 (m, 2H), 4.25 (s, 1H), 4.09 (s, 3H), 3.07 (s, 3H) |
| 47 | DMSO-d$^6$ | 9.06 (s, 1H), 8.15 (d, J = 9.3 Hz, 1H), 7.96 (d, J = 8.3 Hz, 2H), 7.68 (dd, J = 9.3, 2.9 Hz, 1H), 7.33 (d, J = 8.4 Hz, 2H), 7.26 (d, J = 2.9 Hz, 1H), 4.28 (s, 1H), 3.82 (s, 3H), 3.08 (s, 3H). |
| 50 | DMSO-d$^6$ | 9.16 (s, 1H), 8.14 (d, J = 8.7 Hz, 1H), 7.99-7.92 (sym. m, 2H), 7.89 (dd, J = 8.6, 2.0 Hz, 1H), 7.84 (s, 1H), 7.35-7.26 (sym. m, 2H), 4.27 (s, 1H), 3.08 (s, 3H), 2.51 (s, 3H) |
| 53 | DMSO-d$^6$ | 8.60 (d, J = 5.2 Hz, 1 H), 8.16 (s, 1 H), 7.89 (d, J = 9.2 Hz, 1 H), 7.31 (d, J = 2.4 Hz, 1 H), 7.17-7.19 (dd, J = 9.2, 2.4 Hz, 1 H), 6.84 (d, J = 5.2 Hz, 1 H), 3.90 (s, 3 H), 3.54-3.63 (m, 4 H), 3.09 (m, 3 H), 2.89 (s, 4 H), 1.95-1.98 (m, 4 H) |
| 54 | DMSO-d$^6$ | 8.51 (s, 1H), 8.15 (s, 1H), 7.20 (s, 1H), 7.11 (s, 1H), 3.91 (m, 6H), 3.67-3.52 (m, 5H), 3.33-3.22 (m, 3H), 3.17-3.07 (m, 2H), 2.79 (s, 3H), 1.92-1.83 (m, 2H), 1.80-1.63 (m, 4H). |
| 55 | DMSO-d$^6$ | 8.59 (d, J = 5.13 Hz, 1H), 8.15 (s, 1H), 7.88 (d, J = 9.26 Hz, 1H), 7.31 (d, J = 2.63 Hz, 1H), 7.17 (dd, J = 9.26, 2.63 Hz, 1H), 6.86 (d, J = 5.13 Hz, 1H), 3.89 (s, 3H), 3.35-3.24 (m, 2H), 3.19-3.06(m, 6H), 2.80 (s, 3H), 1.87-1.72 (m, 6H) |
| 57 | DMSO-d$^6$ | 8.56 (s, 1H), 7.60-7.62 (m, 1H), 7.51-7.55 (m, 1H), 7.26-7.28 (m, 1H), 4.02 (s, 3H), 3.90-3.93 (m, 2H), 3.45-3.51 (m, 2H), 3.27-3.29 (m, 2H), 3.04 (s, 3H), 1.92-1.97 (m, 4 H), 1.80-1.90 (m, 1H), 1.59-1.61 (m, 1H)) |
| 58 | DMSO-d$^6$ | 9.17 (s, 1H), 7.94 (d, J = 8.8 Hz, 2H), 7.68 (t, J = 8.1 Hz, 1H), 7.49 (t, J = 8.7 Hz, 2H), 7.29 (d, J = 8.9 Hz, 2H), 4.26 (s, 1H), 4.03 (s, 3H), 3.07 (s, 3H) |

TABLE 16-continued

¹H NMR data for examples at 400 MHz

| Compound | Solvent | δ ppm |
|---|---|---|
| 60 | DMSO-d⁶ | 8.71 (d, J = 5.2 Hz, 1H), 8.12 (d, J = 9.1 Hz, 1H), 8.02-7.95 (m, 2H), 7.45 (d, J = 2.5 Hz, 1H), 7.45-7.38 (m, 2H), 7.30 (dd, J = 9.2, 2.6 Hz, 1H), 6.72 (d, J = 5.1 Hz, 1H), 4.28 (s, 1H), 3.94 (s, 3H), 2.75-2.65 (m, 1H), 1.17-1.09 (m, 1H), 1.03-0.87 (m, 3H) |
| 69 | CDCl₃ | 7.38 (d, J = 2.4 Hz, 1H), 7.15-7.08 (m, 1H), 6.73 (d, J = 5.2 Hz, 1H), 3.95 (s, 3H), 3.61 (br d, J = 12.4 Hz, 2H), 3.24-3.13 (m, 2H), 3.03 (s, 3H), 2.88-2.75 (m, 2H), 2.63 (br s, 1H), 2.04-1.82 (m, 4H), 1.65-1.58 (br s, 3H) |
| 72 | CDCl₃ | 8.78 (s, 1H), 7.47-7.33 (m, 2H), 7.11 (d, J = 7.2 Hz, 1H), 4.35 (br d, J = 13.2 Hz, 2H), 4.06 (s, 3H), 3.21-3.05 (m, 4H), 3.02 (s, 3H), 2.62 (br s, 1H), 1.98-1.85 (m, 4H), 1.85-1.72 (m, 1H), 1.57-1.46 (m, 2H) |
| 74 | DMSO-d⁶ | 9.97-10.00 (brs, 1H), 8.62 (d, J = 5.6 Hz 1H), 8.39 (d, J = 7.6 Hz, 1H), 7.90 (d, J = 8.4 Hz, 2H), 7.61 (d, J = 8.4 Hz, 2H), 7.33-7.37 (m, 2H), 6.64 (d, J = 7.2 Hz, 1H), 4.83-4.86 (m, 2H), 4.21 (brs, 1H), 3.92 (s, 3H), 3.02 (s, 3H) |
| 75 | DMSO-d⁶ | 8.69 (d, J = 5.25 Hz, 1 H) 8.14 (d, J = 9.13 Hz, 1 H) 8.01 (s, 1 H) 7.99 (s, 1 H) 7.79 (s, 1 H) 7.77 (s, 1 H) 7.36 (d, J = 2.50 Hz, 1 H) 7.24 (dd, J = 9.07, 2.56 Hz, 1 H) 7.02 (d, J = 5.38 Hz, 1 H) 5.52 (s, 2 H) 3.93 (s, 3 H) 3.10 (s, 3 H). |
| 76 | DMSO-d⁶ | 8.84 (d, J = 5.0 Hz, 1H), 8.71 (d, J = 2.8 Hz, 1H), 8.01-7.94 (m, 2H), 7.84 (d, J = 2.8 Hz, 1H), 7.36-7.29 (m, 2H), 7.07 (d, J = 5.1 Hz, 1H), 4.24 (s, 1H), 4.00 (s, 3H), 3.09 (s, 3H). |
| 77 | DMSO-d⁶ | 9.42 (s, 1H), 8.82 (d, J = 5.2 Hz, 1H), 8.11-8.04 (m, 2H), 7.60-7.52 (m, 2H), 7.26 (s, 1H), 6.61 (d, J = 5.2 Hz, 1H), 4.33 (br, 1H), 4.02 (s, 3H), 3.13 (s, 3H) |
| 79 | DMSO-d⁶ | 2.81 (s, 3 H) 3.67 (s, 1 H) 3.93 (s, 3 H) 4.43 (d, J = 3.31 Hz, 2 H) 6.53 (d, J = 5.29 Hz, 1 H) 7.26-7.32 (m, 3 H) 7.41 (d, J = 2.43 Hz, 1 H) 7.57 (d, J = 8.60 Hz, 2 H) 8.18 (d, J = 9.04 Hz, 1 H) 8.62 (d, J = 5.07 Hz, 1 H) |
| 80 | DMSO-d⁶ | 8.69 (d, J = 5.07 Hz, 1 H), 8.10 (d, J = 9.04 Hz, 1 H), 7.98-8.04 (m, 2 H), 7.37-7.49 (m, 3 H), 7.29 (dd, J = 9.15, 2.54 Hz, 1 H), 6.69 (d, J =5.29 Hz, 1 H), 4.25 (s, 1 H), 3.93 (s, 3 H), 3.09 (s, 3 H) |
| 84 | DMSO-d⁶ | 8.71 (s, 1 H) 8.03-8.09 (m, 2 H) 7.91 (dd, J = 8.25, 1.00 Hz, 1 H) 7.73 (t, J = 8.13 Hz, 1 H) 7.57-7.64 (m, 1 H) 7.57-7.65 (m, 1 H) 7.53 (dd, J = 7.88, 0.75 Hz, 1 H) 4.30 (s, 1 H) 4.01 (s, 3 H) 3.14-3.15 (m, 1 H) 3.15 (d, J = 0.75 Hz, 2 H) |
| 88 | DMSO-d⁶ | 8.86 (d, J = 4.5 Hz, 1H), 7.78 (d, J = 9.2 Hz, 1H), 7.66-7.59 (m, 2H), 7.59-7.52 (m, 2H), 7.48 (d, J = 2.6 Hz, 1H), 7.32 (d, J = 4.5 Hz, 1H), 7.26 (dd, J = 9.2, 2.6 Hz, 1H), 4.57-4.42 (m, 2H), 3.94 (s, 3H), 3.73 (s, 1H), 2.86 (s, 3H) |
| 98 | DMSO-d⁶ | 8.84 (d, J = 4.52 Hz, 1H), 7.76 (d, J = 9.29 Hz, 1H), 7.52-7.43(m, 5H), 7.30-7.21(m, 2H), 3.94 (s, 3H), 3.76 (s, 1H), 3.46-3.39(m, 2H), 3.17-3.09 (m, 2H), 2.95 (s, 3H) |
| 101 | DMSO-d⁶ | 8.75 (d, J = 2.7 Hz, 1H), 8.72 (d, J = 5.1 Hz, 1H), 8.17 (dd, J = 8.9, 4.1 Hz, 2H), 7.96 (dd, J = 8.6, 2.7 Hz, 1H), 7.47 (d, J = 2.5 Hz, 1H), 7.33 (dd, J = 9.2, 2.5 Hz, 1H), 6.77 (d, J = 5.2 Hz, 1H), 4.50 (s, 1H), 3.95 (s, 3H), 3.20 (s, 3H) |
| 103 | DMSO-d⁶ | 8.71 (d, J = 5.2 Hz, 1H), 8.12 (d, J = 9.2 Hz, 1H), 7.97 (d, J = 8.8 Hz, 2H), 7.50-7.39 (m, 3H), 7.32-7.24 (m, 1H), 6.71 (d, J = 5.2 Hz, 1H), 4.23 (s, 1H), 3.94 (s, 3H), 3.22-3.10 (m, 2H), 1.18-1.03 (m, 3H) |
| 107a | DMSO-d⁶ | 9.05 (br d, J = 6.36 Hz, 1 H) 8.22-8.32 (m, 1 H) 7.30-7.63 (m, 3 H) 4.42 (br d, J = 6.14 Hz, 2 H) 3.99 (s, 3 H) 3.75 (br s, 3 H) 3.16 (brs, 1 H) 2.36 (br d, J = 14.69 Hz, 2 H) 2.24-2.48 (m, 1 H) 1.90 (brd, J = 12.93 Hz, 2 H) |
| 107b | acetone-d⁶ | 8.94-9.08 (m, 1 H) 8.32-8.43 (m, 1 H) 8.00 (d, J = 2.19 Hz, 1 H) 7.40-7.52 (m, 2 H) 4.64-4.70 (m, 2 H) 4.04 (br d, J = 3.29 Hz, 3 H) 3.56-3.81 (m, 4 H) 3.24-3.35 (m, 1 H) 2.50-2.71 (m, 3 H) 2.13-2.28 (m, 2 H) |
| 114 | DMSO-d⁶ | 8.70 (d, J = 5.26 Hz, 1 H) 8.02-8.04 (m, 2 H) 7.94 (d, J = 11.84 Hz, 1 H) 7.66 (d, J = 8.11 Hz, 1 H) 7.43-7.46 (m, 2 H) 6.75 (d, J = 5.26 Hz, 1 H) 4.29 (br s, 1 H) 4.03 (s, 3 H) 3.11 (s, 3 H) |
| 115 | CDCl₃ | 8.64 (d, J = 5.2 Hz, 1H), 8.06-7.99 (m, 1H), 7.48 (s, 1H), 7.34 (s, 1H), 7.07 (br d, J = 8.8 Hz, 1H), 7.03-7.00 (m, 1H), 6.74 (d, J = 5.2 Hz, 1H), 4.07 (s, 3H), 4.01 (s, 3H), 3.31 (s, 3H), 3.02 (br s, 1H) |
| 116 | DMSO-d⁶ | 8.54 (d, J = 5.3 Hz, 1H), 8.01 (dd, J = 2.1, 10.1 Hz, 1H), 7.86 (dd, J = 1.2, 8.4 Hz, 1H), 7.63 (t, J = 8.2 Hz, 1H), 7.49 (s, 1H), 7.44 (s, 1H), 6.62 (d, J = 5.1 Hz, 1H), 4.46 (s, 1H), 3.94 (d, J = 9.7 Hz, 6H), 3.16 (s, 3H) |
| 125 | DMSO-d⁶ | 3.12 (s, 3 H) 4.28 (s, 1 H) 6.86 (d, J = 5.04 Hz, 1 H) 7.47 (d, J = 8.55 Hz, 2 H) 7.68 (s, 1 H) 7.86 (br d, J = 1.32 Hz, 1 H) 8.04 (d, J = 8.77 Hz, 2 H) 8.08 (d, J = 8.55 Hz, 1 H) 8.24 (d, J = 8.11 Hz, 1 H) 8.79 (d, J = 5.04 Hz, 1 H) |
| 126 | DMSO-d⁶ | 8.73 (d, J = 5.13 Hz, 1 H) 8.26 (s, 1 H) 8.01-8.07 (m, 2 H) 7.62 (s, 1 H) 7.44-7.50 (m, 2 H) 6.72 (d, J = 5.25 Hz, 1 H) 4.29 (s, 1 H) 4.25-4.32 (m, 1 H) 4.05 (s, 2 H) 4.01-4.08 (m, 1 H) 3.12 (s, 2 H) 3.08 -3.15 (m, 1 H) 2.50 (dt, J = 3.63, 1.81 Hz, 74 H) |

TABLE 16-continued

<sup>1</sup>H NMR data for examples at 400 MHz

| Compound | Solvent | δ ppm |
|---|---|---|
| 127 | DMSO-d$^6$ | 8.71 (s, 1 H) 8.05 (d, J = 8.76 Hz, 2 H) 7.81 (s, 1 H) 7.48 (d, J = 8.76 Hz, 2 H) 7.39 (s, 1 H) 4.28 (s, 1 H) 4.06 (s, 3 H) 3.98 (s, 3 H) 3.12 (s, 3 H) |
| 128 | DMSO-d$^6$ | 3.12 (d, J = 0.75 Hz, 3 H) 4.04 (s, 3 H) 4.29 (s, 1 H) 6.75 (d, J = 5.00 Hz, 1 H) 7.48 (d, J = 8.76 Hz, 2 H) 7.70 (br d, J = 1.38 Hz, 1 H) 8.02-8.08 (m, 3 H) 8.76 (d, J = 5.00 Hz, 1 H) |
| 129 | DMSO-d$^6$ | 8.74 (d, J = 2.7 Hz, 1H), 8.58 (d, J = 5.1 Hz, 1H), 8.17 (d, J = 8.6 Hz, 1H), 7.94 (dd, J = 8.6, 2.7 Hz, 1H), 7.46 (d, J = 5.0 Hz, 2H), 6.78 (d, J = 5.2 Hz, 1H), 4.49 (s, 1H), 3.96 (s, 3H), 3.92 (s, 3H), 3.19 (s, 3H) |
| 130 | DMSO-d$^6$ | 8.76 (d, J = 5.0 Hz, 1H), 8.32 (d, J = 9.1 Hz, 1H), 7.98-7.88 (m, 2H), 7.35 (d, J = 5.0 Hz, 1H), 7.29 (dd, J = 9.0, 1.3 Hz, 3H), 4.22 (s, 1H), 3.68 (s, 3H), 3.07 (s, 3H). |
| 131 | DMSO-d$^6$ | 9.32 (s, 1H), 8.10 (dd, J = 8.6, 1.2 Hz, 1H), 8.03 (td, J = 8.1, 5.4 Hz, 1H), 7.96-7.88 (sym. m, 2H), 7.57 (ddd, J = 11.8, 7.9, 1.2 Hz, 1H), 7.29-7.21 (sym. m, 2H), 4.25 (s, 1H), 3.08 (s, 3H). |
| 133 | DMSO-d$^6$ | 3.10 (s, 3 H) 3.90 (s, 3 H) 4.30 (s, 1 H) 5.48 (s, 2 H) 7.01 (d, J = 5.48 Hz, 1 H) 7.21 (dd, J = 9.21, 2.41 Hz, 1 H) 7.34 (d, J = 2.19 Hz, 1 H) 7.64-7.71 (m, 1 H) 7.84 (d, J = 7.45 Hz, 1 H) 7.94 (br d, J = 7.89 Hz, 1 H) 8.06-8.14 (m, 2 H) 8.67 (d, J = 5.26 Hz, 1 H) |
| 134 | DMSO-d$^6$ | 8.68 (d, J = 5.02 Hz, 1 H), 7.99 (d, J = 8.28 Hz, 2 H), 7.67-7.84 (m, 3 H), 7.49 (t, J = 8.09 Hz, 1 H), 7.20 (d, J = 7.53 Hz, 1 H), 7.15 (d, J = 5.27 Hz, 1 H), 5.50 (s, 2 H), 4.24 (s, 1 H), 3.94 (s, 3 H), 3.08 (s, 3 H) |
| 139 | CDCl$_3$ | 8.67 (s, 1H), 7.75 (d, J = 9.2 Hz, 1H), 7.21 (d, J = 2.8 Hz, 1H), 7.08-7.03 (s, 1H), 4.32 (br d, J = 13.2 Hz, 2H), 3.95 (s, 3H), 3.21-3.06 (m, 4H), 3.02 (s, 3H), 2.61 (br s, 1H), 1.98-1.85 (m, 4H), 1.85-1.71 (m, 1H), 1.26 (s, 2H) |
| 140 | CDCl$_3$ | 8.74 (d, J = 4.8 Hz, 1H), 7.58-7.49 (m, 1H), 7.42-7.38 (m, 1H), 7.01 (d, J = 7.6 Hz, 1H), 6.88 (d, J = 4.8 Hz, 1H), 4.08 (s, 3H), 3.62 (br d, J = 12.4 Hz, 2H), 3.23-3.13 (m, 2H), 3.03 (s, 3H), 2.86-2.74 (m, 2H), 2.63 (br s, 1H), 2.02-1.85 (m, 4H), 1.66-1.56 (m, 3H) |
| 146 | DMSO-d$^6$ | 8.59 (s, 1H), 7.45 (d, J = 4.4 Hz, H), 7.27-7.29 (m, 1H), 4.19-4.22 (m, 2H), 3.93 (s, 3H), 3.73 (s, 1H), 3.10-3.18 (m, 4H), 2.96 (s, 3H), 2.29-2.30 (m, 1 H), 2.02-2.09 (m, 2H), 1.51-1.57 (m, 2H) |
| 149 | CDCl$_3$ | 8.66 (d, J = 5.2 Hz, 1H), 7.98 (d, J = 7.2 Hz, 1H), 7.93 (d, J = 8.4 Hz, 1H), 7.72-7.65 (m, 1H), 7.55-7.49 (m, 1H), 6.96 (d, J = 5.2 Hz, 1H), 3.62 (br s, 1H), 3.52-3.44 (m, 2H), 3.18-3.08 (m, 2H), 2.91 (s, 3H), 2.80-2.70 (m, 2H), 2.01-1.91 (m, 2H), 1.81-1.72 (m, 2H), 1.67-1.46 (m, 3H) |
| 151 | DMSO-d$^6$ | 8.78 (s, 1 H) 7.61 (s, 1 H) 7.05 (s, 1 H) 3.99 (s, 3 H) 3.98 (s, 3 H) 3.57-3.69 (m, 3 H) 3.08-3.18 (m, 2 H) 2.86-2.96 (m, 5 H) 1.89 (brd, J = 11.13 Hz, 2H) 1.72-1.83 (m, 2 H) 1.64 (ddd, J = 10.63, 7.07, 3.69 Hz, 1 H) 1.44-1.58 (m, 2 H) |
| 153 | DMSO-d$^6$ | 9.12 (s, 1H), 7.80 (d, J = 8.07 Hz, 2H), 7.53 (d, J = 8.19 Hz, 2H), 7.44 (s, 1H), 7.33 (s, 1H), 6.12-5.99 (m, 1H), 4.01 (s, 3H), 3.84 (s, 3H), 3.45-3.41 (m, 2H), 3.15 (br dd, J = 9.23, 3.48 Hz, 2H), 2.94 (s, 3H). |
| 154 | DMSO-d$^6$ | 9.29 (s, 1H), 7.73 (d, J = 8.16 Hz, 2H), 7.63 (quin, J = 7.81 Hz, 2H), 7.54 (d, J = 8.03 Hz, 2H), 7.48 (d, J = 6.53 Hz, 1H), 4.02 (s, 3H), 3.76 (s, 1H), 3.48-3.40(m, 2H), 3.20-3.11 (m, 2H), 2.95 (s, 3H) |
| 155 | CDCl$_3$ | 7.76 (d, J = 8.0 Hz, 2H), 7.31 (d, J = 7.8 Hz, 2H), 3.67 (s, 2H), 1.97 (s, 3H), 1.34 (s, 12H). |
| 160 | DMSO-d$^6$ | 8.52 (d, J = 1.75 Hz, 1 H) 7.10-7.24 (m, 2 H) 3.92 (dd, J = 7.13, 1.64 Hz, 6 H) 3.50-3.71 (m, 5 H) 3.15-3.25 (m, 2 H) 2.57 (br s, 1 H) 1.68-1.89 (m, 6 H) 0.84-1.01 (m, 4 H) |
| 161 | DMSO-d$^6$ | 8.71 (d, J = 4.4 Hz, 1 H), 7.46 (s, 1 H), 7.36-7.44 (m, 3 H), 7.25 (d, J = 4.4 Hz, 1 H), 7.19 (s, 1 H), 4.40-4.52 (m, 2 H), 3.96 (s, 3 H), 3.77 (s, 4 H), 3.43-3.58 (m, 2 H), 3.01 (br t, J = 5.6 Hz, 2 H), 2.84 (s, 3 H) |
| 162 | DMSO-d$^6$ | 2.88 (s, 3 H) 3.93 (s, 3 H) 4.24 (s, 2 H) 7.24 (dd, J = 9.26, 2.75 Hz, 1 H) 7.28 (d, J = 4.50 Hz, 1 H) 7.45-7.51 (m, 3 H) 7.53-7.59 (m, 2 H) 7.76 (d, J = 9.26 Hz, 1 H) 8.84 (d, J = 4.50 Hz, 1 H) |
| 165 | DMSO-d$^6$ | 1.41 (q, J = 11.21 Hz, 2 H) 1.74-2.02 (m, 5 H) 3.56 (br d, J = 12.67 Hz, 4 H) 3.69 (s, 3 H) 3.91 (s, 3 H) 3.97 (br t, J = 7.84 Hz, 2 H) 4.05 (s, 3 H) 4.73 (br s, 2 H) 7.53 (d, J = 9.54 Hz, 1 H) 7.94 (d, J = 9.54 Hz, 1 H) 8.63 (s, 1 H) |
| 166 | DMSO-d$^6$ | 8.72 (d, J = 5.26 Hz, 1H), 8.10 (d, J = 9.21 Hz, 1H), 8.05-7.98(m, 2H), 7.48-7.42(m, 3H), 7.33-7.26(m, 1H), 6.74 (d, J = 5.04 Hz, 1H), 4.77 (d, J = 3.51 Hz, 1H), 4.34-4.23(m, 3H), 4.01-3.92 (m, 5H), 1.74 (s, 3H) |
| 167 | DMSO-d$^6$ | 8.69 (s, 1 H) 8.30 (d, J = 8.94 Hz, 1 H) 8.02-8.08 (m, 2 H) 7.56-7.62 (m, 2 H) 7.43 (s, 1 H) 7.42 (d, J = 8.58 Hz, 2 H) 4.32 (s, 1 H) 4.00 (s, 3 H) 3.15 (s, 3 H) |

TABLE 16-continued

<sup>1</sup>H NMR data for examples at 400 MHz

| Compound | Solvent | δ ppm |
|---|---|---|
| 168 | DMSO-d⁶ | 8.86 (s, 1H), 7.83-7.93 (m, 2H), 7.67 (d, J = 8.8 Hz, 1H), 7.48 (d, J = 2.4 Hz, 1H), 7.17-7.28 (m, 1H), 6.97-7.06 (m, 2H), 4.15 (s, 1H), 3.92 (s, 3H), 3.04 (s, 3H), 2.21 (s, 3H). |
| 169 | DMSO-d⁶ | 8.67 (d, J = 5.25 Hz, 1 H) 8.11 (s, 1 H) 7.93 (d, J = 7.88 Hz, 1 H) 7.79-7.87 (m, 2 H) 7.64-7.70 (m, 1 H) 7.54 (d, J = 8.25 Hz, 1 H) 7.07 (d, J = 5.25 Hz, 1 H) 5.49 (s, 2 H) 4.29 (s, 1 H) 3.99 (s, 3 H) 3.09 (s, 3 H) |
| 170 | DMSO-d⁶ | 8.70 (d, J = 5.38 Hz, 1 H) 8.32 (s, 1 H) 8.00 (d, J = 9.13 Hz, 1 H) 7.35 (d, J = 2.50 Hz, 1 H) 7.19 (dd, J = 9.13, 2.50 Hz, 1 H)7.11 (d, J = 5.38 Hz, 1 H) 7.08 (s, 1 H) 7.07-7.09 (m, 1 H) 5.41 (s, 2 H) 4.45 (s, 1 H) 3.91 (s, 3 H) 3.13-3.20 (m, 3 H) |
| 171 | DMSO-d⁶ | 25° C.: 8.60 (s, 1 H) 7.30 (br d, J = 9.21 Hz, 2 H) 4.29-4.49 (m, 2 H) 3.92 (br d, J = 12.28 Hz, 6 H) 3.66 (s, 1 H) 3.42 (br s, 1 H) 2.94-3.17 (m, 4 H) 2.05-2.25 (m, 3 H) 1.68-1.89 (m, 2 H)<br>80° C.: 8.60 (s, 1 H) 7.22-7.41 (m, 2 H) 4.47 (br dd, J = 10.58, 6.39 Hz, 2 H) 3.94 (d, J = 13.01 Hz, 6 H) 3.45 (br s, 1 H) 3.25 (br s, 1 H) 2.96-3.09 (m, 4 H) 2.04-2.28 (m, 3 H) 1.88 (q, J = 12.57 Hz, 2 H) |
| 172 | DMSO-d⁶ | 9.08 (d, J = 2.0 Hz, 1H), 9.03 (s, 1H), 8.70 (d, J = 5.2 Hz, 1H), 8.48 (s, 1H), 8.09 (d, J = 9.2 Hz, 1H), 7.35 (d, J = 2.4 Hz, 1H), 7.21 (dd, J = 9.2, 2.4 Hz, 1H), 7.05 (d, J = 5.2 Hz, 1H), 5.54 (s, 2H), 4.60 (s, 1H), 3.91 (s, 3H), 3.20 (s, 3H). |
| 173 | DMSO-d⁶ | 8.66 (s, 1 H) 8.13 (s, 1 H) 7.91 (d, J = 7.88 Hz, 1 H) 7.82 (d, J = 7.75 Hz, 1 H) 7.65 (t, J = 7.69 Hz, 1 H) 7.40 (s, 1 H) 7.34 (s, 1 H) 5.74 (s, 2 H) 4.27 (s, 1 H) 3.96 (s, 3 H) 3.92 (s, 3 H) 3.08 (s, 3 H) |
| 174 | DMSO-d⁶ | 8.79 (s, 1 H) 8.11 (s, 1 H) 7.93 (br d, J = 7.75 Hz, 1 H) 7.83 (br d, J = 7.63 Hz, 1 H) 7.59-7.74 (m, 3 H) 7.44 (d, J = 7.75 Hz, 1 H) 5.74 (s, 2 H) 4.27 (s, 1 H) 3.97 (s, 3 H) 3.08 (s, 3 H) |
| 175 | DMSO-d⁶ | 8.54 (d, J = 5.25 Hz, 1 H) 8.18 (s, 1 H) 7.92 (br d, J = 7.50 Hz, 1 H) 7.82 (br d, J = 7.75 Hz, 1 H) 7.64-7.70 (m, 1 H) 7.43 (s, 1 H) 7.33 (s, 1 H) 7.32-7.35 (m, 1 H) 6.99 (d, J = 5.38 Hz, 1 H) 5.50 (s, 2 H) 4.29 (s, 1 H) 3.91 (d, J = 7.13 Hz, 6 H) 3.09 (s, 3 H) |
| 176 | DMSO-d⁶ | 8.71 (d, J = 5.2 Hz, 1H), 8.09-8.18 (m, 2H), 7.95 (d, J = 8.0 Hz, 1H), 7.86 (d, J = 7.6 Hz, 1H), 7.64-7.73 (m, 1H), 7.52 (s, 1H), 7.08 (d, J = 5.6 Hz, 1H), 5.50 (s, 2H), 4.30 (s, 1H), 4.01 (s, 3H), 3.10 (s, 3H) |
| 177 | MeOD | 8.61 (d, J = 5.50 Hz, 1H), 8.21 (d, J = 9.26 Hz, 1H), 8.05 (s, 1H), 7.79-7.74 (m, 1H), 7.67 (br d, J = 9.01 Hz, 1H), 7.32 (d, J = 2.50 Hz, 1H), 7.23 (dd, J = 9.19, 2.56 Hz, 1H), 6.98(d, J = 5.50 Hz, 1H), 5.51 (s, 2H), 3.96 (s, 3 H) 3.20 (s, 3H) |
| 178 | DMSO-d⁶ | 8.54 (dd, J = 5.38, 2.13 Hz, 1 H) 8.20 (dd, J = 9.13, 1.63 Hz, 1 H) 8.07 (d, J = 7.75 Hz, 1 H) 7.86 (d, J = 8.00 Hz, 1 H) 7.78 (t, J = 6.57 Hz, 1 H) 7.60 (td, J = 7.75, 2.75 Hz, 1 H) 7.20-7.33 (m, 2 H) 6.81 (t, J = 5.69 Hz, 1 H) 5.98 (quin, J = 5.78 Hz, 1 H) 4.23 (s, 1 H) 3.90 (s, 3 H) 3.00-3.08 (m, 3 H) 1.68-1.76 (m, 3 H) |
| 179 | DMSO-d⁶ | 8.69 (s, 1 H) 7.54-7.62 (m, 2 H) 7.27-7.37 (m, 1 H) 3.96 (s, 3 H) 3.71-3.86 (m, 3H) 3.40-3.54 (m, 2 H) 3.17 (d, J = 6.25 Hz, 2 H) 2.98 (s, 3 H) 2.26-2.40 (m, 1 H) 2.00-2.20 (m, 2 H) 1.56-1.73 (m, 2H) |
| 180 | DMSO-d⁶ | 8.49 (d, J = 7.00 Hz, 1 H) 7.61-7.65 (m, 2 H) 7.53 (dd, J = 5.00, 4.00 Hz, 1 H) 7.24 (d, J = 7.00 Hz, 1 H) 4.17 (br d, J = 13.13 Hz, 2 H) 4.09 (s, 3 H) 4.04 (br d, J = 6.25 Hz, 2 H) 3.81 (s, 3 H) 3.48 (br t, J = 11.82 Hz, 2 H) 2.60-2.70 (m, 1 H) 2.10 (br t, J = 14.63 Hz, 2 H) 1.64-1.77 (m, 2 H) |
| 181 | DMSO-d⁶ | 8.51 (s, 1 H) 7.20 (s, 1 H) 7.07-7.16 (m, 1 H) 3.86-3.99 (m, 6 H) 3.46-3.75 (m, 6 H) 2.79-2.91 (m, 3 H) 1.94-2.10 (m, 3 H) 1.56-1.86 (m, 7H) |
| 182 | DMSO-d⁶ | 8.96 (s, 1H), 7.69-7.62 (m, 1H), 7.45 (d, J = 8.33 Hz, 1H), 7.23 (d, J = 7.67 Hz, 1H), 4.02 (s, 3H), 3.74 (s, 1H), 3.66 (br d, J = 12.28 Hz, 2H), 3.14 (d, J = 6.36 Hz, 2H), 3.04-2.97(m, 2H), 2.96 (s, 3H), 2.29-2.18(m, 1H), 2.15-2.00(m, 2H), 1.68-1.55 (m, 2H) |
| 183 | DMSO-d⁶ | 8.58 (s, 1 H) 7.26 (dd, J = 11.07, 2.52 Hz, 1 H) 7.11 (dd, J = 9.76, 2.52 Hz, 1 H) 4.13 (br d, J = 13.37 Hz, 2 H) 3.95 (s, 3 H) 3.72 (s, 1 H) 3.05-3.20 (m, 4 H) 2.95 (s, 3 H) 2.21-2.36 (m, 1 H) 1.93-2.10 (m, 2H) 1.42-1.59 (m, 2 H) |
| 184 | DMSO-d⁶ | 8.39 (d, J = 5.25 Hz, 1 H) 7.71 (d, J = 13.26 Hz, 1 H) 7.44 (d, J = 8.76 Hz, 1 H) 6.25 (d, J = 5.38 Hz, 1 H) 4.44 (s, 2 H) 4.29 (s, 2 H) 4.02 (s, 3 H) 3.43-3.68 (m, 1 H) 3.25 (dd, J = 7.00, 2.00 Hz, 2 H) 2.91 (s, 3 H) 2.74 (br t, J = 7.88 Hz, 1 H) 2.46-2.54 (m, 2 H) 2.08-2.31 (m, 2 H) |
| 185 | DMSO-d⁶ | 8.58 (s, 1 H), 7.42-7.48 (m, 2 H), 7.26-7.27 (m, 1 H), 5.69 (br s, 1 H), 4.00 (m, 3H), 3.96 (s, 3 H), 3.55 (m, 3H), 3.26-3.30 (m, 1 H), 3.02 (s, 3 H), 1.95-0.97 (m, 2 H), 1.88-1.89 (m, 2 H) |
| 186 | DMSO-d⁶ | 8.22 (d, J = 5.2 Hz, 1 H), 7.16 (d, J = 9.2 Hz, 2 H), 6.14 (d, J = 5.2 Hz, 1 H), 4.36 (s, 2 H), 4.18 (s, 2 H), 3.86 (s, 3 H), 3.85 (s, 3 H), 3.54 (s, 1 H), 3.17 (br d, J = 4.2 Hz, 2 H), 2.82 (s, 3 H), 2.61-2.72 (m, 2H), 2.07-2.18 (m, 2 H) |

TABLE 16-continued

¹H NMR data for examples at 400 MHz

| Compound | Solvent | δ ppm |
|---|---|---|
| 187 | DMSO-d⁶ | 8.59 (s, 1H), 7.46-7.39(m, 2H), 7.25 (dd, J = 5.94, 3.06 Hz, 1H), 4.23-4.13(m, 4H), 3.71 (s, 1H), 3.19-3.07 (m, 4H), 2.95 (s, 3H), 2.29 (br s, 1H), 2.10-1.95(m, 2H), 1.52 (br d, J = 12.13 Hz, 2H), 1.43 (t, J = 7.00 Hz, 3H) |
| 188 | DMSO-d⁶ | 8.16 (s, 1H), 7.44 (s, 1H), 7.12 (s, 1H), 4.53 (s, 2H), 4.34 (s, 2H), 3.94 (d, J = 4.65 Hz, 7H), 3.55 (s, 1H), 3.19 (dd, J = 7.03, 2.63 Hz, 2H), 2.84 (s, 3H), 2.68 (q, J = 8.07 Hz, 2H), 2.21-2.10 (m, 2H) |
| 189 | DMSO-d⁶ | 8.67 (s, 1H), 7.53-7.56 (m, 2H), 7.29-7.32 (m, 1H), 3.94 (s, 3H), 3.77-3.80 (m, 2H), 3.56 (s, 1H), 3.41-3.44 (m, 2H), 3.12 (d, J = 7.0 Hz, 2H), 2.66-2.67 (m, 1H), 2.32-2.37 (m, 1 H), 2.06-2.15 (m, 2H), 1.63-1.66 (m, 2H), 1.05-1.14 (m, 1H), 0.89-0.94 (m, 2H), 0.82-0.87 (m, 1H) |
| 190 | DMSO-d⁶ | 8.58 (s, 1 H) 7.45 (d, J = 4.50 Hz, 2 H) 7.24-7.30 (m, 1 H) 4.20 (br d, J = 12.88 Hz, 2 H) 3.92 (s, 3 H) 3.50 (s, 1 H) 3.15 (br t, J = 12.51 Hz, 2 H) 3.00-3.09 (m, 2 H) 2.58-2.69 (m, 1 H) 2.34 (br d, J = 10.63 Hz, 1 H) 1.97-2.12 (m, 2 H) 1.54 (q, J = 11.67 Hz, 2 H) 1.01-1.09 (m, 1 H) 0.81-0.94 (m, 3 H) |
| 191 | DMSO-d⁶ | 8.57 (s, 1H), 8.14 (s, 1H), 7.39-7.50 (m, 2H), 7.25-7.28 (m, 1H), 3.97-4.20 (m, 3H), 3.81 (s, 3H), 3.44-3.53 (m, 1H), 3.02-3.17 (m, 2H), 2.33-2.47 (m, 3H), 2.12-2.30 (m, 3H), 1.97-2.07(m, 2H), 1.76-1.90(m, 2H), 1.59-1.68(m, 2H) |
| 192 | DMSO-d⁶ | 8.24 (d, J = 5.25 Hz, 1 H) 8.13 (d, J = 13.38 Hz, 1 H) 7.88 (d, J = 8.38 Hz, 2 H) 7.79 (br t, J = 6.00 Hz, 1 H) 7.58 (d, J = 8.38 Hz, 2 H) 7.36 (d, J = 8.76 Hz, 1 H) 6.24 (d, J = 5.38 Hz, 1 H) 4.62 (d, J = 5.88 Hz, 2 H) 4.14 (s, 1 H) 3.95 (s, 3 H) 3.03 (s, 3 H) |
| 193 | DMSO-d⁶ | 8.58 (s, 1H), 7.50-7.40(m, 2H), 7.27 (dd, J = 7.32, 1.44 Hz, 1H), 5.93 (br s, 1H), 4.06-3.95 (m, 3H), 3.92 (s, 3H), 3.55-3.43 (m, 2H), 3.34 (s, 1H), 3.30 (br s, 1H), 2.77-2.68 (m, 1H), 2.06-1.99(m, 2H), 1.95-1.79(m, 2H), 1.11-1.03(m, 1H), 0.98-0.82(m, 3 H) |
| 194 | DMSO-d⁶ | 8.67 (s, 1H), 7.56-7.72 (m, 3H), 6.07 (br s, 1H), 4.70 (br s, 1H), 4.42-4.55 (m, 1H), 3.89-4.23 (m, 7H), 3.59 (br s, 3H), 2.54-2.60 (m, 1H), 2.05-2.18 (m, 1H), 0.91 (br s, 1H), 0.82 (br s, 1H), 0.53 (br s, 1H), 0.35 (br s, 1H) |
| 195 | DMSO-d⁶ | 8.50-8.64 (m, 1 H) 7.41-7.55 (m, 2 H) 7.22-7.35 (m, 1 H) 5.76-5.90 (m, 1 H) 3.97-4.02 (m, 2 H) 3.96 (br d, J = 3.50 Hz, 1 H) 3.92 (s, 3 H) 3.42-3.55 (m, 2 H) 3.19-3.31 (m, 2 H) 3.15-3.18 (m, 1 H) 3.11 (qd, J = 7.34, 2.00 Hz, 2 H) 1.79-2.09 (m, 4 H) 1.19-1.30 (m, 3 H) |
| 196 | DMSO-d⁶ | 8.59 (s, 1 H) 7.40-7.49 (m, 2 H) 7.26 (dd, J = 7.44, 1.06 Hz, 1 H) 5.66 (br s, 1 H) 4.18 (q, J = 7.00 Hz, 2 H) 4.00 (br s, 2 H) 3.96 (br s, 1 H) 3.46-3.58 (m, 2 H) 3.40-3.45 (m, 1 H) 3.27 (s, 1 H) 3.03 (s, 3 H) 1.93-2.01 (m, 2 H) 1.84-1.93 (m, 2 H) 1.43 (t, J = 6.94 Hz, 3 H) |
| 197 | DMSO-d⁶ | 8.69 (s, 1 H) 7.48-7.64 (m, 2 H) 7.29 (dd, J = 5.69, 3.31 Hz, 1 H) 4.20 (q, J = 6.92 Hz, 2 H) 3.79 (br s, 1 H) 3.75 (br d, J = 6.88 Hz, 2 H) 3.44 (brt, J = 12.51 Hz, 2 H) 3.32 (s, 43 H)3.29 (s, 1 H)3.15 (d, J = 6.25 Hz, 2 H) 2.97 (s, 3 H) 2.02-2.17 (m, 2 H) 1.57-1.72 (m, 2 H) 1.44 (t, J = 6.94 Hz, 3H) |
| 198 | DMSO-d⁶ | 1.99 (br s, 2 H), 2.03-2.12 (m, 2 H), 3.05 (s, 3 H), 3.36 (s, 1 H), 3.42-3.50 (m, 1 H), 3.54-3.63 (m, 2 H), 3.65-3.77 (m, 2 H), 3.94 (s, 3 H), 4.02 (s, 1 H), 5.72 (s, 1 H), 7.30 (t, J = 4.4 Hz, 1 H), 7.52-7.59 (m, 2 H), 8.68 (s, 1 H) |
| 199 | DMSO-d⁶ | 8.15 (s, 1 H) 7.40-7.47 (m, 1 H) 7.32-7.39 (m, 1 H) 7.21 (d, J = 7.25 Hz, 1 H) 3.95 (br s, 2 H) 3.90 (s, 3 H) 3.41-3.50 (m, 2 H) 3.39 (s, 1 H) 3.26 (s, 2 H) 3.02 (s, 3 H) 2.52 (br s, 3 H) 1.82-2.00 (m, 4 H) |
| 200 | DMSO-d⁶ | 8.74 (s, 1 H) 7.78 (br d, J = 8.25 Hz, 1 H) 7.52-7.66 (m, 2 H) 6.10 (s, 1 H) 5.96 (s, 1 H) 3.82 (br d, J = 12.76 Hz, 2 H) 3.77 (s, 1 H) 3.48 (br t, J = 12.38 Hz, 2 H) 3.15 (br d, J = 6.13 Hz, 2 H) 2.97 (s, 3 H) 2.01-2.19 (m, 2H) 1.64 (q, J = 10.84 Hz, 2 H) |
| 201 | DMSO-d⁶ | 7.46-7.55 (m, 2 H) 7.24-7.29 (m, 1 H) 3.93 (s, 3 H) 3.68-3.79 (m, 3 H) 3.45 (br t, J = 12.38 Hz, 2 H) 3.15 (d, J = 6.38 Hz, 2 H) 2.97 (s, 3 H) 2.68 (s, 3 H) 2.29 (br d, J = 3.50 Hz, 1 H) 2.00-2.16 (m, 2 H) 1.63 (q, J = 11.34 Hz, 2 H) |
| 202 | DMSO-d⁶ | 7.70 (d, J = 14 Hz, 1H), 7.25-7.26 (m, 2H), 7.02-7.04 (m, 1H), 4.22-4.25 (m, 2H), 3.99 (s, 3H), 3.17-3.24 (dm, 2H), 3.02-3.07 (m, 5H), 2.32 (m, 1 H), 2.02-2.13 (m, 2H), 1.54-1.62 (m, 2H) |
| 203 | DMSO-d⁶ | 8.63 (s, 1H), 7.19-7.35 (m, 2H), 3.91 (s, 3H), 3.65-3.81 (m, 3H), 3.38-3.44 (m, 2H), 3.10 (d, J = 6.4 Hz, 2H), 2.95 (s, 3H), 2.19-2.34 (m, 1H), 1.94-2.12 (m, 2H), 1.50-1.59 (m, 2H) |
| 204 | DMSO-d⁶ | 8.70 (d, J = 4.8 Hz, 1 H), 7.48-7.55 (m, 2 H), 7.41-7.47 (m, 3 H), 7.26 (d, J = 4.8 Hz, 1 H), 7.14 (s, 1 H), 3.94 (s, 3 H), 3.74 (s, 3 H), 3.69 (s, 1 H), 3.42 (dd, J = 9.6, 6.8 Hz, 2 H), 3.31 (s, 3 H), 3.08-3.16 (m, 2 H), 2.89 (s, 3 H ), 2.49 (dt, J = 3.6, 1.6 Hz, 2 H) |

TABLE 16-continued

¹H NMR data for examples at 400 MHz

| Compound | Solvent | δ ppm |
|---|---|---|
| 205 | DMSO-d⁶ | 8.55-8.61 (m, 1 H) 7.55-7.61 (m, 1 H) 7.45-7.51 (m, 1 H) 6.87-6.95 (m, 1 H) 3.94-3.98 (m, 3 H) 3.59-3.67 (m, 1 H) 3.21-3.30 (m, 2 H) 2.99-3.17 (m, 6 H) 2.75-2.81 (m, 3 H) 1.70-1.86 (m, 6 H) |
| 206 | DMSO-d⁶ | 8.33 (s, 1H), 8.15 (s, 1H), 7.21 (s, 1H), 7.13 (s, 1H), 4.23 (br s, 4H), 3.89 (d, J = 2.38 Hz, 6H), 3.55 (br s, 1H), 3.21-3.08 (m, 4H), 2.74 (s, 3H), 1.87 (br t, J = 5.21 Hz, 4 H) |
| 207 | DMSO-d⁶ | 8.32 (s, 1H) 8.16 (s, 1 H) 7.54 (s, 1H) 7.12 (s, 1 H) 4.02 (br t, J = 6.88 Hz, 2 H) 3.90 (d, J = 1.50 Hz, 6 H) 3.70 (s, 2 H) 3.08-3.20 (m, 4 H) 2.75 (s, 3 H) 1.90 (br t, J = 6.88 Hz, 2 H) 1.59-1.73 (m, 4 H) |
| 208 | acetone-d⁶ | 8.50 (d, J = 5.04 Hz, 1 H) 8.15 (s, 1 H) 7.28-7.43 (m, 2 H) 6.90 (d, J = 5.04 Hz, 1 H) 3.96 (d, J = 1.75 Hz, 6 H) 3.33-3.46 (m, 2 H) 3.10-3.32 (m, 6 H) 2.82 (s, 3 H) 1.86-2.00 (m, 6 H) |
| 209 | DMSO-d⁶ | 8.50 (s, 1H), 7.18 (s, 1H), 7.11 (s, 1H), 3.89-3.91 (s, 6H), 3.61 (m, 4H), 3.09-3.16 (m, 4H), 2.73 (s, 3H), 1.60-1.65 (m, 8H) |
| 210 | DMSO-d⁶ | 8.70 (s, 1 H) 7.76 (d, J = 12.63 Hz, 1 H) 7.57 (d, J = 8.50 Hz, 1 H) 4.03 (s, 3 H) 3.66 (d, J = 1.25 Hz, 1 H) 3.53-3.63 (m, 4 H) 3.27-3.33 (m, 2 H) 3.15-3.22 (m, 2 H) 2.82 (d, J = 1.38 Hz, 3 H) 1.76-1.92 (m, 6 H) |
| 211 | DMSO-d⁶ | 8.68-8.87 (m, 1 H) 7.54-7.64 (m, 1 H) 7.02-7.09 (m, 1 H) 3.90-4.05 (m, 6 H) 3.31-3.34 (m, 2 H) 3.28 (br s, 2 H) 3.09-3.21 (m, 4 H) 2.75-2.85 (m, 3 H) 1.69-1.91 (m, 6 H) |
| 212 | MeOD | 8.50 (s, 1H), 7.98 (s, 1H), 7.24 (s, 1H), 4.03 (s, 3H), 3.81-3.84 (m, 4H), 3.41-3.44 (m, 2H), 3.26-3.80 (m, 2H), 2.93 (s, 3H), 1.95-1.99 (m, 2H), 1.80-1.87 (m, 4H) |
| 213 | DMSO-d⁶ | 8.15 (s, 1 H), 8.12-8.18 (m, 1 H), 7.15 (s, 1 H), 7.09 (s, 1 H), 3.91 (s, 3 H), 3.89 (s, 3 H), 3.57 (br d, J = 4.0 Hz, 4 H), 3.23-3.29 (m, 2 H), 3.09-3.16 (m, 2 H), 2.80 (s, 3 H), 2.49 (s, 3 H), 1.85 (t, J = 6.8 Hz, 2H), 1.68-1.80 (m, 4 H) |
| 214 | DMSO-d⁶ | 8.60 (s, 1 H) 7.42-7.53 (m, 2 H) 7.28 (dd, J = 6.25, 2.74 Hz, 1 H) 4.15-4.28 (m, 2 H) 3.92 (s, 3 H) 3.76 (t, J = 7.34 Hz, 2 H) 3.50-3.54 (m, 1 H) 2.99-3.12 (m, 2 H) 2.86 (s, 3 H) 1.98-2.28 (m, 6 H) |
| 215 | DMSO-d⁶ | 8.58 (s, 1 H) 8.15 (s, 1 H) 7.42-7.49 (m, 2 H) 7.27 (dd, J = 7.02, 1.97 Hz, 1 H) 3.92 (s, 3 H) 3.63-3.71 (m, 4 H) 3.28 (br d, J = 7.02 Hz, 2 H) 3.08-3.18 (m, 2 H) 2.80 (s, 3 H) 1.65-1.87 (m, 6 H) |
| 216 | DMSO-d⁶ | 8.32 (s, 1 H), 8.14 (s, 1 H), 7.50 (s, 1 H), 7.11 (s, 1 H), 3.94-4.09 (m, 2 H), 3.89 (s, 3 H), 3.88 (s, 3 H), 3.78-3.87 (m, 2 H), 3.76 (s, 1 H), 3.28-3.38 (m, 2 H), 3.17-3.27 (m, 2 H), 2.81 (s, 3 H), 1.86-2.08 (m, 4 H) |
| 217 | DMSO-d⁶ | 8.46-8.53 (m, 1 H), 8.14 (s, 1 H), 7.50-7.56 (m, 1 H), 7.47 (t, J = 8.0 Hz, 1 H), 7.36 (d, J = 7.6 Hz, 1 H), 4.50 (br s, 4 H), 3.90-3.98 (m, 4 H), 3.42-3.53 (m, 2 H), 3.28 (br d, J = 5.6 Hz, 2 H), 2.83 (s, 3 H), 2.20 (t, J = 6.8 Hz, 2 H) |
| 218 | DMSO-d⁶ | 8.62 (d, J = 6.8 Hz, 1 H), 7.87 (d, J = 12.4 Hz, 1 H), 7.79 (d, J = 8.0 Hz, 1 H), 7.15 (d, J = 7.2 Hz, 1 H), 4.04 (s, 3 H), 3.77 (br s, 3 H), 3.61-3.71 (m, 3 H), 3.45-3.51 (m, 2 H), 3.38-3.45 (m, 1 H), 2.52-2.54 (m, 1 H), 2.03 (t, J = 7.2 Hz, 2 H), 1.78-1.92 (m, 4 H), 1.38-1.47 (m, 1 H), 1.32-1.37 (m, 2 H), 1.23-1.32 (m, 1 H) |
| 219 | DMSO-d⁶ | 8.91 (s, 1 H) 7.97 (s, 1 H) 7.80 (s, 1 H) 4.08 (s, 3 H) 3.60-3.65 (m, 1 H) 3.35-3.43 (m, 4 H) 3.25-3.31 (m, 2 H) 3.15 (d, J = 4.13 Hz, 2 H) 2.81 (d, J = 1.50 Hz, 3 H) 1.74-1.92 (m, 6 H) |
| 220 | DMSO-d⁶ | 8.13-8.20 (m, 1 H) 7.75-7.86 (m, 1 H) 4.06 (s, 3 H) 3.62-3.67 (m, 1 H) 3.30 (br d, J = 7.25 Hz, 6 H) 3.16-3.24 (m, 2 H) 2.78-2.86 (m, 6H) 1.89 (t, J = 7.00 Hz, 2 H) 1.70-1.83 (m, 4 H) |
| 221 | DMSO-d⁶ | 1.37 (t, J = 7.2 Hz, 3 H), 1.73-1.89 (m, 4 H), 1.96-2.06 (m, 2 H), 3.40-3.49 (m, 2 H), 3.60 (br t, J = 6.8 Hz, 2 H), 3.79-3.88 (m, 2 H), 4.04 (s, 3 H), 4.06-4.19 (m, 4 H), 7.66 (d, J = 7.8 Hz, 1 H), 7.97 (d, J = 12.2 Hz, 1 H), 8.82 (s, 1 H) |
| 222 | DMSO-d⁶ | 2.21 (br t, J = 6.8 Hz, 2 H), 2.81 (s, 3 H), 3.23-3.29 (m, 2 H), 3.47 (br d, J = 9.2 Hz, 2 H), 3.90 (s, 3 H), 4.68-4.83 (m, 4 H), 7.25 (d, J = 7.8 Hz, 1 H), 7.39 (t, J = 8.0 Hz, 1 H), 7.62 (d, J = 8.0 Hz, 1 H), 8.25 (s, 1 H), 8.41 (s, 1 H) |
| 223 | DMSO-d⁶ | 8.43 (s, 1 H) 7.78 (d, J = 8.50 Hz, 1 H) 7.39 (t, J = 8.19 Hz, 1 H) 7.26 (d, J = 7.88 Hz, 1 H) 4.02 (s, 2 H) 3.71 (d, J = 8.13 Hz, 2 H) 3.57 (br s, 1 H) 2.89 (s, 3 H) 2.18 (br t, J = 6.69 Hz, 2 H) |
| 224 | DMSO-d⁶ | 1.62-1.77 (m, 4 H), 1.82 (t, J = 6.8 Hz, 2 H), 2.80 (s, 3 H), 3.06-3.15 (m, 2 H), 3.21-3.34 (m, 2 H), 3.56-3.70 (m, 4 H), 3.99 (s, 3 H), 7.38 (d, J = 8.4 Hz, 1 H), 7.66 (d, J = 12.4 Hz, 1 H), 8.16 (s, 1 H), 8.56 (s, 1 H) |
| 225 | DMSO-d⁶ | 8.74 (s, 1H), 8.28 (s, 1H), 7.34 (m, 1H), 4.09-4.20 (m, 7H), 3.73-3.83 (m, 2H), 3.58-3.65 (m, 2H), 3.32-3.38 (m, 1H), 2.20 (t, J = 7.2 Hz, 2H), 1.95-2.11 (m, 4H), 1.34-1.62 (m, 4H) |
| 226 | DMSO-d⁶ | 8.71 (d, J = 5.13 Hz, 1 H) 8.33 (s, 1 H) 7.50 (s, 1 H) 6.96 (d, J = 5.25 Hz, 1 H) 4.03 (s, 3 H) 3.63 (s, 1 H) 3.19-3.30 (m, 4 H) 3.14 (br d, J = 4.50 Hz, 2 H) 2.81 (d, J = 1.38 Hz, 3 H) 1.75-1.89 (m, 6 H) |

TABLE 16-continued

<sup>1</sup>H NMR data for examples at 400 MHz

| Compound | Solvent | δ ppm |
|---|---|---|
| 227 | DMSO-d<sup>6</sup> | 1.71-1.82 (m, 4H), 1.83-1.89 (m, 2 H), 2.81 (s, 3 H), 3.11-3.19 (m, 2 H), 3.27-3.46 (m, 6 H), 3.65 (br s, 1 H), 3.91 (s, 3 H), 3.93 (s, 3 H), 7.26 (s, 1 H), 7.33 (s, 1 H), 8.23 (s, 1 H), 8.54 (d, J = 4.4 Hz, 1 H) |
| 228 | DMSO-d<sup>6</sup> | 7.58 (s, 1H), 7.23 (s, 1H), 3.97 (d, J = 1.50 Hz, 6H), 3.62 (s, 1H), 3.31-3.16(m, 8H), 2.80 (d, J = 9.63 Hz, 6H), 1.89 (br t, J = 7.00 Hz, 2H), 1.83-1.68(m, 4H) |
| 229 | DMSO-d<sup>6</sup> | 9.12 (d, J = 6.6 Hz, 1 H) 8.22 (t, J = 10.6 Hz, 1 H) 7.95 (d, J = 7.5 Hz, 1 H) 7.51 (br d, J = 6.6 Hz, 1 H) 4.49-4.66 (m, 2 H) 4.07 (s, 3 H) 3.82-3.91 (m, 1 H) 3.68 (s, 3 H) 3.49-3.65 (m, 2 H) 3.36-3.48 (m, 1H) 2.99 (dt, J = 14.1, 7.1 Hz, 1 H) 2.21-2.35 (m, 1 H) 1.90-2.05 (m, 1H) |
| 229a | DMSO-d<sup>6</sup> | 8.64 (d, J = 5.2 Hz, 1H), 7.80 (d, J = 12.0 Hz, 1H), 7.52 (d, J = 8.4 Hz, 1H), 6.96 (d, J = 5.2 Hz, 1H), 4.14-4.28 (m, 2H), 3.99 (s, 3H), 3.66 (br s, 1H), 3.46-3.56 (m, 1H), 3.20-3.31 (m, 2H), 3.02-3.14 (m, 1H), 2.74-2.88 (m, 4H), 2.07-2.19 (m, 1H), 1.78-1.86 (m, 1H). |
| 229b | DMSO-d<sup>6</sup> | 8.65 (d, J = 5.2 Hz, 1H), 7.80 (d, J = 12.0 Hz, 1H), 7.52 (d, J = 8.4 Hz, 1H), 6.97 (d, J = 5.6 Hz, 1H), 4.14-4.30 (m, 2H), 3.99 (s, 3H), 3.65 (s, 1H), 3.48-3.57 (m, 1H), 3.34-3.39 (m, 1H), 3.15-3.25 (m, 1H), 3.05-3.12 (m, 1H), 2.74-2.86 (m, 4H), 2.06-2.19 (m, 1H), 1.72-1.86 (m, 1H) |
| 230 | DMSO-d<sup>6</sup> | 8.66 (d, J = 5.2 Hz, 1H), 7.81 (dd, J = 12.0, 4.4 Hz, 1H), 7.52 (d, J = 8.4 Hz, 1H), 6.97 (d, J = 5.2 Hz, 1H), 4.17-4.30 (m, 2H), 4.10 br s, 1H), 3.99 (s, 3H), 3.48-3.59 (m, 1H), 3.28-3.41 (m, 2H), 3.21-3.28 (m, 1H), 3.14-3.20 (m, 3H), 3.05-3.13 (m, 1H), 2.77-2.85 (m, 4H), 2.09-2.19 (m, 1H), 1.79-1.82 (m, 1H) |
| 231 | DMSO-d<sup>6</sup> | 8.82 (d, J = 4.4 Hz, 1 H), 8.08 (d, J = 9.2 Hz, 1 H), 7.84-7.89 (m, 2 H), 7.49 (d, J = 4.4 Hz, 1 H), 7.45 (d, J = 2.8 Hz, 1 H), 7.27-7.35 (m, 3 H), 5.72 (s, 2 H), 4.08 (s, 1 H), 3.93 (s, 3 H), 3.02 (s, 3 H) |
| 232 | DMSO-d<sup>6</sup> | 8.84 (d, J = 4.4 Hz, 1 H), 8.10 (d, J = 9.2 Hz, 1 H), 7.65 (s, 1 H), 7.51-7.58 (m, 3H), 7.46 (d, J = 2.4 Hz, 1 H), 7.37-7.42 (m, 1 H), 7.31-7.36 (m, 1 H), 5.72 (s, 2 H), 4.22 (s, 1 H), 3.94 (s, 3 H), 3.25-3.30 (m, 1 H), 3.06-3.10 (m, 3 H), 2.99-3.05 (m, 1 H), 2.52-2.56 (m, 1 H), 1.23 (s, 1 H) |
| 233 | DMSO-d<sup>6</sup> | 8.88 (d, J = 4.88 Hz, 1H), 8.38 (d, J = 9.38 Hz, 1H), 8.25 (s, 1H), 7.49 (d, J = 2.50 Hz, 1H), 7.45 (d, J = 4.75 Hz, 1H), 7.33 (dd, J = 9.38, 2.63 Hz, 1H), 4.38(s, 2H), 3.95 (s, 3H), 3.78 (br s, 1H), 3.66-3.49(m, 2H), 2.95-2.88 (m, 2H), 2.85 (s, 3H) |
| 234 | DMSO-d<sup>6</sup> | 8.85 (d, J = 5.04 Hz, 1H), 8.29-8.22 (m, 1H), 8.21-8.15 (m, 1H), 7.93-7.88 (m, 1H), 7.50-7.43(m, 2H), 7.36-7.29 (m, 1H), 4.03-3.97(m, 3H), 3.61-3.52 (m, 2H), 3.22-3.14(m, 2H), 3.07 (s, 3H), 1.95-1.86(m, 1H) |
| 235 | DMSO-d<sup>6</sup> | 8.64 (d, J = 5.2 Hz, 1 H), 8.17 (s, 1 H), 8.09 (d, J = 9.2 Hz, 1 H), 7.32 (d, J = 2.4 Hz, 1 H), 7.19 (dd, J = 9.2, 2.4 Hz, 1 H), 6.97 (d, J = 5.2 Hz, 1 H), 4.89 (dt, J = 6.8, 3.2 Hz, 1 H), 3.90 (s, 3 H) 3.33-3.46 (m, 2 H) 3.18-3.31 (m, 2 H) 2.80 (s, 3 H) 2.03-2.14 (m, 2 H) 1.90 (brd, J = 7.00 Hz, 2 H) |
| 236 | DMSO-d<sup>6</sup> | 8.59 (s, 1H), 7.40-7.49 (m, 2H), 7.24-7.29 (m, 1H), 3.92 (s, 3H), 3.51-3.65 (m, 9H), 2.88 (s, 3H), 1.68-2.02 (m, 4H) |
| 237 | DMSO-d<sup>6</sup> | 8.33 (s, 1 H), 7.18 (s, 1 H), 7.12 (s, 1 H), 4.57 (br s, 2 H), 4.39 (br s, 2 H), 3.90 (s, 6 H), 3.55 (s, 1 H), 3.19 (dd, J = 7.2, 2.4 Hz, 2 H), 2.85 (s, 3 H), 2.65-2.74 (m, 1 H), 2.43-2.49 (m, 2 H), 2.15 (q, J = 10.8 Hz, 2 H) |
| 238 | DMSO-d<sup>6</sup> | 8.43 (s, 1H), 8.15 (s, 1H), 7.77 (d, J = 8.4 Hz, 1H), 7.35-7.40 (m, 1H), 7.25 (d, J = 7.2 Hz, 1H), 4.06-4.18 (m, 1H), 3.80-3.97 (m, 5H), 3.65-3.77 (m, 1H), 3.24-3.41 (m, 2H), 2.96 (s, 3H), 2.72-2.86 (m, 1H), 2.21-2.32 (m, 1H), 1.71-1.88 (m, 1H) |
| 238a | DMSO-d<sup>6</sup> | 8.43 (s, 1H), 7.77 (d, J = 8.4 Hz, 1H), 7.35-7.39 (m, 1H), 7.25 (d, J = 7.6 Hz, 1H), 4.08-4.17 (m, 1H), 3.85-3.95 (m, 5H), 3.78 (s, 1H), 3.67-3.76 (m, 1H), 3.32-3.39 (m, 1H), 3.14-3.29 (m, 1H), 2.96 (s, 3H), 2.73-2.85 (m, 1H), 2.19-2.32 (m, 1H), 1.72-1.88 (m, 1H) |
| 238b | DMSO-d<sup>6</sup> | 8.43 (s, 1H), 7.77 (d, J = 8.4 Hz, 1H), 7.35-7.39 (m, 1H), 7.25 (d, J = 8.0 Hz, 1H), 4.08-4.12 (m, 1H), 3.83-3.95 (m, 4H), 3.61-3.82 (m, 2H), 3.24-3.33 (m, 2H), 2.96 (s, 3H), 2.73-2.84 (m, 1H), 2.18-2.32 (m, 1H), 1.74-1.89 (m, 1H) |
| 239 | DMSO-d<sup>6</sup> | 8.43 (s, 1 H) 8.16 (s, 1 H) 7.76 (d, J = 8.63 Hz, 1 H) 7.37 (t, J = 8.25 Hz, 1 H) 7.25 (d, J = 7.75 Hz, 1 H) 4.07-4.14 (m, 1 H) 3.89 (s, 6 H) 3.65-3.75 (m, 2 H) 3.22-3.38 (m, 2 H) 2.96 (s, 3 H) 2.73-2.84 (m, 1 H) 2.19-2.31 (m, 1 H) 1.72-1.89 (m, 1 H) |
| 240 | DMSO-d<sup>6</sup> | 8.52 (s, 1 H) 7.20 (s, 1 H) 7.13 (s, 1 H) 5.74 (br s, 1H) 4.18 (br s, 1 H) 3.92 (d, J = 7.00 Hz, 6 H) 3.67-3.69 (m, 1 H) 3.61 (br s, 2 H) 3.37-3.46 (m, 4 H) 3.36-3.39 (m, 3 H) 2.98-3.22 (m, 2 H) 1.85 (br t, J = 7.07 Hz, 2 H) 1.74 (br s, 4 H) 1.36 (s, 3 H) 1.23 (s, 3 H) |

TABLE 16-continued

$^1$H NMR data for examples at 400 MHz

| Compound | Solvent | δ ppm |
|---|---|---|
| 241 | DMSO-d$^6$ | 8.52 (s, 1 H) 7.60 (s, 1 H) 7.24 (s, 1 H) 5.93 (s, 1 H) 5.79 (s, 1 H) 4.02 (s, 3 H) 3.71-3.87 (m, 4 H) 3.41 -3.51 (m, 2 H) 3.25-3.31 (m, 2 H) 2.95 (s, 3 H) 1.99 (t, J = 7.13 Hz, 2 H) 1.80-1.93 (m, 4 H) |
| 242 | DMSO-d$^6$ | 8.61 (d, J = 5.29 Hz, 1 H) 8.12-8.14 (m, 1 H) 8.06-8.11 (m, 1 H) 7.25-7.30 (m, 1 H) 7.14-7.21 (m, 1 H) 6.89-6.95 (m, 1 H) 4.94-5.01 (m, 1 H) 3.87-3.90 (m, 3 H) 3.03-3.08 (m, 1 H) 2.81-2.85 (m, 3 H) 2.15-2.24 (m, 2 H) 1.97 (br d, J = 9.04 Hz, 2 H) 1.61-1.94 (m, 5H) |
| 243 | DMSO-d$^6$ | 8.58-8.69 (m, 1 H) 8.13-8.19 (m, 1 H) 7.98-8.07 (m, 1 H) 7.27-7.35 (m, 1 H) 7.14-7.23 (m, 1 H) 6.98-7.06 (m, 1 H) 4.61-4.76 (m, 1 H) 3.87-3.95 (m, 3 H) 3.05 (tt, J = 11.80, 3.33 Hz, 1 H) 2.84-2.91 (m, 3 H) 2.18-2.37 (m, 4 H) 1.52-1.81 (m, 4 H) |
| 244 | DMSO-d$^6$ | 8.64 (d, J = 5.26 Hz, 1 H) 8.03 (s, 1 H) 7.75-7.91 (m, 3 H) 7.63 (t, J = 7.78 Hz, 1 H) 7.51 (d, J = 8.33 Hz, 1 H) 7.04 (d, J = 5.26 Hz, 1 H) 5.47 (s, 2 H) 4.26 (s, 1 H) 3.96 (s, 3 H) 2.59-2.69 (m, 1 H) 1.04-1.12 (m, 1 H) 0.79-0.99 (m, 3 H) |
| 245 | DMSO-d$^6$ | 8.54 (dd, J = 5.32, 2.06 Hz, 1 H) 8.20 (dd, J = 9.13, 1.38 Hz, 1 H) 8.07 (br d, J = 7.50 Hz, 1 H) 7.86 (br d, J = 7.88 Hz, 1 H) 7.78 (br t, J = 6.44 Hz, 1 H) 7.60 (td, J = 7.72, 2.69 Hz, 1 H) 7.19-7.33 (m, 2 H) 7.19-7.33 (m, 1 H) 6.81 (t, J = 5.57 Hz, 1 H) 5.93-6.04 (m, 1 H) 4.22 (br s, 1 H) 3.90 (s, 3 H) 3.04 (d, J = 3.88 Hz, 3 H) 1.72 (d, J = 6.25 Hz, 3 H) |
| 246 | DMSO-d$^6$ | 8.57 (s, 1 H) 7.39-7.55 (m, 2 H) 7.28 (d, J = 7.02 Hz, 1 H) 5.92 (br s, 1 H) 4.27 (br s, 2 H) 3.92 (s, 3 H) 3.85 (br d, J = 8.99 Hz, 1 H) 3.83-3.90 (m, 1 H) 3.77-3.82 (m, 1 H) 3.77-3.82 (m, 1 H) 3.74 (br s, 1 H) 2.88 (s, 3 H) 2.57 (br s, 2 H) |

Biological Example B-1

Inhibition of ENPP1 Hydrolysis of 2′,3′-cGAMP

Assay 1: Test compounds were plated in a 3× dilution scheme in a 384 well plate. To 50 nL of test compound in DMSO was added 2.5 µL ENPP-1 ECD in Assay Buffer (Tris-HCl pH 8.0 (50 mM), NaCl (150 mM), and 0.01% Triton X-100 in water (2.5 nM final concentration). Enzyme was omitted in control wells reserved to define maximum inhibition (max). Control wells were reserved to define no inhibition (min), and DMSO was used in place of compound solution. The plate was centrifuged for 30 s, and the mixture was incubated for 30 min. 2.5 µL of 2,3-cGAMP in Assay Buffer (final conc: 24 µM; K$_M$=24 µM) was added and the plate was centrifuged and incubated for 30 min. AMP-Glo™ Reagent I (Promega Corp.; 5 µL) was added, the plate was centrifuged for 1 min and incubated for 60 min. AMP Detection solution (100 µL) was added to each well, the plate centrifuged and incubated for 60 min. Luminescence was measured with an Envision plate reader, and % Inhibition was calculated for each well as: (([max−min]−[test−min])/[max−min]. IC$_{50}$ values were calculated from concentration vs. % Inhibition data via a four-parameter variable slope model and converted to K$_I$ values via the Cheng/Prusoff Equation (K$_I$=IC$_{50}$/(1+[substrate]/K$_M$). Known ENPP1 inhibitors have the following IC$_{50}$ values in Assay 1:

8-(3-cyano-6-fluoro-7-methoxyquinolin-4-yl)-2,8-diaz-aspiro[4.5]decane-2-sulfonamide, 2.9 nM;

4-[(6,7-dimethoxyquinolin-4-yl)oxy]benzene-1-sulfonamide, 190 nM;

N-{4-[(6,7-dimethoxyquinolin-4-yl)oxy]phenyl}aminosulfonamide, 490 nM;

7-(6,7-dimethoxyquinazolin-4-yl)-1,2,3,4-tetrahydroisoquinoline-2-sulfonamide, 11 nM;

N-{[4-(7-methoxyquinolin-4-yl)phenyl]methyl}aminosulfonamide, 29 nM;

N-{2-[1-(6,7-dimethoxyquinazolin-4-yl)piperidin-4-yl]ethyl}aminosulfonamide, 31 nM.

Compound 1 had a K$_I$ of 5.1 nM. Compound 1 has an IC$_{50}$ of 17 nM. Compound 8 has an IC$_{50}$ of 6.9 nM. Compound 80 has an IC$_{50}$ of 1.4 nM. Compound 161 has an IC$_{50}$ of 1.3 nM. Additional results are summarized in Table 17 and Table 18.

Assay 2: Compared to the conditions in Assay 1, this assay has a larger dynamic range and ensures the system is under steady-state conditions by reducing the enzyme concentration in the assay. This allows discrimination among very potent compounds and allows for conversion of IC$_{50}$ data to K$_I$s.

Test compounds were plated in a 3× dilution scheme in a 384 well plate. To 50 nL of test compound in DMSO was added 2.5 µL ENPP-1 ECD in Assay Buffer (Tris-HCl pH 8.0 (50 mM), NaCl (150 mM), and 0.01% Triton X-100 in water (0.25 nM final ENPP-1 concentration). Enzyme was omitted in control wells reserved to define maximum inhibition (max). Control wells were reserved to define no inhibition (min), and DMSO was used in place of compound solution. The plate was centrifuged for 30 s, and the mixture was incubated for 30 min. 2.5 µL of 2,3-cGAMP in Assay Buffer (final conc: 24 µM; K$_M$=24 µM) was added and the plate was centrifuged and incubated for 30 min. AMP-Glom Reagent I (Promega Corp.; 5 µL) was added, the plate was centrifuged for 1 min and incubated for 60 min. AMP Detection solution (10 µL) was added to each well, the plate centrifuged and incubated for 60 min. Luminescence was measured with an Envision plate reader, and % Inhibition was calculated for each well as: (([max −min]−[test−min])/[max−min]. IC$_{50}$ values were calculated from concentration vs. % Inhibition data via a four-parameter variable slope model and converted to K$_I$ values via the Cheng/Prusoff Equation (K$_I$=(IC$_{50}$+[E]/2)/(1+[substrate]/K$_M$). Known inhibitors of ENPP1 have the following K$_I$s in Assay 2:

8-(3-cyano-6-fluoro-7-methoxyquinolin-4-yl)-2,8-diaz-aspiro[4.5]decane-2-sulfonamide, 0.47 nM 4-[(6,7-dimethoxyquinolin-4-yl)oxy]benzene-1-sulfonamide, 32 nM
N-{4-[(6,7-dimethoxyquinolin-4-yl)oxy]phenyl}aminosulfonamide, 70 nM
N-{[4-(7-methoxyquinolin-4-yl)phenyl]methyl}aminosulfonamide, 4.9 nM
N-{2-[1-(6,7-dimethoxyquinazolin-4-yl)piperidin-4-yl]ethyl}aminosulfonamide, 2.3 nM Results are summarized in Table 17 and Table 18.

Biological Example B-2

Inhibition of ENPP1 Hydrolysis of AMP p-Nitrophenyl Ester on MDA-MB-231 Cells (Assay 3)

ENPP1 is normally expressed on the human metastatic breast cancer cell line MDA-MB-231. Hydrolysis of the p-nitrophenyl ester of AMP (pNP-AMP), an isostere of ATP, is selectively catalyzed by ENPP1 in the supernatant of MDA-MB-231 cell cultures. Inhibition of the hydrolysis of pNP-AMP by MDA-MB-231 at pH 7.4 and 37° C., is a good model of physiologically relevant activity of membrane-bound ENPP1 at disease-relevant expression levels.

MDA-MB-231 cells were harvested using TypLE Express Enzyme digestion and suspended in 100 µL of Leibovitz's L-15 Medium, 20% FBS, seeding the cells in a 96-well assay plate with 4.5×10⁴ cells/well. Cells were incubated at 37° C. with 1% $CO_2$ for 24 h. In a separate dilution plate, 2× of top dose of compound was prepared in phenol-red free 1640 medium without FBS and then 1:3 serial diluted in the same medium. The cell culture medium of L15 medium was aspirated carefully and cells were washed with PBS once, and 50 µL per well of test compound or DMSO blank were added to the assay plate. Substrate mix (50 µL; 0.5 mM pNP-AMP in phenol-red free 1640 media without FBS) was added for a pNP-AMP final concentration of 0.25 mM. The system was incubated at 37° C. for 3 h. Release of para-nitrophenol was measured by absorbance at 405 nM on an Envision plate reader, and % Inhibition was calculated for each well as: (([max−min]−[test−min])/[max−min]. $IC_{50}$ values were calculated from concentration vs. % Inhibition data via a four-parameter variable slope model and converted to apparent $K_I$ ($K_{I,app}$) values via the Cheng/Prusoff Equation ($K_{I,app}=IC_{50}/(1+[substrate]/K_M)$). Known ENPP1 inhibitors have the following apparent $K_I$s in Assay 3:
8-(3-cyano-6-fluoro-7-methoxyquinolin-4-yl)-2,8-diazaspiro[4.5]decane-2-sulfonamide, 24 nM
4-[(6,7-dimethoxyquinolin-4-yl)oxy]benzene-1-sulfonamide, 380 nM
N-{4-[(6,7-dimethoxyquinolin-4-yl)oxy]phenyl}aminosulfonamide, 920 nM
7-(6,7-dimethoxyquinazolin-4-yl)-1,2,3,4-tetrahydroisoquinoline-2-sulfonamide, 23 nM
N-{[4-(7-methoxyquinolin-4-yl)phenyl]methyl}aminosulfonamide, 330 nM
N-{2-[1-(6,7-dimethoxyquinazolin-4-yl)piperidin-4-yl]ethyl}aminosulfonamide, 120 nM Results for Assays 1 and 2 are summarized in Table 17 below. Table 17 Legend: Assay 1 $IC_{50}$ values, A: >1000 nM; B: ≤1000 but >10 nM; C: ≤10 nM; Assay 2 $K_I$ values, D: >300 nM; E: ≤300 but >3 nM; F: ≤3 nM.

A more detailed and expanded summary of results for Assays 1, 2, and 3 is provided below in Table 18.

TABLE 17

| Compound | Assay 1 ($IC_{50}$) | Assay 2 ($K_I$) |
|---|---|---|
| 1 | B | E |
| 1R | A | D |
| 1S | B | F |
| 6 | A | — |
| 8 | C | F |
| 10 | B | F |
| 12 | B | E |
| 14 | B | E |
| 18 | B | E |
| 22 | A | D |
| 26 | A | — |
| 37 | C | F |
| 37a | — | E |
| 37b | — | F |
| 43 | C | F |
| 44 | B | F |
| 44a | B | F |
| 44b | A | D |
| 47 | B | — |
| 50 | A | — |
| 52 | B | E |
| 52a | — | E |
| 52b | — | E |
| 53 | B | E |
| 54 | C | F |
| 54a | C | F |
| 54b | C | F |
| 55 | C | F |
| 55a | C | F |
| 55b | B | E |
| 57 | B | E |
| 58 | B | — |
| 60 | C | F |
| 60a | C | F |
| 60b | B | E |
| 69 | B | E |
| 72 | B | E |
| 74 | B | F |
| 75 | C | F |
| 75a | C | F |
| 75b | A | E |
| 76 | A | — |
| 77 | B | — |
| 78 | — | E |
| 79 | B | E |
| 80 | C | F |
| 80a | C | F |
| 80b | B | E |
| 84 | A | E |
| 88 | B | — |
| 94 | C | F |
| 94a | — | F |
| 94b | — | E |
| 98 | B | E |
| 101 | B | E |
| 103 | C | F |
| 103a | A | D |
| 103b | C | F |
| 114 | C | F |
| 114a | C | F |
| 114b | B | E |
| 115 | B | E |
| 116 | B | E |
| 117 | B | E |
| 118 | B | E |
| 119 | B | E |
| 120 | C | F |
| 120a | C | F |
| 120b | B | E |
| 121 | — | E |
| 122 | — | F |
| 123 | — | F |
| 124 | — | F |
| 125 | B | — |
| 126 | B | E |
| 127 | B | E |
| 128 | B | — |

TABLE 17-continued

| Compound | Assay 1 (IC$_{50}$) | Assay 2 (K$_I$) |
|---|---|---|
| 129 | B | E |
| 130 | A | — |
| 131 | A | — |
| 132 | — | F |
| 133 | C | F |
| 133a | C | F |
| 133b | A | E |
| 134 | A | — |
| 135 | C | F |
| 136 | C | F |
| 137 | B | E |
| 138 | B | E |
| 139 | B | F |
| 140 | B | E |
| 141 | C | F |
| 141a | — | F |
| 141b | — | E |
| 142 | C | F |
| 142a | — | E |
| 142b | — | F |
| 143 | — | F |
| 144 | — | F |
| 145 | — | E |
| 146 | — | F |
| 147 | — | E |
| 148 | — | E |
| 149 | A | D |
| 150 | C | F |
| 151 | C | F |
| 152 | C | F |
| 153 | B | E |
| 154 | A | — |
| 155 | A | — |
| 156 | — | F |
| 156a | — | F |
| 156b | — | F |
| 157 | — | F |
| 158 | — | F |
| 159 | — | F |
| 160 | — | F |
| 161 | C | F |
| 161a | — | F |
| 161b | — | F |
| 162 | B | E |
| 163 | — | E |
| 164 | — | E |
| 165 | A | D |

TABLE 18

| Compound | Assay 1 (IC$_{50}$) | Assay 2 (K$_I$) | Assay 3 (K$_{I, app}$) |
|---|---|---|---|
| 1 | 17 | 3.5 | 61 |
| 1R | 3200 | 330 | — |
| 1S | 13 | 0.87 | 45 |
| 6 | >30000 | — | — |
| 8 | 4.1 | 0.69 | 27 |
| 10 | 23 | 2.8 | — |
| 12 | 30 | 8.6 | 190 |
| 14 | 110 | 15 | — |
| 18 | 180 | 24 | — |
| 22 | 1200 | 310 | — |
| 26 | 8800 | — | — |
| 37 | 2.9 | 0.41 | 28 |
| 37a | — | 21 | — |
| 37b | — | 0.28 | 21 |
| 43 | 3.9 | 0.49 | 29 |
| 44 | 15 | 1.6 | 110 |
| 44a | 11 | 1 | 110 |
| 44b | 1900 | 350 | — |
| 47 | 180 | — | — |
| 50 | 2600 | — | — |
| 52 | 35 | 6.3 | 280 |
| 52a | — | 110 | — |
| 52b | — | 3.5 | — |
| 53 | 44 | 4.6 | 160 |
| 54 | 0.71 | 0.014 | 0.88 |
| 54a | 0.34 | 0.0075 | 0.32 |
| 54b | 7.6 | 1.3 | 130 |
| 55 | 2 | 0.14 | 25 |
| 55a | 0.76 | 0.09 | 8.7 |
| 55b | 45 | 7.3 | — |
| 57 | 31 | 5.3 | 120 |
| 58 | 51 | — | — |
| 60 | 2.8 | 0.34 | 23 |
| 60a | 1.3 | 0.099 | 11 |
| 60b | 520 | 93 | — |
| 69 | 55 | 10 | — |
| 72 | 120 | 18 | 430 |
| 74 | 11 | 1.7 | — |
| 75 | 4.4 | 0.49 | 31 |
| 75a | 3 | 0.38 | 22 |
| 75b | — | 98 | — |
| 76 | 23000 | — | — |
| 77 | 57 | — | — |
| 78 | — | 150 | — |
| 79 | 740 | 220 | — |
| 80 | 6.2 | 1.1 | 29 |
| 80a | 2.2 | 0.26 | 13 |
| 80b | 180 | 13 | — |
| 84 | 1300 | 210 | — |
| 88 | 920 | — | — |
| 94 | 6.6 | 1.3 | 83 |
| 94a | — | 0.78 | 46 |
| 94b | — | 9 | — |
| 98 | 140 | 25 | — |
| 101 | 40 | 5.4 | 300 |
| 103 | 9 | 1.3 | 49 |
| 103a | 1600 | 450 | — |
| 103b | 2.2 | 0.31 | 30 |
| 107 | — | 80 | — |
| 107a | — | 27 | — |
| 107b | — | 74 | — |
| 114 | 2.8 | 0.27 | 19 |
| 114a | 0.94 | 0.088 | 6.3 |
| 114b | 77 | >25 | — |
| 115 | 85 | 13 | — |
| 116 | 220 | 25 | — |
| 117 | 180 | 94 | — |
| 118 | 160 | 36 | — |
| 119 | 66 | 17 | — |
| 120 | 1.1 | 0.12 | 6.2 |
| 120a | 0.46 | 0.05 | 6.5 |
| 120b | 37 | 4.8 | — |
| 121 | — | 4.2 | 250 |
| 122 | — | 1.6 | — |
| 123 | — | 1.5 | 60 |
| 124 | — | 0.73 | 30 |
| 125 | 340 | 110 | — |
| 126 | 39 | 11 | — |
| 127 | 30 | 5 | 380 |
| 128 | 310 | — | — |
| 129 | 260 | 39 | — |
| 130 | 8100 | — | — |
| 131 | >30000 | — | — |
| 132 | — | 1.1 | 45 |
| 133 | 1.4 | 0.12 | 13 |
| 133a | 0.5 | 0.055 | 4.1 |
| 133b | >100 | 49 | — |
| 134 | 1100 | — | — |
| 135 | 7.8 | 1.4 | 110 |
| 136 | 2 | 0.32 | 29 |
| 137 | 200 | 38 | — |
| 138 | 37 | 4.6 | 140 |
| 139 | 15 | 2.4 | — |
| 140 | 880 | 180 | — |
| 141 | 2.1 | 0.25 | 16 |
| 141a | — | 0.26 | 28 |
| 141b | — | 31 | — |
| 142 | 6.3 | 1.2 | 86 |

TABLE 18-continued

| Compound | Assay 1 (IC$_{50}$) | Assay 2 (K$_I$) | Assay 3 (K$_{I, app}$) |
|---|---|---|---|
| 142a | — | 25 | — |
| 142b | — | 0.8 | 52 |
| 143 | — | 1 | 180 |
| 144 | — | 0.28 | 19 |
| 145 | — | 8.7 | — |
| 146 | — | 0.36 | 15 |
| 146a | — | 0.12 | 4.5 |
| 146b | — | 66 | — |
| 147 | — | 9.9 | — |
| 148 | — | 56 | — |
| 149 | 1400 | 410 | — |
| 150 | 8.6 | 1.3 | 62 |
| 151 | 6.2 | 0.57 | 59 |
| 152 | 2.4 | 0.41 | 26 |
| 153 | 54 | 12 | — |
| 154 | 1800 | — | — |
| 155 | 14000 | — | — |
| 156 | — | 0.03 | 4.1 |
| 156a | — | 0.016 | 1.7 |
| 156b | — | 2.9 | — |
| 157 | — | 2.7 | — |
| 158 | — | 0.44 | — |
| 159 | — | 0.025 | 3.6 |
| 160 | — | 0.021 | 0.45 |
| 160a | — | 0.007 | 0.22 |
| 160b | — | 1.7 | — |
| 161 | 1.3 | 0.051 | 3.7 |
| 161a | — | 0.015 | 5.2 |
| 161b | — | 0.64 | — |
| 162 | 40 | 6.9 | — |
| 163 | — | 21 | — |
| 164 | — | 97 | — |
| 165 | >30000 | 1400 | — |
| 166 | — | 3.1 | 230 |
| 167 | — | 7.9 | — |
| 168 | — | 0.84 | 40 |
| 169 | — | 0.051 | 1.5 |
| 169a | — | 15 | >190 |
| 169b | — | 0.018 | 1.5 |
| 170 | — | 0.7 | 25 |
| 171 | — | 49 | — |
| 172 | — | 11 | — |
| 173 | — | 0.17 | 9.2 |
| 174 | — | 5.2 | 240 |
| 175 | — | 0.037 | 3.5 |
| 175a | — | 0.011 | 0.53 |
| 175b | — | 4.1 | — |
| 176 | — | 0.094 | 7.2 |
| 177 | — | 0.03 | 1.5 |
| 177a | — | 20 | — |
| 177b | — | 0.0085 | 0.48 |
| 178 | — | 2.6 | — |
| 178a | — | — | — |
| 178b | — | 34 | — |
| 179 | — | 0.048 | 3.3 |
| 179a | — | 9.1 | — |
| 179b | — | 0.014 | 0.63 |
| 180 | — | 16 | — |
| 181 | — | 0.16 | 28 |
| 182 | — | 3.1 | — |
| 183 | — | 5.2 | — |
| 183a | — | 2.9 | — |
| 183b | — | >150 | — |
| 184 | — | 0.13 | 5.5 |
| 184a | — | 0.1 | 1.7 |
| 184b | — | 2.5 | 58 |
| 185 | — | 0.028 | 0.45 |
| 185a | — | 0.013 | 0.32 |
| 185b | — | 2.8 | — |
| 186 | — | 0.38 | 17 |
| 187 | — | 0.19 | 4.4 |
| 188 | — | 0.074 | 6.5 |
| 189 | — | 0.033 | 0.45 |
| 189a | — | 8.8 | — |
| 189b | — | 0.0075 | 0.31 |
| 190 | — | 0.19 | 7.3 |
| 191 | — | 0.34 | 15 |
| 192 | — | 0.58 | — |
| 193 | — | 0.023 | 0.62 |
| 193a | — | 54 | — |
| 193b | — | 0.012 | 0.36 |
| 194 | — | 40 | — |
| 195 | — | 0.2 | — |
| 195a | — | 0.052 | — |
| 195b | — | 7.7 | — |
| 196 | — | 0.091 | 2.3 |
| 197 | — | 0.04 | 2.3 |
| 198 | — | 0.014 | 0.2 |
| 198a | — | 0.0025 | 0.086 |
| 198b | — | 1.2 | — |
| 199 | — | 0.43 | 8.8 |
| 200 | — | 0.019 | 0.41 |
| 201 | — | 0.69 | 12 |
| 202 | — | 370 | — |
| 203 | — | 1.7 | — |
| 204 | — | 28 | — |
| 205 | — | 0.032 | 2.2 |
| 205a | — | 5 | — |
| 205b | — | 0.0057 | 0.12 |
| 206 | — | 17 | — |
| 207 | — | 0.037 | 3.3 |
| 208 | — | 0.021 | 0.21 |
| 208a | — | 1.1 | 55 |
| 208b | — | 0.0078 | 0.16 |
| 209 | — | 17 | — |
| 210 | — | 0.024 | 2.5 |
| 211 | — | 0.022 | 0.97 |
| 211a | — | 0.023 | 2.2 |
| 211b | — | 0.5 | — |
| 212 | — | 0.047 | 4.4 |
| 213 | — | 0.058 | 2.8 |
| 214 | — | 110 | — |
| 215 | — | 3.8 | — |
| 216 | — | 5.5 | — |
| 217 | — | 0.29 | 8 |
| 218 | — | 0.022 | 0.69 |
| 218a | — | 0.0078 | 0.29 |
| 218b | — | 1.5 | — |
| 219 | — | 0.091 | — |
| 219a | — | 0.071 | 1.2 |
| 219b | — | 2 | — |
| 220 | — | 0.25 | 11 |
| 221 | — | 0.12 | 4.6 |
| 222 | — | 0.07 | 1.1 |
| 222a | — | 0.034 | 1.2 |
| 222b | — | 1.3 | — |
| 223 | — | 0.11 | 3.2 |
| 223a | — | 0.047 | 3.1 |
| 223b | — | 19 | 460 |
| 224 | — | 0.019 | 1.1 |
| 225 | — | 0.096 | 6.8 |
| 226 | — | 1.2 | 43 |
| 227 | — | 0.018 | 0.51 |
| 228 | — | 0.25 | 8.7 |
| 229a | — | 39 | — |
| 229b | — | 0.37 | 3.6 |
| 230a | — | 11 | — |
| 230b | — | 0.38 | 6.6 |
| 231 | — | 1.2 | 56 |
| 232 | — | 3.3 | — |
| 233 | — | >500 | — |
| 234 | — | >500 | — |
| 235 | — | 8 | — |
| 236 | — | 86 | >580 |
| 237 | — | 0.028 | 1.2 |
| 237a | — | 2.4 | — |
| 237b | — | 0.005 | 0.17 |
| 238a | — | 66 | 260 |
| 238b | — | 13 | — |
| 239 | — | 0.81 | 15 |
| 239a | — | 0.43 | 5.4 |
| 239b | — | 83 | — |
| 240 | — | 0.069 | 5.4 |
| 241 | — | 0.031 | 1.2 |

TABLE 18-continued

| Compound | Assay 1 ($IC_{50}$) | Assay 2 ($K_I$) | Assay 3 ($K_{I, app}$) |
|---|---|---|---|
| 242 | — | >500 | — |
| 243 | — | 4.3 | — |
| 244 | — | 0.018 | 0.55 |
| 245 | — | 0.23 | 5.7 |
| 246 | — | 19 | — |

Biological Example B-3

Evaluation of Effect of ENPP1 Inhibitors on Mouse Model of Tumor Growth

EMT6 cells (ATCC, CRL-2755™) are maintained in vitro as a monolayer culture in Waymouth's medium supplemented with 15% heat inactivated fetal bovine serum, 100 U/mL penicillin and 100 µg/mL streptomycin at 37° C. in an atmosphere of 5% $CO_2$ in air. The tumor cells are routinely subcultured twice weekly by trypsin-EDTA treatment. The cells growing to a confluency around 70%-80% are harvested and counted for tumor inoculation. Each mouse is inoculated subcutaneously at the right flank with $2 \times 10^5$ EMT6 cells suspended in 0.1 mL base medium for tumor development, with n=10 mice inoculated per treatment group. Once primary tumor size reaches an average of 50 $mm^3$, animals are randomized using block randomization by Excel based on tumor size. Animals are then dosed once daily by oral gavage (10 mL/kg) with vehicle control (0.5% methylcellulose and 1% Tween-80 in water) or test compound as suspension in vehicle. Mice are dosed continuously, for example once daily or twice daily, until individual tumors reached the experimental endpoint of 1,500 $mm^3$ in size, after which animals are euthanized and tumors harvested for downstream analysis.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiments, methods, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

What is claimed is:

1. A compound of Formula (I):

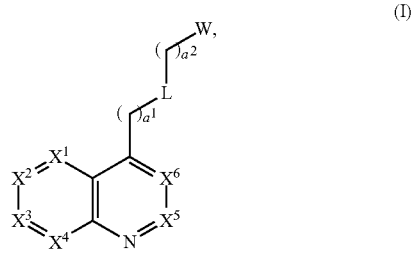

(I)

or a pharmaceutically acceptable salt thereof, wherein W is

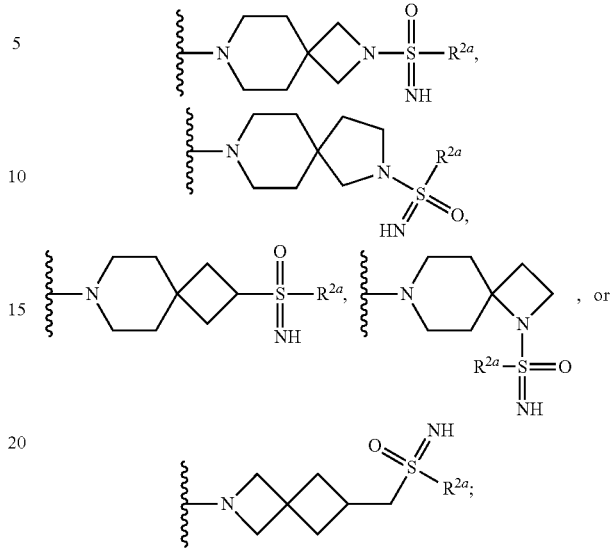

$R^{2a}$ is hydrogen, optionally substituted $C_{1-6}$ alkyl, optionally substituted $C_{3-6}$ cycloalkyl, optionally substituted 3-6 membered heterocycloalkyl, or optionally substituted $C_{1-6}$ haloalkyl;

$X^1$ is —$CR^{1b}$— or —N—;
$X^2$ is —$CR^{2b}$— or —N—;
$X^3$ is —$CR^{3b}$— or —N—;
$X^4$ is —$CR^{4b}$— or —N—;
$X^5$ is —$CR^{5b}$— or —N—;
$X^6$ is —$CR^{6b}$— or —N—;

$R^{1b}$-$R^{6b}$ are each independently hydrogen, halogen, hydroxyl, $C_{1-4}$ alkoxy optionally substituted with one or more halo substituents, cyano, $C_{1-3}$ alkyl, $C_{1-3}$ haloalkyl, nitro, —$NR^{1c}R^{2c}$, —$NHC(O)R^{3c}$, or —$C(O)NR^{4c}R^{5c}$;

L is a bond, —O—, —C(O)—, —$NR^{6c}$—, or —$OCR^{7c}$—*, wherein * represents the point of attachment to

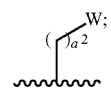

$R^{1c}$-$R^{7c}$ are each independently hydrogen or $C_{1-3}$ alkyl; and $a^1$ and $a^2$ are each independently 0, 1, 2, or 3.

2. The compound of claim 1, or a pharmaceutically acceptable salt thereof, wherein $R^{2a}$ is $C_{1-6}$ alkyl.

3. The compound of claim 2, or a pharmaceutically acceptable salt thereof, wherein $R^{2a}$ is methyl.

4. The compound of claim 1, or a pharmaceutically acceptable salt thereof, wherein the

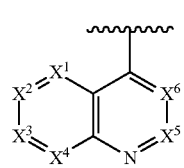

portion of Formula (I) is

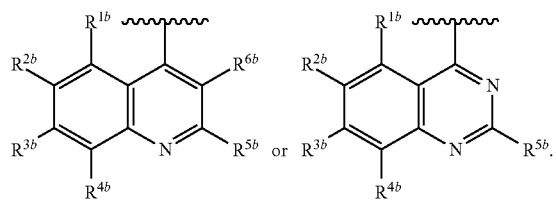

5. The compound of claim 1, or a pharmaceutically acceptable salt thereof, wherein the

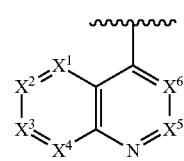

portion of Formula (I) is

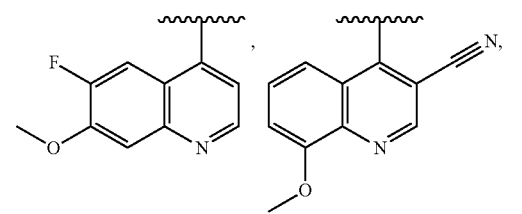

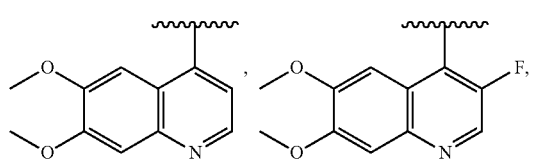

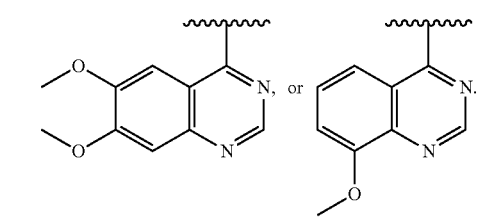

6. The compound of claim 1, or a pharmaceutically acceptable salt thereof, wherein L is a bond.

7. The compound of claim 1, or a pharmaceutically acceptable salt thereof, wherein L is —O—.

8. The compound of claim 1, or a pharmaceutically acceptable salt thereof, wherein $a^1$ is 0 and $a^2$ is 0.

9. The compound of claim 1, or a pharmaceutically acceptable salt thereof, wherein the compound is selected from the group consisting of

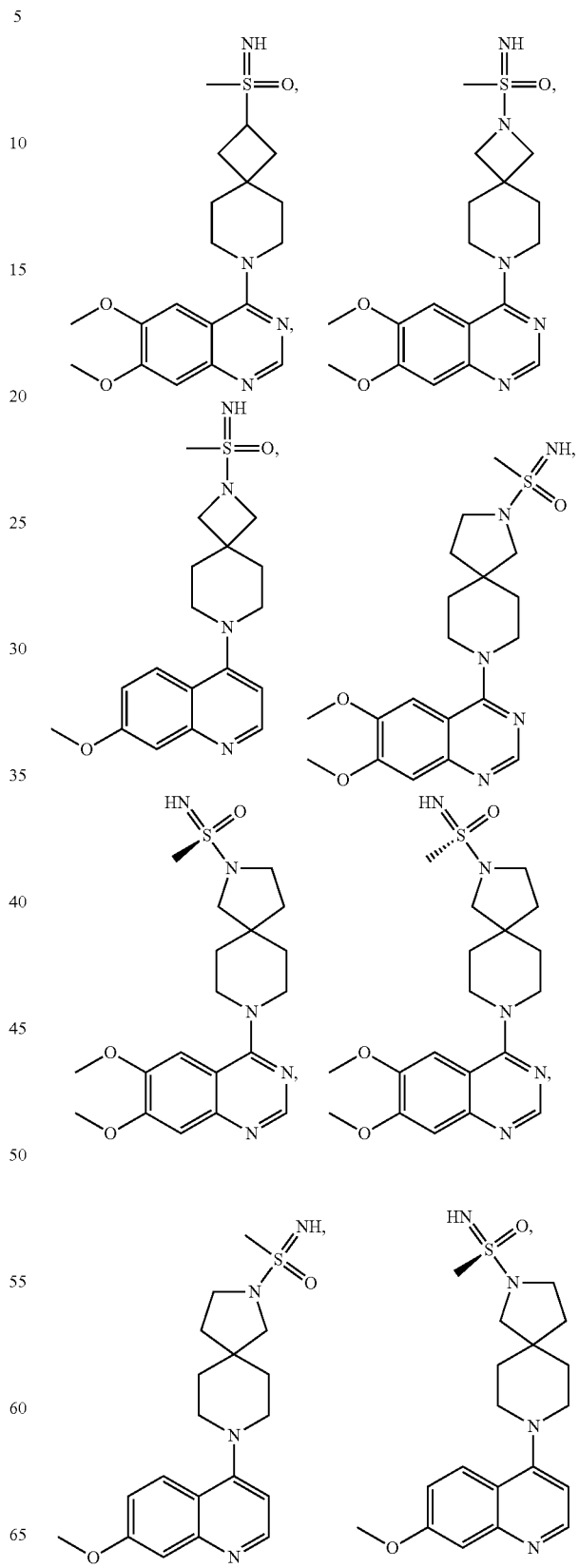

399
-continued
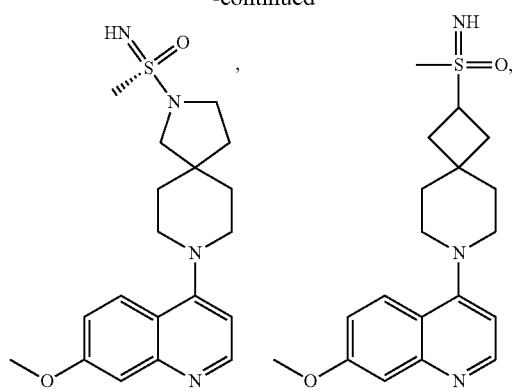
400
-continued
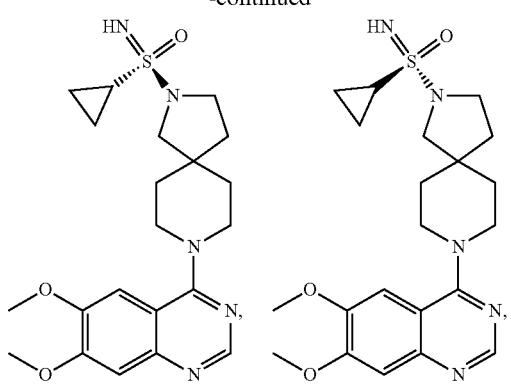
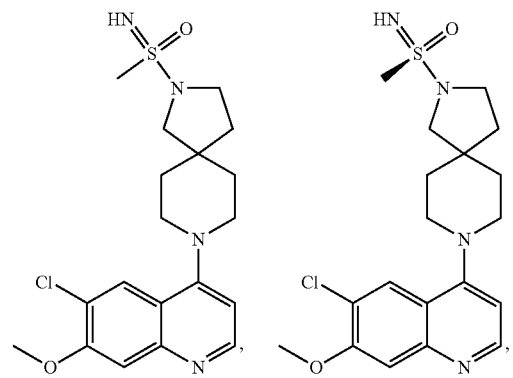
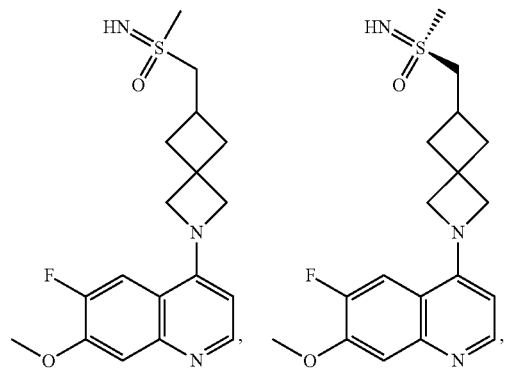
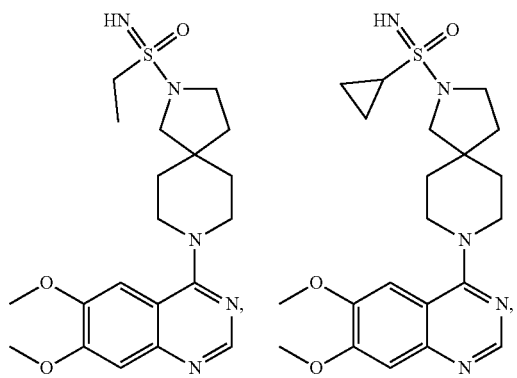
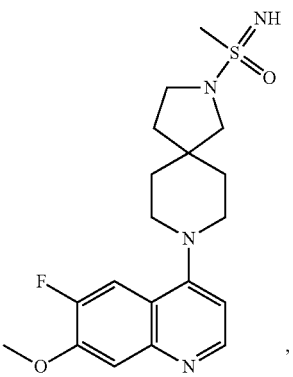

401
-continued
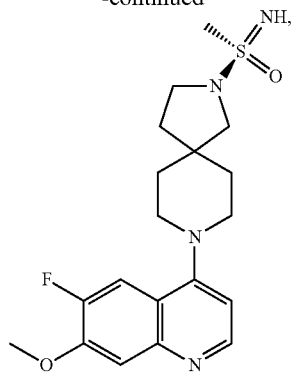
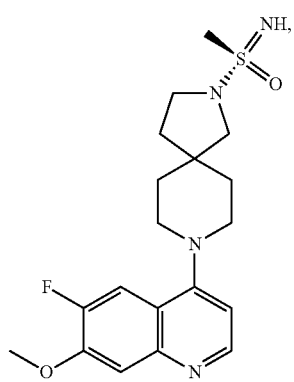
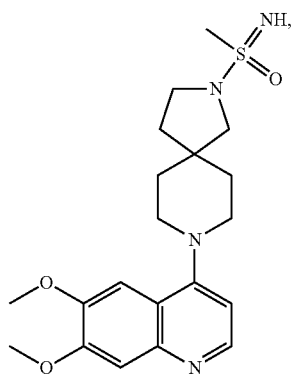
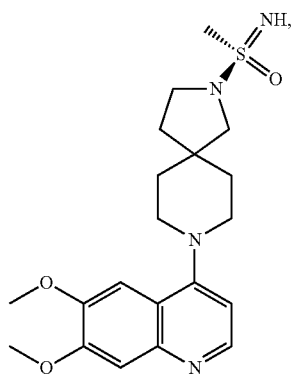
402
-continued
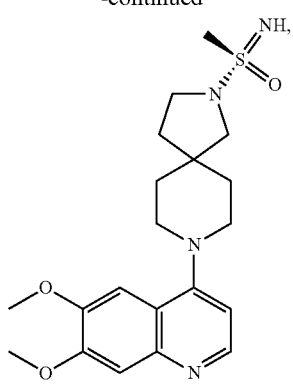
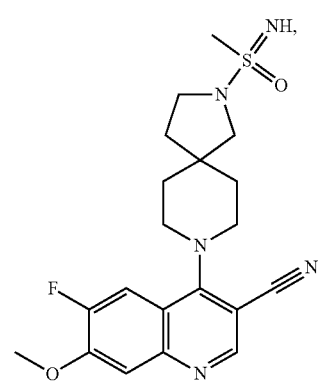
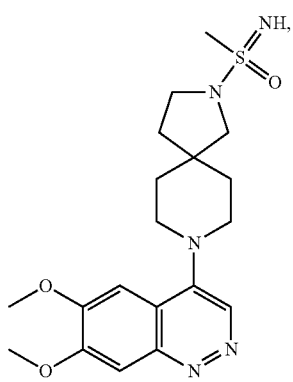
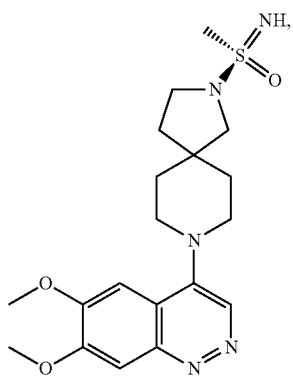

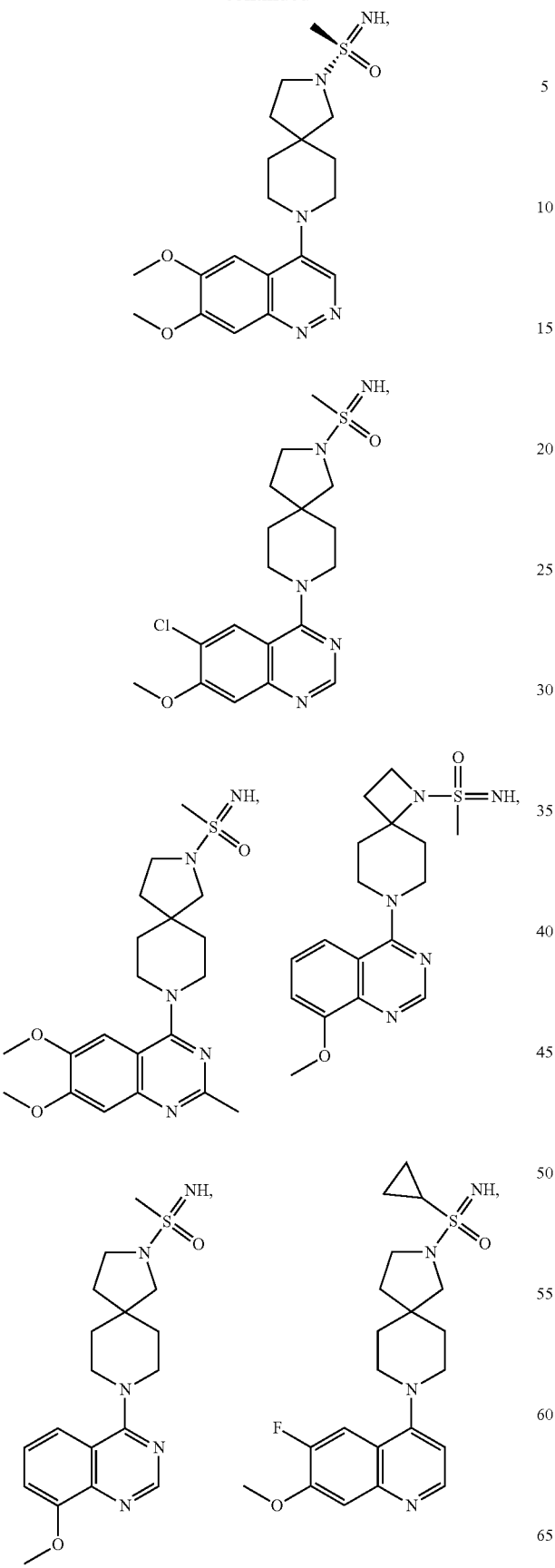
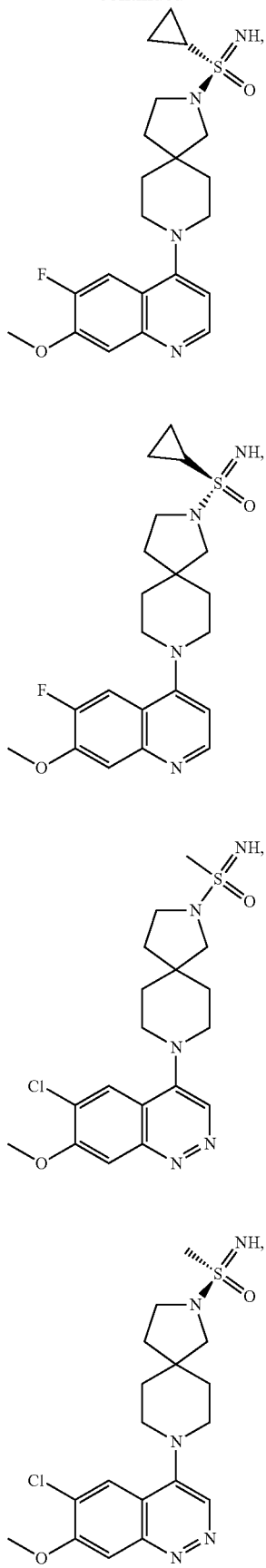

405
-continued
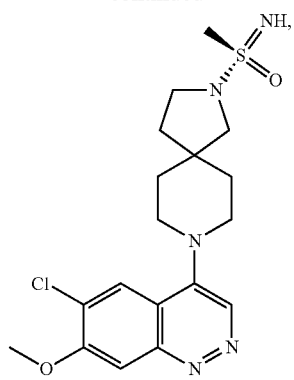
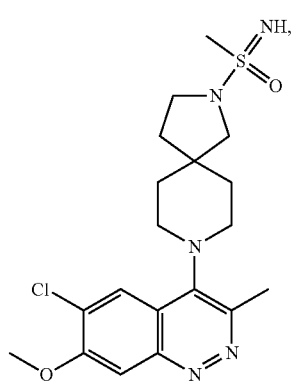
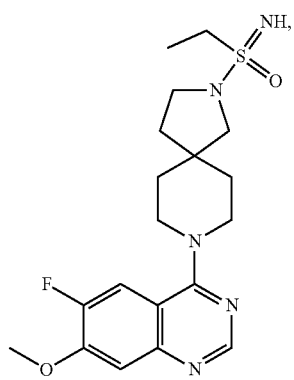
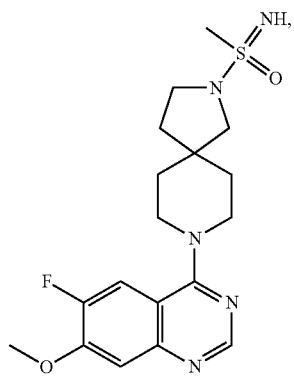
406
-continued
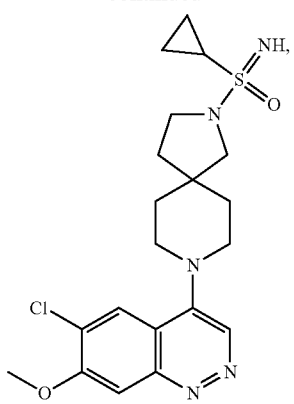
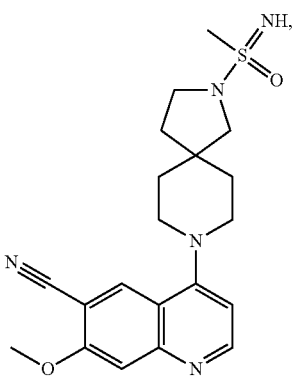
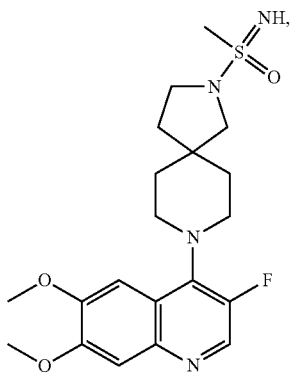
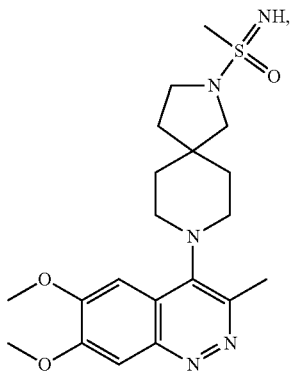

407
-continued
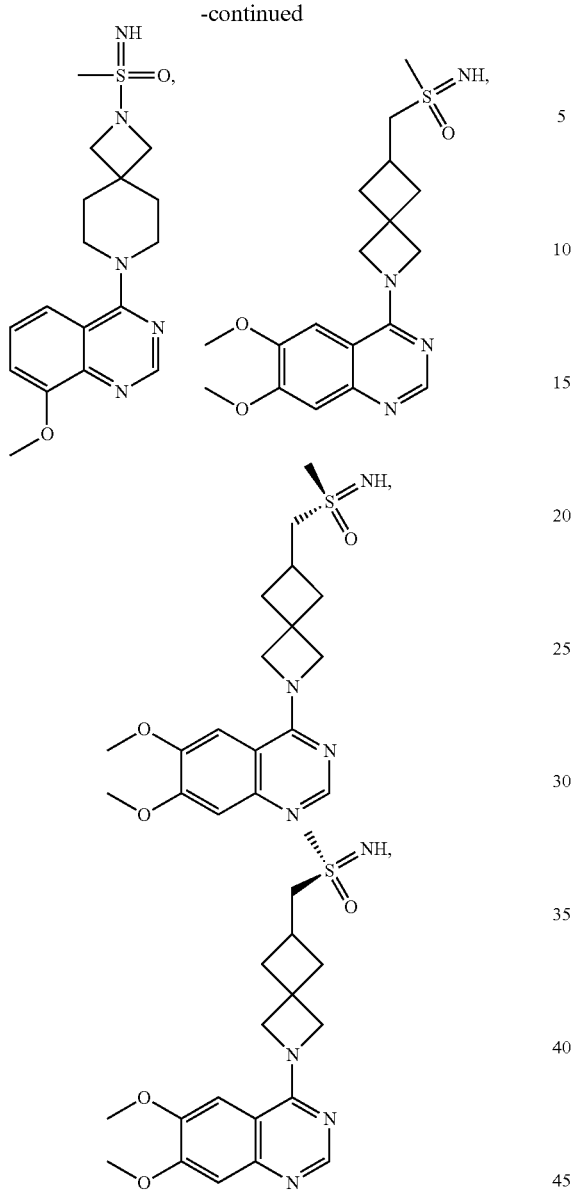
408
-continued
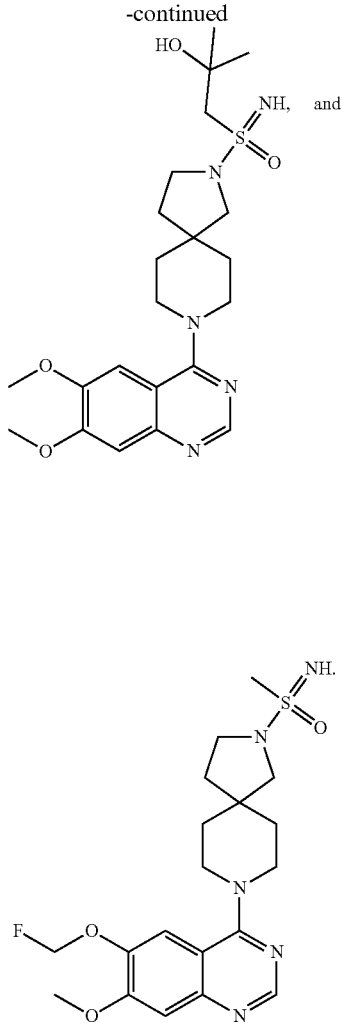
10. A pharmaceutical composition comprising a compound of claim 1, or a pharmaceutically acceptable salt thereof, and a pharmaceutically acceptable carrier or excipient.
* * * * *